US012460193B2

(12) United States Patent
Liu et al.

(10) Patent No.: US 12,460,193 B2
(45) Date of Patent: Nov. 4, 2025

(54) COMPOSITIONS FOR PREVENTING OR TREATING CORONAVIRUS INFECTIONS

(71) Applicant: InvisiShield Technologies Ltd., Emeryville, CA (US)

(72) Inventors: Cheng Liu, Orinda, CA (US); Hongbing Zhang, Moraga, CA (US); Ziyou Cui, Seattle, WA (US); Zhiyuan Yang, Richmond, CA (US); Jinyun Chen, Emeryville, CA (US); Jingbao Liu, Castro Valley, CA (US); Guangyan Xiong, Emeryville, CA (US); Warner Greene, Hillsborough, CA (US)

(73) Assignee: INVISISHIELD TECHNOLOGIES LTD., Emeryville, CA (US)

( * ) Notice: Subject to any disclaimer, the term of this patent is extended or adjusted under 35 U.S.C. 154(b) by 0 days.

(21) Appl. No.: 18/914,016

(22) Filed: Oct. 11, 2024

(65) Prior Publication Data

US 2025/0109390 A1 Apr. 3, 2025

Related U.S. Application Data

(63) Continuation of application No. PCT/US2023/065732, filed on Apr. 13, 2023.

(60) Provisional application No. 63/418,570, filed on Oct. 23, 2022, provisional application No. 63/331,216, filed on Apr. 14, 2022.

(51) Int. Cl.

*A61P 31/14* (2006.01)
*A61K 38/00* (2006.01)
*C12N 9/48* (2006.01)

(52) U.S. Cl.

CPC .............. *C12N 9/485* (2013.01); *A61P 31/14* (2018.01); *C12Y 304/17023* (2013.01); *A61K 38/00* (2013.01); *C07K 2319/00* (2013.01)

(58) Field of Classification Search

CPC ...................................................... C12N 9/485
See application file for complete search history.

(56) References Cited

U.S. PATENT DOCUMENTS

| | | | |
|---|---|---|---|
| 4,816,567 | A | 3/1989 | Cabilly |
| 5,591,828 | A | 1/1997 | Bosslet |
| 5,821,333 | A | 10/1998 | Carter |
| 7,642,228 | B2 | 1/2010 | Carter |
| 10,787,501 | B1 | 9/2020 | Babb et al. |
| 10,954,289 | B1 | 3/2021 | Babb et al. |
| 10,975,139 | B1 | 4/2021 | Babb et al. |
| 11,440,952 | B2 | 9/2022 | Liu et al. |
| 2011/0287009 | A1 | 11/2011 | Scheer |
| 2018/0230447 | A1 | 8/2018 | Batlle et al. |
| 2020/0095327 | A1 | 3/2020 | Chang et al. |
| 2021/0261650 | A1 | 8/2021 | Corti et al. |
| 2021/0277092 | A1 | 9/2021 | Crowe, Jr. et al. |
| 2021/0292392 | A1 | 9/2021 | Zhang et al. |
| 2021/0292393 | A1 | 9/2021 | Westendorf et al. |
| 2021/0300999 | A1 | 9/2021 | Crowe, Jr. et al. |
| 2022/0033522 | A1 | 2/2022 | Ganesan et al. |
| 2022/0119501 | A1 | 4/2022 | Liu et al. |
| 2023/0141962 | A1 | 5/2023 | Liu |

FOREIGN PATENT DOCUMENTS

| | | | |
|---|---|---|---|
| CN | 111303280 | A | 6/2020 |
| EP | 0404097 | A2 | 12/1990 |
| WO | 1993011161 | A1 | 6/1993 |
| WO | 1996034103 | A1 | 10/1996 |
| WO | 2003063772 | A2 | 8/2003 |
| WO | 2008016729 | A1 | 2/2008 |
| WO | 2013055958 | A1 | 4/2013 |
| WO | 2021158521 | A1 | 8/2021 |
| WO | 2021168305 | A1 | 8/2021 |
| WO | 2021195326 | A1 | 9/2021 |
| WO | 2021195485 | A1 | 9/2021 |
| WO | WO 2021189104 | * | 9/2021 |
| WO | 2021216547 | A1 | 10/2021 |
| WO | 2022082217 | A1 | 4/2022 |
| WO | WO 2022075667 | * | 4/2022 |

OTHER PUBLICATIONS

Qiu et al., "Receptor utilization of angiotensin converting enzyme 2 (ACE2) indicates a narrower host range of SARS-CoV-2 than that of SARS-CoV", bioRxiv, 2020, 20 pages. doi: https://doi.org/10.1101/2020.06.13.149930.*

Human ACE2 NCBI seqeunces NM_021804.2, Jun. 2019. Retrieved from < https://www.ncbi.nlm.nih.gov/nuccore/NM_021804.2 > on May 13, 2025.*

Dog ACE2 NCBI sequences NW_020267596.1, Jul. 2018. Retrived from < https://www.ncbi.nlm.nih.gov/nuccore/NW_020267596.1?report=genbank > on May 13, 2025.*

Abhinandan, K.R. et al. (Aug. 2008, e-pub. Jul. 9, 2008). "Analysis and Improvements to Kabat and Structurally Correct Numbering of Antibody Variable Domains," Molecular Immunology 45(14):3832-3839.

Adolf-Bryfogle, J. et al. (2015, e-pub. Nov. 11, 2014). "PylgClassify: A Database of Antibody CDR Structural Classifications," Nucleic Acids Res. 43:D432-D438.

(Continued)

*Primary Examiner* — Suzanne M Noakes
(74) *Attorney, Agent, or Firm* — MORRISON & FOERSTER LLP

(57) ABSTRACT

The present application relates to compositions for preventing or treating infections. In some embodiments, the present application provides chimeric proteins comprising a target-binding moiety comprising an extracellular binding domain (EBD) of an angiotensin-converting enzyme 2 (ACE2) protein or a fragment thereof that specifically binds to an S protein, and a positively charged mucoadhesive peptide fragment. Compositions comprising the chimeric proteins described herein are useful for preventing or treating a viral infection in an individual, such as a coronavirus infection.

30 Claims, 17 Drawing Sheets

Specification includes a Sequence Listing.

(56) References Cited

OTHER PUBLICATIONS

Al-Lazikani, B. et al. (1997). “Standard Conformations for the Canonical Structures of Immunoglobulins,” J. Mol. Biol. 273:927-948.
Alves, N.J. (2019, Feb. 15, 2019). “Antibody Conjugation and Formulation,” Antibody Therapeutics 2(1):33-39.
Azhar, E.M et al. (Jun. 26, 2014). “Evidence for Camel-to Human Transmission of MERS-Coronavirus,” New England Journal of Medicine 370(26):2499-2505.
Beyerstedt, S. et al. (2021, e-pub. Jan. 3, 2021). “ COVID-19: Angiotensin-Converting Enzyme 2 (ACE2) Expression and Tissue Susceptibility to SARS-COV-2 Infection,” Eur. J. Clin. Microbiol. Infect. Dis. 40:905-919.
Bird, R.E. et al. (Oct. 21, 1988). “Single-Chain Antigen-Binding Proteins,” Science 242(4877):423-426.
Blume, C. et al. (Feb. 2021). “A Novel Ace2 Isoform Is Expressed in Human Respiratory Epithelia and Is Upregulated in Response to Interferons and RNA Respiratory Virus Infection,” Nature 53:205-214.
Bottermann, M. et al. (Apr. 10, 2019). “Complement C4 Prevents Viral Infection Through Capsid Inactivation,” Cell Host & Microbe 25:617-629.
BPS Bioscience: ACE-2, His-tag. Available online at https://bpsbioscience.com/ace2-his-tag-11003 [Retrieved online Dec. 21, 2021] https://web.archive.org/web/2020*/https://bpsbioscience.com/ace2-his-tag-11003 published on Jun. 30, 2020 as per Wayback Machine, last visited on Jan. 28, 2022, 3 pages.
Branttie, J.M. et al. (Feb. 25, 2020). “Parainfluenza Virus 5 Fusion Protein Maintains Pre-Fusion Stability but Not Fusogenic Activity Following Mutation of a Transmembrane Leucine/Isoleucine Domain,” J. Gen. Virol. 101 (5):467-472.
Burton, D.R. (1985). “Immunoglobulin G: Functional Sites,” Molec. Immunol. 22(3):161-206.
CELERION Applied Translational Medicine. (May 6, 2015). “Intranasal Drug Delivery: Drug Development Considerations,” slide presentation by Morimoto, B. H. PhD, Executive Director, Applied Translational Medicine, 28 pages.
Cheadle, C. et al. (Jan. 1992). “Cloning and Expression of the Variable Regions of Mouse Myeloma Protein Mopc315 in *E. Coli*: Recovery of Active Fv Fragments,” Molecular Immunology 29(1):21-30.
Chivers, C.E. et al. (2011). “How the Biotin-Streptavidin Interaction was Made Even Stronger: Investigation via Crystallography and a Chimaeric Tetramer,” Biochem J. 435(Pt 1):55-63.
Chothia, C. et al. (Aug. 20, 1987). “Canonical Structures for the Hypervariable Regions of Immunoglobulins,” J. Mol. Biol. 196(4):901-917.
Chowdhury, P.S. (2008). “Engineering Hot Spots for Affinity Enhancement of Antibodies,” Methods Mol. Biol. 207:179-196.
Clinical Trials. Eli Lilly and Company (Aug. 2, 2020). A Study of LY3819253 (LY-CoV555) and LY3832479 (LY-CoV016) in Preventing S AR S -C oV-2 Infection and COVID-19 in Nursing Home Residents and Staff (BLAZE-2). Identifier NCT04497987 Located at https://clinicaltrials.gov/ct2/show/NCT04497987 last visited on Jan. 19, 2022, 27 pages.
Clinical Trials. Regeneron Pharmaceuticals (Jul. 26, 2020-Present). Study Assessing the Safety, Tolerability, Pharmacokinetics, and Immunogenicity of Repeated Subcutaneous Doses of Anti-Spike (S) SARS-CoV-2 Monoclonal Antibodies (REGN10933+REGN10987) in Adult Volunteers as Related to COVID-19. Identifier: NCT04519437, 19 pages.
Clinical Trials. Regeneron Pharmaceuticals (Jun. 11, 2020-Present). Safety, Tolerability, and Efficacy of Anti Spike (S) SARS-CoV-2 Monoclonal Antibodies for Hospitalized Adult Patients With COVID-19. Identifier NCT04426695, 35 pages.
Clinical Trials. Regeneron Pharmaceuticals (Jun. 16, 2020-Present). Safety, Tolerability, and Efficacy of Anti Spike (S) SARS-CoV-2 Monoclonal Antibodies for the Treatment of Ambulatory Adult and Pediatric Patients With COVID-19. Identifier NCT04425629, 32 pages.
Clinical Trials. Regeneron Pharmaceuticals (Jun. 30, 2020-Present). COVID-19 Study Assessing the Efficacy and Safety of Anti-Spike SARS CoV-2 Monoclonal Antibodies for Prevention of SARS CoV-2 Infection Asymptomatic in Healthy Adults and Adolescents Who Are Household Contacts to an Individual With a Positive SARS-CoV-2 RT-PCR Assay. Identifier NCT04452318, 42 pages.
Clinical Trials. Shanghai Junshi Bioscience Co., Ltd. (Jun. 5, 2020-Present). Tolerability, Safety, Pharmacokinetic Profile and Immunogenicity of a Recombinant Humanized Anti-SARS-CoV-2 Monoclonal Antibody (J5016) for Injection in Chinese Health Subjects. Identifier NCT04441918, 20 pages.
Clinical Trials. Vir Biotechnology, Inc. (Aug. 27, 2020-present). VIR-7831 for the Early Treatment of COVID-19 in Outpatients (COMET-ICE). Identifier NCT04545060, 17 pages.
Cohen, J. (Nov. 10, 2020). “Can a Nose-Full of Chicken Antibodies Ward Off Coronavirus Infections?,” Science Insider, located at https://www.science.org/content/article/can-nose-full-chicken-antibodies-ward-coronavirus-infections#.YfRjAoyfAO4.mailto , last visited on Jan. 30, 2022, 2 pages.
Crowe, J.E. Jr, et al. (Feb. 1994). “Recombinant Human Respiratory Syncytial Virus (RSV) Monoclonal Antibody Fab is Effective Therapeutically When Introduced Directly into the Lungs of RSV-Infected Mice,” Proc Natl Acad Sci USA 91(4):1386-1390.
Cui, Y. et al. (2017, e-pub. Jan. 4, 2017). “Monoclonal Antibodies: Formulations of Marketed Products and Recent Advances in Novel Delivery System,” Drug Development and Industrial Pharmacy 11:28, 40 pages.
Cunningham, B.C. et al. (Jun. 2, 1989). “High-Resolution Epitope Mapping of hGH-Receptor Interactions by Alanine-Scanning Mutagenesis,” Science 244:1081-1085.
Dall’acqua, W. et al. (1998). “Contribution of Domain Interface Residues to the Stability of Antibody CH3 Domain Homodimers,” Biochemistry 37(26):9266-9273.
Dolton, G. et al. (2014). “Comparison of Peptide-Major Histocompatibility Complex Tetramers and Dextramers for the Identification of Antigen-Specific T Cells, ”Clin. Exp. Immunol. 177(1):47-63.
Ehrenmann, F. et al. (Jan. 2010, e-pub. Nov. 9, 2009). “IMGT/3Dstructure-DB and IMGT/DomainGapAlign: A Database and a Tool for Immunoglobulins or Antibodies, T Cell Receptors, MHC, IgSF and MhcSF,” Nucleic Acids Res. 38: D301-D307.
Ehrick, J.D. et al. (2013, e-pub. Jun. 22, 2013). “Considerations for the Development of Nasal Dosage Forms,” WEB PDF, Sterile Product Development, pp. 99-144, located at https://link.springer.com/content/pdf/10.1007/978-1-4614-7978-9_5.pdf, last visited on Jan. 31, 2022, 46 pages.
Eroshenko, N. et al. (Jul. 2020, e-pub. Jun. 17, 2020). “Implications of Antibody-Dependent Enhancement of Infection for SARS-CoV-2 Countermeasures,” Nat. Biotechnol. 38:789-791.
Eureka Therapeutics. (Dec. 14, 2020). “Eureka Therapeutics Announces Successful Preclinical Results of InvisiMask™ Human Antibody Nasal Spray Against SARS-CoV-2 Infection,” Press Release, located at https://www.eurekatherapeutics.com/media/press-releases/121420/, last visited on Jan. 28, 2022, 3 pages.
Eureka Therapeutics. (Dec. 14, 2020). “InvisiMask™ Nasal Spray,” Web Brochure (FAQ), located at https://www.eurekatherapeutics.com/faqpdf/?utm_source=faq_pdf&utm_medium=hyperlink&utm_campaign=invisimask_faq, last visited on Jan. 28, 2022, 6 pages.
Eureka Therapeutics. (Dec. 14, 2020). “InvisiMask™ Nasal Spray,” Web Brochure, located at https://www.eurekatherapeutics.com/COVID19/, last visited on Jan. 28, 2022, 5 pages.
Fan, C-Y. et al. (Nov. 2008). “Production of Multivalent Protein Binders Using a Self-Trimerizing Collagen-Like Peptide Scaffold,” FASEB J. 22:3795-3804.
FDA. CDER. CMC. (Jul. 2002). “Guidance for Industry, Nasal Spray and Inhalation Solution, Suspension, and Spray Drug Products—Chemistry, Manufacturing, and Controls Documentation,” Brochure, U.S. Department of Health and Human Services, Food and Drug Administration, Center for Drug Evaluation and Research (CDER), CMC, 49 pages.

(56) References Cited

OTHER PUBLICATIONS

Ferkol, T et al. (Feb. 1995). "Gene Transfer into the Airway Epithelium of Animals by Targeting the 1-3 Polymeric Immunoglobulin Receptor," The Journal of Clinical Investigation 95(2):493-502.
Forster, P. et al. (Apr. 28, 2020). "Phylogenetic Network Analysis of SARS-CoV-2 Genomes," PNAS 117 (17):9241-9243.
Ge, J. et al. (Apr. 2013). "RNA Pesudouridylation: New Insights Into an Old Modification," Trends Biochem. Sci. 38 (4):210-218, 20 pages.
GenBank Accession No. NC045512.2, last updated Jul. 18, 2020, "Severe Acute Respiratory Syndrome Coronavirus 2 Isolate Wuhan-Hu-1, Complete Genome," located at "https://www.ncbi.nlm.nih.gov/nuccore/NC_045512.2/", last visited on Jan. 25, 2023, 16 pages.
Gencel-Augusto, J. et al. (2020). "p53 Tetramerization: at the Center of the Dominant-Negative Effect of Mutant p53," Genes Dev. 34(17-18):1128-1146.
GeneBank Accession No. AAP41037, last updated May 27, 2020, located at http://www.ncbi.nlm.nih.gov/protein/AAP41037.1, last visited Dec. 11, 2024, three pages.
Gizurarson, S. (2012). "Anatomical and Historical Factors Affecting Intranasal Drug and Vaccine Delivery," Current Drug Delivery 9(6):566-582.
Globaldata. (Sep. 17, 2020). "A Nasal Spray Vaccine for COVID-19," Analyst Briefing by Scotty Chung-Siu, MPH, Senior Analyst, 3 pages.
Goldsby, R.A. et al. (2003). "Antibodies: Structure and Function. Part II Generation of B-Cell and T-Cell Responses," Chapter 4 in Immunology, W.H. Freeman, pp. 82-85.
Gomez, C.E. et al. (Mar. 11, 2021). "Emerging SARS-CoV-2 Variants and Impact in Global Vaccination Programs against SARS-CoV-2/COVID-19," Vaccines 9(3):243, 13 pages.
Greenberg, A.S. et al. (Mar. 9, 1995). "A New Antigen Receptor Gene Family That Undergoes Rearrangement and Extensive Somatic Diversification in Sharks" Nature 374(6518):168-173.
Guan, Y. et al. (Aug. 10, 2003). "Isolation and Characterization of Viruses Related to the SARS Coronavirus from Animals in Southern China," Science 30:276-278.
Guillaume, P. et al. (Feb. 14, 2003, e-pub. Oct. 28, 2002). "Soluble Major Histocompatibility Complex-Peptide Octamers with impaired CD8 Binding Selectively Induce Fas-dependent Apoptosis," J. Biol. Chem. 278 (7):4500-4509.
Halwe, S. et al. (Jul. 29, 2021). "Intranasal Administration of a Monoclonal Neutralizing Antibody Protects Mice against SARS-CoV-2 Infection," Viruses 13(8):1498, 39 pages.
Hamers-Casterman, C. et al. (Jun. 3, 1993). "Naturally Occurring Antibodies Devoid of Light Chains," Nature 363:446-448.
Hassanzadeh-Ghassabeh, G. et al. (2013, e-pub. Jun. 4, 2013). "Nanobodies and their Potential Applications," Nanomedicine (Lond) 8(6):1013-1026.
He, Y. et al. (2006). "Cross-Neutralization of Human and Palm Civet Severe Acute Respiratory Syndrome Coronaviruses by Antibodies Targeting the Receptor-Binding Domain of Spike Protein," The Journal of Immunology 176:6085-6092.
Heurich, A. et al. (Jan. 2014). "TMPRSS2 and ADAM17 Cleave ACE2 Differentially and Only Proteolysis by TMPRSS2 Augments Entry Driven by the Severe Acute Respiratory Syndrome Coronavirus Spike Protein," J. Virol. 88 (2):1293-1307.
Higgins, T.S. et al. (2020). "Intranasal Antiviral Drug Delivery and Coronavirus Disease (COVID-19): A State-of-the-Art Review," Preprint Manuscript, Intranasal Antiviral Agents and COVID-19, 37 pages.
Hoffman, M. et al. (Apr. 16, 2020). "SARS-CoV-2 Cell Entry Depends on ACE2 and TMPRSS2 and Is Blocked by a Clinically Proven Protease Inhibitor," Cell 181:271-280.
Holler, N. et al. (2000). "Development if Improved Soluble Inhibitors of FasL and CD49K Based on Oligomerized Receptors," J. Immunol. Methods 237:159-173.
Holliger, P. et al. (Jul. 1993). "'Diabodies'": Small Bivalent and Bispecific Antibody Fragments, Proceedings of the National Academy of Sciences USA 90:6444-6448.
Honegger, A. et al. (Jun. 8, 2001). "Yet Another Numbering Scheme for Immunoglobulin Variable Domains: An Automatic Modeling and Analysis Tool," J. Mol. Biol. 309:657-670.
Hoogenboom, H.R. (2001). "Overview of Antibody Phage-Display Technology and Its Applications," Methods Mol Biol 178:1-37.
Huber-Lang, M. et al. (Jun. 2006, e-pub. May 21, 2006). "Generation of C5a in the Absence of C3: A New Complement Activation Pathway," Nature Medicine 12(6):682-687.
Hulswit, R.J. et al. (Feb. 12, 2019). "Human Coronaviruses OC43 and HKU1 Bind to 9-O-Acetylated Sialic Acids via a Conserved Receptor-Binding site in Spike Protein Domain A," PNAS 116(7):2681-2690.
Huston, J.S. et al. (Aug. 1988). "Protein Engineering of Antibody Binding Sites: Recovery of Specific Activity in an Anti-Digoxin Single-chain Fv Analogue Produced in *Escherichia coli*," Proc. Natl. Acad. Sci. USA 85:5879-5883.
Illum, L. (Dec. 2002). "Nasal Drug Delivery: New Developments and Strategies," Drug Discovery Today 7 (23):1184-1189.
Illum, L. et al. (1994). "Chitosan as a Novel Nasal Delivery System for Peptide Drugs," Pharmaceutical Research 11 (8):1186-1189.
International Preliminary Report on Patentability issued on Oct. 8, 2024, for PCT Application No. PCT/US2023/065732, filed on Apr. 13, 2023, 5 pages.
International Preliminary Report on Patentability mailed Apr. 27, 2023, for International Patent Application No. PCT/US2021/071893, filed Oct. 14, 2021, 11 pages.
International Search Report and Written Opinion mailed on Aug. 21, 2023, for PCT Application No. PCT/US23/65732, filed on Apr. 13, 2023, 10 pages.
International Search Report and Written Opinion of the International Searching Authority mailed Jan. 4, 2022, for International Patent Application No. PCT/US2021/071893, filed Oct. 14, 2021, 19 pages.
Jansen, F.K. et al. (1982). "Immunotoxins: Hybrid Molecules Combining High Specificity and Potent Cytotoxicity," Immunol. Rev. 62:185-216.
Jones, P.T. et al. (May 29, 1986). "Replacing the Complementarity-Determining Regions in a Human Antibody With Those From a Mouse," Nature 321:522-525.
Kabat, E.A. et al. (Oct. 10, 1977). "Unusual Distributions of Amino Acids in Complementarity-Determining (Hypervariable) Segments of Heavy and Light Chains of Immunoglobulins and Their Possible Roles in Specificity of Antibody-Combining Sites," J. Biol. Chem. 252(19):6609-6616.
Kaye, R.S. et al. (2008, e-pub. Nov. 24, 2008). "Development and Testing of Particulate Formulations for the Nasal Delivery of Antibodies," Journal of Controlled Release 135(2009):127-135.
Killen, J.A. et al. (Nov. 1, 1984). "Specific Killing of Lymphocytes That Cause Experimental Autoimmune Myasthenia Gravis by Ricin Toxin-Acetylcholine Receptor Conjugates," J. Immunol. 133(5):2549-2553.
Koussoroplis, S.J. et al. (2014, e-pub. May 17, 2014). "PEGylation of Antibody Fragments Greatly Increases Their Local Residence Time Following Delivery to the Respiratory Tract," J Control Release 187:91-100.
Kulkarni, V. (Jun. 2012). "Formulation and Characterization of Nasal Sprays, An Examination of Nasal Spray Formulation Parameters and Excipients and Their Influence on Key in Vitro Tests," WEB PDF, Inhalation, located at https://www.dptlabs.com/wp-content/uploads/2012/08/Formulation_and_Characterization_of_Nasal_Sprays.pdf , last visited on Jan. 31, 2022, 5 pages.
Kuznetsov, A. et al. (2022, e-pub. Dec. 1, 2021). "ACE2 Peptide Fragment Interaction with Different S1 Protein Sites," Int. J. Pept. Res Ther. 28(1):1-7.
Lefranc, M.-P. et al. (2015, e-pub. Nov. 5, 2014). "IMGT®, The International ImMunoGeneTics Information System® 25 Years on," Nucleic Acids Res. 43:D413-D422.
Lefranc, M.P. et al. (Jan. 2003). "IMGT Unique Numbering for Immunoglobulin and T Cell Receptor Variable Domains and Ig Superfamily V-Like Domains," Dev. Comp. Immunol. 27(1):55-77.

(56) References Cited

OTHER PUBLICATIONS

Li, F. (2016, e-pub. Aug. 25, 2016). "Structure, Function, and Evolution of Coronavirus Spike Proteins," Annu Rev Virol. 3(1):237-261.
Li, F. et al. (Sep. 16, 2005). "Structure of SARS Coronavirus Spike Receptor-Binding Domain Complexed with Receptor," Science 309:1864-1968.
Li, Q. et al. (Jun. 18, 2020). "Genetic Variability of Human Angiotensin-Converting Enzyme 2 (hACE2) Among Various Ethnic Populations," Mol. Genet. Genomic Med. 8(8):e1344, 6 pages.
Li, W. et al. (2005). "Receptor and viral determinants of SARS-coronavirus adaptation to human ACE2," The EMBO Journal 24(8):1634-1643.
Liu, L. et al. (Aug. 20, 2020, e-pub. Jul. 22, 2020). "Potent Neutralizing Antibodies Against Multiple Epitopes on SARS-CoV-2 Spike," Nature 584:450-456, 26 pages.
Lobner, E. et al. (2016). "Engineered IgG1-Fc—One Fragment to Bind Them All," Immunol. Rev. 270(1)113-131.
Lu, F. et al. (Aug. 2015). "Bat-to-Human: Spike Features Determining 'Host Jump' of Coronaviruses SRS-CoV, MERS-CoV, and Beyond," Tends in Microbiology 29(8):468-478.
Lu, G. et al. (Aug. 8, 2013). "Molecular Basis of Binding Between Novel Human Coronavirus MERS-CoV and its Receptor CD26," Nature 500:227-232.
Maccallum, R.M. et al. (1996). "Antibody-Antigen Interactions: Contact Analysis and Binding Site Topography," J. Mol. Biol. 262:732-745.
Marple, B, et al. (2004). "Review Article, Safety Review of Benzalkonium Chloride Used as a Preservative in Intranasal Solutions: An Overview of Conflicting Data and Opinions," Otolaryngol Head Neck Surg 130:131-41.
Mellors, J. et al. (Jul. 9, 2020). "Viral Evasion of the Complement System and Its Importance for Vaccines and Therapeutics," Frontiers in Immunology 11(1450):1-20.
Millet, J. K. et al. (Apr. 16, 2015). "Host Cell Proteases: Critical Determinants of Coronavirus Tropism and Pathogenesis," Virus Res. 202:120-134.
Mohebbi, A. et al. (Aug. 17, 2020). "Susceptibility of the Iranian Population to Severe Acute Respiratory Syndrome Coronavirus 2 Infection Based on Variants of Angiotensin I Converting Enzyme 2," Future Virol. 10:2217-2235.
Mordhorst, S. et al. (Nov. 23, 2020, E-PUB. Sep. 17, 2020). "Posttranslationally Acting Arginases Provide a Ribosomal Route to Non-Proteinogenic Ornithine Residues in Diverse Peptide Sequences," Angewandte Chemie 59(48):21442-21447.
Morimoto, B. H. (PhD) (May 6, 2015). "Intranasal Drug Delivery: Drug Development Considerations," slide presentation for CELERION Applied Translational Medicine, 28 pages.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Napolitano, G. et al. (2016). "TFEB at a Glance," J. Cell Sci. 129(13):2475-2481.
Partial European Search Report for European Patent Application No. 21881327.7, mailed on Sep. 10, 2024, Filed May 16, 2023, 10 pages.
Plückthun, A. (1994). "Antibodies from *Escherichia coli*," in Chapter 11 the Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Raag, R. et al. (Jan. 1995). "Single-chain Fvs," The FASEB Journal 9:73-80.
Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.
Riche, D. O. (Feb. 2021). "Two Different Antibody-Dependent Enhancement (ADE) Risks for SARS-CoV-2 Antibodies," Front. Immunol. 12:640093, 9 pages.
Riechmann, L. et al. (Mar. 24, 1988). "Reshaping Human Antibodies for Therapy," Nature 332:323-329.
Riediker, M. et al. (Jul. 27, 2020). "Estimation of Viral Aerosol Emissions From Simulated Individuals With Asymptomatic to Moderate Coronavirus Disease 2019," JAMA Netw Open. 3(7):e2013807, 10 pages.
Rudikoff, S. et al. (Mar. 1982). "Single Amino Acid Substitution Altering Antigen-Binding Specificity," Proc. Natl. Acad. Sci. USA 79:1979-1983.
Scheraga. H.A. (1992). "Predicting Three Dimensional Structures of Oligopeptides," Chapter 2 in Review in Computational Chemistry III, pp. 73-142.
Shikov, A.E. et al. (Sep. 29, 2020). "Analysis of the Spectrum of ACE2 Variation Suggests a Possible Influence of Rare and Common Variants on Susceptibility to COVID-19 and Severity of Outcome," Front Genet. 11:551220, 10 pages.
Suh, W. et al. (2001). "Anti-JL1 Antibody-Conjugated Poly (L-lysine) for Targeted Gene Delivery to Leukemia T Cells," Journal of Controlled Release 72(2001):171-178.
Sui, J. et al. (Feb. 24, 2004). "Potent Neutralization of Severe Acute Respiratory Syndrome (SARS) Coronavirus by a Human mAb to S1 Protein That Blocks Receptor Association," 101(8):2536-2541.
Tanaka, S. et al. (2021, e-pub. Jun. 17, 2021). "An ACE2 Triple Decoy That Neutralizes SARS-CoV-2 Shows Enhanced Affinity for Virus Variants," Nature 11:12740-12753.
Tang, J.W. et al. (Apr. 2021). "Emergence of a New SARS-CoV-2 variant in the UK,"Journal of Infection 82(4):e27-e28.
Taylor, P.C. et al. (Jun. 2021). "Neutralizing Monoclonal Antibodies for Treatment of COVID-19," Nat Rev Immunol 21:382-393.
Thorat, S. (2016). "Formulation and Product Development of Nasal Spray: An Overview," Scholars Journal of Applied Medical Sciences (SJAMS) 4(8D):2976-2985.
Tuekprakhon, A. et al. (2022). "Antibody Escape of SARS-CoV-2 Omicron BA.4 and BA.5 From Vaccine and BA. 1 Serum," Cell 185(14):2422-2433.
UniProtKB ID PODTC2, located at http://www.uniprot.org/uniprotkb/P59594/entry, last visited on Dec. 10, 2024, nine pages.
Van Den Brink, E.N. et al. (Feb. 2005). "Molecular and Biological Characterization of Human Monoclonal Antibodies Binding to the Spike and Nucleocapsid Proteins of Severe Acute Respiratory Syndrome Coronavirus," Journal of Virology 79(3):1635-1644.
Viana, R. et al. (2022, e-pub. Jan. 7, 2022). "Rapid Epidemic Expansion of the SARS-CoV-Omicron Variant in Southern Africa," Nature 603:679-686.
Vitetta, E.S. et al. (Nov. 20, 1987). "Redesigning Nature's Poisons to Create Anti-Tumor Reagents," Science 238:1098-1104.
Walls, A. C. et al. (Apr. 16, 2020). "Structure, Function, and Antigenicity of the SARS-CoV-2 Spike Glycoprotein," Cell 180(2):281-292, 38 pages.
Walsh, S. et al. (Oct. 2004). "Extended Nasal Residence Time of Lysostaphin and an Anti-Staphylococcal Monoclonal Antibody by Delivery in Semisolid or Polymeric Carriers," Pharm Res. 21(10):1770-1775.
Wang, Q. et al. (Jan. 19, 2023). "Alarming Antibody Evasion Properties of Rising SARS-CoV-2 BQ and XBB Subvariants," Cell 186:279-286.
Wang, Q. et al. (May 14, 2020). "Structural and Functional Basis of SARS-CoV-2 Entry by Using Human ACE2," Cell 181(4):894-904.
Wang, W. et al. (Jan. 2007). "Antibody Structure, Instability, and Formulation," J. Pharm. Sci. 96(1):1-26.
Ward, E.S. et al. (Oct. 12, 1989). "Binding Activities of a Repertoire of Single Immunoglobulin Variable Domains Secreted From *Escherichia coli*," Nature 341:544-546.
Weltzin, R. et al. (Jul. 1999). "Intranasal Antibody Prophylaxis for Protection Against Viral Disease," Clinical Microbiology Review 12(3):383-393.
Wevers, B.A. et al. (2009). "Recently Discovered Human Coronaviruses," Clin. Lab Med. 29(4):715-724.
Widjaja, I. et al. (2019, e-pub. Apr. 2, 2019). "Towards a Solution to MERS: Protective Human Monoclonal Antibodies Targeting

(56) References Cited

OTHER PUBLICATIONS

Different Domains and Functions of the MERS-Coronavirus Spike Glycoprotein," Emerging Microbes & Infections 8(1):516-530.
Woo, P.C.Y. et al. (2009). "Coronavirus Diversity, Phylogeny and Interspecies Jumping," Exp. Biol. Med. 234:1117-1127.
Yang, X. et al. (May 2002). "Highly Stable Trimers Formed by Human Immunodeficiency Virus Type 1 Envelope Glycoproteins Fused With the Trimeric Motif of T4 Bacteriophage Fibritin," J. Virol. 76(9):4634-4642.
Ye, J. et al. (Jul. 2013). "IgBLAST: An Immunoglobulin Variable Domain Sequence Analysis Tool," Nucleic acids research 41(W1):W34-W40.
Zhang, H. et al. (Dec. 9, 2020). "Intranasal Administration of SARS-CoV-2 Neutralizing Human Antibody Prevents Infection in Mice." bioRxiv located at https://doi.org/10.1101/2020.12.08.416677, last visited on Jan. 30, 2022, 14 pages.
Zheng, J. et al. (Jan. 28, 2021, e-pub. Nov. 9, 2020). "COVID-19 Treatments and Pathogenesis Including Anosmia in K18-hACE2 Mice," Nature 589:603-607.
Zheng, M et al. (2021, e-pub. Dec. 13, 2020). "Poly(alpha-L-Lysine }-Based Nanomaterials for Versatile Biomedical 1-3 C—Applications: Current Advances and Perspectives," Bioactive Materials 6(7):1878-1909.
Zhou, P. et al. (Mar. 12, 2020, e-pub. Feb. 3, 2020). "A Pneumonia Outbreak Associated With a New Coronavirus of Probable Bat Origin," Nature 579:270-273, 20 pages.
Zhu, N. et al. (Feb. 20, 2020, e-pub. Jan. 24, 2020). "A Novel Coronavirus From Patients With Pneumonia in China 2019," N Engl. J. Med. 382(8):727-733.
Zhu, Z. et al. (Jul. 17, 2007). "Potent Cross-Reactive Neutralization of SARS Coronavirus Isolates by Human Monoclonal Antibodies," PNAS 104(29):12123-12128.
Zola, H. (1987). Monoclonal Antibodies: A Manual of Techniques, CRC Press Inc. pp. 147-158.

* cited by examiner

FIG. 2

```
CLUSTAL O sequence alignment

CHICKEN_tr|F1NHR4            MLLHFWLLCGLSAVVTPQDVT-QEAQTFLAEFNVPAEDISYENSLASWNYNTNITEETAR   59
GUINEA_PIG_tr|H0VSF6         MSGSFWFLLNLVAVTTAQFNLEEQAKTFLDEFNLEAEDLYYQSSLASWNYNTNITDENVQ   60
MOUSE_UPKB:Q8R0I0            MSSSSWLLLSLVAVTTAQSLTEENAKTFLNNFNQEAEDLSYQSSLASWNYNTNITEENAQ   60
SWINE_tr|K7GLM4              MSGSFWLLLSLIPVTAAQSTTEELAKTFLEKFNLEAEDLAYQSSLASWNYNTNITDENIQ   60
BOVINE_UPKB:Q58DD0           MTGSFWLLLSLVAVTAAQSTTEEQAKTFLEKFNHEAEDLSYQSSLASWNYNTNITDENVQ   60
RABBIT_tr|G1TEF4             MSGSSWLLLSLVAVTAAQSTIEELAKTFLEKFNQEAEDLSYQSALASWDYNTNITEENVQ   60
MACAQUE_tr|F7AH40            MSGSSWLLLSLVAVTAAQSTIEEQAKTFLDKFNHEAEDLFYQSSLASWNYNTNITEENVQ   60
[redacted]                   MSSSSWLLLSLVAVTAAQSTIEEQAKTFLDKFNHEAEDLFYQSSLASWNYNTNITEENVQ   60
CHIMPANZEE_tr|A0A2J8KU96     MSGSSWLLLSLVAVTAAQSTIEEQAKTFLDKFNHEAEDLFYQSSLASWNYNTNITEENVQ   60
EQUINE_tr|F6V9L3             MSGSSWLLLSLVAVTAAQSTTEDLAKTFLEKFNSEAEELSHQSSLASWSYNTNITDENVQ   60
FERRET_UPKB:Q2WG88           MLGSSWLLLSLAALTAAQSTTEDLAKTFLEKFNYEAEELSYQNSLASWNYNTNITDENIQ   60
MINK_UPKB:A0A7T0Q2W2         MLGSSWLLLSLAALTAAQSTTEDLAKTFLEKFNYEAEELSYQNSLASWNYNTNITDENIQ   60
CANINE_tr|J9P7Y2             MSGSSWLLLSLAALTAAQS-TEDLVKTFLEKFNYEAEELSYQSSLASWNYNINITDENVQ   59
FELINE_tr|A0A5F5XDN9         MSGSFWLLLSFAALTAAQSTTEELAKTFLEKFNHEAEELSYQSSLASWNYNTNITDENVQ   60
                             *    *:* .:   :.: *     : .:*** :** .**:: ::.:****.** ***:*. :

CHICKEN_tr|F1NHR4            KMSEAGAKWAAFYEEASRNASRFSLANIQDAVTRLQIQSLQDRGSSVLSPEKYSRLNSVM   119
GUINEA_PIG_tr|H0VSF6         KMSEAGGILSAFYEEQSNLAKAYPLQDIQNLTVKRQLRILQQSGSSSFSADKNKQLSTIL   120
MOUSE_UPKB:Q8R0I0            KMSEAAAKWSAFYEEQSKTAQSFSLQEIQTPIIKRQLQALQQSGSSALSADKNKQLNTIL   120
SWINE_tr|K7GLM4              KMNDARAKWSAFYEEQSRIAKTYPLDEIQTLILKRQLQALQQSGTSGLSADKSKRLNTIL   120
BOVINE_UPKB:Q58DD0           KMNEARAKWSAFYEEQSRMAKTYSLEEIQNLTLKRQLKALQHSGTSALSAEKSKRLNTIL   120
RABBIT_tr|G1TEF4             KMNDAEAKWSAFYEEQSKLAKTYPSQEVQNLTVKRQLQALQQSGSSALSADKSKQLNTIL   120
MACAQUE_tr|F7AH40            NMNNAGEKWSAFLKEQSTLAQMYPLQEIQNLTVKLQLQALQQNGSSVLSEDKSKRLNTIL   120
[redacted]                   NMNNAGDKWSAFLKEQSTLAQMYPLQEIQNLTVKLQLQALQQNGSSVLSEDKSKRLNTIL   120
CHIMPANZEE_tr|A0A2J8KU96     NMNNAGDKWSAFLKEQSTLAQMYPLQEIQNLTVKLQLQALQQNGSSVLSEDKSKRLNTIL   120
EQUINE_tr|F6V9L3             KMNEAGARWSAFYEEQCKLAKTYPLEEIQNLTVKRQLQALQQSGSSVLSADKSKRLNEIL   120
FERRET_UPKB:Q2WG88           KMNIAGAKWSAFYEEESQHAKTYPLEEIQDFIIKRQLRALQQSGSSVLSADKREKLNTIL   120
MINK_UPKB:A0A7T0Q2W2         KMNIAGAKWSAFYEEESQHAKTYPLEEIQDFIIKRQLRALQQSGSSVLSADKPERLNTIL   120
CANINE_tr|J9P7Y2             KMNNAGAKWSAFYEEQSKLAKTYPLEEIQDSTVKRQLRALQHSGSSVLSADKNQRLNTIL   119
FELINE_tr|A0A5F5XDN9         KMNEAGAKWSAFYEEQSKLAKTYPLAEIHNTTVKRQLQALQQSGSSVLSADKSQRLNTIL   120
                             :*. *     :** :* .  *. :    :::     : *:: **. *:* :* :* .:*. ::

CHICKEN_tr|F1NHR4            NSMSTIYSTGVVCKATEPFDCLVLEPGLDDIMANSIDYHERLWAWEGWRADVGRMMRPLY   179
GUINEA_PIG_tr|H0VSF6         NTMSTLYSTGKVCYPSDPQECLLLEPGLADIMSKSTDYNLRLWAWEGWRSKVGKQLRPLY   180
MOUSE_UPKB:Q8R0I0            NTMSTIYSTGKVCNPKNPQECLLLEPGLDEIMATSTDYNSRLWAWEGWRAEVGKQLRPLY   180
SWINE_tr|K7GLM4              NTMSTIYSSGKVLDPNNPQECLVLEPGLDEIMENSKDYSRRLWAWESWRAEVGKQLRPLY   180
BOVINE_UPKB:Q58DD0           NKMSTIYSTGKVLDPN-TQECLALEPGLDDIMENSRDYNRRLWAWEGWRAEVGKQLRPLY   179
RABBIT_tr|G1TEF4             STMSTIYSTGKVCNQSNPQECFLLEPGLDEIMAKSTDYNERLWAWEGWRSVVGKQLRPLY   180
MACAQUE_tr|F7AH40            NTMSTIYSTGKVCNPNNPQECLLLDPGLNEIMEKSLDYNERLWAWEGWRSEVGKQLRPLY   180
[redacted]                   NTMSTIYSTGKVCNPDNPQECLLLEPGLNEIMANSLDYNERLWAWESWRSEVGKQLRPLY   180
CHIMPANZEE_tr|A0A2J8KU96     NTMSAIYSTGKVCNPNNPQECLLLEPGLNEIMANSLDYNERLWAWESWRSEVGKQLRPLY   180
EQUINE_tr|F6V9L3             NTMSTIYSTGKVCNPSNPQECLLLEPGLDAIMENSKDYNQRLWAWEGWRSEVGKQLRPLY   180
FERRET_UPKB:Q2WG88           NAMSTIYSTGKACNPNNPQECLLLEPGLDDIMENSKDYNERLWAWEGWRSEVGKQLRPLY   180
MINK_UPKB:A0A7T0Q2W2         NAMSTIYSTGKACNPNNPQECLLLEPGLDDIMENSKDYNERLWAWEGWRSEVGKQLRPLY   180
CANINE_tr|J9P7Y2             NSMSTIYSTGKACNPSNPQECLLLEPGLDDIMENSKDYNERLWAWEGWRSEVGKQLRPLY   179
FELINE_tr|A0A5F5XDN9         NAMSTIYSTGKACNPNNPQECLLLEPGLDDIMENSKDYNERLWAWEGWRAEVGKQLRPLY   180
                             . **::**:* .        :*: *:***  ** .* **  ******.**: **: :****

CHICKEN_tr|F1NHR4            EEYVELKNEAARLNNYSDYGDYWRANYETDYPEEYKYSRDQLVQDVEKTFEQIKPLYQHL   239
GUINEA_PIG_tr|H0VSF6         EEYVALKNEMARANKYEDYGDYWRRDYEVEDMDGYNYSRNQLIEDVERTFAEIKPLYEQL   240
MOUSE_UPKB:Q8R0I0            EEYVVLKNEMARANNYNDYGDYWRGDYEAEGADSYNYNRNQLIEDVERTFAEIKPLYEHL   240
SWINE_tr|K7GLM4              EEYVVLENEMARANNYEDYGDYWRGDYEVTGTGDYDYSRNQLMEDVERTFAEIKPLYEHL   240
BOVINE_UPKB:Q58DD0           EEYVVLENEMARANNYEDYGDYWRGDYEVTGAGDYDYSRDQLMKDVERTFAEIKPLYEQL   239
RABBIT_tr|G1TEF4             EEYVVLKNEMARANNYEDYGDYWRADYEAEGADGYDYSRSQLIDDVERTFSEIKPLYEQL   240
MACAQUE_tr|F7AH40            EEYVVLKNEMARANHYKDYGDYWRGNYEVNGVDGYDYNRDQLIEDVERTFEEIKPLYEHL   240
[redacted]                   EEYVVLKNEMARANHYEDYGDYWRGDYEVNGVDGYDYSRGQLIEDVEHTFEEIKPLYEHL   240
CHIMPANZEE_tr|A0A2J8KU96     EEYVVLKNEMARANHYEDYGDYWRGDYEVNGVDGYDYSRGQLIEDVEHTFEEIKPLYEHL   240
EQUINE_tr|F6V9L3             EEYVVLKNEMARANNYEDYGDYWRGDYEAEGPSGYDYSRDQLIEDVERTFAEIKPLYEHL   240
FERRET_UPKB:Q2WG88           EEYVALKNEMARANNYEDYGDYWRGDYEEEWADGYSYSRNQLIEDVEHTFTQIKPLYEHL   240
MINK_UPKB:A0A7T0Q2W2         EEYVALKNEMARANNYEDYGDYWRGDYEEEWADGYNYSRNQLIEDVEHTFTQIKPLYEHL   240
CANINE_tr|J9P7Y2             EEYVALKNEMARANNYEDYGDYWRGDYEEEWENGYNYSRNQLIDDVEHTFTQIMPLYQHL   239
FELINE_tr|A0A5F5XDN9         EEYVALKNEMAKSKQYEDYGDYWRGDYEEEWTDGYNYSRSQLIKDVEHTFTQIKPLYQHL   240
                             **** *:** *: ::*.******* :**       *.*.*.**:.***:** :* ***::*
```

FIG. 2 (continued)

```
CHICKEN_tr|F1NHR4            HAYVRHRLEQVYGSELINPTGCLPAHLLGDMWGRFWTNLYNLTVPYPEKPNIDVTSAMAQ   299
GUINEA_PIG_tr|H0VSF6         HAYVRTKLMETYPS-RISPVGCLPAHLLGDMWGRFWTELYSLTVPFQQKPNIDVTDAMES   299
MOUSE_UPKB:Q8R0I0            HAYVRRKLMDTYPS-YISPTGCLPAHLLGDMWGRFWTNLYPLTVPFAQKPNIDVTDAMMN   299
SWINE_tr|K7GLM4              HAYVRAKLMDAYPS-RISPTGCLPAHLLGDMWGRFWTNLYPLTVPFGEKPSIDVTEAMVN   299
BOVINE_UPKB:Q58DD0           HAYVRAKLMNTYPS-YISPTGCLPAHLLGDMWGRFWTNLYSLTVPFEHKPSIDVTEKMEN   298
RABBIT_tr|G1TEF4             HAFVRTKLMDAYPS-RISPTGCLPAHLLGDMWGRFWTNLYSLTVPFGQKPNIDVTDTMVN   299
MACAQUE_tr|F7AH40            HAYVRAKLMNAYPS-YISPTGCLPAHLLGDMWGRFWTNLYSLTVPFGQKPNIDVTDAMVN   299
hACE2_UPKB:Q9BYF1            HAYVRAKLMNAYPS-YISPIGCLPAHLLGDMWGRFWTNLYSLTVPFGQKPNIDVTDAMVD   299
CHIMPANZEE_tr|A0A2J8KU96     HAYVRAKLMNAYPS-YISPIGCLPAHLLGDMWGRFWTNLYSLTVPFGQKPNIDVTDAMVD   299
EQUINE_tr|F6V9L3             HAYVRAKLMDTYPS-HINPTGCLPAHLLGDMWGRFWTNLYSLTVPFGQKPNIDVTDAMVD   299
FERRET_UPKB:Q2WG88           HAYVRAKLMDAYPS-RISPTGCLPAHLLGDMWGRFWTNLYPLMVPFRQKPNIDVTDAMVN   299
MINK_UPKB:A0A7T0Q2W2         HAYVRAKLMDAYPS-RISPTGCLPAHLLGDMWGRFWTNLYPLMVPFGQKPNIDVTDAMVN   299
CANINE_tr|J9P7Y2             HAYVRTKLMDTYPS-YISPTGCLPAHLLGDMWGRFWTNLYPLTVPFGQKPNIDVTNAMVN   298
FELINE_tr|A0A5F5XDN9         HAYVRAKLMDTYPS-RISPTGCLPAHLLGDMWGRFWTNLYPLTVPFGQKPNIDVTDAMVN   299
                             **:** :* ..* *  *.* ******************:** * **: .**.****. * .

CHICKEN_tr|F1NHR4            KNWDAMKIFKTAEAFFASIGLYNMTEGFWTNSMLTEPTDNRKVVCHPTAWDMGKNDYRIK   359
GUINEA_PIG_tr|H0VSF6         QSWDAEKIFKEAEKFFVSVGLPPMTQGFWKNSMLTEPGDGQKVVCHPTAWDMGKNDFRIK   359
MOUSE_UPKB:Q8R0I0            QGWDAERIFQEAEKFFVSVGLPHMTQGFWANSMLTEPADGRKVVCHPTAWDLGHGDFRIK   359
SWINE_tr|K7GLM4              QSWDAIRIFEEAEKFFVSIGLPNMTQGFWNNSMLTEPGDGRKVVCHPTAWDLGKGDFRIK   359
BOVINE_UPKB:Q58DD0           QSWDAERIFKEAEKFFVSISLPYMTQGFWDNSMLTEPGDGRKVVCHPTAWDLGKGDFRIK   358
RABBIT_tr|G1TEF4             QGWDAERIFKEAEKFFVSVGLPSMTQGFWENSMLTEPGDGRKVVCHPTAWDLGKGDFRIK   359
MACAQUE_tr|F7AH40            QAWNAQRIFKEAEKFFVSVGLPNMTQGFWENSMLTDPGNVQKVVCHPTAWDLGKGDFRII   359
hACE2_UPKB:Q9BYF1            QAWDAQRIFKEAEKFFVSVGLPNMTQGFWENSMLTDPGNVQKAVCHPTAWDLGKGDFRIL   359
CHIMPANZEE_tr|A0A2J8KU96     QAWDAQRIFKEAEKFFVSVGLPNMTQGFWENSMLTDPGNVQKAVCHPTAWDLGKGDFRIL   359
EQUINE_tr|F6V9L3             QSWDAKRIFEEAEKFFVSVGLPNMTQGFWENSMLTEPGDGRKVVCHPTAWDLGKGDFRIK   359
FERRET_UPKB:Q2WG88           QSWDAKRIFEEAETFFVSVGLPNMTEGFWQNSMLTEPGDNRKVVCHPTAWDLGKRDFRIK   359
MINK_UPKB:A0A7T0Q2W2         QSWDAKRIFKEAEKFFVSVGLPNMTEGFWQNSMLTEPGDNRKVVCHPTAWDLGKHDFRIK   359
CANINE_tr|J9P7Y2             QSWDAKKIFKEAEKFFVSVGLPNMTQEFWENSMLTEPSDSRKVVCHPTAWDLGKGDFRIK   358
FELINE_tr|A0A5F5XDN9         QSWDAKRIFKEAEKFFVSVGLPNMTQGFWENSMLTEPGDSRKVVCHPTAWDLGKGDFRIK   359
                             : *:* :**: ** **.*:.*  **: ** *****:* : :*.********:*: *:**

CHICKEN_tr|F1NHR4            MCTKVTMDDFLTAHHEMGHIEYDMAYSVQPFLLRNGANEGFHEAVGEIMSLSAATPQHLK   419
GUINEA_PIG_tr|H0VSF6         MCTKVTMDHFLTAHHEMGHIQYDMAYAIQPFLLRDGANEGFHEAIGEIMSLSAATPEHLK   419
MOUSE_UPKB:Q8R0I0            MCTKVTMDNFLTAHHEMGHIQYDMAYARQPFLLRNGANEGFHEAVGEIMSLSAATPKHLK   419
SWINE_tr|K7GLM4              MCTKVTMDDFLTAHHEMGHIQYDMAYAIQPYLLRNGANEGFHEAVGEIMSLSAATPHYLK   419
BOVINE_UPKB:Q58DD0           MCTKVTMDDFLTAHHEMGHIQYDMAYAAQPYLLRNGANEGFHEAVGEIMSLSAATPHYLK   418
RABBIT_tr|G1TEF4             MCTKVTMDNFLTAHHEMGHIQYDMAYATQPFLLRNGANEGFHEAVGEIMSLSAATPEHLK   419
MACAQUE_tr|F7AH40            MCTKVTMDDFLTAHHEMGHIQYDMAYAAQPFLLRNGANEGFHEAVGEIMSLSAATPKHLK   419
hACE2_UPKB:Q9BYF1            MCTKVTMDDFLTAHHEMGHIQYDMAYAAQPFLLRNGANEGFHEAVGEIMSLSAATPKHLK   419
CHIMPANZEE_tr|A0A2J8KU96     MCTKVTMDDFLTAHHEMGHIQYDMAYAAQPFLLRNGANEGFHEAVGEIMSLSAATPKHLK   419
EQUINE_tr|F6V9L3             MCTKVTMDDFLTAHHEMGHIQYDMAYAVQPYLLRNGANEGFHEAVGEIMSLSAATPNHLK   419
FERRET_UPKB:Q2WG88           MCTKVTMDDFLTAHHEMGHIQYDMAYAEQPFLLRNGANEGFHEAVGEIMSLSAATPNHLK   419
MINK_UPKB:A0A7T0Q2W2         MCTKVTMDDFLTAHHEMGHIQYDMAYAAQPFLLRNGANEGFHEAVGEIMSLSAATPNHLK   419
CANINE_tr|J9P7Y2             MCTKVTMDDFLTAHHEMGHIQYDMAYAAQPFLLRNGANEGFHEAVGEIMSLSAATPNHLK   418
FELINE_tr|A0A5F5XDN9         MCTKVTMDDFLTAHHEMGHIQYDMAYAVQPFLLRNGANEGFHEAVGEIMSLSAATPNHLK   419
                             ********.***********:*****:  **:***:*********:***********.:**

CHICKEN_tr|F1NHR4            SLDLLEPTFQEDEETEINFLLKQALTIVGTMPFTYMLEKWRWM-VFNGEITKQEWTKRWW   478
GUINEA_PIG_tr|H0VSF6         SIGLLPPDFHEDNGTF---FHGFTHALLGTLPFTFMLEKVERGWSSRVKIPKSSGLKN-V   475
MOUSE_UPKB:Q8R0I0            SIGLLPSDFQEDSETEINFLLKQALTIVGTLPFTYMLEKWRWM-VFRGEIPKEQWMKKWW   478
SWINE_tr|K7GLM4              ALGLLPPDFYEDSETEINFLLKQALTIVGTLPFTYMLEKWRWM-VFKGEIPKEQWMQKWW   478
BOVINE_UPKB:Q58DD0           ALGLLAPDFHEDNETEINFLLKQALTIVGTLPFTYMLEKWRWM-VFKGEIPKQQWMEKWW   477
RABBIT_tr|G1TEF4             STGLLPYDFHEDNETEINFLLKQALTIVGTLPFTYMLEKWRWM-VFKGEIPKEQWMQKWW   478
MACAQUE_tr|F7AH40            SIGLLSPDFQEDNETEINFLLKQALTIVGTLPFTYMLEKWRWM-VFKGEIPKDQWMKKWW   478
hACE2_UPKB:Q9BYF1            SIGLLSPDFQEDNETEINFLLKQALTIVGTLPFTYMLEKWRWM-VFKGEIPKDQWMKKWW   478
CHIMPANZEE_tr|A0A2J8KU96     SIGLLSPDFQEDNETEINFLLKQALTIVGTLPFTYMLEKWRWM-VFKGEIPKDQWMKKWW   478
EQUINE_tr|F6V9L3             AIGLLPPDFYEDSETEINFLLKQALTIVGTLPFTYMLEKWRWM-VFKGEIPKEEWMKKWW   478
FERRET_UPKB:Q2WG88           NIGLLPPDFSEDSETDINFLLKQALTIVGTLPFTYMLEKWRWM-VFKGEIPKEQWMQKWW   478
MINK_UPKB:A0A7T0Q2W2         NIGLLPPDFSEDSETDINFLLKQALTIVGTLPFTYMLEKWRWM-VFKGEIPKEQWMQKWW   478
CANINE_tr|J9P7Y2             NIGLLPPSFFEDSETEINFLLKQALTIVGTLPFTYMLEKWRWM-VFKGEIPKDQWMKTWW   477
FELINE_tr|A0A5F5XDN9         TIGLLSPGFSEDSETEINFLLKQALTIVGTLPFTYMLEKWRWM-VFKGEIPKEQWMQKWW   478
                              :.**   * **. *    :    : ::**:***:****  .      . :* :..  :
```

FIG. 2 (continued)

```
CHICKEN_tr|F1NHR4              KMKREIVGVVEPVPHDETYCDPAALFHVANDYSFIRYYTRTIYQFQFQEALCKAANHTGP   538
GUINEA_PIG_tr|H0VSF6           ADEVKIVGVVEPLPHDETYCDPASLFHVSNDYSFIRYYTRTIYQFQFQEALCKAANHVGP   535
MOUSE_UPKB:Q8R0I0              EMKREIVGVVEPLPHDETYCDPASLFHVSNDYSFIRYYTRTIYQFQFQEALCQAAKYNGS   538
SWINE_tr|K7GLM4                EMKREIVGVVEPLPHDETYCDPACLFHVAEDYSFIRYYTRTIYQFQFHEALCRTAKHEGP   538
BOVINE_UPKB:Q58DD0             EMKREIVGVVEPLPHDETYCDPACLFHVAEDYSFIRYYTRTIYQFQFHEALCKTAKHEGA   537
RABBIT_tr|G1TEF4               EMKREIVGVVEPMPHDETYCDPAALFHVANDYSFIRYYTRTIYQFQFQEALCQAAQHEGP   538
MACAQUE_tr|F7AH40              EMKREIVGVVEPVPHDETYCDPASLFHVSNDYSFIRYYTRTLYQFQFQEALCQAAKHEGP   538
hACE2_UPKB:Q9BYF1              EMKREIVGVVEPVPHDETYCDPASLFHVSNDYSFIRYYTRTLYQFQFQEALCQAAKHEGP   538
CHIMPANZEE_tr|A0A2J8KU96       EMKREIVGVVEPVPHDETYCDPASLFHVSNDYSFIRYYTRTLYQFQFQEALCQAAKHEGP   538
EQUINE_tr|F6V9L3               EMKREIVGVVEPVPHDETYCDPAALFHVANDYSFIRYYTRTIYQFQFQEALCQTAKHEGP   538
FERRET_UPKB:Q2WG88             EMKRDIVGVVEPLPHDETYCDPAALFHVANDYSFIRYYTRTIYQFQFQEALCQIAKHEGP   538
MINK_UPKB:A0A7T0Q2W2           EMKRDIVGVVEPLPHDETYCDPAALFHVANDYSFIRYYTRTIYQFQFQEALCQIAKHEGP   538
CANINE_tr|J9P7Y2               EMKRNIVGVVEPVPHDETYCDPASLFHVANDYSFIRYYTRTIYQFQFQEALCQIAKHEGP   537
FELINE_tr|A0A5F5XDN9           EMKREIVGVVEPVPHDETYCDPASLFHVANDYSFIRYYTRTIYQFQFQEALCRIAKHEGP   538
                                 :  .*******:**********.****::***********:*****:****: *:: *

CHICKEN_tr|F1NHR4              LHKCDITNSTAAGGNLRQLLELGKSKPWTQALESATGEKYMNATPLLHYFEPLFNWLQKN   598
GUINEA_PIG_tr|H0VSF6           LHKCDISNSTEAGQKLLNMLKLGKSEPWTLALESIVGTKNMDVKPLLNYFQPLSTWLQDQ   595
MOUSE_UPKB:Q8R0I0              LHKCDISNSTEAGQKLLKMLSLGNSEPWTKALENVVGARNMDVKPLLNYFQPLFDWLKEQ   598
SWINE_tr|K7GLM4                LYKCDISNSTEAGQKLLQMLSLGKSEPWTLALENIVGVKTMDVKPLLSYFEPLLTWLKAQ   598
BOVINE_UPKB:Q58DD0             LFKCDISNSTEAGQRLLQMLRLGKSEPWTLALENIVGIKTMDVKPLLNYFEPLFTWLKEQ   597
RABBIT_tr|G1TEF4               LHKCDISNSTEAGQKLLNMLRLGKSEPWTLALENVVGAKNMDVRPLLNYFEPLFTWLKEQ   598
MACAQUE_tr|F7AH40              LHKCDISNSTEAGQKLLNMLKLGKSEPWTLALENVVGAKNMNVRPLLNYFEPLFTWLKDQ   598
hACE2_UPKB:Q9BYF1              LHKCDISNSTEAGQKLFNMLRLGKSEPWTLALENVVGAKNMNVRPLLNYFEPLFTWLKDQ   598
CHIMPANZEE_tr|A0A2J8KU96       LHKCDISNSTEAGQKLFNMLRLGKSEPWTLALENVVGAKNMNVRPLLNYFEPLFTWLKDQ   598
EQUINE_tr|F6V9L3               LHKCDISNSTEAGQKLLQMLSLGKSEPWTLALERIVGVKNMDVRPLLNYFEPLFTWLKDQ   598
FERRET_UPKB:Q2WG88             LYKCDISNSSEAGQKLHEMLSLGRSKPWTFALERVVGAKTMDVRPLLNYFEPLFTWLKEQ   598
MINK_UPKB:A0A7T0Q2W2           LYKCDISNSREAGQKLHEMLSLGRSKPWTFALERVVGAKTMDVRPLLNYFEPLFTWLKEQ   598
CANINE_tr|J9P7Y2               LHKCDISNSSEAGQKLLEMLKLGKSKPWTYALEIVVGAKNMDVRPLLNYFEPLFTWLKEQ   597
FELINE_tr|A0A5F5XDN9           LHKCDISNSSEAGKKLLQMLTLGKSKPWTLALEHVVGEKKMNVTPLLKYFEPLFTWLKEQ   598
                               *.****:**  ** .* ::* **.*:*** ***  .* : *:. *** **:**  **: :

CHICKEN_tr|F1NHR4              NSGRSIGWNTDWTPYSDNAIKVRISLKAALGDDAYVWDASELFLFKSSIAYAMRKYFAKE   658
GUINEA_PIG_tr|H0VSF6           NRNSFVGWNTEWSPYSEESIKVRISLKSALGEDAYKWDDNEMYLFRSSVAYAMRKYFLDV   655
MOUSE_UPKB:Q8R0I0              NRNSFVGWNTEWSPYADQSIKVRISLKSALGANAYEWTNNEMFLFRSSVAYAMRKYFSII   658
SWINE_tr|K7GLM4                NGNSSVGWNTDWTPYADQSIKVRISLKSALGKEAYEWNDNEMYLFRSSIAYAMRNYFSSA   658
BOVINE_UPKB:Q58DD0             NRNSFVGWSTEWTPYSDQSIKVRISLKSALGENAYEWNDNEMYLFQSSVAYAMRKYFSEA   657
RABBIT_tr|G1TEF4               NRNSFVGWSTEWTPYADQSIKVRISLKTALGDQAYEWNDSEMYLFRSSVAYAMRKYFSEV   658
MACAQUE_tr|F7AH40              NKNSFVGWSTDWSPYADQSIKVRISLKSALGDKAYEWNDNEMYLFRSSVAYAMRTYFLEI   658
hACE2_UPKB:Q9BYF1              NKNSFVGWSTDWSPYADQSIKVRISLKSALGDKAYEWNDNEMYLFRSSVAYAMRQYFLKV   658
CHIMPANZEE_tr|A0A2J8KU96       NKNSFVGWSTDWSPYADQSIKVRISLKSALGDKAYEWNDNEMYLFRSSVAYAMRQYFLKV   658
EQUINE_tr|F6V9L3               NKNSFVGWSTNWSPYADQSIKVRISLKSALGEKSYEWNDNEMYLFQSSVAYAMRVYFLKA   658
FERRET_UPKB:Q2WG88             NRNSFVGWNTDWSPYADQSIKVRISLKSALGEKAYEWNDNEMYFFQSSIAYAMREYFSKV   658
MINK_UPKB:A0A7T0Q2W2           NRNSFVGWNTDWSPYADQSIKVRISLKSALGEKAYEWNDNEMYFFQSSIAYAMREYFSKV   658
CANINE_tr|J9P7Y2               NRNSFVGWNTDWSPYADQSIKVRISLKSALGEKAYEWNNNEMYLFRSSIAYAMRQYFSEV   657
FELINE_tr|A0A5F5XDN9           NRNSFVGWNTDWRPYADQSIKVRISLKSALGDEAYEWNDNEMYLFRSSVAYAMREYFSKV   658
                               *  .   :**.*:* **::::*********:***  .:* *   .*:::*:**:***** **

CHICKEN_tr|F1NHR4              KEQNVDFQVTDIHVGEETQRVSFYLTVSMPGNVSDIVPRADVEKAIRMSRGRISEAFRLD   718
GUINEA_PIG_tr|H0VSF6           KNQTVLFSWEDVRVSDWTHRVSFTFFVTEPNNVSNIIPRTEVEDAIRLSRSRINDVF---   712
MOUSE_UPKB:Q8R0I0              KNQTVPFLEEDVRVSDLKPRVSFYFFVTSPQNVSDVIPRSEVEDAIRMSRGRINDVFGLN   718
SWINE_tr|K7GLM4                KNETIPFGAEDVWVSDLKPRISFNFFVTSPANMSDIIPRSDVEKAISMSRSRINDAFRLD   718
BOVINE_UPKB:Q58DD0             KNETVLFGEDNVWVSDKKPRISFNFFVTSPNNVSDIIPRTEVENAIRLSRDRINDVFQLD   717
RABBIT_tr|G1TEF4               KNQTILFGEEDVRVSDLKPRISFNFFVTAPNNVNDIIPRNEVEEAISMSRSRINDIFRLD   718
MACAQUE_tr|F7AH40              KHQTILFGEEDVRVADLKPRISFNFYVTAPKNVSDIIPRTEVEEAIRISRSRINDAFRLN   718
hACE2_UPKB:Q9BYF1              KNQMILFGEEDVRVANLKPRISFNFFVTAPKNVSDIIPRTEVEKAIRMSRSRINDAFRLN   718
CHIMPANZEE_tr|A0A2J8KU96       KNQMILFGEEDVRVANLKPRISFNFFVTAPKNVSDIIPRTEVEKAIRKSRSRINDAFRLN   718
EQUINE_tr|F6V9L3               KNQTILFGEEDVWVSDLKPRISFNFFVTSPKNASDIIPRTDVEEAIRMSRSRINDAFRLD   718
FERRET_UPKB:Q2WG88             KNQTIPFVGKDVRVSDLKPRISFNFIVTSPENMSDIIPRADVEEAIRKSRGRINDAFRLD   718
MINK_UPKB:A0A7T0Q2W2           KKQTIPFVDKDVRVSDLKPRISFNFIVTSPENMSDIIPRADVEEAIRKSRGRINDAFRLD   718
CANINE_tr|J9P7Y2               KNQTIPFVEDNVWVSDLKPRISFNFFVTSPGNVSDIIPRTEVEEAIRMYRSRINDVFRLD   717
FELINE_tr|A0A5F5XDN9           KNQTIPFVEDNVWVSNLKPRISFNFFVTASKNVSDVIPRSEVEEAIRMSRSRINDAFRLD   718
                               :.: : *   :: *.: . *:** : *:   * .:::*: :**.**    *.**.: *
```

FIG. 2 (continued)

```
CHICKEN_tr|F1NHR4              DNTLEFDGIVPTLATPYKPPVTIWLILFGVVMSLIVIGVIVLIITGQRDKKKKARGRANE   778
GUINEA_PIG_tr|H0VSF6           ---------LSGIYPTLSPPYEPPVTIWLIVFGVVMGLVVVGIVVLVITGIRDRRKKKQKQREE   767
MOUSE_UPKB:Q8R0I0              DNSLEFLGIHPTLEPPYQPPVTIWLIIFGVVMALVVVGIIILIVTGIKGRKKKNETKREE   778
SWINE_tr|K7GLM4                DNTLEFLGIQPTLGPPDEPPVTVWLIIFGVVMGLVVVGIVVLIFTGIRDRRKKKQASSEE   778
BOVINE_UPKB:Q58DD0             DNSLEFLGIQPTLGPPYEPPVTIWLIIFGVVMGVVVIGIVVLIFTGIRNRRKKNQASSEE   777
RABBIT_tr|G1TEF4               DNSLEFVGIQPTLEPPYESPVPIWLVVFGVVMGMIVIGIVVLIFTGIKDRRKQKQAKREE   778
MACAQUE_tr|F7AH40              DNSLEFLGIQTTLAPPYQSPVTTWLIVFGVVMGVIVAGIVVLIFTGIRDRKKKNQARSEE   778
hACE2_UPKB:Q9BYF1              DNSLEFLGIQPTLGPPNQPPVSIWLIVFGVVMGVIVVGIVILIFTGIRDRKKKNKARSGE   778
CHIMPANZEE_tr|A0A2J8KU96       DNSLEFLGIQPTLGPPNQPPVSIWLIVFGVVMGVIVVGIVILIFTGIRDRKKKNKARSEE   778
EQUINE_tr|F6V9L3               DNTLEFLGIQPTLGPPYQPPVTVWLIAFGVVMGLVVVGIVVLIATGIRGRRKKNQARSEE   778
FERRET_UPKB:Q2WG88             DNSLEFLGIQPTLEPPYQPPVTIWLIVFGVVMGVVVVGIFLLIFSGIRNRRKNNQARSEE   778
MINK_UPKB:A0A7T0Q2W2           DNSLEFLGIQPTLEPPYQPPVTIWLIVFGVVMGVVVVGIFLLIFSGIRNRRKNNQARSEE   778
CANINE_tr|J9P7Y2               DNSLEFLGIQPTLGPPYEPPVTIWLIVFGVVMGVVVVGIVLLIFSGIRNRRKNDQARGEE   777
FELINE_tr|A0A5F5XDN9           DNSLEFLGIQPTLSPPYQPPVTIWLIVFGVVMGVVVVGIVLLIVSGIRNRRKNNQARSEE   778
                                     ; **   **  * ; **  **; *****.::* *:.;*; :* :.::*; .    *

CHICKEN_tr|F1NHR4              AGSNCEVNPYD-----EDGPSNKGFEQSEETQTSF     808
GUINEA_PIG_tr|H0VSF6           ---------NPYSSVDIGKGENNTAFQNSEDNQTSF     794
MOUSE_UPKB:Q8R0I0              ---------NPYDSMDIGKGESNAGFQNSDDAQTSF     805
SWINE_tr|K7GLM4                ---------NPYGSMDLSKGESNSGFQNGDDIQTSF     805
BOVINE_UPKB:Q58DD0             ---------NPYGSVDLNKGENNSGFQNIDDVQTSL     804
RABBIT_tr|G1TEF4               ---------NPYGFVDMSKGENNSGFQNSDDIQTSF     805
MACAQUE_tr|F7AH40              ---------NPYASIDINKGENNPGFQNTDDVQTSF     805
hACE2_UPKB:Q9BYF1              ---------NPYASIDISKGENNPGFQNTDDVQTSF     805
CHIMPANZEE_tr|A0A2J8KU96       ---------NPYASVDISKGENNPGFQNTDDVQTSF     805
EQUINE_tr|F6V9L3               ---------NPYASVDLSKGENNPGFQNGDDVQTSF     805
FERRET_UPKB:Q2WG88             ---------NPYASVDLSKGENNPGFQNVDDVQTSF     805
MINK_UPKB:A0A7T0Q2W2           ---------NPYASVDLSKGENNPGFQNVDDVQTSF     805
CANINE_tr|J9P7Y2               ---------NPYASVDLSKGENNPGFQNVDDAQTSF     804
FELINE_tr|A0A5F5XDN9           ---------NPYASVDLSKGENNPGFQHADDVQTSF     805
                                        ***      .*..* .*:: :: ***:
```

FIG. 7A
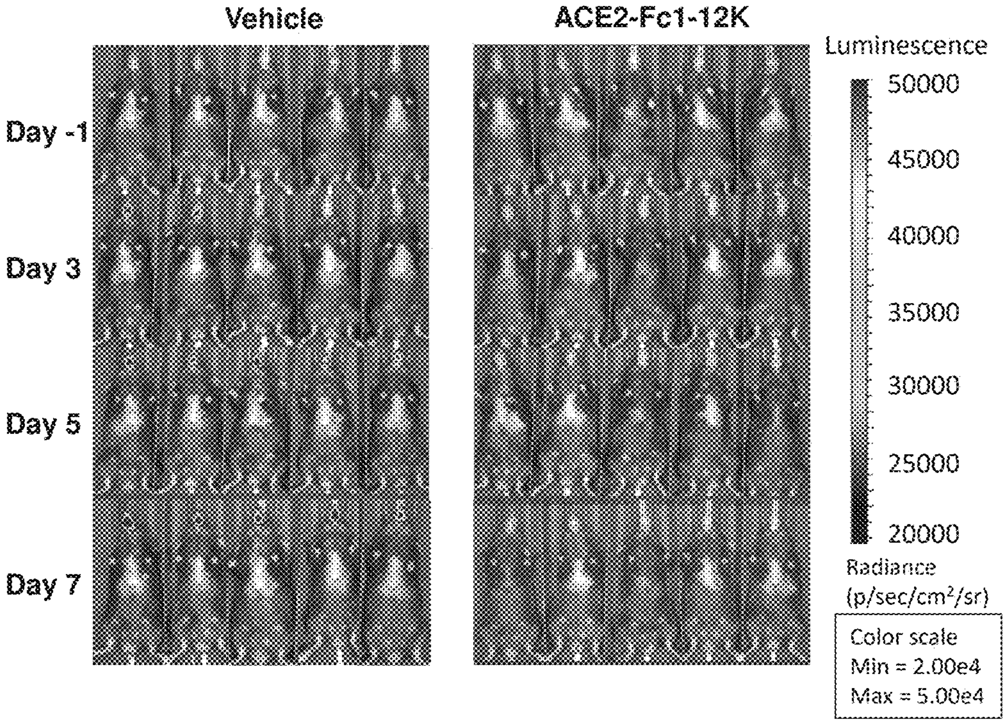
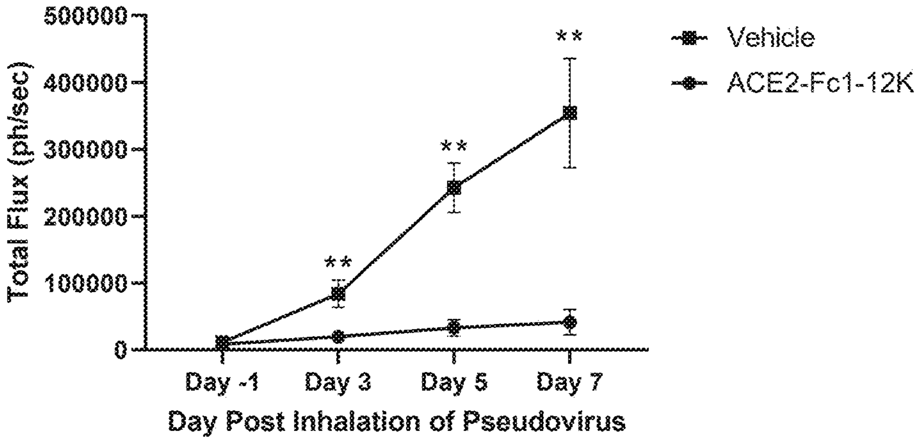

| Spike Protein S1 | ḱ a | kd | KD |
|---|---|---|---|
| Wide Type | 1.89E+05 | 1.15E-02 | 6.09E-08 |
| Alpha | 2.81E+05 | 3.42E-03 | 1.22E-08 |
| Beta | 1.90E+05 | 3.75E-03 | 1.98E-08 |
| Delta | 2.81E+05 | 2.92E-03 | 1.04E-08 |
| Omicron | 4.02E+05 | 2.63E-03 | 6.53E-09 |
| Omicron BA.2 | 1.02E+05 | 3.87E-03 | 3.80E-08 |

COMPOSITIONS FOR PREVENTING OR TREATING CORONAVIRUS INFECTIONS

CROSS REFERENCE TO RELATED APPLICATIONS

This application is a continuation of International Application No. PCT/US2023/065732, filed on Apr. 13, 2023, which claims priority benefit of U.S. Provisional Application No. 63/331,216, filed on Apr. 14, 2022, and U.S. Provisional Application 63/418,570, filed on Oct. 23, 2022, the contents of each of which are hereby incorporated by reference in their entireties.

REFERENCE TO AN ELECTRONIC SEQUENCE LISTING

The content of the electronic sequence listing (256442000301 subseqlist.xml; Size: 164,949 bytes; and Date of Creation: Nov. 21, 2024) is herein incorporated by reference in its entirety.

FIELD

The invention relates to compositions and methods for preventing or treating coronavirus infections.

BACKGROUND

Respiratory microbial infections, including viral and bacterial infections, are a leading cause of adult and pediatric illness and mortality worldwide. There is a large unmet need for novel treatment and prevention methods that more effectively target these infections. The rapid spread and high morbidity and mortality of coronavirus infection, including SARS-CoV-2 infection, the virus that causes COVID-19, has resulted in severe human health and economic impacts in 2020-2022. The number of SARS-CoV-2 infection cases and hospitalizations have surged as increases in social activity and mobility have led to increased incidences of viral transmission. SARS-CoV-2 infection is transmitted primarily from person-to-person through respiratory droplets when an infected person talks, sneezes, or coughs. Infectious droplets can land in the mouths or noses of people who are nearby or possibly be inhaled into the lungs, with the upper respiratory mucosal surfaces being the initial and predominant sites for the viral infection. In addition, airborne transmission of the virus can occur through aerosol particles that linger in the air for longer periods of time and can travel further from their origin than droplets. Facemasks are being used as the first line of defense, but they are passive barriers to infection and their efficacy is imperfect. Therapeutic discovery and prevention efforts are necessary to halt the pandemic spread of coronavirus, such as SARS-CoV-2.

Therapeutic drug development for COVID-19 treatment includes small-molecule and large-molecule (e.g., inhibitory polypeptide) drug candidates. A number of inhibitory polypeptides that target the Receptor Binding Domain (RBD) of SARS-CoV-2 spike(S) protein are currently being developed. Angiotensin-converting enzyme 2 (ACE2) mediates viral entry into cells, via binding of the S protein through the S1 subunit of the RBD. Therefore, ACE2 inhibitory peptides represent promising therapeutics to prevent coronavirus infection.

The current pharmaceutical prevention strategy for COVID-19 is focused on the development of SARS-CoV-2 vaccines; however, such vaccine approaches may be burdened by viral gene mutations and the possibility of antibody-dependent enhancement (ADE, Ricke, *Front Immunol.* 2021; 12:640093). Therefore, safe and flexible methods to prevent coronavirus infection are of urgent demand.

BRIEF SUMMARY

The present application provides compositions and methods for preventing or treating an infection caused by a coronavirus or a variant thereof. Thus, one aspect of the present application provides a chimeric protein comprising: (a) a target-binding moiety comprising an extracellular binding domain (EBD) of an angiotensin-converting enzyme 2 (ACE2) protein or a fragment thereof that specifically binds to a spike(S) protein; and (b) a mucoadhesive peptide fragment comprising at least about 5 positively charged amino acid residues, wherein the mucoadhesive peptide fragment facilitates attachment of the chimeric protein to a mucosa.

In some embodiments, the chimeric protein comprises a single polypeptide chain.

In some embodiments, the chimeric protein comprises two or more polypeptide chains. In some embodiments, the chimeric protein comprises two or more mucoadhesive peptide fragments. In some embodiments, each of the two or more mucoadhesive peptide fragments comprises at least about 5 positively charged amino acid residues. In some embodiments, the mucoadhesive peptide fragment comprises at least about 6 positively charged amino acid residues.

In some embodiments, the positively charged amino acid residues are selected from the group consisting of lysine, arginine, histidine, ornithine, and combinations thereof. In some embodiments, the positively charged amino acid residues comprise lysines. In some embodiments, the mucoadhesive peptide fragment comprises about 5, about 6, about 12, or about 30 lysines. In some embodiments, the positively charged amino acid residues comprise arginines. In some embodiments, the mucoadhesive peptide fragment comprises about 5, about 6, about 12, or about 30 arginines. In some embodiments, the positively charged amino acid residues comprise histidines. In some embodiments, the mucoadhesive peptide fragment comprises about 5, about 6, about 12, or about 30 histidines. In some embodiments, the positively charged amino acid residues comprise ornithines. In some embodiments, the mucoadhesive peptide fragment comprises about 5, about 6, about 12, or about 30 ornithines.

In some embodiments, the mucoadhesive peptide fragment comprises at least 5 contiguous positively charged amino acids. In some embodiments, the positively charged amino acid residues are interspersed with one or more non-positively charged amino acid residues. In some embodiments, the non-positively charged amino acid residues are non-polar amino acids or polar uncharged amino acids. In some embodiments, the non-positively charged amino acid residues are selected from the group consisting of isoleucine, valine, alanine, tryptophan, leucine, glycine, methionine, proline, phenylalanine, threonine, cysteine, tyrosine, glutamine, serine, and asparagine, and combinations thereof. In some embodiments, at least 50% of the amino acid residues in the mucoadhesive peptide fragment are positively charged amino acid residues.

In some embodiments, the mucoadhesive peptide fragment is no more than about 15 kD. In some embodiments, the mucoadhesive peptide fragment has an isoelectric point (pI) higher than the pH of the mucosa. In some embodiments, the half-life of the chimeric protein on the mucosa is at least 12 hours. In some embodiments, the mucoadhesive peptide fragment does not facilitate penetration of the chimeric protein into a cell of the mucosa. In some embodiments, the mucoadhesive peptide fragment does not disrupt folding of the chimeric protein within a host cell expressing the chimeric protein. In some embodiments, the mucoadhesive peptide fragment does not block secretion of the chimeric protein from a host cell expressing the chimeric protein. In some embodiments, the mucoadhesive peptide fragment does not interfere with the binding between the target-binding moiety and the S protein.

In some embodiments, the mucoadhesive peptide fragment comprises an amino acid sequence of any one of SEQ ID NOs: 28-62 and 128-134, or a variant thereof comprising at least about 90% sequence identity to the amino acid sequence of any one of SEQ ID NOs: 28-62 and 128-134.

In some embodiments, the mucoadhesive peptide fragment is fused to the target-binding moiety via a bond.

In some embodiments, the mucoadhesive peptide fragment is fused to the target-binding moiety via a peptide linker. In some embodiments, the peptide linker comprises one or more oligomerization and/or multimerization domains. In some embodiments, the peptide linker comprises the constant region of a heavy chain of a full-length antibody or a fragment thereof. In some embodiments, the peptide linker comprises the constant region of a light chain of a full-length antibody or a fragment thereof. In some embodiments, the linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof. In some embodiments, the linker comprises an Fc region or a fragment thereof. In some embodiments, the linker comprises a detectable enzymatic tag. In some embodiments, the enzymatic tag is an alkaline phosphatase. In some embodiments, the enzymatic tag is a glutathione-s-transferase. In some embodiments, the peptide linker comprises a basic helix-loop-helix leucine zipper (bZIP) domain. In some embodiments, the peptide linker comprises a bZIP isoleucine zipper domain. In some embodiments, the peptide linker comprises a bZIP-leucine/isoleucine zipper domain. In some embodiments, the peptide linker comprises a collagen-like peptide. In some embodiments, the peptide linker comprises a p53 tetramerization domain. In some embodiments, the peptide linker comprises a streptavidin (SA) protein. In some embodiments, the peptide linker comprises a SA protein and a dextran scaffold. In some embodiments, the peptide linker comprises a SA protein and one or more maleimide polymers (DMGS). In some embodiments, the peptide linker comprises a bacteriophage T7 fibritin protein or a portion thereof. In some embodiments, the peptide linker comprises a cartilage oligomeric matrix protein (COMP) protein.

In some embodiments, the mucoadhesive peptide fragment is fused to a C-terminus of the target-binding moiety.

In some embodiments, the target-binding moiety comprises the EBD of a human ACE2 (hACE2) protein or a fragment or variant thereof. In some embodiments, the target-binding moiety comprises amino acids 30-41 of a full-length hACE2 protein, or a variant thereof comprising at least about 90% sequence identity to amino acids 30-41 of a full-length hACE2 protein. In some embodiments, the target-binding moiety comprises the amino acid sequence of SEQ ID NO: 102, or a variant thereof comprising at least about 90% sequence identity to the amino acid sequence of SEQ ID NO: 102. In some embodiments, the target-binding moiety comprises amino acids 24-42 of a full-length hACE2 protein, or a variant thereof comprising at least about 90% sequence identity to amino acids 24-42 of a full-length hACE2 protein. In some embodiments, the target-binding moiety comprises the amino acid sequence of SEQ ID NO: 8, or a variant thereof comprising at least about 90% sequence identity to the amino acid sequence of SEQ ID NO: 8. In some embodiments, the target-binding moiety comprises the amino acid sequence of any one of SEQ ID NOs: 1-7, 9-14, and 135, or a variant thereof comprising at least about 90% sequence identity to the amino acid sequence of any one of SEQ ID NOs: 1-7, 9-14, and 135. In some embodiments, the chimeric protein comprises the amino acid sequence of any one of SEQ ID NOs: 84-88 and 136-140, or a variant thereof comprising at least about 90% sequence identity to the amino acid sequence of any one of SEQ ID NOs: 84-88 and 136-140.

In some embodiments, the target-binding moiety comprises the EBD of an animal ACE2 protein or a fragment or variant thereof. In some embodiments, the animal ACE2 protein is a murine, guinea pig, equine, ferret, macaque, chimpanzee, swine, canine, feline, bovine, rabbit, mink, or chicken ACE2 protein or a fragment or variant thereof. In some embodiments, the target-binding moiety comprises amino acids 30-41 of a full-length animal ACE2 protein, or a variant thereof comprising at least about 90% sequence identity to amino acids 30-41 of a full-length animal ACE2 protein, wherein the full-length animal ACE2 protein is not a chicken or canine ACE2 protein. In some embodiments, the target-binding moiety comprises amino acids 29-40 of a full-length animal ACE2 protein, or a variant thereof comprising at least about 90% sequence identity to amino acids 29-40 of a full-length animal ACE2 protein, wherein the full-length animal ACE2 protein is a chicken or canine ACE2 protein. In some embodiments, the target-binding moiety comprises the amino acid sequence of any one of SEQ ID NOs: 110-122, or a variant thereof comprising at least about 90% sequence identity to any one of SEQ ID NOS: 110-122. In some embodiments, the target-binding moiety comprises the amino acid sequence of any one of SEQ ID NOs: 15-27, or a variant thereof comprising at least about 90% sequence identity to the amino acid sequence of any one of SEQ ID NOs: 15-27. In some embodiments, the chimeric protein comprises the amino acid sequence of any one of SEQ ID NOs: 89-93, or a variant thereof comprising at least about 90% sequence identity to the amino acid sequence of any one of SEQ ID NOs: 89-93.

In some embodiments, the mucosa is selected from the group consisting of nasal mucosa, larynx mucosa, trachea mucosa, bronchi mucosa, lung mucosa, eye mucosa, and combinations thereof.

In some aspects, provided herein is a pharmaceutical composition comprising the chimeric protein of any of the proceeding embodiments, and a pharmaceutically acceptable carrier. In some embodiments, the pharmaceutical composition comprises a plurality of the chimeric proteins, and wherein at least two of the plurality of the chimeric proteins are different from each other. In some embodiments, the pharmaceutically acceptable carrier comprises about 0.05% to about 0.2% (w/w) methionine. In some embodiments, the pharmaceutically acceptable carrier has a pH of about 4.5 to about 7.5. In some embodiments, the pharmaceutically acceptable carrier comprises about 20 mM to about 50 mM citrate. In some embodiments, the pharmaceutically acceptable carrier comprises about 100 mM to about 150 mM NaCl. In some embodiments, the pharmaceutically acceptable carrier comprises about 0.01% to about 0.1% (w/w) polysorbate 80. In some embodiments, the pharmaceutically acceptable carrier comprises about 1% to about 10% (w/w) glycerin. In some embodiments, the pharmaceutically acceptable carrier comprises about 0.05% to about 0.2% (w/w) potassium sorbate. In some embodiments, the pharmaceutically acceptable carrier: (i) comprises about 0.05% to about 0.2% (w/w) methionine; (ii) has a pH of about 4.5 to about 7.5; (iii) comprises about 20 mM to about 50 mM citrate; (iv) comprises about 100 mM to about 150 mM NaCl; (v) comprises about 0.01% to about 0.1% (w/w) polysorbate 80; (vi) comprises about 1% to about 10% (w/w) glycerin; and/or (vii) comprises about 0.05% to about 0.2% (w/w) potassium sorbate. In some embodiments, the pharmaceutical composition is formulated for intranasal administration, intraocular administration, and/or intrabronchial administration.

In some aspects, provided herein is an isolated nucleic acid or a set of isolated nucleic acids encoding the chimeric protein of any of the preceding embodiments.

In other aspects, provided herein is a vector or a set of vectors comprising the nucleic acid or the set of nucleic acids of the preceding embodiment.

In further aspects, provided herein is a host cell comprising the chimeric protein of any of the preceding embodiments, the nucleic acid or set of nucleic acids of the preceding embodiment, the vector or set of vectors of the preceding embodiment.

In additional aspects, provided herein is a method of preparing a chimeric protein, comprising: (a) culturing a host cell of the preceding embodiment under a condition effective to express the chimeric protein; and (b) obtaining the expressed chimeric protein from the host cell.

In other aspects, provided herein is a method of preventing or treating an infection caused by a virus in an individual, comprising administering to the individual an effective amount of the chimeric protein of any of the preceding embodiments, or the pharmaceutical composition of any of the preceding embodiments. In some embodiments, the chimeric protein or the pharmaceutical composition is administered to the individual before the individual is exposed to the virus. In some embodiments, the chimeric protein or the pharmaceutical composition is administered to the individual within about 72 hours after the individual is exposed to the virus. In some embodiments, the chimeric protein or the pharmaceutical composition is administered topically onto the mucosa. In some embodiments, the chimeric protein or the pharmaceutical composition is administered via a nasal spray, an inhaler, a nebulizer, or an eye drop. In some embodiments, the chimeric protein or the pharmaceutical composition is administered once daily.

In some aspects, provided herein is in vitro method of killing or neutralizing a virus, comprising contacting a virus with the chimeric protein of any of the preceding embodiments in the presence of at least one component of the complement system. In some embodiments, the chimeric protein comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof. In some embodiments, the at least one component of the complement system is C1, C4, or membrane attack complex (MAC). In some embodiments, the at least one component of the complement system is C1. In some embodiments, the at least one component of the complement system is C4. In some embodiments, the C4 is involved in the neutralization of the virus. In some embodiments, the at least one component of the complement system is MAC. In some embodiments, the MAC is involved in the killing of the virus.

In some aspects, provided herein is a method of killing or neutralizing a virus in an individual, comprising administering to the individual an effective amount of the chimeric protein of any of the preceding embodiments, or the pharmaceutical composition of the preceding embodiments. In some embodiments, the chimeric protein, or a pharmaceutical composition comprising the chimeric protein and a pharmaceutically acceptable carrier, comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof.

In some aspects, provided herein is a method of activating the complement pathway in an individual, comprising administering to the individual an effective amount of any of the preceding embodiments, or the pharmaceutical composition of the preceding embodiments. In some embodiments, the chimeric protein, or a pharmaceutical composition comprising the chimeric protein and a pharmaceutically acceptable carrier, comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof.

In some embodiments, at least one virus is killed on the mucosa. In some embodiments, at least one virus is neutralized on the mucosa.

In some aspects, provided herein is a method of preventing, treating, or reducing infection caused by a virus in an individual, comprising administering to the individual an effective amount of any of the preceding embodiments, or the pharmaceutical composition of the preceding embodiments, wherein at least one virus is killed or neutralized on the mucosa. In some embodiments, the chimeric protein, or a pharmaceutical composition comprising the chimeric protein and a pharmaceutically acceptable carrier, comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof.

In some embodiments, the chimeric protein activates the complement pathway in the individual. In some embodiments, the killing or neutralization is via activation of the complement pathway.

In some embodiments, the virus is a coronavirus. In some embodiments, the virus is selected from the group consisting of SARS-CoV, SARS-CoV-2, and HCoV-NL63. In some embodiments, the S protein comprises the amino acid sequence of any one of SEQ ID NOs: 96-100, 103, 123-127, and 141-143, or a variant thereof comprising at least about 90% sequence identity to the amino acid sequence of any one of SEQ ID NOs: 96-100, 103, 123-127, and 141-143.

Also provided are kits and articles of manufacture (e.g., a nasal spray medicament) comprising any one of the compositions described above and instructions for any one of the methods described above.

BRIEF DESCRIPTION OF THE DRAWINGS

The drawings illustrate certain embodiments of the features and advantages of this disclosure. These embodiments are not intended to limit the scope of the appended claims in any manner.

FIG. 2 shows a CLUSTAL Omega multiple sequence alignment of several human ACE2 (hACE2) and animal ACE2 sequences. Asterisks indicate conserved amino acid residues, and the spike protein S1 subunit binding site that serves as the base for the fragment ACE12 in hACE2 is underlined. SEQ ID NOs corresponding to the ACE2 proteins in the alignment are as follows, in the order displayed: SEQ ID NO: 27 (chicken), SEQ ID NO: 16 (guinea pig), SEQ ID NO: 15 (mouse), SEQ ID NO: 20 (swine), SEQ ID NO: 23 (bovine), SEQ ID NO: 24 (rabbit), SEQ ID NO: 18 (macaque), SEQ ID NO: 1 (human), SEQ ID NO: 19 (chimpanzee), SEQ ID NO: 17 (equine), SEQ ID NO: 25 (ferret), SEQ ID NO: 26 (mink), SEQ ID NO: 21 (canine) and SEQ ID NO: 22 (feline).

FIG. 7A shows the bioluminescent imaging (BLI) of hACE2 transgenic mice administered with SARS-CoV-2 Delta variant pseudoviruses. Mice were first instilled nasally with ACE2 mucoadhesive protein (right panel) or with vehicle only (buffer, left panel) and later (after 10 hours) inoculated intranasally with Delta pseudotyped lentivirus particles. The bottom panel shows a graph of the luciferase emission (bioluminescence) one day before inoculation and on days 3, 5 and 7 post inoculation. This data demonstrates the ability of ACE2-Fc1-12K chimeric protein to protect mice from SARS-CoV-2 Delta variant pseudoviral infection in an in vivo animal model.

DETAILED DESCRIPTION

Figure 1:
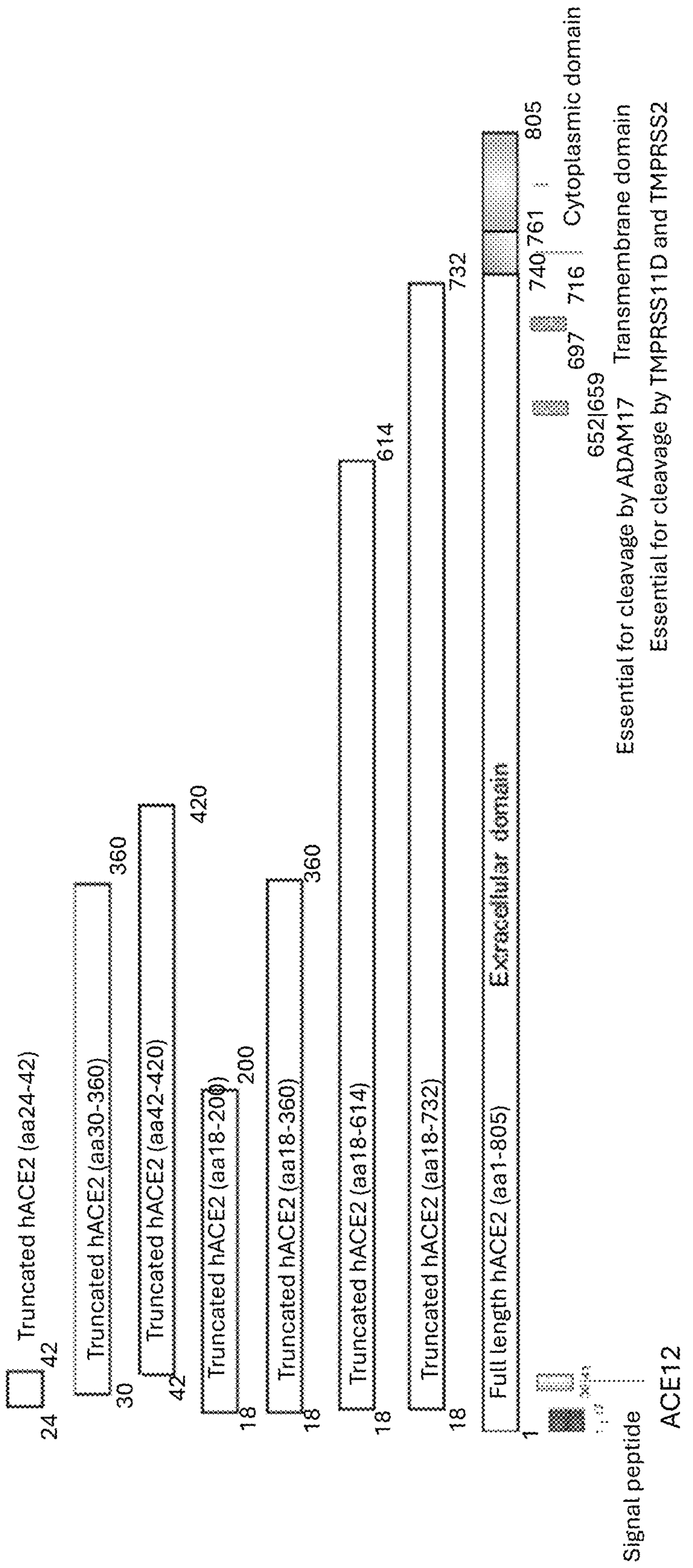
FIG. 1 shows various human ACE2 protein constructs and important features.

The present application provides compositions and methods for preventing or treating an infection caused by a virus (e.g., a coronavirus) that infects through a mucosa in an individual by targeting the virus using a chimeric protein comprising an angiotensin-converting enzyme 2 (ACE2) fragment (e.g., an extracellular binding domain (EBD) of an ACE2 protein or a fragment thereof) that has a positively charged mucoadhesive peptide fragment ("ACE2 chimeric proteins"), optionally via a peptide linker.

Accordingly, one aspect of the present application provides a chimeric protein comprising: (a) a target-binding moiety comprising an extracellular binding domain (EBD) of an angiotensin-converting enzyme 2 (ACE2) protein or a fragment thereof that specifically binds to a spike(S) protein; and (b) a mucoadhesive peptide fragment comprising at least about 5 positively charged amino acid residues (e.g., lysines or histidines), wherein the mucoadhesive peptide fragment facilitates attachment of the chimeric protein to a mucosa. In some embodiments, the S protein is from a coronavirus (e.g., SARS-CoV-2). In some embodiments, the target-binding moiety is fused to the mucoadhesive peptide fragment via a peptide linker (e.g., an immunoglobulin Fc region or a fragment thereof).

For example, the compositions described herein may comprise a chimeric protein or cocktails of different chimeric proteins, comprising an ACE2 fragment that targets SARS-CoV-2 spike(S) protein, and is modified with a positively charged peptide that prevents the SARS-CoV-2 virus from reaching its primary target cell population in the respiratory tract (e.g., nasal) mucosa for human or animal infection. The compositions can be administered via the nasal passages using a respiratory spray.

Inventors of the present application developed chimeric proteins comprising ACE2 fragments fused to a positively charged mucoadhesive peptide fragment, optionally via a peptide linker, that recognize the S1 subunit of the S protein of a coronavirus, such as SARS-CoV-2. The chimeric proteins have significantly enhanced affinity to mucin molecules compared to unmodified ACE2 fragments, which leads to improved stability in respiratory mucosa. The chimeric proteins show improved potency as compared to unmodified ACE2 fragments in blocking SARS-CoV-2 infection in a cell-based assay. Additionally, the chimeric proteins activate innate immune functions, and are able to kill SARS-CoV-2 virus via activation of the complement pathway. Administration of an exemplary chimeric protein into mouse nostrils blocks the infection of mice that are exposed to high titer SARS-CoV-2 pseudovirus at least 10 hours after the initial treatment. The protection against SARS-CoV-2 is effective in both nasal and lung areas seven days after viral exposure. The exemplary chimeric proteins are highly stable and maintain SARS-CoV-2 neutralizing activity in a nasal spray formulation. Nasal spray of the chimeric proteins can be developed as an affordable and effective prophylactic product to protect people from infection by exposure to SARS-CoV-2 virus in the air (e.g., via the nasal passages). The chimeric proteins may serve as universal binders, universal blockers, and/or universal capturers of viruses, such as coronaviruses, whereby the chimeric protein is capable of binding to the S protein of a coronavirus of any variant thereof, regardless of the variant type, as long as the virus normally enters host cells through the molecule that the target-binding moiety in the chimeric protein is derived from. For examples, the ACE2 chimeric proteins disclosed herein are universal binders, universal blockers, and/or universal capturers of all coronaviruses that enter host cells through the ACE2 receptor molecule, including SARS-CoV-2, SARS-CoV, and HCoV-NL63.

Compared to other methods that block microbial infection, which involve systemic administration of molecules (e.g., inhibitory polypeptides) that do not have a positively charged mucoadhesive peptide fragment, the methods described herein require administration of much less protein, leading to a large cost reduction that is critical for any pandemic situation. The compositions may also be self-administered, which greatly relieves the burden on an overwhelmed health care system.

Accordingly, one aspect of the present application provides a chimeric protein comprising: (a) a target-binding moiety comprising an extracellular binding domain (EBD) of an angiotensin-converting enzyme 2 (ACE2) protein or a fragment thereof that specifically binds to a spike(S) protein; and (b) a mucoadhesive peptide fragment comprising at least about 5 positively charged amino acid residues (e.g., lysines or histidines), wherein the mucoadhesive peptide fragment facilitates attachment of the chimeric protein to a mucosa. In some embodiments, the S protein is from a coronavirus (e.g., SARS-CoV-2). In some embodiments, the target-binding moiety is fused to the mucoadhesive peptide fragment via a peptide linker (e.g., an immunoglobulin Fc region or a fragment thereof).

The chimeric proteins provided herein are useful for treating or preventing an infection by a coronavirus in an individual, as well as for killing or neutralizing a coronavirus in an individual via activation of the complement pathway.

I. Definitions

The term "target-binding moiety" is used herein to refer to a molecule or a fragment thereof that is capable of specifically binding to a target. A target-binding moiety may have one or more target-binding sites.

As used herein, a "mucoadhesive peptide fragment" refers to a peptide that carries one or more positive charges and is capable of interacting with a mucosa, e.g., via electrostatic interactions.

As used herein, a "receptor" refers to a receptor on a host cell that facilitates or mediates microbial entry into the host cell. A receptor may be membrane-bound or a soluble receptor.

As used herein, "treatment" or "treating" is an approach for obtaining beneficial or desired results including clinical results. For purposes of this application, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease. The methods of the present application contemplate any one or more of these aspects of treatment.

"Preventing," as used herein, includes providing prophylaxis with respect to the occurrence or recurrence of a disease in a subject that may be predisposed to the disease but has not yet been diagnosed with the disease.

An "effective amount" of an agent refers to an amount effective, at dosages and for periods of time necessary, to achieve the desired therapeutic or prophylactic result. An effective amount herein may vary according to factors such as the disease state, age, sex, and weight of the patient, and the ability of the chimeric protein (e.g., the target-binding moiety) to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. For purposes of this application, an effective amount of a drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. The effective amount can be ascertained by measuring relevant physiological effects, and it can be adjusted in connection with the dosing regimen and diagnostic analysis of the subject's condition, and the like.

The terms "individual," "subject" and "patient" are used interchangeably herein to describe a mammal, including humans. In some embodiments, the individual is human. In some embodiments, an individual suffers from a respiratory infection. In some embodiments, the individual is in need of treatment.

The terms "polypeptide" and "protein" are used interchangeably to refer to a polymer of amino acid residues and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present application, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts, which produce the proteins or errors due to PCR amplification.

As use herein, the term "specifically binds," "specifically recognizing," or "is specific for" refers to measurable and reproducible interactions, such as binding between a target and a target-binding moiety that is determinative of the presence of the target in the presence of a heterogeneous population of molecules, including biological molecules. For example, target-binding moiety that specifically recognizes a target (which can be an epitope) is target-binding moiety that binds this target with greater affinity, avidity, more readily, and/or with greater duration than its bindings to other targets. In some embodiments, target-binding moiety that specifically recognizes an antigen reacts with one or more antigenic determinants of the antigen (such as SARS-CoV-2 S protein) with a binding affinity that is at least about 10 times its binding affinity for other targets (such as MERS-CoV S protein, or a non-respiratory-pathogen protein).

The "$CH_1$ domain" of a human IgG Fc region (also referred to as "$C_1$" of "H1" domain) usually extends from about amino acid 118 to about amino acid 215 (EU numbering system).

"Hinge region" is generally defined as stretching from Glu216 to Pro230 of human $IgG_1$ (Burton, *Molec. Immunol.* 22:161-206 (1985)). Hinge regions of other IgG isotypes may be aligned with the $IgG_1$ sequence by placing the first and last cysteine residues forming inter-heavy chain S—S bonds in the same positions.

The "$CH_2$ domain" of a human IgG Fc region (also referred to as "$C_2$" of "H2" domain) usually extends from about amino acid 231 to about amino acid 340. The $CH_2$ domain is unique in that it is not closely paired with another domain. Rather, two N-linked branched carbohydrate chains are interposed between the two $CH_2$ domains of an intact native IgG molecule. It has been speculated that the carbohydrate may provide a substitute for the domain-domain pairing and help stabilize the $CH_2$ domain. Burton, Molec Immunol. 22:161-206 (1985).

The "$CH_3$ domain" (also referred to as "$C_2$" or "H3" domain) comprises the stretch of residues C-terminal to a $CH_2$ domain in an Fc region (i.e., from about amino acid residue 341 to the C-terminal end of an antibody sequence, typically at amino acid residue 446 or 447 of an IgG).

The "$CH_4$ domain" found in IgE and IgM molecules, is situated C-terminal to the $CH_3$ domain, comprising residues 466-572 of human IgM and residues 323-427 of hIgE. The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments, the two or more substantially similar values differ by no more than about any one of 5%, 10%, 15%, 20%, 25%, or 50%. The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments, the two or more substantially similar values differ by no more than about any one of 5%, 10%, 15%, 20%, 25%, or 50%.

A polypeptide "variant" means a biologically active polypeptide having at least about 80% amino acid sequence identity and no more than 100% identity with the native sequence polypeptide after aligning the sequences and introducing gaps, if necessary, to achieve the maximum percent sequence identity. Such variants include, for instance, polypeptides wherein one or more amino acid residues are added, or deleted, at the N- or C-terminus of the polypeptide. In some embodiments, a variant has at least about 80% amino acid sequence identity. In some embodiments, a variant has at least about 90% amino acid sequence identity. In some embodiments, a variant has at least about 95% amino acid sequence identity with the native sequence polypeptide.

As used herein, "Percent (%) amino acid sequence identity" with respect to a peptide or polypeptide sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Non-limiting exemplary mammalian cells include, but are not limited to, NSO cells, PER.C6® cells (Crucell), and 293 and CHO cells, and their derivatives, such as 293-6E and DG44 cells, respectively.

As used herein, a "variant" virus refers to an isolate of a virus whose genome sequence differs from that of a reference virus and the difference in the genome sequence confers new phenotypic properties such as increased fitness compared to the reference virus. When referring to a viral species in the present application, such as SARS-CoV-2, it is understood that the species encompass variants as well as the reference virus that was first isolated and identified. In some embodiments, the variant virus described herein is a "variant of interest", i.e., a variant with specific genetic markers that have been associated with changes to receptor binding, reduced neutralization by antibodies generated against previous infection or vaccination, reduced efficacy of treatments, potential diagnostic impact, and/or predicted increase in transmissibility and/or disease severity. In some embodiments, the variant virus described herein is a "variant of concern", i.e., a variant for which there is evidence of an increase in transmissibility, more severe disease (e.g., increased hospitalizations and/or deaths), significant reduction in neutralization by antibodies generated during previous infection or vaccination, reduced effectiveness of treatments or vaccines, and/or diagnostic detection failures. In some embodiments, the variant virus described herein is a "variant of high consequence", i.e., a variant of high consequence has clear evidence that prevention measures or medical countermeasures (MCMs) have significantly reduced effectiveness relative to previously circulating variants.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, "a pharmaceutically acceptable carrier" refers to a pharmaceutically acceptable substrate, composition or vehicle used in the process of drug delivery, which may have one or more ingredients including, but not limited to, excipient(s), binder(s), diluent(s), solvent(s), filler(s), and/or stabilizer(s).

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter.

As used herein and in the appended claims, the singular forms "a," "an," and "the" include plural referents unless the context clearly dictates otherwise.

II. Chimeric Proteins

The present application provides chimeric proteins (such as fusion proteins, i.e., ACE2 chimeric proteins) comprising: (a) a target-binding moiety comprising an extracellular binding domain (EBD) of an angiotensin-converting enzyme 2 (ACE2) protein or a fragment thereof that specifically binds to a spike(S) protein (e.g., the S protein of a coronavirus, the S1 subunit of the S protein, or the S1 subunit of the coronavirus S protein); and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having at least about 5 (e.g., about 5 to about 30, such as about 12) lysines (including for example at least about 5 (e.g., about 5 to about 30, such as about 12) contiguous lysines). In some embodiments, the positively charged amino acid residues are histidines. In some embodiments, the mucoadhesive peptide fragment is a polyhistidine peptide having at least about 5 (e.g., about 5 to about 30, such as about 12) histidines (including for example at least about 5 (e.g., about 5 to about 30, such as about 12) contiguous histidines). In some embodiments, the positively charged amino acid residues are arginines. In some embodiments, the mucoadhesive peptide fragment is a polyarginine peptide having at least about 5 (e.g., about 5-30 such as 12) arginines (including for example at least about 5 (e.g., about 5-30 such as 12) contiguous arginines). In some embodiments, the positively charged amino acid residues are ornithines. In some embodiments, the mucoadhesive peptide fragment is a polyornithine peptide having at least about 5 (e.g., about 5 to about 30, such as about 12) ornithines (including for example at least about 5 (e.g., about 5 to about 30, such as about 12) contiguous ornithines). In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the target-binding moiety. In some embodiments, the mucoadhesive peptide fragment is non-covalently associated with the target-binding moiety, e.g., via an oligomerization and/or multimerization domain. In some embodiments, the S protein is from a virus, e.g., a coronavirus. In some embodiments, the virus causes a respiratory infection, e.g., a coronavirus infection. In some embodiments, the mucosa is selected from the group consisting of nasal mucosa, larynx mucosa, trachea mucosa, bronchi mucosa, lung mucosa, eye mucosa, and combinations thereof. In some embodiments, the target-binding moiety is directly fused to the mucoadhesive peptide fragment. In some embodiments, the target-binding moiety is fused to the mucoadhesive peptide fragment via peptide linker. In some embodiments, the peptide linker comprises the amino acid sequence of any one of the peptide linkers described in Table 9.

In some embodiments, there is provided a chimeric protein comprising: (a) a target-binding moiety comprising an EBD of a human ACE2 (hACE2) protein or a fragment thereof that specifically binds to an S protein of a coronavirus; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the target-binding moiety specifically binds an S1 subunit of the S protein of the coronavirus. In some embodiments, the S protein is any one of the S proteins described in Table 5. In some embodiments, the coronavirus is SARS-CoV-2 or a variant thereof. In some embodiments, the target-binding moiety comprises the amino acid sequence of any one of the hACE2 proteins or fragments thereof described in Table 3, e.g., in some embodiments, the target-binding moiety comprises the amino acid sequence of any one of SEQ ID NOs: 1-7, 9-14, and 135, or a variant thereof having at least about 90% (such as about n % sequence identity, where n % is selected from 91%, 92%, 93%, 94%, 95%, 96%, 97%, 98%, and 99%) sequence identity to the amino acid sequence of any one of SEQ ID NOs: 1-7, 9-14, and 135. In some embodiments, the target-binding moiety comprises the amino acid sequence of SEQ ID NO: 8, or a variant thereof comprising at least about 90% sequence identity to the amino acid sequence of SEQ ID NO: 8. In some embodiments, the target-binding moiety comprises the amino acid sequence of SEQ ID NO: 102, or a variant thereof comprising at least about 90% (such as about n % sequence identity, where n % is selected from 91%, 92%, 93%, 94%, 95%, 96%, 97%, 98%, and 99%) sequence identity to the amino acid sequence of SEQ ID NO: 102. In some embodiments, the chimeric protein comprises the amino acid sequence of any one of the hACE2 chimeric proteins described in Table 1, e.g., in some embodiments, the chimeric protein comprises the amino acid sequence of any one of SEQ ID NOs: 84-88 and 136-140, or a variant thereof having at least about 90% (such as about n % sequence identity, where n % is selected from 91%, 92%, 93%, 94%, 95%, 96%, 97%, 98%, and 99%) sequence identity to the amino acid sequence of any one of SEQ ID NOs: 84-88 and 136-140. In some embodiments, the mucoadhesive peptide fragment comprises the amino acid sequence of any one of the mucoadhesive peptide fragments described in Table 8. In some embodiments, the target-binding moiety is directly fused to the mucoadhesive peptide fragment. In some embodiments, the target-binding moiety is fused to the mucoadhesive peptide fragment via peptide linker. In some embodiments, the peptide linker comprises the amino acid sequence of any one of the peptide linkers described in Table 9.

In some embodiments, there is provided a chimeric protein comprising: (a) a target-binding moiety comprising an EBD of an animal ACE2 protein or a fragment thereof that specifically binds to an S protein of a coronavirus; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the target-binding moiety specifically binds an S1 subunit of the S protein of the coronavirus. In some embodiments, the S protein is any one of the S proteins described in Table 5. In some embodiments, the coronavirus is SARS-CoV-2 or a variant thereof. In some embodiments, the target-binding moiety comprises the amino acid sequence of any one of the animal ACE2 proteins or fragments thereof described in Table 4, e.g., in some embodiments, the target-binding moiety comprises the amino acid sequence of any one of SEQ ID NOs: 15-27, or a variant thereof having at least about 90% (such as about n % sequence identity, where n % is selected from 91%, 92%, 93%, 94%, 95%, 96%, 97%, 98%, and 99%) sequence identity to the amino acid sequence of any one of SEQ ID NOs: 15-27. In some embodiments, the chimeric protein comprises the amino acid sequence of any one of the animal ACE2 chimeric proteins described in Table 1, e.g., in some embodiments, the chimeric protein comprises the amino acid sequence of any one of SEQ ID NOs: 89-93, or a variant thereof having at least about 90% (such as about n % sequence identity, where n % is selected from 91%, 92%, 93%, 94%, 95%, 96%, 97%, 98%, and 99%) sequence identity to the amino acid sequence of any one of SEQ ID NOs: 89-93. In some embodiments, the mucoadhesive peptide fragment comprises the amino acid sequence of any one of the mucoadhesive peptide fragments described in Table 8. In some embodiments, the target-binding moiety is directly fused to the mucoadhesive peptide fragment. In some embodiments, the target-binding moiety is fused to the mucoadhesive peptide fragment via peptide linker. In some embodiments, the peptide linker comprises the amino acid sequence of any one of the peptide linkers described in Table 9.

In some embodiments, the half-life of the chimeric protein on the mucosa is at least about n hours, where n is selected from 6 hours, 8 hours, 10 hours, 12 hours, 14 hours, 16 hours, 18 hours, 20 hours 22 hours, 24 hours, 30 hours, 36 hours, 48 hours, or more. In some embodiments, the half-life of the chimeric protein on the mucosa is at least 12 hours. In some embodiments, the half-life of the chimeric protein on the mucosa is at least 24 hours.

The half-life of the chimeric protein on the mucosa may be determined using known in vitro assays in the art. In view of the size and polar properties of the chimeric protein, mucosal (e.g., nasal) absorption of the chimeric protein is minimal because of low membrane permeability of the chimeric protein. However, mucociliary clearance of the chimeric protein may play a role in the half-life of the chimeric proteins. The mucoadhesive peptide fragment can improve the retention time of the chimeric protein on the mucosa. For example, an in vitro model cell system, such as mucosal epithelial cells, may be used to determine the amount of the chimeric protein remaining on cell/mucin surface by FACS or immunofluorescence. As another example, mucosa related components, such as mucin, could be used to incubate with a chimeric protein and determine the amount of the chimeric protein associated with mucin by ELISA.

In some embodiments, the chimeric protein comprises a target-binding moiety comprising between about 12 amino acids (aa) and about 805 aa of a full-length hACE2 protein or a fragment thereof (e.g., an EBD of an ACE2 protein or a fragment thereof, such as SEQ ID NO: 1), such as between about 12 aa and about 700 aa, between about 15 aa and about 500 aa, between about 100 aa and about 300 aa, between about 200 aa and about 400 aa, between about 300 aa and about 500 aa, between about 400 aa and about 600 aa, between about 500 aa and about 700 aa, between about 600 aa and about 805 aa, between about 12 aa and about 20 aa, between about 15 aa and about 20 aa, between about 21 aa and about 42 aa, between about 30 aa and about 41 aa, or between about 500 aa and about 805 aa. In some embodiments, the chimeric protein comprises a target-binding moiety comprising greater than about 12 aa of a full-length hACE2 protein or a fragment thereof, such any greater than about n, where n is selected from 13 aa, 14 aa, 15 aa, 16 aa, 17 aa, 18 aa, 19, aa, 20 aa, 30 aa, 40 aa, 50 aa, 100 aa, 150 aa, 200 aa, 250 aa, 300 aa, 350 aa, 400 aa, 450 aa, 500 aa, 550 aa, 600 aa, 650 aa, 700 aa, 750 aa, 800 aa, 850 aa, or more. In some embodiments, the chimeric protein comprises a target-binding moiety comprising less than about 805 aa of a full-length hACE2 protein or a variant thereof, such as less than about n, where n is selected from 800 aa, 750 aa, 700 aa, 650 aa, 600 aa, 550 aa, 500 aa, 450 aa, 400 aa, 350 aa, 300 aa, 250 aa, 200 aa, 150 aa, 100 aa, 50 aa, 40 aa, 30 aa, 20 aa, 19aa, 18aa, 17aa, 16aa, 15 aa, 14 aa, 13 aa, 12 aa, or less. In some embodiments, the chimeric protein comprises a target-binding moiety comprising any of about 805 aa, about 714 aa, about 596 aa, about 380 aa, about 342 aa, about 331 aa, about 182 aa, about 19 aa, or about 12 aa, of a full-length hACE2 protein or a variant thereof.

In some embodiments, the chimeric protein comprises a target-binding moiety comprising between about 12 aa and about 805 aa of a full-length animal ACE2 protein or a variant thereof, such as between about 12 aa and about 700 aa, between about 15 aa and about 500 aa, between about 100 aa and about 300 aa, between about 200 aa and about 400 aa, between about 300 aa and about 500 aa, between about 400 aa and about 600 aa, between about 500 aa and about 700 aa, between about 600 aa and about 805 aa, between about 15 aa and about 20 aa, between about 12 aa and about 20 aa, between about 21 aa and about 42 aa, between about 30 aa and about 41 aa, or between about 500 aa and about 805 aa, of a full-length animal ACE2 protein or a variant thereof. In some embodiments, the chimeric protein comprises a target-binding moiety comprising greater than about 12 aa of a full-length animal ACE2 protein or a variant thereof, such any greater than about n, where n is selected from 13 aa, 14 aa, 15 aa, 16 aa, 17 aa, 18 aa, 19, aa, 20 aa, 30 aa, 40 aa, 50 aa, 100 aa, 150 aa, 200 aa, 250 aa, 300 aa, 350 aa, 400 aa, 450 aa, 500 aa, 550 aa, 600 aa, 650 aa, 700 aa, 750 aa, 800 aa, 850 aa, or more, of a full-length animal ACE2 protein or a variant thereof. In some embodiments, the chimeric protein comprises a target-binding moiety comprising less than about 805 aa of a full-length animal ACE2 protein or a variant thereof, such as less than about n, where n is selected from 800 aa, 750 aa, 700 aa, 650 aa, 600 aa, 550 aa, 500 aa, 450 aa, 400 aa, 350 aa, 300 aa, 250 aa, 200 aa, 150 aa, 100 aa, 40 aa, 30 aa, 50 aa, 20 aa, 19aa, 18aa, 17aa, 16aa, 15 aa, 14 aa, 13 aa, 12 aa, or less, of a full-length animal ACE2 protein or a variant thereof. In some embodiments, the chimeric protein comprises a target-binding moiety comprising any of about 805 aa, about 714 aa, about 596 aa, about 380 aa, about 342 aa, about 331 aa, about 182 aa, about 19 aa, or about 12 aa, of a full-length animal ACE2 protein or a variant thereof.

In some embodiments, the chimeric protein comprises a target-binding moiety comprising a fragment that selectively recognizes an S1 subunit of the S protein and is capable of interfering with S1 binding to a full-length ACE2. In some embodiments, the chimeric protein comprises a target-binding moiety comprising amino acids 24-42 of a full-length ACE2 protein (e.g., a full-length hACE2 protein) or a variant thereof. In some embodiments, the chimeric protein comprises a target-binding moiety comprising between about 12 aa and about 19 aa, such as between about 12 aa and about 14 aa, between about 13 aa and about 15 aa, between about 14 aa and about 16 aa, between about 15 aa and about 17 aa, between about 16 aa and about 18 aa, between about 17 aa and about 19 aa, or between about 18 aa and about 19 aa of amino acids 24-42, of a full-length ACE2 protein or a variant thereof. In some embodiments, the chimeric protein comprises a target-binding moiety comprising at least about 12 aa, such as at least about n, where n is selected from 13aa, 14 aa, 15 aa, 16 aa, 17 aa, and 18 aa, of SEQ ID NO: 8. In some embodiments, the chimeric protein comprises a target-binding moiety comprising greater than about 12 aa, such as greater than about n, where n is selected from 13 aa, 14 aa, 15 aa, 16 aa, 17 aa, and 18 aa, of SEQ ID NO: 8. In some embodiments, the chimeric protein comprises a target-binding moiety comprising less than about 20 aa, such as at less than about n, where n is selected from 19 aa, 18 aa, 17 aa, 16 aa, 15 aa, 14 aa, 13 aa, 12 aa, or fewer, of SEQ ID NO: 8. In some embodiments, the chimeric protein comprises a target-binding moiety comprising about 19 aa of SEQ ID NO: 8. In some embodiments, the chimeric protein comprises a target-binding moiety comprising the amino acid sequence of SEQ ID NO: 8, or a variant thereof comprising at least about 90% (such as about n % sequence identity, where n % is selected from 91%, 92%, 93%, 94%, 95%, 96%, 97%, 98%, and 99%) sequence identity to the amino acid sequence of SEQ ID NO: 8.

In some embodiments, the chimeric protein comprises a target-binding moiety comprising amino acids 30-41 of a full-length ACE2 protein (e.g., a full-length hACE2 protein or a full-length animal ACE2 protein) or a variant thereof. In some embodiments, the chimeric protein comprises a target-binding moiety comprising the amino acid sequence of any one of SEQ ID NOs: 102, 111-120, and 122, or a variant thereof comprising at least about 90% (such as about n % sequence identity, where n % is selected from 91%, 92%, 93%, 94%, 95%, 96%, 97%, 98%, and 99%) sequence identity to any one of SEQ ID NOs: 102, 111-120, and 122. In some embodiments, the full-length ACE2 protein or a variant thereof is a hACE2 protein or variant thereof. In some embodiments, the full-length ACE2 protein or variant thereof is not a canine or a chicken full-length ACE2 protein or variant thereof.

In some embodiments, the chimeric protein comprises a target-binding moiety comprising amino acids 29-40 of a full-length ACE2 protein (e.g., a full-length animal ACE2 protein) or a variant thereof. In some embodiments, the chimeric protein comprises a target-binding moiety comprising the amino acid sequence of SEQ ID NO: 110 or 121, or a variant thereof comprising at least about 90% (such as about n % sequence identity, where n % is selected from 91%, 92%, 93%, 94%, 95%, 96%, 97%, 98%, and 99%) sequence identity to SEQ ID NO: 110 or 121. In some embodiments, the full-length ACE2 protein or variant thereof is a canine or a chicken ACE2 protein or a variant thereof.

Exemplary chimeric proteins comprising a target-binding moiety that specifically binds to an S protein of a coronavirus and a mucoadhesive peptide fragment comprising at least about 5 (e.g., about 5 to about 30) positively charged amino acid residues are provided herein. In some embodiments, the chimeric protein comprises any of the ACE2 proteins or fragments thereof described in Tables 3 and 4 (e.g., hACE2 or animal ACE2 proteins or fragments thereof, respectively). In some embodiments, the chimeric protein comprises any of the mucoadhesive peptide fragments described in Table 8. In some embodiments, the target-binding moiety is directly fused with the mucoadhesive peptide fragment. In some embodiments, the target-binding moiety is fused with the mucoadhesive peptide fragment via a peptide linker. In some embodiments, the chimeric protein comprises any of the peptide linkers described in Table 9.

In some embodiments, the chimeric protein comprises: (a) a target-binding moiety comprising an EBD of ACE2 (e.g., SEQ ID NO: 1) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding moiety is directly fused to the mucoadhesive peptide fragment. In some embodiments, the chimeric protein comprises any of the mucoadhesive peptide fragments described in Table 8.

In some embodiments, the chimeric protein comprises: (a) a target-binding moiety comprising an EBD of ACE2 (e.g., SEQ ID NO: 1) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding is fused to the mucoadhesive peptide via a peptide linker. In some embodiments, the peptide linker is any of the peptide linkers described in Table 9. In some embodiments, the chimeric protein comprises: (a) a target-binding moiety comprising an EBD of ACE2 (e.g., SEQ ID NO: 1) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding is fused to the mucoadhesive peptide fragment via an immunoglobulin Fc region or a fragment thereof. In some embodiments, the chimeric protein comprises any of the mucoadhesive peptide fragments described in Table 8.

In some embodiments, the chimeric protein comprises: (a) a target-binding moiety comprising an EBD of ACE2 (e.g., SEQ ID NO: 1) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, wherein the target-binding is fused to the mucoadhesive peptide fragment via an immunoglobulin Fc region or a fragment thereof, and wherein the mucoadhesive peptide fragment comprises a polycationic peptide. In some embodiments, the polycationic peptide is a polylysine peptide (e.g., a 6K, a 12K, or a 30K peptide). In some embodiments, the polycationic peptide is a polyhistidine peptide (e.g., a 5H, a 6H, a 12H, or a 30H peptide).

In some embodiments, the chimeric protein comprises: (a) a target-binding moiety comprising ACE614 (e.g., SEQ ID NO: 2) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding moiety is directly fused to the mucoadhesive peptide fragment. In some embodiments, the chimeric protein comprises any of the mucoadhesive peptide fragments described in Table 8.

In some embodiments, the chimeric protein comprises: (a) a target-binding moiety comprising ACE614 (e.g., SEQ ID NO: 2) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding is fused to the mucoadhesive peptide via a peptide linker. In some embodiments, the peptide linker is any of the peptide linkers described in Table 9. In some embodiments, the chimeric protein comprises: (a) a target-binding moiety comprising ACE614 (e.g., SEQ ID NO: 2) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding is fused to the mucoadhesive peptide fragment via an immunoglobulin Fc region or a fragment thereof. In some embodiments, the chimeric protein comprises any of the mucoadhesive peptide fragments described in Table 8.

In some embodiments, the chimeric protein comprises: (a) a target-binding moiety comprising ACE614 (e.g., SEQ ID NO: 2) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, wherein the target-binding is fused to the mucoadhesive peptide fragment via an immunoglobulin Fc region or a fragment thereof, and wherein the mucoadhesive peptide fragment comprises a polycationic peptide. In some embodiments, the polycationic peptide is a polylysine peptide (e.g., a 6K, a 12K, or a 30K peptide). In some embodiments, the polycationic peptide is a polyhistidine peptide (e.g., a 5H, a 6H, a 12H, or a 30H peptide).

In some embodiments, the chimeric protein comprises: (a) a target-binding moiety comprising ACE740 (e.g., SEQ ID NO: 135) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding moiety is directly fused to the mucoadhesive peptide fragment. In some embodiments, the chimeric protein comprises any of the mucoadhesive peptide fragments described in Table 8.

In some embodiments, the chimeric protein comprises: (a) a target-binding moiety comprising ACE740 (e.g., SEQ ID NO: 135) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding is fused to the mucoadhesive peptide via a peptide linker. In some embodiments, the peptide linker is any of the peptide linkers described in Table 9. In some embodiments, the chimeric protein comprises: (a) a target-binding moiety comprising ACE740 (e.g., SEQ ID NO: 135) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, and wherein the target-binding is fused to the mucoadhesive peptide fragment via an immunoglobulin Fc region or a fragment thereof. In some embodiments, the chimeric protein comprises any of the mucoadhesive peptide fragments described in Table 8.

In some embodiments, the chimeric protein comprises: (a) a target-binding moiety comprising ACE740 (e.g., SEQ ID NO: 135) or a fragment thereof that specifically binds to an S protein; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa, wherein the target-binding is fused to the mucoadhesive peptide fragment via an immunoglobulin Fc region or a fragment thereof, and wherein the mucoadhesive peptide fragment comprises a polycationic peptide. In some embodiments, the polycationic peptide is a polylysine peptide (e.g., a 6K, a 12K, or a 30K peptide). In some embodiments, the polycationic peptide is a polyhistidine peptide (e.g., a 5H, a 6H, a 12H, or a 30H peptide).

Table 1 describes the sequences of the exemplary chimeric proteins provided herein.

TABLE 1

Exemplary chimeric proteins

| Chimeric protein name; ACE2 fragment; Species; Linker; Mucoadhesive peptide | Sequence (Linker is BOLD; Mucoadhesive peptide is ITALICIZED) | SEQ ID NO |
|---|---|---|
| ACE740-Fc1-5H; ACE740; Human; Immunoglobulin Fc region ($CH_2CH_3$): "Fc1"; 5H | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYGDY<br>WRGDYEVNGVDGYDYSRGQLIEDVEHTFEEIKPLYEHLHAYVRAKL<br>MNAYPSYISPIGCLPAHLLGDMWGRFWTNLYSLTVPFGQKPNIDVT<br>DAMVDQAWDAQRIFKEAEKFFVSVGLPNMTQGFWENSMLTDPGNVQ | 136 |

TABLE 1-continued

| Exemplary chimeric proteins | | |
|---|---|---|
| Chimeric protein name;<br>ACE2 fragment;<br>Species;<br>Linker;<br>Mucoadhesive peptide | Sequence (Linker is BOLD;<br>Mucoadhesive peptide is ITALICIZED) | SEQ ID NO |
| | KAVCHPTAWDLGKGDFRILMCTKVTMDDFLTAHHEMGHIQYDMAYA<br>AQPFLLRNGANEGFHEAVGEIMSLSAATPKHLKSIGLLSPDFQEDN<br>ETEINFLLKQALTIVGTLPFTYMLEKWRWMVFKGEIPKDQWMKKWW<br>EMKREIVGVVEPVPHDETYCDPASLFHVSNDYSFIRYYTRTLYQFQ<br>FQEALCQAAKHEGPLHKCDISNSTEAGQKLFNMLRLGKSEPWTLAL<br>ENVVGAKNMNVRPLLNYFEPLFTWLKDQNKNSFVGWSTDWSPYADQ<br>SIKVRISLKSALGDKAYEWNDNEMYLFRSSVAYAMRQYFLKVKNQM<br>ILFGEEDVRVANLKPRISFNFFVTAPKNVSDIIPRTEVEKAIRMSR<br>SRINDAFRLNDNSLEFLGIQPTLGPPNQPPVS**TCPPCPAPELLGGP**<br>**SVFLFPPKPKDTLMISRTPEVTCVVVDVSHEDPEVKFNWYVDGVEV**<br>**HNAKTKPREEQYNSTYRVVSVLTVLHQDWLNGKEYKCKVSNKALPA**<br>**PIEKTISKAKGQPREPQVYTLPPSRDELTKNQVSLTCLVKGFYPSD**<br>**IAVEWESNGQPENNYKTTPPVLDSDGSFFLYSKLTVDKSRWQQGNV**<br>**FSCSVMHEALHNHYTQKSLSLSPG***HHHHH* | |
| ACE740-Fc1-6H;<br>ACE740;<br>Human;<br>Immunoglobulin Fc region ($CH_2CH_3$): "Fc1";<br>6H | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYGDY<br>WRGDYEVNGVDGYDYSRGQLIEDVEHTFEEIKPLYEHLHAYVRAKL<br>MNAYPSYISPIGCLPAHLLGDMWGRFWTNLYSLTVPFGQKPNIDVT<br>DAMVDQAWDAQRIFKEAEKFFVSVGLPNMTQGFWENSMLTDPGNVQ<br>KAVCHPTAWDLGKGDFRILMCTKVTMDDFLTAHHEMGHIQYDMAYA<br>AQPFLLRNGANEGFHEAVGEIMSLSAATPKHLKSIGLLSPDFQEDN<br>ETEINFLLKQALTIVGTLPFTYMLEKWRWMVFKGEIPKDQWMKKWW<br>EMKREIVGVVEPVPHDETYCDPASLFHVSNDYSFIRYYTRTLYQFQ<br>FQEALCQAAKHEGPLHKCDISNSTEAGQKLENMLRLGKSEPWTLAL<br>ENVVGAKNMNVRPLLNYFEPLFTWLKDQNKNSFVGWSTDWSPYADQ<br>SIKVRISLKSALGDKAYEWNDNEMYLFRSSVAYAMRQYFLKVKNQM<br>ILFGEEDVRVANLKPRISFNFFVTAPKNVSDIIPRTEVEKAIRMSR<br>SRINDAFRLNDNSLEFLGIQPTLGPPNQPPVS**TCPPCPAPELLGGP**<br>**SVFLFPPKPKDTLMISRTPEVTCVVVDVSHEDPEVKFNWYVDGVEV**<br>**HNAKTKPREEQYNSTYRVVSVLTVLHQDWLNGKEYKCKVSNKALPA**<br>**PIEKTISKAKGQPREPQVYTLPPSRDELTKNQVSLTCLVKGFYPSD**<br>**IAVEWESNGQPENNYKTTPPVLDSDGSFFLYSKLTVDKSRWQQGNV**<br>**FSCSVMHEALHNHYTQKSLSLSPG***HHHHHH* | 137 |
| ACE740-Fc1-7X-1;<br>ACE740;<br>Human;<br>Immunoglobulin Fc region ($CH_2CH_3$): "Fc1";<br>7X-1 | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYGDY<br>WRGDYEVNGVDGYDYSRGQLIEDVEHTFEEIKPLYEHLHAYVRAKL<br>MNAYPSYISPIGCLPAHLLGDMWGRFWTNLYSLTVPFGQKPNIDVT<br>DAMVDQAWDAQRIFKEAEKFFVSVGLPNMTQGFWENSMLTDPGNVQ<br>KAVCHPTAWDLGKGDFRILMCTKVTMDDFLTAHHEMGHIQYDMAYA<br>AQPFLLRNGANEGFHEAVGEIMSLSAATPKHLKSIGLLSPDFQEDN<br>ETEINFLLKQALTIVGTLPFTYMLEKWRWMVFKGEIPKDQWMKKWW<br>EMKREIVGVVEPVPHDETYCDPASLFHVSNDYSFIRYYTRTLYQFQ<br>FQEALCQAAKHEGPLHKCDISNSTEAGQKLFNMLRLGKSEPWTLAL<br>ENVVGAKNMNVRPLLNYFEPLFTWLKDQNKNSFVGWSTDWSPYADQ<br>SIKVRISLKSALGDKAYEWNDNEMYLFRSSVAYAMRQYFLKVKNQM<br>ILFGEEDVRVANLKPRISFNFFVTAPKNVSDIIPRTEVEKAIRMSR<br>SRINDAFRLNDNSLEFLGIQPTLGPPNQPPVS**TCPPCPAPELLGGP**<br>**SVFLFPPKPKDTLMISRTPEVTCVVVDVSHEDPEVKFNWYVDGVEV**<br>**HNAKTKPREEQYNSTYRVVSVLTVLHQDWLNGKEYKCKVSNKALPA**<br>**PIEKTISKAKGQPREPQVYTLPPSRDELTKNQVSLTCLVKGFYPSD**<br>**IAVEWESNGQPENNYKTTPPVLDSDGSFFLYSKLTVDKSRWQQGNV**<br>**FSCSVMHEALHNHYTQKSLSLSPG***KKKGKKK* | 138 |
| ACE740-Fc1-12X-7;<br>ACE740;<br>Human;<br>Immunoglobulin Fc region ($CH_2CH_3$): "Fc1";<br>12X-7 | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYGDY<br>WRGDYEVNGVDGYDYSRGQLIEDVEHTFEEIKPLYEHLHAYVRAKL<br>MNAYPSYISPIGCLPAHLLGDMWGRFWTNLYSLTVPFGQKPNIDVT<br>DAMVDQAWDAQRIFKEAEKFFVSVGLPNMTQGFWENSMLTDPGNVQ<br>KAVCHPTAWDLGKGDFRILMCTKVTMDDFLTAHHEMGHIQYDMAYA<br>AQPFLLRNGANEGFHEAVGEIMSLSAATPKHLKSIGLLSPDFQEDN<br>ETEINFLLKQALTIVGTLPFTYMLEKWRWMVFKGEIPKDQWMKKWW<br>EMKREIVGVVEPVPHDETYCDPASLFHVSNDYSFIRYYTRTLYQFQ | 139 |

TABLE 1-continued

Exemplary chimeric proteins

| Chimeric protein name;<br>ACE2 fragment;<br>Species;<br>Linker;<br>Mucoadhesive peptide | Sequence (Linker is BOLD;<br>Mucoadhesive peptide is ITALICIZED) | SEQ ID NO |
|---|---|---|
| | FQEALCQAAKHEGPLHKCDISNSTEAGQKLFNMLRLGKSEPWTLAL<br>ENVVGAKNMNVRPLLNYFEPLFTWLKDQNKNSFVGWSTDWSPYADQ<br>SIKVRISLKSALGDKAYEWNDNEMYLFRSSVAYAMRQYFLKVKNQM<br>ILFGEEDVRVANLKPRISFNFFVTAPKNVSDIIPRTEVEKAIRMSR<br>SRINDAFRLNDNSLEFLGIQPTLGPPNQPPVS**TCPPCPAPELLGGP**<br>**SVFLFPPKPKDTLMISRTPEVTCVVVDVSHEDPEVKFNWYVDGVEV**<br>**HNAKTKPREEQYNSTYRVVSVLTVLHQDWLNGKEYKCKVSNKALPA**<br>**PIEKTISKAKGQPREPQVYTLPPSRDELTKNQVSLTCLVKGFYPSD**<br>**IAVEWESNGQPENNYKTTPPVLDSDGSFFLYSKLTVDKSRWQQGNV**<br>**FSCSVMHEALHNHYTQKSLSLSPG***KKAHHGKKAHHV* | |
| ACE740-Fc1-12X-8;<br>ACE740;<br>Human;<br>Immunoglobulin Fc region ($CH_2CH_3$): "Fc1";<br>12X-8 | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYGDY<br>WRGDYEVNGVDGYDYSRGQLIEDVEHTFEEIKPLYEHLHAYVRAKL<br>MNAYPSYISPIGCLPAHLLGDMWGRFWTNLYSLTVPFGQKPNIDVT<br>DAMVDQAWDAQRIFKEAEKFFVSVGLPNMTQGFWENSMLTDPGNVQ<br>KAVCHPTAWDLGKGDFRILMCTKVTMDDFLTAHHEMGHIQYDMAYA<br>AQPFLLRNGANEGFHEAVGEIMSLSAATPKHLKSIGLLSPDFQEDN<br>ETEINFLLKQALTIVGTLPFTYMLEKWRWMVFKGEIPKDQWMKKWW<br>EMKREIVGVVEPVPHDETYCDPASLFHVSNDYSFIRYYTRTLYQFQ<br>FQEALCQAAKHEGPLHKCDISNSTEAGQKLENMLRLGKSEPWTLAL<br>ENVVGAKNMNVRPLLNYFEPLFTWLKDQNKNSFVGWSTDWSPYADQ<br>SIKVRISLKSALGDKAYEWNDNEMYLFRSSVAYAMRQYFLKVKNQM<br>ILFGEEDVRVANLKPRISFNFFVTAPKNVSDIIPRTEVEKAIRMSR<br>SRINDAFRLNDNSLEFLGIQPTLGPPNQPPVS**TCPPCPAPELLGGP**<br>**SVFLFPPKPKDTLMISRTPEVTCVVVDVSHEDPEVKFNWYVDGVEV**<br>**HNAKTKPREEQYNSTYRVVSVLTVLHQDWLNGKEYKCKVSNKALPA**<br>**PIEKTISKAKGQPREPQVYTLPPSRDELTKNQVSLTCLVKGFYPSD**<br>**IAVEWESNGQPENNYKTTPPVLDSDGSFFLYSKLTVDKSRWQQGNV**<br>**FSCSVMHEALHNHYTQKSLSLSPG***KKARRGKKARRV* | 140 |
| ACE614-Fc1-12K;<br>ACE614;<br>Human;<br>Immunoglobulin Fc region ($CH_2CH_3$): "Fc1";<br>12K | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYGDY<br>WRGDYEVNGVDGYDYSRGQLIEDVEHTFEEIKPLYEHLHAYVRAKL<br>MNAYPSYISPIGCLPAHLLGDMWGRFWTNLYSLTVPFGQKPNIDVT<br>DAMVDQAWDAQRIFKEAEKFFVSVGLPNMTQGFWENSMLTDPGNVQ<br>KAVCHPTAWDLGKGDFRILMCTKVTMDDFLTAHHEMGHIQYDMAYA<br>AQPFLLRNGANEGFHEAVGEIMSLSAATPKHLKSIGLLSPDFQEDN<br>ETEINFLLKQALTIVGTLPFTYMLEKWRWMVFKGEIPKDQWMKKWW<br>EMKREIVGVVEPVPHDETYCDPASLFHVSNDYSFIRYYTRTLYQFQ<br>FQEALCQAAKHEGPLHKCDISNSTEAGQKLENMLRLGKSEPWTLAL<br>ENVVGAKNMNVRPLLNYFEPLFTWLKDQNKNSFVGWSTDWSPYA**TC**<br>**PPCPAPELLGGPSVFLFPPKPKDTLMISRTPEVTCVVVDVSHEDPE**<br>**VKFNWYVDGVEVHNAKTKPREEQYNSTYRVVSVLTVLHQDWLNGKE**<br>**YKCKVSNKALPAPIEKTISKAKGQPREPQVYTLPPSRDELTKNQVS**<br>**LTCLVKGFYPSDIAVEWESNGQPENNYKTTPPVLDSDGSFFLYSKL**<br>**TVDKSRWQQGNVFSCSVMHEALHNHYTQKSLSLSPGK**GGGGS*KKKK*<br>*KKKKKKKK* | 84 |
| ACE614-Fc1-12H;<br>ACE614;<br>Human;<br>Immunoglobulin Fc region ($CH_2CH_3$): "Fc1";<br>12H | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYGDY<br>WRGDYEVNGVDGYDYSRGQLIEDVEHTFEEIKPLYEHLHAYVRAKL<br>MNAYPSYISPIGCLPAHLLGDMWGRFWTNLYSLTVPFGQKPNIDVT<br>DAMVDQAWDAQRIFKEAEKFFVSVGLPNMTQGFWENSMLTDPGNVQ<br>KAVCHPTAWDLGKGDFRILMCTKVTMDDFLTAHHEMGHIQYDMAYA<br>AQPFLLRNGANEGFHEAVGEIMSLSAATPKHLKSIGLLSPDFQEDN<br>ETEINFLLKQALTIVGTLPFTYMLEKWRWMVFKGEIPKDQWMKKWW<br>EMKREIVGVVEPVPHDETYCDPASLFHVSNDYSFIRYYTRTLYQFQ<br>FQEALCQAAKHEGPLHKCDISNSTEAGQKLENMLRLGKSEPWTLAL<br>ENVVGAKNMNVRPLLNYFEPLFTWLKDQNKNSFVGWSTDWSPYA**TC**<br>**PPCPAPELLGGPSVFLFPPKPKDTLMISRTPEVTCVVVDVSHEDPE**<br>**VKFNWYVDGVEVHNAKTKPREEQYNSTYRVVSVLTVLHQDWLNGKE**<br>**YKCKVSNKALPAPIEKTISKAKGQPREPQVYTLPPSRDELTKNQVS** | 85 |

TABLE 1-continued

| Exemplary chimeric proteins | | |
|---|---|---|
| Chimeric protein name;<br>ACE2 fragment;<br>Species;<br>Linker;<br>Mucoadhesive peptide | Sequence (Linker is BOLD;<br>Mucoadhesive peptide is ITALICIZED) | SEQ ID NO |
| | **LTCLVKGFYPSDIAVEWESNGQPENNYKTTPPVLDSDGSFFLYSKL**<br>**TVDKSRWQQGNVFSCSVMHEALHNHYTQKSLSLSPGK***HHHHHHHHH*<br>*HHH* | |
| ACE200-bIZIP-35X-1;<br>ACE200;<br>Human;<br>Leucine/Isoleucine zipper: "bIZIP";<br>35X-1 | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYG**LS**<br>**IIAICLGSLGLILIIILLSVVVWKLL***GRHKAKNHIRRPKSRWKKWHK*<br>*YRKVHRHKVHKGRR* | 86 |
| ACE200-$CH_2$-$CH_2$-12X-4;<br>ACE200;<br>Human;<br>Immunoglobulin Fc region $CH_2CH_2$;<br>12X-4 | STIEEQAKTFLDKFNHEAEDLFYQSSLASWNYNTNITEENVQNMNN<br>AGDKWSAFLKEQSTLAQMYPLQEIQNLTVKLQLQALQQNGSSVLSE<br>DKSKRLNTILNTMSTIYSTGKVCNPDNPQECLLLEPGLNEIMANSL<br>DYNERLWAWESWRSEVGKQLRPLYEEYVVLKNEMARANHYEDYG**TC**<br>**PPCPAPELLGGPSVFLFPPKPKDTLMISRTPEVTCVVVDVSHEDPE**<br>**VKFNWYVDGVEVHNAKTKPREEQYNSTYRVVSVLTVLHQDWLNGKE**<br>**YKCKVSNKALPAPIEKTISKAKGQPRE***KRAHOKCORKSH* | 87 |
| ACE19-SA-50X-1;<br>ACE19;<br>Human;<br>Streptavidin ("SA");<br>50X-1 | QAKTFLDKFNHEAEDLFYQ**MAEAGITGTWYNQLGSTFIVTAGADGA**<br>**LTGTYESAVGNAEGDYVLTGRYDSAPATDGSGTALGWTVAWKNNYR**<br>**NAHSATTWSGQYVGGAEARINTQWLLTSGTTEANAWKSTLVGHDTF**<br>**TKVKPSAAS***HNKRFKKGRHVRHSRHKSHRRTHKYHHWRHYRKVHRC*<br>*KKAHKSHHRVHHK* | 88 |
| cACE614-Fc1-12H;<br>cACE614;<br>Canine;<br>Immunoglobulin Fc region ($CH_2CH_3$): "Fc1";<br>12H | STEDLVKTFLEKFNYEAEELSYQSSLASWNYNINITDENVQKMNNA<br>GAKWSAFYEEQSKLAKTYPLEEIQDSTVKRQLRALQHSGSSVLSAD<br>KNQRLNTILNSMSTIYSTGKACNPSNPQECLLLEPGLDDIMENSKD<br>YNERLWAWEGWRSEVGKQLRPLYEEYVALKNEMARANNYEDYGDYW<br>RGDYEEEWENGYNYSRNQLIDDVEHTFTQIMPLYQHLHAYVRTKLM<br>DTYPSYISPTGCLPAHLLGDMWGRFWTNLYPLTVPFGQKPNIDVTN<br>AMVNQSWDARKIFKEAEKFFVSVGLPNMTQEFWENSMLTEPSDSRK<br>VVCHPTAWDLGKGDFRIKMCTKVTMDDFLTAHHEMGHIQYDMAYAA<br>QPFLLRNGANEGFHEAVGEIMSLSAATPNHLKNIGLLPPSFFEDSE<br>TEINFLLKQALTIVGTLPFTYMLEKWRWMVFKGEIPKDQWMKTWWE<br>MKRNIVGVVEPVPHDETYCDPASLFHVANDYSFIRYYTRTIYQFQF<br>QEALCQIAKHEGPLHKCDISNSSEAGQKLLEMLKLGKSKPWTYALE<br>IVVGAKNMDVRPLLNYFEPLFTWLKEQNRNSFVGWNTDWSPYADQS<br>IKVRISLKSALGEKAYEWNNNEMYLFRSSIAYAMRQYFSEVKNQTI<br>PFVEDNVWVSDLKPRISFNFFVTSPGNVSDIIPRTEVEEAIRMYRS<br>RINDVFRLDDNSLEFLGIQPTLGPPYEPPVTIWLIVFGVVMGVVVV<br>GIVLLIFSGIRNRRKNDQARGEENPYASVDLSKGENNPGFQNVDDA<br>QTSF**ATCPPCPAPELLGGPSVFLFPPKPKDTLMISRTPEVTCVVVD**<br>**VSHEDPEVKFNWYVDGVEVHNAKTKPREEQYNSTYRVVSVLTVLHQ**<br>**DWLNGKEYKCKVSNKALPAPIEKTISKAKGQPREPQVYTLPPSRDE**<br>**LTKNQVSLTCLVKGFYPSDIAVEWESNGQPENNYKTTPPVLDSDGS**<br>**FFLYSKLTVDKSRWQQGNVFSCSVMHEALHNHYTQKSLSLSPGK***HH*<br>*HHHHHHHHHH* | 89 |
| cACE200-$(GPP)_{10}$-40X-2;<br>cACE200;<br>Canine;<br>$(GPP)_{10}$;<br>40X-2 | STEDLVKTFLEKFNYEAEELSYQSSLASWNYNINITDENVQKMNNA<br>GAKWSAFYEEQSKLAKTYPLEEIQDSTVKRQLRALQHSGSSVLSAD<br>KNQRLNTILNSMSTIYSTGKACNPSNPQECLLLEPGLDDIMENSKD<br>YNERLWAWEGWRSEVGKQLRPLYEEYVALKNEMARANNYEDYGD**GP**<br>**PGPPGPPGPPGPPGPPGPPGPPGPPGPP***WRKVHHYKKQHKNRAHGK*<br>*LKLRAKIHQRSRMHGKQKHYHR* | 90 |
| mACE614-COMP-6X-5;<br>mACE614;<br>Mouse;<br>cartilage oligomeric matrix protein ("COMP");<br>6X-5 | SLTEENAKTFLNNFNQEAEDLSYQSSLASWNYNTNITEENAQKMSE<br>AAAKWSAFYEEQSKTAQSFSLQEIQTPIIKRQLQALQQSGSSALSA<br>DKNKQLNTILNTMSTIYSTGKVCNPKNPQECLLLEPGLDEIMATST<br>DYNSRLWAWEGWRAEVGKQLRPLYEEYVVLKNEMARANNYNDYGDY<br>WRGDYEAEGADGYNYNRNQLIEDVERTFAEIKPLYEHLHAYVRRKL<br>MDTYPSYISPTGCLPAHLLGDMWGRFWTNLYPLTVPFAQKPNIDVT<br>DAMMNQGWDAERIFQEAEKFFVSVGLPHMTQGFWANSMLTEPADGR<br>KVVCHPTAWDLGHGDFRIKMCTKVTMDNFLTAHHEMGHIQYDMAYA<br>RQPFLLRNGANEGFHEAVGEIMSLSAATPKHLKSIGLLPSDFQEDS<br>ETEINFLLKQALTIVGTLPFTYMLEKWRWMVFRGEIPKEQWMKKWW<br>EMKREIVGVVEPLPHDETYCDPASLFHVSNDYSFIRYYTRTIYQFQ<br>FQEALCQAAKYNGSLHKCDISNSTEAGQKLLKMLSLGNSEPWTKAL<br>ENVVGARNMDVKPLLNYFQPLFDWLKEQNRNSFVGWNTEWSPYA**GP**<br>**QMLRELGETNAALQDVRELLRQQVREITFLKNTVMEBDAC***KKHHRR* | 91 |

TABLE 1-continued

Exemplary chimeric proteins

| Chimeric protein name; ACE2 fragment; Species; Linker; Mucoadhesive peptide | Sequence (Linker is BOLD; Mucoadhesive peptide is ITALICIZED) | SEQ ID NO |
|---|---|---|
| gACEΔ360-Fc1-120; gACEΔ360; Chicken (*Gallus domesticus*); Immunoglobulin Fc region ($CH_2CH_3$): "Fc1"; 120 | AEFNVRAEDISYENSLASWNYNTNITEETARKMSEAGAKWAAFYEEASRNASRFSLANIQDAVTRLQIQSLQDRGSSVLSPEKYSRLNSVMNSMSTIYSTGVVCKATEPFDCLVLEPGLDDIMANSIDYHERLWAWEGWRADVGRMMRPLYEEYVELKNEAARLNNYSDYGDYWRANYETDYPEEYKYSRDQLVQDVEKTFEQIKPLYQHLHAYVRHRLEQVYGSELINPTGCLPAHLLGDMWGRFWTNLYNLTVPYPEKPNIDVTSAMAQKNWDAMKIFKTAEAFFASIGLYNMTEGFWTNSMLTEPTDNRKVVCHPTAWDMGKNDYRIKMA**TCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK***OOOOOOOOOOOO* | 92 |
| nACEΔ420-T4F-12X-1; nACEΔ420; Mink (*Neovison vison*); T4 Fibritin ("T4F"); 12X-1 | YQNSLASWNYNTNITDENIQKMNIAGAKWSAFYEEESQHAKTYPLEEIQDPIIKRQLRALQQSGSSVLSADKRERLNTILNAMSTIYSTGKACNPNNPQECLLLEPGLDDIMENSKDYNERLWAWEGWRSEVGKQLRPLYEEYVALKNEMARANNYEDYGDYWRGDYEEEWADGYNYSRNQLIEDVEHTFTQIKPLYEHLHAYVRAKLMDAYPSRISPTGCLPAHLLGDMWGRFWTNLYPLMVPFGQKPNIDVTDAMVNQSWDARRIFKEAEKFFVSVGLPNMTEGFWQNSMLTEPGDNRKVVCHPTAWDLGKHDFRIKMCTKVTMDDFLTAHHEMGHIQYDMAYAAQPFLLRNGANEGFHEAVGEIMSLSAATPNHLKF**GYIPEAPRDGQAYVRKDGEWVLLSTFL***HHKKOOHHKKOO* | 93 |

Additional ACE2 chimeric proteins comprising any of the target-binding moieties or variants thereof specifically binding an S protein, the mucoadhesive peptide fragments, and/or linkers provided herein are also contemplated. It should be understood that various other chimeric proteins comprising target-binding moieties comprising an EBD of known ACE2 proteins or fragments thereof (e.g., hACE2 or animal ACE2 proteins, or fragments thereof), such as those described in Tables 3 and 4, or variants known in the art, fused with any of the mucoadhesive peptide fragments, such as those described in Table 8, and/or linkers, such as those described in Table 9, provided herein may be encompassed by the scope of this invention.

Using the hACE2 protein sequences disclosed in Table 3, and fragments thereof, exemplary human-derived hACE2 chimeric proteins and chimeric protein fragments may be designed. In some embodiments, the chimeric protein comprises: (a) a target-binding moiety comprising the amino acid sequence of any one of SEQ ID NOs: 1-7, 9-14, and 135, i.e., described in Table 3; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the chimeric protein comprises a target-binding moiety comprising an EBD of a hACE2 protein or a fragment thereof and one or more of the mucoadhesive peptide fragments described herein, such as any of the chimeric proteins comprising a hACE2 protein provided in Table 1 above, e.g., ACE740-Fc1-5H, ACE740-Fc1-6H, ACE740-Fc1-7X-1, ACE740-Fc1-12X-7, ACE740-Fc1-12X-8, ACE614-Fc1-12K, ACE614-Fc1-12H, ACE200-bIZIP-35X-1, ACE200-$CH_2$—$CH_2$-12X-4, and ACE19-SA-50X-1.

In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of any one of SEQ ID NOs: 84-88 and 136-140. In some embodiments, the chimeric protein comprises the amino acid sequence of any one of SEQ ID NOs: 84-88 and 136-140.

In some embodiments, there is provided a chimeric protein comprising: (a) a target-binding moiety comprising the amino acid sequence of SEQ ID NO: 135, i.e., ACE740 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises an Fc region (e.g., an immunoglobulin Fc region) or a fragment thereof. In some embodiments, the peptide linker comprises the amino acid sequence of SEQ ID NO: 63, i.e., "Fc1" as described in Table 9. In some embodiments, the mucoadhesive peptide fragment comprises the amino acid sequence of SEQ ID NO: 128, i.e., "5H" in Table 8. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 136. In some embodiments, the chimeric protein comprises the amino acid sequence of SEQ ID NO: 136. In some embodiments, the chimeric protein is ACE740-Fc1-5H, as described in Table 1. In some embodiments, the mucoadhesive peptide fragment comprises the amino acid sequence of SEQ ID NO: 28, i.e., “6H” as described in Table 8. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 137. In some embodiments, the chimeric protein comprises the amino acid sequence of SEQ ID NO: 137. In some embodiments, the chimeric protein is ACE740-Fc1-6H, as described in Table 1. In some embodiments, the mucoadhesive peptide fragment comprises the amino acid sequence of SEQ ID NO: 129, i.e., “7X-1” as described in Table 8. In some embodiments, the chimeric protein comprises an amino acid sequence having at least about 90% sequence identity (such as about sequence identity, where n is selected from 91%, 92%, 93%, 94%, 95%, 96%, 97%, 98%, and 99%) to the amino acid sequence of SEQ ID NO: 138. In some embodiments, the chimeric protein comprises the amino acid sequence of SEQ ID NO: 138. In some embodiments, the chimeric protein is ACE740-Fc1-7X-1, as described in Table 1. In some embodiments, the mucoadhesive peptide fragment comprises the amino acid sequence of SEQ ID NO: 130, i.e., “12X-7” as described in Table 8. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 139. In some embodiments, the chimeric protein comprises the amino acid sequence of SEQ ID NO: 139. In some embodiments, the chimeric protein is ACE740-Fc1-12X-7, as described in Table 1. In some embodiments, the mucoadhesive peptide fragment comprises the amino acid sequence of SEQ ID NO: 131, i.e., “12X-8” as described in Table 8. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 140. In some embodiments, the chimeric protein comprises the amino acid sequence of SEQ ID NO: 140. In some embodiments, the chimeric protein is ACE740-Fc1-12X-8, as described in Table 1.

In some embodiments, there is provided a chimeric protein comprising: (a) a target-binding moiety comprising the amino acid sequence of SEQ ID NO: 2, i.e., ACE614 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises an Fc region (e.g., an immunoglobulin Fc region) or a fragment thereof. In some embodiments, the peptide linker comprises the amino acid sequence of SEQ ID NO: 63, i.e., “Fc1” as described in Table 9. In some embodiments, the mucoadhesive peptide fragment comprises the amino acid sequence of SEQ ID NO: 32, i.e., “12K” in Table 8. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 84. In some embodiments, the chimeric protein comprises the amino acid sequence of SEQ ID NO: 84. In some embodiments, the chimeric protein is ACE614-Fc1-12K, as described in Table 1. In some embodiments, the mucoadhesive peptide fragment comprises the amino acid sequence of SEQ ID NO: 29, i.e., “12H” as described in Table 8. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 85. In some embodiments, the chimeric protein comprises the amino acid sequence of SEQ ID NO: 85. In some embodiments, the chimeric protein is ACE614-Fc1-12H, as described in Table 1.

In some embodiments, there is provided a chimeric protein comprising: (a) a target-binding moiety comprising the amino acid sequence of SEQ ID NO: 6, i.e., ACE200 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises a basic helix-loop-helix zipper (bZIP) domain. In some embodiments, the peptide linker comprises a leucine/isoleucine zipper (bIZIP) domain. In some embodiments, the peptide linker comprises the amino acid sequence of SEQ ID NO: 72, i.e., “bIZIP” as described in Table 9. In some embodiments, the mucoadhesive peptide fragment comprises the amino acid sequence of SEQ ID NO: 57, i.e., “35X-1” in Table 8. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 86. In some embodiments, the chimeric protein comprises the amino acid sequence of SEQ ID NO: 86. In some embodiments, the chimeric protein is ACE200-bIZIP-35X-1, as described in Table 1. In some embodiments, the mucoadhesive peptide fragment comprises the amino acid sequence of SEQ ID NO: 50, i.e., “12X-4” as described in Table 8. In some embodiments, the peptide linker comprises an Fc region (e.g., an immunoglobulin Fc region) or a fragment thereof. In some embodiments, the peptide linker comprises the amino acid sequence of SEQ ID NO: 66, i.e., “$CH_2$” as described in Table 9. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 87. In some embodiments, the chimeric protein comprises the amino acid sequence of SEQ ID NO: 87. In some embodiments, the chimeric protein is ACE200-$CH_2$—$CH_2$-12X-4, as described in Table 1.

In some embodiments, there is provided a chimeric protein comprising: (a) a target-binding moiety comprising the amino acid sequence of SEQ ID NO: 8, i.e., ACE19 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the mucoadhesive peptide fragment comprises the amino acid sequence of SEQ ID NO: 61, i.e., "50X-1" in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises a streptavidin (SA) moiety. In some embodiments, the peptide linker comprises the amino acid sequence of SEQ ID NO: 76, i.e., "SA" as described in Table 9. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 88. In some embodiments, the chimeric protein comprises the amino acid sequence of SEQ ID NO: 88. In some embodiments, the chimeric protein is ACE19-SA-50X-1, as described in Table 1.

In some embodiments, there is provided a chimeric protein comprising: (a) a target-binding moiety comprising the amino acid sequence of SEQ ID NO: 1, i.e., hACE2 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-84, 94, and 109, as described in Table 9.

In some embodiments, there is provided a chimeric protein comprising: (a) a target-binding moiety comprising the amino acid sequence of SEQ ID NO: 3, i.e., ACE360 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-84, 94, and 109, as described in Table 9.

In some embodiment, there is provided a chimeric protein comprising: (a) a target-binding moiety comprising the amino acid sequence of SEQ ID NO: 4, i.e., ACEΔ360 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 5, i.e., ACE732 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 7, i.e., ACEΔ420 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 102, i.e., ACE12 as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 9, i.e., ACE2 K26R as described in Table 3, or a fragment thereof; and (b) a mucoadhesive peptide fragment comprising at least about 5

(e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 10, i.e., ACE2 I468V as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 11, i.e., ACE2 N638S as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 12, i.e., ACE2 N720D as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 13, i.e., ACE2 HN-HN as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 14, i.e., ACE2 TY-HA as described in Table 3, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

Using the animal ACE2 protein sequences disclosed in Table 4, and fragments thereof corresponding to the various partial hACE2 fragments disclosed in Table 3 (e.g., fragments with equivalent sequence boundaries and lengths), exemplary animal-derived ACE2 chimeric proteins and chimeric protein fragments may be designed. In some embodiments, the target-binding moiety comprising an animal ACE2 protein described herein is a murine, guinea pig, equine, ferret, macaque, chimpanzee, swine, canine, feline, bovine, rabbit, mink, or chicken ACE2 protein or a fragment or variant thereof. In some embodiments, the chimeric protein comprises: (a) a target-binding moiety comprising the amino acid sequence of any one of SEQ ID NOs: 15-27, i.e., described in Table 4; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the chimeric protein comprises: (a) a target-binding moiety comprising the amino acid sequence of any one of SEQ ID NOs: 2-7 and 8-14 (e.g., fragments with equivalent sequence boundaries and lengths to animal ACE2 proteins), i.e., described in Table 3; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the chimeric protein comprises a target-binding moiety comprising an EBD of an animal ACE2 protein or a fragment thereof and one or more of the mucoadhesive peptide fragments described herein, such as any of the chimeric proteins comprising an animal ACE2 protein provided in Table 1 above, e.g., cACE614-Fc1-12H, cACE200-$(GPP)_{10}$-40X-2, mACE614-COMP-6X-5, gACEΔ360-FC1-12O, nACEΔ420-T4F-12X.

In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of any one of SEQ ID NOs: 89-93. In some embodiments, the chimeric protein comprises the amino acid sequence of any one of SEQ ID NOs: 89-93.

In some embodiments, there is provided a chimeric protein comprising: (a) a target-binding moiety comprising the amino acid sequence of SEQ ID NO: 104, i.e., cACE614, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOS: 28-62 and 128-134, as described in Table 8. In some embodiments, the mucoadhesive peptide fragment comprises the amino acid sequence of SEQ ID NO: 32, i.e., "12K" in Table 8. In some embodiments, the mucoadhesive peptide fragment comprises the amino acid sequence of SEQ ID NO: 28, i.e., "12H" in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises an Fc region (e.g., an immunoglobulin Fc region) or a fragment thereof. In some embodiments, the peptide linker comprises the amino acid sequence of SEQ ID NO: 63, i.e., "Fc1" as described in Table 9. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 89. In some embodiments, the chimeric protein comprises the amino acid sequence of SEQ ID NO: 89. In some embodiments, the chimeric protein is cACE614-Fc1-12H, as described in Table 1.

In some embodiments, there is provided a chimeric protein comprising: (a) a target-binding moiety comprising the amino acid sequence of SEQ ID NO: 105, i.e., cACE200, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOS: 28-62 and 128-134, as described in Table 8. In some embodiments, the mucoadhesive peptide fragment comprises the amino acid sequence of SEQ ID NO: 58, i.e., "40X-2" in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises a collagen-like protein (GPP) comprising repeated Glycine-X-Y repeats $(GPP)_n$, where n≥1. In some embodiments, the peptide linker comprises the amino acid sequence of SEQ ID NO: 109, i.e., "(GPP) 10" as described in Table 9. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 90. In some embodiments, the chimeric protein comprises the amino acid sequence of SEQ ID NO: 90. In some embodiments, the chimeric protein is cACE200-(GPP) 10-40X-2, as described in Table 1.

In some embodiments, there is provided a chimeric protein comprising: (a) a target-binding moiety comprising the amino acid sequence of SEQ ID NO: 106, i.e., mACE614, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOS: 28-62 and 128-134, as described in Table 8. In some embodiments, the mucoadhesive peptide fragment comprises the amino acid sequence of SEQ ID NO: 45, i.e., "6X-5" in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises a cartilage oligomeric matrix protein (COMP), or a fragment thereof. In some embodiments, the peptide linker comprises the amino acid sequence of SEQ ID NO: 77, i.e., "COMP" as described in Table 9. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 91. In some embodiments, the chimeric protein comprises the amino acid sequence of SEQ ID NO: 91. In some embodiments, the chimeric protein is mACE614-COMP-6X-5, as described in Table 1.

In some embodiments, there is provided a chimeric protein comprising: (a) a target-binding moiety comprising the amino acid sequence of SEQ ID NO: 107, i.e., gACEΔ360, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOS: 28-62 and 128-134, as described in Table 8. In some embodiments, the mucoadhesive peptide fragment comprises the amino acid sequence of SEQ ID NO: 38, i.e., "120" in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises an Fc region (e.g., an immunoglobulin Fc region) or a fragment thereof. In some embodiments, the peptide linker comprises the amino acid sequence of SEQ ID NO: 63, i.e., "Fc1" as described in Table 9. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 92. In some embodiments, the chimeric protein comprises the amino acid sequence of SEQ ID NO: 92. In some embodiments, the chimeric protein is gACEΔ360-Fc1-120, as described in Table 1.

In some embodiments, there is provided a chimeric protein comprising: (a) a target-binding moiety comprising the amino acid sequence of SEQ ID NO: 108, i.e., nACEΔ420, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the mucoadhesive peptide fragment comprises the amino acid sequence of SEQ ID NO: 47, i.e., "12X-1" in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9. In some embodiments, the peptide linker comprises a T4 fibritin domain or a fragment thereof. In some embodiments, the peptide linker comprises the amino acid sequence of SEQ ID NO: 74, i.e., "T4F" as described in Table 9. In some embodiments, the chimeric protein comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 93. In some embodiments, the chimeric protein comprises the amino acid sequence of SEQ ID NO: 93. In some embodiments, the chimeric protein is nACEΔ420-T4F-12X-1, as described in Table 1.

In some embodiments, there is provided a chimeric protein comprising: (a) a target-binding moiety comprising the amino acid sequence of SEQ ID NO: 15, i.e., mouse ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 16, i.e., guinea pig ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 17, i.e., equine ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 18, i.e., macaque ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 19, i.e., chimpanzee ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 20, i.e., swine ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 21, i.e., canine ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 22, i.e., feline ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 23, i.e., bovine ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94 and 109, as described in Table 9.

In some embodiments, there is provided a chimeric protein comprising: (a) a target-binding moiety comprising the amino acid sequence of SEQ ID NO: 24, i.e., rabbit ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94 and 109, as described in Table 9.

In some embodiments, there is provided a chimeric protein comprising: (a) a target-binding moiety comprising the amino acid sequence of SEQ ID NO: 25, i.e., ferret ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 26, i.e., mink ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

In some embodiments, there is provided a chimeric protein comprising: (a) a target-binding moiety comprising the amino acid sequence of SEQ ID NO: 27, i.e., chicken ACE2 as described in Table 4, or a fragment thereof; and (b) a mucoadhesive peptide fragment comprising at least about 5 (e.g., about 5 to about 30) positively charged amino acid residues, wherein the mucoadhesive peptide fragment facilitates attachment of the chimeric protein to a mucosa. In some embodiments, the mucoadhesive peptide fragment comprises the amino acid sequence of any one of SEQ ID NOs: 28-62 and 128-134, as described in Table 8. In some embodiments, the target-binding moiety is fused to the mucoadhesive peptide fragment via a peptide linker. In some embodiments, the peptide linker comprises the amino acid sequence of any one of SEQ ID NOs: 63-83, 94, and 109, as described in Table 9.

Without being bound by any theory or hypothesis, coronavirus infection (e.g., SARS-CoV-2 infection) occurs mainly through respiratory droplets and possible airborne transmission. Upper respiratory surfaces are the dominant and initial sites for coronavirus infection. The nasal epithelium produces a physical glycoprotein barrier to inhaled particles including allergens and pathogens, preventing penetration to the epithelial surface of mucosal tissues. One major component of the mucosal layer of nasal and respiratory tract are mucins, a family of large glycoproteins that coat the surface of the respiratory epithelium. Mucins, the primary non-aqueous component of mucus, are a complex and heterogeneous structure, which carry a highly negative charge. The inventors of the present application, in some embodiments, engineered a peptide comprising at least 5 positively charged amino acids (e.g., lysines, histidines, arginines, ornithines, or combinations thereof) which, when covalently linked to a target-binding moiety, confers to the conjugate (i.e., ACE2 chimeric protein) positive charges. The target-binding moiety (e.g., an EBD of an ACE2 protein or a fragment thereof) with its positively charged C-terminal peptide can form a layer of coronavirus-binding moieties that can line the nasal/respiratory tract and prevent the virus from binding to the viral receptor-expressing epithelial cells. A positively charged target-binding moiety could also bind the phospholipid bilayer of cell membranes, also negatively charged. This "sticky" property of the polymeric positively charged amino acid chain imparts to the target-binding moiety a longer half-life in the respiratory mucosal epithelium, providing a lengthened period of protection. Therefore, the engineered target-binding moiety-mucoadhesive polymer conjugate can block coronavirus entry into the cells of the respiratory cavity, even if the virus might penetrate the mucosal barrier and reach viral receptor-positive epithelial cells. In other embodiments, the positively charged mucoadhesive amino acids can be interspersed with non-positively charged amino acids without disrupting the mucoadhesive properties of the chimeric protein. Furthermore, the target-binding moiety of the ACE2 chimeric protein may be fused to the mucoadhesive peptide fragment via a peptide linker.

The different aspects and embodiments are discussed in various sections below in further detail.

A. Target-Binding Moieties

The chimeric proteins described herein comprise a target-binding moiety comprising an inhibitory polypeptide, i.e., an EBD of an ACE2 protein (such as SEQ ID NO: 101) or a fragment thereof that specifically binds to an S protein. In some embodiments, the target-binding moiety comprises an inhibitory polypeptide that inhibits binding of the S protein to a receptor on a cell of a mucosa. In some embodiments, the target-binding moiety comprises a natural receptor of the S protein or a fragment derived from the natural receptor. In some embodiments, the target-binding moiety comprises an EBD of the natural receptor, e.g., ACE2, or a fragment thereof. In some embodiments, the ACE2 is a hACE2 protein. In some embodiments, the ACE2 is an animal ACE2 protein.

In some embodiments, the target-binding moiety comprises a purification tag, e.g., a His tag, such as DYKDDDDKHHHHHH (SEQ ID NO: 95).

In some embodiments, the S protein is from a virus, such as a coronavirus. In some embodiments, the virus causes respiratory infections.

In humans, coronaviruses cause mild to severe respiratory tract illnesses ranging from the common cold to more serious diseases such as coronavirus disease 2019 (COVID-19), Severe Acute Respiratory Syndrome (SARS) and Middle East Respiratory Syndrome (MERS). The target-binding moieties described herein may target any one of these viruses, or other future viruses comprising S proteins.

Exemplary viruses, targets, and target-binding moieties are further described below.

Coronaviruses

A target-binding moiety (e.g., an EBD of an ACE2 protein or a fragment thereof) of the prevent invention specifically binds to a spike protein (also referred to as spike glycoprotein, or S protein) of a virus. In some embodiments, the virus is a coronavirus. In some embodiments, the virus is selected from the group consisting of SARS-CoV, SARS-CoV-2, and HCoV-NL63, including variants thereof. In some embodiments, the virus is SARS-CoV-2. In some embodiments, the virus is a reference coronavirus or a coronavirus having substantially the same genomic sequence (e.g., fewer than any one of 200, 100, 50, 20, 10, 5, 4, 3, 2, or 1 mutation(s)) and phenotypes as the reference coronavirus. In some embodiments, the virus is a variant coronavirus that has one or more mutations in the genomic sequence compared to the reference coronavirus, wherein the one or more mutations contribute to phenotypic differences, such as increased viral fitness, including for example, infectivity, virulence, and/or drug resistance.

In some embodiments, the virus is SARS-CoV-2. In some embodiments, the virus is a reference SARS-CoV-2 (e.g., WIV4, i.e., hCoV-19/WIV04/2019 or BetaCoV/WIV04/2019) or a SARS-CoV-2 virus having substantially the same genomic sequence (e.g., fewer than any one of 200, 100, 50, 20, 10, 5, 4, 3, 2, or 1 mutations) and phenotypes as the reference SARS-CoV-2. The genome sequence of the reference SARS-CoV-2 WIV4 can be found on Genbank (NCBI Reference Sequence: NC_045512.2), which is also known as 2019-nCOV. In some embodiments, the SARS-CoV-2 is a variant, such as a variant of interest, a variant of concern, or a variant of high consequence. In some embodiments, the SARS-CoV-2 is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (also known as B.1.1.28.1) variant, an A.23.1 variant, a CAL.20C variant, a B.1.427 variant, a B.1.429 variant, a B.1.525 variant, a P.1.351 variant and a B.1.1.529 variant. In some embodiments, the SARS-CoV-2 variant is a B.1.1.7 variant. In some embodiments, the SARS-CoV-2 variant is a B.1.351 variant. In some embodiments, the SARS-CoV-2 variant is a B.1.617.2 variant. In some embodiments, the SARS-CoV-2 variant is a B.1.1.529 variant. Other variants of SARS-CoV-2 are known in the art. For example, See, Gomez et al., *Vaccines* 9 (3): 243, 2021 and Tang et al., *Journal of Infection* 82: e27-e28 (2021), which are incorporated herein by reference in their entirety. In some embodiments, the SARS-CoV-2 variant has one or more mutations (e.g., insertion, deletion, and/or substitution) in the S protein. In some embodiments, the one or more mutations in the S protein may affect viral fitness, such as infectivity, virulence, and/or drug resistance (e.g., resistance to neutralizing antibodies and/or resistance to a vaccine). For example, the SARS-CoV-2 variant may have L452R and/or E484K substitutions in the S protein. In some embodiments, the one or more mutations in the S protein do not substantially alter viral fitness. In some embodiments, the SARS-CoV-2 variant does not have a mutation in the S protein.

In some embodiments, the S protein is an S protein of a coronavirus. In some embodiments, the target-binding moiety specifically binds the S1 subunit of the S protein. In some embodiments, the target-binding moiety specifically binds the S2 subunit of the S protein.

In some embodiments, the target-binding moiety is an inhibitory polypeptide that inhibits binding of the S protein to a receptor on a cell of the mucosa. In some embodiments, the target-binding moiety comprises a natural receptor of the S protein or a fragment derived from the natural receptor of a coronavirus. In some embodiments, the target-binding moiety comprises an EBD of the natural receptor of a coronavirus. In some embodiments, the target-binding moiety comprises an EBD of ACE2 or a fragment thereof. In some embodiments, the target-binding moiety comprises a truncated version of ACE2.

In nature, the S protein of coronaviruses mediates viral entry into the host cells. Table 2 below shows identified viral receptors for various coronaviruses. See, also, Raj V S et al. Chapter 15 of Helena Jane Maier et al. (eds.), Coronaviruses: Methods and Protocols, *Methods in Molecular Biology*, vol. 1282, Springer Science+Business Media New York 2015; Li F. *Annu Rev Virol.,* 3 (1): 237-261 (2016); Hulswit 2019 and Zhou et al., *Nature* 579:270 (2020), which are incorporated herein by reference in their entirety.

TABLE 2

Host viral receptors for coronaviruses.

| Viral receptor on host cells | Coronavirus (underlined are human coronaviruses) |
|---|---|
| Aminopeptidase N (APN) | <u>HCoV-229E</u>, TGEV, PEDV, PRCV, FIPV, CCoV |
| Angiotensin-converting enzyme 2 (ACE2) | SARS-CoV-2, SARS-CoV, <u>HCoV-NL63</u> |
| Dipeptidyl peptidase 4 (DPP4, also known as CD26) | MERS-CoV, HKU4 |

TABLE 2-continued

| Host viral receptors for coronaviruses. | |
|---|---|
| Viral receptor on host cells | Coronavirus (underlined are human coronaviruses) |
| N-acetyl-9-O-acetylneuraminic acid (9-O-Ac-Neu5Ac) | HCoV-OC43, HCoV-HKU1, BCoV |
| Murine carcinoembryonic antigen related adhesion molecule 1 (mCEACAM) | MHV |

Provided herein are chimeric proteins comprising target-binding moieties comprising an EBD of an ACE2 host viral receptor, or a fragment thereof, of a coronavirus. The ACE2 protein or a fragment thereof may be derived from any coronavirus comprising an ACE2 viral receptor. Chimeric proteins based on these host receptors are contemplated herein (see, Table 1). In some embodiments, the coronavirus is SARS-CoV-2, SARS-CoV, or HCoV-NL63, or a variant thereof.

ACE2 is the cellular receptor for coronavirus infection (e.g., SARS-CoV-2 infection) and mediates binding of the viral S protein present on the surface of viral particles, enabling viral entry into susceptible host cells of the respiratory tract. ACE2 is a metallocarboxyl peptidase of 805 amino acids and is comprised of an extracellular catalytic domain (e.g., an EBD), a transmembrane region, and a short intracellular domain, that is highly conserved among vertebrates. A catalytically active fragment of ACE2 membrane-bound protein can be released from its membrane tether by the action of the ADAM10/ADAM17 metalloproteinases or cleaved by the transmembrane protease TMPRSS2 at the cell membrane. ADAM17 and TMPRSS2 are expressed in cells in the lung and play an important role in coronavirus entry into cells of the respiratory tract. ACE2 and TMPRSS2 are co-expressed in many tissues throughout the body and can be easily detected in the respiratory system (e.g., expression occurs in type II pneumocytes and enterocytes, alveolar cells, bronchial transient epithelial secretory cells, respiratory epithelial cells, and in the oral cavity and tongue (Beyerstedt et al. 2021; Heurich et al. 2014)). In cells of the nasal epithelium, ACE2 is highly expressed in adults, with lower expression shown in children.

A 19 amino-acid ACE2 fragment QAKTFLDKFNHEAEDLFYQ ("ACE19", SEQ ID NO: 8 in Table 1), comprising the S1 binding site DKFNHEAEDLFY (SEQ ID NO: 102; underlined portion of the above ACE19), was found to selectively recognize the SARS-CoV-2 virus S protein S1 subunit and interfere with S1 binding (Kuznetsov et al. *Int J Pept Res Ther.* 28:7, 2022; Mohebbi et al. *Future Virol.* 10:2217-2235 (2020)).

Provided herein are target-binding moieties comprising an EBD of an ACE2 protein or a fragment thereof. In some embodiments, the ACE2 protein is a hACE2 protein or a fragment thereof. In some embodiments, the ACE2 protein is an animal ACE2 protein or a fragment thereof. hACE2 and animal ACE2 proteins are known in the art. Tables 3-4 show exemplary hACE2 (Table 3) and animal ACE2 (Table 4) proteins and fragments thereof.

TABLE 3

| Exemplary hACE2 proteins and fragments and variants thereof | | |
|---|---|---|
| SEQ ID NO | Sequence | Protein description |
| 1 | MSSSSWLLLSLVAVTAAQSTIEEQAKTFLDKFNHEAEDLFYQSSLASWNY NTNITEENVQNMNNAGDKWSAFLKEQSTLAQMYPLQEIQNLTVKLQLQA LQQNGSSVLSEDKSKRLNTILNTMSTIYSTGKVCNPDNPQECLLLEPGLNEI MANSLDYNERLWAWESWRSEVGKQLRPLYEEYVVLKNEMARANHYED YGDYWRGDYEVNGVDGYDYSRGQLIEDVEHTFEEIKPLYEHLHAYVRAK LMNAYPSYISPIGCLPAHLLGDMWGRFWTNLYSLTVPFGQKPNIDVTDAM VDQAWDAQRIFKEAEKFFVSVGLPNMTQGFWENSMLTDPGNVQKAVCH PTAWDLGKGDFRILMCTKVTMDDFLTAHHEMGHIQYDMAYAAQPFLLR NGANEGFHEAVGEIMSLSAATPKHLKSIGLLSPDFQEDNETEINFLLKQAL TIVGTLPFTYMLEKWRWMVFKGEIPKDQWMKKWWEMKREIVGVVEPVP HDETYCDPASLFHVSNDYSFIRYYTRTLYQFQFQEALCQAAKHEGPLHKC DISNSTEAGQKLFNMLRLGKSEPWTLALENVVGAKNMNVRPLLNYFEPLF TWLKDQNKNSFVGWSTDWSPYADQSIKVRISLKSALGDKAYEWNDNEM YLFRSSVAYAMRQYFLKVKNQMILFGEEDVRVANLKPRISFNFFVTAPKN VSDIIPRTEVEKAIRMSRSRINDAFRLNDNSLEFLGIQPTLGPPNQPPVSIWLI VFGVVMGVIVVGIVILIFTGIRDRKKKNKARSGENPYASIDISKGENNPGFQ NTDDVQTSF | hACE2 Full length hACE2 UPKB:Q9BYF1 Blume et al., *Nature* 53:205-214 (2021) |
| 2 | STIEEQAKTFLDKFNHEAEDLFYQSSLASWNYNTNITEENVQNMNNAGDK WSAFLKEQSTLAQMYPLQEIQNLTVKLQLQALQQNGSSVLSEDKSKRLNT ILNTMSTIYSTGKVCNPDNPQECLLLEPGLNEIMANSLDYNERLWAWESW RSEVGKQLRPLYEEYVVLKNEMARANHYEDYGDYWRGDYEVNGVDGY DYSRGQLIEDVEHTFEEIKPLYEHLHAYVRAKLMNAYPSYISPIGCLPAHL LGDMWGRFWTNLYSLTVPFGQKPNIDVTDAMVDQAWDAQRIFKEAEKF FVSVGLPNMTQGFWENSMLTDPGNVQKAVCHPTAWDLGKGDFRILMCT KVTMDDFLTAHHEMGHIQYDMAYAAQPFLLRNGANEGFHEAVGEIMSLS AATPKHLKSIGLLSPDFQEDNETEINFLLKQALTIVGTLPFTYMLEKWRW MVFKGEIPKDQWMKKWWEMKREIVGVVEPVPHDETYCDPASLFHVSND | ACE614 hACE2 fusion fragment aa19-614 of full-length human ACE2 protein PDB:6LZG Wang et al., *Cell* 181(4):894-904 (2020) |

TABLE 3-continued

Exemplary hACE2 proteins and fragments and variants thereof

| SEQ ID NO | Sequence | Protein description |
|---|---|---|
| | YSFIRYYTRTLYQFQFQEALCQAAKHEGPLHKCDISNSTEAGQKLENMLR<br>LGKSEPWTLALENVVGAKNMNVRPLLNYFEPLFTWLKDQNKNSFVGWS<br>TDWSPYA | |
| 3 | STIEEQAKTFLDKFNHEAEDLFYQSSLASWNYNTNITEENVQNMNNAGDK<br>WSAFLKEQSTLAQMYPLQEIQNLTVKLQLQALQQNGSSVLSEDKSKRLNT<br>ILNTMSTIYSTGKVCNPDNPQECLLLEPGLNEIMANSLDYNERLWAWESW<br>RSEVGKQLRPLYEEYVVLKNEMARANHYEDYGDYWRGDYEVNGVDGY<br>DYSRGQLIEDVEHTFEEIKPLYEHLHAYVRAKLMNAYPSYISPIGCLPAHL<br>LGDMWGRFWTNLYSLTVPFGQKPNIDVTDAMVDQAWDAQRIFKEAEKF<br>FVSVGLPNMTQGFWENSMLTDPGNVQKAVCHPTAWDLGKGDFRILM | ACE360<br>aa19-360 of full-length human ACE2 protein |
| 4 | DKFNHEAEDLFYQSSLASWNYNTNITEENVQNMNNAGDKWSAFLKEQST<br>LAQMYPLQEIQNLTVKLQLQALQQNGSSVLSEDKSKRLNTILNTMSTIYST<br>GKVCNPDNPQECLLLEPGLNEIMANSLDYNERLWAWESWRSEVGKQLRP<br>LYEEYVVLKNEMARANHYEDYGDYWRGDYEVNGVDGYDYSRGQLIED<br>VEHTFEEIKPLYEHLHAYVRAKLMNAYPSYISPIGCLPAHLLGDMWGRFW<br>TNLYSLTVPFGQKPNIDVTDAMVDQAWDAQRIFKEAEKFFVSVGLPNMT<br>QGFWENSMLTDPGNVQKAVCHPTAWDLGKGDFRILM | ACEΔ360<br>aa30-360 of full-length human ACE2 protein |
| 5 | STIEEQAKTFLDKFNHEAEDLFYQSSLASWNYNTNITEENVQNMNNAGDK<br>WSAFLKEQSTLAQMYPLQEIQNLTVKLQLQALQQNGSSVLSEDKSKRLNT<br>ILNTMSTIYSTGKVCNPDNPQECLLLEPGLNEIMANSLDYNERLWAWESW<br>RSEVGKQLRPLYEEYVVLKNEMARANHYEDYGDYWRGDYEVNGVDGY<br>DYSRGQLIEDVEHTFEEIKPLYEHLHAYVRAKLMNAYPSYISPIGCLPAHL<br>LGDMWGRFWTNLYSLTVPFGQKPNIDVTDAMVDQAWDAQRIFKEAEKF<br>FVSVGLPNMTQGFWENSMLTDPGNVQKAVCHPTAWDLGKGDFRILMCT<br>KVTMDDFLTAHHEMGHIQYDMAYAAQPFLLRNGANEGFHEAVGEIMSLS<br>AATPKHLKSIGLLSPDFQEDNETEINFLLKQALTIVGTLPFTYMLEKWRW<br>MVFKGEIPKDQWMKKWWEMKREIVGVVEPVPHDETYCDPASLFHVSND<br>YSFIRYYTRTLYQFQFQEALCQAAKHEGPLHKCDISNSTEAGQKLFNMLR<br>LGKSEPWTLALENVVGAKNMNVRPLLNYFEPLFTWLKDQNKNSFVGWS<br>TDWSPYADQSIKVRISLKSALGDKAYEWNDNEMYLFRSSVAYAMRQYFL<br>KVKNQMILFGEEDVRVANLKPRISFNFFVTAPKNVSDIIPRTEVEKAIRMSR<br>SRINDAFRLNDNSLEFLGIQPTLG | ACE732<br>aa19-732 of full-length human ACE2 protein |
| 135 | STIEEQAKTFLDKFNHEAEDLFYQSSLASWNYNTNITEENVQNMNNAGDK<br>WSAFLKEQSTLAQMYPLQEIQNLTVKLQLQALQQNGSSVLSEDKSKRLNT<br>ILNTMSTIYSTGKVCNPDNPQECLLLEPGLNEIMANSLDYNERLWAWESW<br>RSEVGKQLRPLYEEYVVLKNEMARANHYEDYGDYWRGDYEVNGVDGY<br>DYSRGQLIEDVEHTFEEIKPLYEHLHAYVRAKLMNAYPSYISPIGCLPAHL<br>LGDMWGRFWTNLYSLTVPFGQKPNIDVTDAMVDQAWDAQRIFKEAEKF<br>FVSVGLPNMTQGFWENSMLTDPGNVQKAVCHPTAWDLGKGDFRILMCT<br>KVTMDDFLTAHHEMGHIQYDMAYAAQPFLLRNGANEGFHEAVGEIMSLS<br>AATPKHLKSIGLLSPDFQEDNETEINFLLKQALTIVGTLPFTYMLEKWRW<br>MVFKGEIPKDQWMKKWWEMKREIVGVVEPVPHDETYCDPASLFHVSND<br>YSFIRYYTRTLYQFQFQEALCQAAKHEGPLHKCDISNSTEAGQKLENMLR<br>LGKSEPWTLALENVVGAKNMNVRPLLNYFEPLFTWLKDQNKNSFVGWS<br>TDWSPYADQSIKVRISLKSALGDKAYEWNDNEMYLFRSSVAYAMRQYFL<br>KVKNQMILFGEEDVRVANLKPRISFNFFVTAPKNVSDIIPRTEVEKAIRMSR<br>SRINDAFRLNDNSLEFLGIQPTLGPPNQPPVS | ACE740<br>aa19-740 of full-length human ACE2 protein |
| 6 | STIEEQAKTFLDKFNHEAEDLFYQSSLASWNYNTNITEENVQNMNNAGDK<br>WSAFLKEQSTLAQMYPLQEIQNLTVKLQLQALQQNGSSVLSEDKSKRLNT<br>ILNTMSTIYSTGKVCNPDNPQECLLLEPGLNEIMANSLDYNERLWAWESW<br>RSEVGKQLRPLYEEYVVLKNEMARANHYEDYG | ACE200<br>aa19-200 of full-length human ACE2 protein |
| 7 | YQSSLASWNYNTNITEENVQNMNNAGDKWSAFLKEQSTLAQMYPLQEIQ<br>NLTVKLQLQALQQNGSSVLSEDKSKRLNTILNTMSTIYSTGKVCNPDNPQ<br>ECLLLEPGLNEIMANSLDYNERLWAWESWRSEVGKQLRPLYEEYVVLKN<br>EMARANHYEDYGDYWRGDYEVNGVDGYDYSRGQLIEDVEHTFEEIKPL<br>YEHLHAYVRAKLMNAYPSYISPIGCLPAHLLGDMWGRFWTNLYSLTVPF<br>GQKPNIDVTDAMVDQAWDAQRIFKEAEKFFVSVGLPNMTQGFWENSML<br>TDPGNVQKAVCHPTAWDLGKGDFRILMCTKVTMDDFLTAHHEMGHIQY<br>DMAYAAQPFLLRNGANEGFHEAVGEIMSLSAATPKHLKS | ACEΔ420<br>aa42-420 of full-length human ACE2 protein |
| 8 | QAKTFLDKFNHEAEDLFYQ | ACE19<br>aa24-42 of full-length human ACE2 protein<br>Kuznetsov et al., *Int J Pept Res Ther* 28(1):7 (2022) |

TABLE 3-continued

Exemplary hACE2 proteins and fragments and variants thereof

| SEQ ID NO | Sequence | Protein description |
|---|---|---|
| 102 | DKFNHEAEDLFY | ACE12<br>aa30-41 of full-length human ACE2 protein<br>Mohebbi et al. *Future Virol.* 10:2217-2235 (2020) |
| 9 | MSSSSWLLLSLVAVTAAQSTIEEQARTFLDKFNHEAEDLFYQSSLASWNY<br>NTNITEENVQNMNNAGDKWSAFLKEQSTLAQMYPLQEIQNLTVKLQLQA<br>LQQNGSSVLSEDKSKRLNTILNTMSTIYSTGKVCNPDNPQECLLLEPGLNEI<br>MANSLDYNERLWAWESWRSEVGKQLRPLYEEYVVLKNEMARANHYED<br>YGDYWRGDYEVNGVDGYDYSRGQLIEDVEHTFEEIKPLYEHLHAYVRAK<br>LMNAYPSYISPIGCLPAHLLGDMWGRFWTNLYSLTVPFGQKPNIDVTDAM<br>VDQAWDAQRIFKEAEKFFVSVGLPNMTQGFWENSMLTDPGNVQKAVCH<br>PTAWDLGKGDFRILMCTKVTMDDFLTAHHEMGHIQYDMAYAAQPFLLR<br>NGANEGFHEAVGEIMSLSAATPKHLKSIGLLSPDFQEDNETEINFLLKQAL<br>TIVGTLPFTYMLEKWRWMVFKGEIPKDQWMKKWWEMKREIVGVVEPVP<br>HDETYCDPASLFHVSNDYSFIRYYTRTLYQFQFQEALCQAAKHEGPLHKC<br>DISNSTEAGQKLFNMLRLGKSEPWTLALENVVGAKNMNVRPLLNYFEPLF<br>TWLKDQNKNSFVGWSTDWSPYADQSIKVRISLKSALGDKAYEWNDNEM<br>YLFRSSVAYAMRQYFLKVKNQMILFGEEDVRVANLKPRISFNFFVTAPKN<br>VSDIIPRTEVEKAIRMSRSRINDAFRLNDNSLEFLGIQPTLGPPNQPPVSIWLI<br>VFGVVMGVIVVGIVILIFTGIRDRKKKNKARSGENPYASIDISKGENNPGFQ<br>NTDDVQTSF | ACE2 K26R<br>Point mutant K26R<br>Li et al., *Mol Genet Genomic Med.* 8(8):e1342 (2020) |
| 10 | MSSSSWLLLSLVAVTAAQSTIEEQAKTFLDKFNHEAEDLFYQSSLASWNY<br>NTNITEENVQNMNNAGDKWSAFLKEQSTLAQMYPLQEIQNLTVKLQLQA<br>LQQNGSSVLSEDKSKRLNTILNTMSTIYSTGKVCNPDNPQECLLLEPGLNEI<br>MANSLDYNERLWAWESWRSEVGKQLRPLYEEYVVLKNEMARANHYED<br>YGDYWRGDYEVNGVDGYDYSRGQLIEDVEHTFEEIKPLYEHLHAYVRAK<br>LMNAYPSYISPIGCLPAHLLGDMWGRFWTNLYSLTVPFGQKPNIDVTDAM<br>VDQAWDAQRIFKEAEKFFVSVGLPNMTQGFWENSMLTDPGNVQKAVCH<br>PTAWDLGKGDFRILMCTKVTMDDFLTAHHEMGHIQYDMAYAAQPFLLR<br>NGANEGFHEAVGEIMSLSAATPKHLKSIGLLSPDFQEDNETEINFLLKQAL<br>TIVGTLPFTYMLEKWRWMVFKGEVPKDQWMKKWWEMKREIVGVVEPV<br>PHDETYCDPASLFHVSNDYSFIRYYTRTLYQFQFQEALCQAAKHEGPLHK<br>CDISNSTEAGQKLFNMLRLGKSEPWTLALENVVGAKNMNVRPLLNYFEP<br>LFTWLKDQNKNSFVGWSTDWSPYADQSIKVRISLKSALGDKAYEWNDNE<br>MYLFRSSVAYAMRQYFLKVKNQMILFGEEDVRVANLKPRISFNFFVTAPK<br>NVSDIIPRTEVEKAIRMSRSRINDAFRLNDNSLEFLGIQPTLGPPNQPPVSIW<br>LIVFGVVMGVIVVGIVILIFTGIRDRKKKNKARSGENPYASIDISKGENNPG<br>FQNTDDVQTSF | ACE2 I468V<br>Point mutant I468V<br>Li et al., *Mol Genet Genomic Med.* 8(8):e1342 (2020) |
| 11 | MSSSSWLLLSLVAVTAAQSTIEEQAKTFLDKFNHEAEDLFYQSSLASWNY<br>NTNITEENVQNMNNAGDKWSAFLKEQSTLAQMYPLQEIQNLTVKLQLQA<br>LQQNGSSVLSEDKSKRLNTILNTMSTIYSTGKVCNPDNPQECLLLEPGLNEI<br>MANSLDYNERLWAWESWRSEVGKQLRPLYEEYVVLKNEMARANHYED<br>YGDYWRGDYEVNGVDGYDYSRGQLIEDVEHTFEEIKPLYEHLHAYVRAK<br>LMNAYPSYISPIGCLPAHLLGDMWGRFWTNLYSLTVPFGQKPNIDVTDAM<br>VDQAWDAQRIFKEAEKFFVSVGLPNMTQGFWENSMLTDPGNVQKAVCH<br>PTAWDLGKGDFRILMCTKVTMDDFLTAHHEMGHIQYDMAYAAQPFLLR<br>NGANEGFHEAVGEIMSLSAATPKHLKSIGLLSPDFQEDNETEINFLLKQAL<br>TIVGTLPFTYMLEKWRWMVFKGEIPKDQWMKKWWEMKREIVGVVEPVP<br>HDETYCDPASLFHVSNDYSFIRYYTRTLYQFQFQEALCQAAKHEGPLHKC<br>DISNSTEAGQKLFNMLRLGKSEPWTLALENVVGAKNMNVRPLLNYFEPLF<br>TWLKDQNKNSFVGWSTDWSPYADQSIKVRISLKSALGDKAYEWNDSEM<br>YLFRSSVAYAMRQYFLKVKNQMILFGEEDVRVANLKPRISFNFFVTAPKN<br>VSDIIPRTEVEKAIRMSRSRINDAFRLNDNSLEFLGIQPTLGPPNQPPVSIWLI<br>VFGVVMGVIVVGIVILIFTGIRDRKKKNKARSGENPYASIDISKGENNPGFQ<br>NTDDVQTSF | ACE2 N638S<br>Point mutant N638S<br>Li et al., *Mol Genet Genomic Med.* 8(8):e1342 (2020) |
| 12 | MSSSSWLLLSLVAVTAAQSTIEEQAKTFLDKFNHEAEDLFYQSSLASWNY<br>NTNITEENVQNMNNAGDKWSAFLKEQSTLAQMYPLQEIQNLTVKLQLQA<br>LQQNGSSVLSEDKSKRLNTILNTMSTIYSTGKVCNPDNPQECLLLEPGLNEI<br>MANSLDYNERLWAWESWRSEVGKQLRPLYEEYVVLKNEMARANHYED<br>YGDYWRGDYEVNGVDGYDYSRGQLIEDVEHTFEEIKPLYEHLHAYVRAK<br>LMNAYPSYISPIGCLPAHLLGDMWGRFWTNLYSLTVPFGQKPNIDVTDAM<br>VDQAWDAQRIFKEAEKFFVSVGLPNMTQGFWENSMLTDPGNVQKAVCH<br>PTAWDLGKGDFRILMCTKVTMDDFLTAHHEMGHIQYDMAYAAQPFLLR<br>NGANEGFHEAVGEIMSLSAATPKHLKSIGLLSPDFQEDNETEINFLLKQAL<br>TIVGTLPFTYMLEKWRWMVFKGEIPKDQWMKKWWEMKREIVGVVEPVP<br>HDETYCDPASLFHVSNDYSFIRYYTRTLYQFQFQEALCQAAKHEGPLHKC | ACE2 N720D<br>Point mutant N720D<br>Shikov et al., *Front Genet.* 2020; 11:551220 (2020) |

TABLE 3-continued

| SEQ ID NO | Sequence | Protein description |
|---|---|---|
| Exemplary hACE2 proteins and fragments and variants thereof | | |
| | DISNSTEAGQKLFNMLRLGKSEPWTLALENVVGAKNMNVRPLLNYFEPLF<br>TWLKDQNKNSFVGWSTDWSPYADQSIKVRISLKSALGDKAYEWNDNEM<br>YLFRSSVAYAMRQYFLKVKNQMILFGEEDVRVANLKPRISFNFFVTAPKN<br>VSDIIPRTEVEKAIRMSRSRINDAFRLNDNSLEFLGIQPTLGPPNQPPVSIWLI<br>VFGVVMGVIVVGIVILIFTGIRDRKKKNKARSGENPYASIDISKGENNPGFQ<br>NTDDVQTSF | |
| 13 | MSSSSWLLLSLVAVTAAQSTIEEQAKTFLDKFNHEAEDLFYQSSLASWNY<br>NTNITEENVQNMNNAGDKWSAFLKEQSTLAQMYPLQEIQNLTVKLQLQA<br>LQQNGSSVLSEDKSKRLNTILNTMSTIYSTGKVCNPDNPQECLLLEPGLNEI<br>MANSLDYNERLWAWESWRSEVGKQLRPLYEEYVVLKNEMARANHYED<br>YGDYWRGDYEVNGVDGYDYSRGQLIEDVEHTFEEIKPLYEHLHAYVRAK<br>LMNAYPSYISPIGCLPAHLLGDMWGRFWTNLYSLTVPFGQKPNIDVTDAM<br>VDQAWDAQRIFKEAEKFFVSVGLPNMTQGFWENSMLTDPGNVQKAVCH<br>PTAWDLGKGDFRILMCTKVTMDDFLTAHNEMGNIQYDMAYAAQPFLLR<br>NGANEGFHEAVGEIMSLSAATPKHLKSIGLLSPDFQEDNETEINFLLKQAL<br>TIVGTLPFTYMLEKWRWMVFKGEIPKDQWMKKWWEMKREIVGVVEPVP<br>HDETYCDPASLFHVSNDYSFIRYYTRTLYQFQFQEALCQAAKHEGPLHKC<br>DISNSTEAGQKLFNMLRLGKSEPWTLALENVVGAKNMNVRPLLNYFEPLF<br>TWLKDQNKNSFVGWSTDWSPYADQSIKVRISLKSALGDKAYEWNDNEM<br>YLFRSSVAYAMRQYFLKVKNQMILFGEEDVRVANLKPRISFNFFVTAPKN<br>VSDIIPRTEVEKAIRMSRSRINDAFRLNDNSLEFLGIQPTLGPPNQPPVSIWLI<br>VFGVVMGVIVVGIVILIFTGIRDRKKKNKARSGENPYASIDISKGENNPGFQ<br>NTDDVQTSF | ACE2 HN-HN<br>Point mutant<br>H374N and H378N<br>Tanaka et al.,<br>*Nature* 11:12740-<br>12752 (2021) |
| 14 | MSSSSWLLLSLVAVTAAQSTIEEQAKYFLDKFNAEAEDLFYQSSLASWNY<br>NTNITEENVQNMNNAGDKWSAFLKEQSTLAQMYPLQEIQNLTVKLQLQA<br>LQQNGSSVLSEDKSKRLNTILNTMSTIYSTGKVCNPDNPQECLLLEPGLNEI<br>MANSLDYNERLWAWESWRSEVGKQLRPLYEEYVVLKNEMARANHYED<br>YGDYWRGDYEVNGVDGYDYSRGQLIEDVEHTFEEIKPLYEHLHAYVRAK<br>LMNAYPSYISPIGCLPAHLLGDMWGRFWTNLYSLTVPFGQKPNIDVTDAM<br>VDQAWDAQRIFKEAEKFFVSVGLPNMTQGFWENSMLTDPGNVQKAVCH<br>PTAWDLGKGDFRILMCTKVTMDDFLTAHHEMGHIQYDMAYAAQPFLLR<br>NGANEGFHEAVGEIMSLSAATPKHLKSIGLLSPDFQEDNETEINFLLKQAL<br>TIVGTLPFTYMLEKWRWMVFKGEIPKDQWMKKWWEMKREIVGVVEPVP<br>HDETYCDPASLFHVSNDYSFIRYYTRTLYQFQFQEALCQAAKHEGPLHKC<br>DISNSTEAGQKLFNMLRLGKSEPWTLALENVVGAKNMNVRPLLNYFEPLF<br>TWLKDQNKNSFVGWSTDWSPYADQSIKVRISLKSALGDKAYEWNDNEM<br>YLFRSSVAYAMRQYFLKVKNQMILFGEEDVRVANLKPRISFNFFVTAPKN<br>VSDIIPRTEVEKAIRMSRSRINDAFRLNDNSLEFLGIQPTLGPPNQPPVSIWLI<br>VFGVVMGVIVVGIVILIFTGIRDRKKKNKARSGENPYASIDISKGENNPGFQ<br>NTDDVQTSF | ACE2 TY-HA<br>Point mutant T27Y<br>and H34A<br>Tanaka et al.,<br>*Nature* 11:12740-<br>12752 (2021) |

TABLE 4

| SEQ ID NO | Sequence | Protein description |
|---|---|---|
| Exemplary animal ACE2 proteins and fragments and variants thereof | | |
| 15 | MSSSSWLLLSLVAVTTAQSLTEENAKTFLNNFNQEAEDLSYQSSLASWNY<br>NTNITEENAQKMSEAAAKWSAFYEEQSKTAQSFSLQEIQTPIIKRQLQALQ<br>QSGSSALSADKNKQLNTILNTMSTIYSTGKVCNPKNPQECLLLEPGLDEIM<br>ATSTDYNSRLWAWEGWRAEVGKQLRPLYEEYVVLKNEMARANNYNDY<br>GDYWRGDYEAEGADGYNYNRNQLIEDVERTFAEIKPLYEHLHAYVRRKL<br>MDTYPSYISPTGCLPAHLLGDMWGRFWTNLYPLTVPFAQKPNIDVTDAM<br>MNQGWDAERIFQEAEKFFVSVGLPHMTQGFWANSMLTEPADGRKVVCH<br>PTAWDLGHGDFRIKMCTKVTMDNFLTAHHEMGHIQYDMAYARQPFLLR<br>NGANEGFHEAVGEIMSLSAATPKHLKSIGLLPSDFQEDSETEINFLLKQAL<br>TIVGTLPFTYMLEKWRWMVFRGEIPKEQWMKKWWEMKREIVGVVEPLP<br>HDETYCDPASLFHVSNDYSFIRYYTRTIYQFQFQEALCQAAKYNGSLHKC<br>DISNSTEAGQKLLKMLSLGNSEPWTKALENVVGARNMDVKPLLNYFQPL<br>FDWLKEQNRNSFVGWNTEWSPYADQSIKVRISLKSALGANAYEWTNNE<br>MFLFRSSVAYAMRKYFSIIKNQTVPFLEEDVRVSDLKPRVSFYFFVTSPQN<br>VSDVIPRSEVEDAIRMSRGRINDVFGLNDNSLEFLGIHPTLEPPYQPPVTIW<br>LIIFGVVMALVVVGIIILIVTGIKGRKKKNETKREENPYDSMDIGKGESNAG<br>FQNSDDAQTSF | Mouse full-length<br>ACE2<br>Reference:<br>UPKB:Q8R0I0 |
| 16 | MSGSFWFLLNLVAVTTAQFNLEEQAKTFLDEFNLKAEDLYYQSSLASWN<br>YNTNITDENVQKMSEAGGILSAFYEEQSNLAKAYPLQDIQNLTVKRQLRI | Guinea pig full-<br>length ACE2 |

TABLE 4-continued

Exemplary animal ACE2 proteins and fragments and variants thereof

| SEQ ID NO | Sequence | Protein description |
|---|---|---|
| | LQQSGSSGFSADKNKQLSTILNTMSTLYSTGKVCYPSDPQECLLLEPGLAD<br>IMSKSTDYNLRLWAWEGWRSKVGKQLRPLYEEYVALKNEMARANKYE<br>DYGDYWRRDYEVEDMDGYNYSRNQLIEDVERTFAEIKPLYEQLHAYVRT<br>KLMETYPSRISPVGCLPAHLLGDMWGRFWTELYSLTVPFQQKPNIDVTDA<br>MESQSWDAEKIFKEAEKFFVSVGLPPMTQGFWKNSMLTEPGDGQKVVC<br>HPTAWDMGKNDFRIKMCTKVTMDHFLTAHHEMGHIQYDMAYAIQPFLL<br>RDGANEGFHEAIGEIMSLSAATPEHLKSIGLLPPDFHEDNGTFFHGFTHAL<br>LGTLPFTFMLEKVERGWSSRVKIPKSSGLKNVADEVKIVGVVEPLPHDET<br>YCDPASLFHVSNDYSFIRYYTRTIYQFQFQEALCKAANHVGPLHKCDISNS<br>TEAGQKLLNMLKLGKSEPWTLALESIVGTKNMDVKPLLNYFQPLSTWLQ<br>DQNRNSFVGWNTEWSPYSEESIKVRISLKSALGEDAYKWDDNEMYLFRS<br>SVAYAMRKYFLDVKNQTVLFSWEDVRVSDWTHRVSFTFFVTEPNNVSNI<br>IPKTEVEDAIRLSRSRINDVFLSGIYPTLSPPYEPPVTIWLIVFGVVMGLVVV<br>GIVVLVITGIRDRRKKKQKQREENPYSSVDIGKGENNTAFQNSEDNQTSF | Reference:<br>tr\|H0VSF6 |
| 17 | MSGSSWLLLSLVAVTAAQSTTEDLAKTFLEKFNSEAEELSHQSSLASWSY<br>NTNITDENVQKMNEAGARWSAFYEEQCKLAKTYPLEEIQNLTVKRQLQA<br>LQQSGSSVLSADKSKRLNEILNTMSTIYSTGKVCNPSNPQECLLLEPGLDAI<br>MENSKDYNQRLWAWEGWRSEVGKQLRPLYEEYVVLKNEMARANNYED<br>YGDYWRGDYEAEGPSGYDYSRDQLIEDVERTFAEIKPLYEHLHAYVRAK<br>LMDTYPSHINPTGCLPAHLLGDMWGRFWTNLYSLTVPFGQKPNIDVTDA<br>MVDQSWDAKRIFEEAEKFFVSVGLPNMTQGFWENSMLTEPGDGRKVVC<br>HPTAWDLGKGDFRIKMCTKVTMDDFLTAHHEMGHIQYDMAYAVQPYLL<br>RNGANEGFHEAVGEIMSLSAATPNHLKAIGLLPPDFYEDSETEINFLLKQA<br>LTIVGTLPFTYMLEKWRWMVFKGEIPKEEWMKKWWEMKREIVGVVEPV<br>PHDETYCDPAALFHVANDYSFIRYYTRTIYQFQFQEALCQTAKHEGPLHK<br>CDISNSTEAGQKLLQMLSLGKSEPWTLALERIVGVKNMDVRPLLNYFEPL<br>FTWLKDQNKNSFVGWSTNWSPYADQSIKVRISLKSALGEKSYEWNDNE<br>MYLFQSSVAYAMRVYFLKAKNQTILFGEEDVWVSDLKPRISFNFFVTSPK<br>NASDIIPRTDVEEAIRMSRSRINDAFRLDDNTLEFLGIQPTLGPPYQPPVTV<br>WLIAFGVVMGLVVVGIVVLIATGIRGRRKKNQARSEENPYASVDLSKGEN<br>NPGFQNGDDVQTSF | Equine full-length ACE2<br>Reference:<br>tr\|F6V9L3 |
| 18 | MSGSSWLLLSLVAVTAAQSTIEEQAKTFLDKFNHEAEDLFYQSSLASWNY<br>NTNITEENVQNMNNAGEKWSAFLKEQSTLAQMYPLQEIQNLTVKLQLQA<br>LQQNGSSVLSEDKSKRLNTILNTMSTIYSTGKVCNPNNPQECLLLDPGLNE<br>IMEKSLDYNERLWAWEGWRSEVGKQLRPLYEEYVVLKNEMARANHYK<br>DYGDYWRGNYEVNGVDGYDYNRDQLIEDVERTFEEIKPLYEHLHAYVR<br>AKLMNAYPSYISPTGCLPAHLLGDMWGRFWTNLYSLTVPFGQKPNIDVT<br>DAMVNQAWNAQRIFKEAEKFFVSVGLPNMTQGFWENSMLTDPGNVQK<br>VVCHPTAWDLGKGDFRIIMCTKVTMDDFLTAHHEMGHIQYDMAYAAQP<br>FLLRNGANEGFHEAVGEIMSLSAATPKHLKSIGLLSPDFQEDNETEINFLL<br>KQALTIVGTLPFTYMLEKWRWMVFKGEIPKDQWMKKWWEMKREIVGV<br>VEPVPHDETYCDPASLFHVSNDYSFIRYYTRTLYQFQFQEALCQAAKHEG<br>PLHKCDISNSTEAGQKLLNMLKLGKSEPWTLALENVVGAKNMNVRPLLN<br>YFEPLFTWLKDQNKNSFVGWSTDWSPYADQSIKVRISLKSALGDKAYEW<br>NDNEMYLFRSSVAYAMRTYFLEIKHQTILFGEEDVRVADLKPRISFNFYV<br>TAPKNVSDIIPRTEVEEAIRISRSRINDAFRLNDNSLEFLGIQTTLAPPYQSP<br>VTTWLIVFGVVMGVIVAGIVVLIFTGIRDRKKKNQARSEENPYASIDINKG<br>ENNPGFQNTDDVQTSF | Macaque full-length ACE2<br>Reference:<br>tr\|F7AH40 |
| 19 | MSGSSWLLLSLVAVTAAQSTIEEQAKTFLDKFNHEAEDLFYQSSLASWNY<br>NTNITEENVQNMNNAGDKWSAFLKEQSTLAQMYPLQEIQNLTVKLQLQA<br>LQQNGSSVLSEDKSKRLNTILNTMSAIYSTGKVCNPNNPQECLLLEPGLNE<br>IMANSLDYNERLWAWESWRSEVGKQLRPLYEEYVVLKNEMARANHYE<br>DYGDYWRGDYEVNGVDGYDYSRGQLIEDVEHTFEEIKPLYEHLHAYVR<br>AKLMNAYPSYISPIGCLPAHLLGDMWGRFWTNLYSLTVPFGQKPNIDVTD<br>AMVDQAWDAQRIFKEAEKFFVSVGLPNMTQGFWENSMLTDPGNVQKA<br>VCHPTAWDLGKGDFRILMCTKVTMDDFLTAHHEMGHIQYDMAYAAQPF<br>LLRNGANEGFHEAVGEIMSLSAATPKHLKSIGLLSPDFQEDNETEINFLLK<br>QALTIVGTLPFTYMLEKWRWMVFKGEIPEDQWMKKWWEMKREIVGVV<br>EPVPHDETYCDPASLFHVSNDYSFIRYYTRTLYQFQFQEALCQAAKHEGP<br>LHKCDISNSTEAGQKLFNMLRLGKSEPWTLALENVVGAKNMNVRPLLNY<br>FEPLFTWLKDQNKNSFVGWSTDWSPYADQSIKVRISLKSALGDKAYEWN<br>DNEYLFRSSVAYAMRQYFLKVKNQMILFGEEDVRVANLKPRISFNFFVTA<br>PKNVSDIIPRTEVEKAIRKSRSRINDAFRLNDNSLEFLGIQPTLGPPNQPPVS<br>IWLIVFGVVMGVIVVGIVILIFTGIRDRKKKNKARSEENPYASVDTSKGEN<br>NPGFQNTDDVQTSF | Chimpanzee full-length ACE2<br>Reference:<br>tr\|A0A2J8KU96 |
| 20 | MSGSFWLLLSLIPVTAAQSTTEELAKTFLEKFNLEAEDLAYQSSLASWNY<br>NTNITDENIQKMNDARAKWSAFYEEQSRIAKTYPLDEIQTLILKRQLQALQ<br>QSGTSGLSADKSKRLNTILNTMSTIYSSGKVLDPNNPQECLVLEPGLDEIM<br>ENSKDYSRRLWAWESWRAEVGKQLRPLYEEYVVLENEMARANNYEDY<br>GDYWRGDYEVTGTGDYDYSRNQLMEDVERTFAEIKPLYEHLHAYVRAK | Swine full-length ACE2<br>Reference:<br>tr\|K7GLM4 |

TABLE 4-continued

Exemplary animal ACE2 proteins and fragments and variants thereof

| SEQ ID NO | Sequence | Protein description |
|---|---|---|
| | LMDAYPSRISPTGCLPAHLLGDMWGRFWTNLYPLTVPFGEKPSIDVTEAM<br>VNQSWDAIRIFEEAEKFFVSIGLPNMTQGFWNNSMLTEPGDGRKVVCHPT<br>AWDLGKGDFRIKMCTKVTMDDFLTAHHEMGHIQYDMAYAIQPYLLRNG<br>ANEGFHEAVGEIMSLSAATPHYLKALGLLPPDFYEDSETEINFLLKQALTI<br>VGTLPFTYMLEKWRWMVFKGEIPKEQWMQKWWEMKREIVGVVEPLPH<br>DETYCDPACLFHVAEDYSFIRYYTRTIYQFQFHEALCRTAKHEGPLYKCDI<br>SNSTEAGQKLLQMLSLGKSEPWTLALENIVGVKTMDVKPLLSYFEPLLTW<br>LKAQNGNSSVGWNTDWTPYADQSIKVRISLKSALGKEAYEWNDNEMYL<br>FRSSIAYAMRNYFSSAKNETIPFGAEDVWVSDLKPRISFNFFVTSPANMSDI<br>IPRSDVEKAISMSRSRINDAFRLDDNTLEFLGIQPTLGPPDEPPVTVWLIIFG<br>VVMGLVVVGIVVLIFTGIRDRRKKKQASSEENPYGSMDLSKGESNSGFQN<br>GDDIQTSF | |
| 21 | MSGSSWLLLSLAALTAAQSTEDLVKTFLEKFNYEAEELSYQSSLASWNYN<br>INITDENVQKMNNAGAKWSAFYEEQSKLAKTYPLEEIQDSTVKRQLRAL<br>QHSGSSVLSADKNQRLNTILNSMSTIYSTGKACNPSNPQECLLLEPGLDDI<br>MENSKDYNERLWAWEGWRSEVGKQLRPLYEEYVALKNEMARANNYED<br>YGDYWRGDYEEEWENGYNYSRNQLIDDVEHTFTQIMPLYQHLHAYVRT<br>KLMDTYPSYISPTGCLPAHLLGDMWGRFWTNLYPLTVPFGQKPNIDVTN<br>AMVNQSWDARKIFKEAEKFFVSVGLPNMTQEFWENSMLTEPSDSRKVVC<br>HPTAWDLGKGDFRIKMCTKVTMDDFLTAHHEMGHIQYDMAYAAQPFLL<br>RNGANEGFHEAVGEIMSLSAATPNHLKNIGLLPPSFFEDSETEINFLLKQAL<br>TIVGTLPFTYMLEKWRWMVFKGEIPKDQWMKTWWEMKRNIVGVVEPV<br>PHDETYCDPASLFHVANDYSFIRYYTRTIYQFQFQEALCQIAKHEGPLHKC<br>DISNSSEAGQKLLEMLKLGKSKPWTYALEIVVGAKNMDVRPLLNYFEPLF<br>TWLKEQNRNSFVGWNTDWSPYADQSIKVRISLKSALGEKAYEWNNNEM<br>YLFRSSIAYAMRQYFSEVKNQTIPFVEDNVWVSDLKPRISFNFFVTSPGNV<br>SDIIPRTEVEEAIRMYRSRINDVFRLDDNSLEFLGIQPTLGPPYEPPVTIWLI<br>VFGVVMGVVVVGIVLLIFSGIRNRRKNDQARGEENPYASVDLSKGENNP<br>GFQNVDDAQTSF | Canine full-length ACE2 Reference: tr\|J9P7Y2 |
| 22 | MSGSFWLLLSFAALTAAQSTTEELAKTFLEKFNHEAEELSYQSSLASWNY<br>NTNITDENVQKMNEAGAKWSAFYEEQSKLAKTYPLAEIHNTTVKRQLQA<br>LQQSGSSVLSADKSQRLNTILNAMSTIYSTGKACNPNNPQECLLLEPGLDD<br>IMENSKDYNERLWAWEGWRAEVGKQLRPLYEEYVALKNEMAKSKQYE<br>DYGDYWRGDYEEEWTDGYNYSRSQLIKDVEHTFTQIKPLYQHLHAYVR<br>AKLMDTYPSRISPTGCLPAHLLGDMWGRFWTNLYPLTVPFGQKPNIDVT<br>DAMVNQSWDARRIFKEAEKFFVSVGLPNMTQGFWENSMLTEPGDSRKV<br>VCHPTAWDLGKGDFRIKMCTKVTMDDFLTAHHEMGHIQYDMAYAVQPF<br>LLRNGANEGFHEAVGEIMSLSAATPNHLKTIGLLSPGFSEDSETEINFLLKQ<br>ALTIVGTLPFTYMLEKWRWMVFKGEIPKEQWMQKWWEMKREIVGVVEP<br>VPHDETYCDPASLFHVANDYSFIRYYTRTIYQFQFQEALCRIAKHEGPLHK<br>CDISNSSEAGKKLLQMLTLGKSKPWTLALEHVVGEKKMNVTPLLKYFEP<br>LFTWLKEQNRNSFVGWNTDWRPYADQSIKVRISLKSALGDEAYEWNDN<br>EMYLFRSSVAYAMREYFSKVKNQTIPFVEDNVWVSNLKPRISFNFFVTAS<br>KNVSDVIPRSEVEEAIRMSRSRINDAFRLDDNSLEFLGIQPTLSPPYQPPVTI<br>WLIVFGVVMGVVVVGIVLLIVSGIRNRRKNNQARSEENPYASVDLSKGEN<br>NPGFQHADDVQTSF | Feline full-length ACE2 Reference: tr\|A0A5F5XDN9 |
| 23 | MTGSFWLLLSLVAVTAAQSTTEEQAKTFLEKFNHEAEDLSYQSSLASWN<br>YNTNITDENVQKMNEARAKWSAFYEEQSRMAKTYSLEEIQNLTLKRQLK<br>ALQHSGTSALSAEKSKRLNTILNKMSTIYSTGKVLDPNTQECLALEPGLDD<br>IMENSRDYNRRLWAWEGWRAEVGKQLRPLYEEYVVLENEMARANNYE<br>DYGDYWRGDYEVTGAGDYDYSRDQLMKDVERTFAEIKPLYEQLHAYVR<br>AKLMHTYPSYISPTGCLPAHLLGDMWGRFWTNLYSLTVPFEHKPSIDVTE<br>KMENQSWDAERIFKEAEKFFVSISLPYMTQGFWDNSMLTEPGDGRKVVC<br>HPTAWDLGKGDFRIKMCTKVTMDDFLTAHHEMGHIQYDMAYAAQPYLL<br>RNGANEGFHEAVGEIMSLSAATPHYLKALGLLAPDFHEDNETEINFLLKQ<br>ALTIVGTLPFTYMLEKWRWMVFKGEIPKQQWMEKWWEMKREIVGVVEP<br>LPHDETYCDPACLFHVAEDYSFIRYYTRTIYQFQFHEALCKTAKHEGALF<br>KCDISNSTEAGQRLLQMLRLGKSEPWTLALENIVGIKTMDVKPLLNYFEP<br>LFTWLKEQNRNSFVGWSTEWTPYSDQSIKVRISLKSALGENAYEWNDNE<br>MYLFQSSVAYAMRKYFSEARNETVLFGEDNVWVSDKKPRISFKFFVTSPN<br>NVSDIIPRTEVENAIRLSRDRINDVFQLDDNSLEFLGIQPTLGPPYEPPVTIW<br>LIIFGVVMGVVVIGIVVLIFTGIRNRRKKNQASSEENPYGSVDLNKGENNS<br>GFQNIDDVQTSL | Bovine full-length ACE2 Reference: UPKB:Q58DD0 |
| 24 | MSGSSWLLLSLVAVTAAQSTIEELAKTFLEKFNQEAEDLSYQSALASWDY<br>NTNITEENVQKMNDAEAKWSAFYEEQSKLAKTYPSQEVQNLTVKRQLQ<br>ALQQSGSSALSADKSKQLNTILSTMSTIYSTGKVCNQSNPQECFLLEPGLD<br>EIMAKSTDYNERLWAWEGWRSVVGKQLRPLYEEYVVLKNEMARANNY<br>EDYGDYWRADYEAEGADGYDYSRSQLIDDVERTFSEIKPLYEQLHAFVR<br>TKLMDAYPSRISPTGCLPAHLLGDMWGRFWTNLYSLTVPFGQKPNIDVT<br>DTMVNQGWDAERIFKEAEKFFVSVGLPSMTQGFWENSMLTEPGDGRKV | Rabbit full-length ACE2 Reference: tr\|G1TEF4 |

TABLE 4-continued

Exemplary animal ACE2 proteins and fragments and variants thereof

| SEQ ID NO | Sequence | Protein description |
| --- | --- | --- |
| | VCHPTAWDLGKGDFRIKMCTKVTMDNFLTAHHEMGHIQYDMAYATQPF<br>LLRNGANEGFHEAVGEIMSLSAATPEHLKSIGLLPYDFHEDNETEINFLLK<br>QALTIVGTLPFTYMLEKWRWMVFKGEIPKEQWMQKWWEMKREIVGVV<br>EPMPHDETYCDPAALFHVANDYSFIRYYTRTIYQFQFQEALCQAAQHEGP<br>LHKCDISNSTEAGQKLLNMLRLGRSEPWTLALENVVGAKNMDVRPLLNY<br>FEPLFTWLKEQNRNSFVGWSTEWTPYADQSIKVRISLKTALGDQAYEWN<br>DSEMYLFRSSVAYAMRKYFSEVKNQTILFGEEDVRVSDLKPRISFNFFVTA<br>PNNVNDIIPRNEVEEAISMSRSRINDIFRLDDNSLEFVGIQPTLEPPYESPVPI<br>WLVVFGVVMGMIVIGIVVLIFTGIKDRRKQKQAKREENPYGFVDMSKGE<br>NNSGFQNSDDIQTSF | |
| 25 | MLGSSWLLLSLAALTAAQSTTEDLAKTFLEKFNYEAEELSYQNSLASWN<br>YNTNITDENIQKMNIAGAKWSAFYEEESQHAKTYPLEEIQDPIIKRQLRAL<br>QQSGSSVLSADKRERLNTILNAMSTIYSTGKACNPNNPQECLLLEPGLDDI<br>MENSKDYNERLWAWEGWRSEVGKQLRPLYEEYVALKNEMARANNYED<br>YGDYWRGDYEEEWADGYSYSRNQLIEDVEHTFTQIKPLYEHLHAYVRAK<br>LMDAYPSRISPTGCLPAHLLGDMWGRFWTNLYPLMVPFRQKPNIDVTDA<br>MVNQSWDARRIFEEAETFFVSVGLPNMTEGFWQNSMLTEPGDNRKVVC<br>HPTAWDLGKRDFRIKMCTKVTMDDFLTAHHEMGHIQYDMAYAEQPFLL<br>RNGANEGFHEAVGEIMSLSAATPNHLKNIGLLPPDFSEDSETDINFLLKQA<br>LTIVGTLPFTYMLEKWRWMVFKGEIPKEQWMQKWWEMKRDIVGVVEPL<br>PHDETYCDPAALFHVANDYSFIRYYTRTIYQFQFQEALCQIAKHEGPLYK<br>CDISNSSEAGQKLHEMLSLGRSKPWTFALERVVGAKTMDVRPLLNYFEPL<br>FTWLKEQNRNSFVGWNTDWSPYADQSIKVRISLKSALGEKAYEWNDNE<br>MYFFQSSIAYAMREYFSKVKNQTIPFVGKDVRVSDLKPRISFNFIVTSPEN<br>MSDIIPRADVEEAIRKSRGRINDAFRLDDNSLEFLGIQPTLEPPYQPPVTIWL<br>IVFGVVMGVVVVGIFLLIFSGIRNRRKNNQARSEENPYASVDLSKGENNP<br>GFQNVDDVQTSF | Ferret full-length ACE2 Reference: UPKB:Q2WG88 |
| 26 | MLGSSWLLLSLAALTAAQSTTEDLAKTFLEKFNYEAEELSYQNSLASWN<br>YNTNITDENIQKMNIAGAKWSAFYEEESQHAKTYPLEEIQDPIIKRQLRAL<br>QQSGSSVLSADKRERLNTILNAMSTIYSTGKACNPNNPQECLLLEPGLDDI<br>MENSKDYNERLWAWEGWRSEVGKQLRPLYEEYVALKNEMARANNYED<br>YGDYWRGDYEEEWADGYNYSRNQLIEDVEHTFTQIKPLYEHLHAYVRA<br>KLMDAYPSRISPTGCLPAHLLGDMWGRFWTNLYPLMVPFGQKPNIDVTD<br>AMVNQSWDARRIFKEAEKFFVSVGLPNMTEGFWQNSMLTEPGDNRKVV<br>CHPTAWDLGKHDFRIKMCTKVTMDDFLTAHHEMGHIQYDMAYAAQPFL<br>LRNGANEGFHEAVGEIMSLSAATPNHLKNIGLLPPDFSEDSETDINFLLKQ<br>ALTIVGTLPFTYMLEKWRWMVFKGEIPKEQWMQKWWEMKRDIVGVVE<br>PLPHDETYCDPAALFHVANDYSFIRYYTRTIYQFQFQEALCQIAKHEGPLY<br>KCDISNSREAGQKLHEMLSLGRSKPWTFALERVVGAKTMDVRPLLNYFE<br>PLFTWLKEQNRNSFVGWNTDWSPYADQSIKVRISLKSALGEKAYEWNDN<br>EMYFFQSSIAYAMREYFSKVKKQTIPFVDKDVRVSDLKPRISFNFIVTSPEN<br>MSDIIPRADVEEAIRKSRGRINDAFRLDDNSLEFLGIQPTLEPPYQPPVTIWL<br>IVFGVVMGVVVVGIFLLIFSGIRNRRKNNQARSEENPYASVDLSKGENNP<br>GFQNVDDVQTSF | Mink full-length ACE2 Reference: UPKB:A0A7T0Q2W2 |
| 27 | MLLHFWLLCGLSAVVTPQDVTQEAQTFLAEFNVRAEDISYENSLASWNY<br>NTNITEETARKMSEAGAKWAAFYEEASRNASRFSLANIQDAVTRLQIQSL<br>QDRGSSVLSPEKYSRLNSVMNSMSTIYSTGVVCKATEPFDCLVLEPGLDDI<br>MANSIDYHERLWAWEGWRADVGRMMRPLYEEYVELKNEAARLNNYSD<br>YGDYWRANYETDYPEEYKYSRDQLVQDVEKTFEQIKPLYQHLHAYVRH<br>RLEQVYGSELINPTGCLPAHLLGDMWGRFWTNLYNLTVPYPEKPNIDVTS<br>AMAQKNWDAMKIFKTAEAFFASIGLYNMTEGFWTNSMLTEPTDNRKVV<br>CHPTAWDMGKNDYRIKMCTKVTMDDFLTAHHEMGHIEYDMAYSVQPF<br>LLRNGANEGFHEAVGEIMSLSAATPQHLKSLDLLEPTFQEDEETEINFLLK<br>QALTIVGTMPFTYMLEKWRWMVFNGEITKQEWTKRWWKMKREIVGVV<br>EPVPHDETYCDPAALFHVANDYSFIRYYTRTIYQFQFQEALCKAANHTGP<br>LHKCDITNSTAAGGNLRQLLELGKSKPWTQALESATGEKYMNATPLLHY<br>FEPLFNWLQKNNSGRSIGWNTDWTPYSDNAIKVRISLKAALGDDAYVWD<br>ASELFLFKSSIAYAMRKYFAKEKEQNVDFQVTDIHVGEETQRVSFYLTVS<br>MPGNVSDIVPRADVEKAIRMSRGRISEAFRLDDNTLEFDGIVPTLATPYKP<br>PVTIWLILFGVVMSLIVIGVIVLIITGQRDKRKKARGRANEAGSNCEVNPY<br>DEDGRSNKGFEQSEETQTSF | Chicken full-length ACE2 Reference: tr\|F1NHR4 |
| 110 | AEFNVRAEDISY | ACE12-2 aa 29-40 of chicken full-length ACE2 protein |
| 111 | DEFNLKAEDLYY | ACE12-3 aa 30-41 of guinea pig full-length ACE2 protein |

TABLE 4-continued

Exemplary animal ACE2 proteins and fragments and variants thereof

| SEQ ID NO | Sequence | Protein description |
|---|---|---|
| 112 | NNFNQEAEDLSY | ACE12-4 aa 30-41 of mouse full-length ACE2 protein |
| 113 | EKFNLEAEDLAY | ACE12-5 aa 30-41 of swine full-length ACE2 protein |
| 114 | EKFNHEAEDLSY | ACE12-6 aa 30-41 of bovine full-length ACE2 protein |
| 115 | EKFNQEAEDLSY | ACE12-7 aa 30-41 of rabbit full-length ACE2 protein |
| 116 | DKFNHEAEDLFY | ACE12-8 aa 30-41 of macaque full-length ACE2 protein |
| 117 | DKFNHEAEDLFY | ACE12-9 aa 30-41 of chimpanzee full-length ACE2 protein |
| 118 | EKFNSEAEELSH | ACE12-10 aa 30-41 of equine full-length ACE2 protein |
| 119 | EKFNYEAEELSY | ACE12-11 aa 30-41 of ferret full-length ACE2 protein |
| 120 | EKFNYEAEELSY | ACE12-12 aa 30-41 of mink full-length ACE2 protein |
| 121 | EKFNYEAEELSY | ACE12-13 aa 29-40 of canine full-length ACE2 protein |
| 122 | EKFNHEAEELSY | ACE12-14 aa 30-41 of feline full-length ACE2 protein |

New ACE2 proteins or fragments thereof may be established against an S protein (e.g., an S1 subunit of an S protein) of a coronavirus or variant thereof using art-known techniques, and the sequences of such proteins, or a fragment thereof, may be used as the target-binding moiety of a chimeric protein of the present disclosure. In some embodiments, the coronavirus is a known coronavirus. In some embodiments, the coronavirus is a variant of a known coronavirus. In some embodiments, the coronavirus is a future coronavirus. In some embodiments, the coronavirus is a variant of a future coronavirus. In some embodiments, the target-binding moiety comprises a derivative of any one of the hACE2 or animal ACE2 proteins described herein (e.g., a fragment of any one of the hACE2 or animal ACE2 proteins described herein, or a variant of any one of the hACE2 or animal ACE2 proteins described herein).

In some embodiments, the target-binding moiety comprises between about 12 amino acids (aa) and about 805 aa of a full-length hACE2 protein or a fragment or variant thereof (e.g., an EBD of an ACE2 protein or a fragment or variant thereof, such as SEQ ID NO: 1), such as between about 12 aa and about 700 aa, between about 15 aa and about 500 aa, between about 100 aa and about 300 aa, between about 200 aa and about 400 aa, between about 300 aa and about 500 aa, between about 400 aa and about 600 aa, between about 500 aa and about 700 aa, between about 600 aa and about 805 aa, between about 12 aa and about 20 aa, between about 15 aa and about 20 aa, between about 21 aa and about 42 aa, between about 30 aa and about 41 aa, or between about 500 aa and about 805 aa, of a full-length hACE2 protein or a fragment or variant thereof. In some embodiments, the target-binding moiety comprises greater than about 12 aa of a full-length hACE2 protein or a fragment or variant thereof, such any greater than about n, where n is selected from 13 aa, 14 aa, 15 aa, 16 aa, 17 aa, 18 aa, 19, aa, 20 aa, 30 aa, 40 aa, 50 aa, 100 aa, 150 aa, 200 aa, 250 aa, 300 aa, 350 aa, 400 aa, 450 aa, 500 aa, 550 aa, 600 aa, 650 aa, 700 aa, 750 aa, 800 aa, 850 aa, or more, of a full-length hACE2 protein or a fragment thereof. In some embodiments, the target-binding moiety comprises less than about 805 aa of a full-length hACE2 protein or a fragment or variant thereof, such as less than about n, where n is selected from 800 aa, 750 aa, 700 aa, 650 aa, 600 aa, 550 aa, 500 aa, 450 aa, 400 aa, 350 aa, 300 aa, 250 aa, 200 aa, 150 aa, 100 aa, 50 aa, 40 aa, 30 aa, 20 aa, 19aa, 18aa, 17aa, 16aa, 15 aa, 14 aa, 13 aa, 12 aa, or less, of a full-length hACE2 protein or a fragment or variant thereof. In some embodiments, the target-binding moiety comprises any of about 805 aa, about 722 aa, about 714 aa, about 596 aa, about 380 aa, about 342 aa, about 331 aa, about 182 aa, about 19 aa, or about 12 aa of a full-length hACE2 protein or a fragment or variant thereof.

In some embodiments, the target-binding moiety comprises between about 12 aa and about 805 aa of a full-length animal ACE2 protein or a fragment or a variant thereof, such as between about 12 aa and about 700 aa, between about 15 aa and about 500 aa, between about 100 aa and about 300 aa, between about 200 aa and about 400 aa, between about 300 aa and about 500 aa, between about 400 aa and about 600 aa, between about 500 aa and about 700 aa, between about 600 aa and about 805 aa, between about 15 aa and about 20 aa, between about 12 aa and about 20 aa, between about 21 aa and about 42 aa, between about 30 aa and about 41 aa, or between about 500 aa and about 805 aa, of a full-length animal ACE2 protein or a fragment or a variant thereof. In some embodiments, the target-binding moiety comprises greater than about 12 aa of a full-length animal ACE2 protein or a fragment or variant thereof, such any greater than about n, where n is selected from 13 aa, 14 aa, 15 aa, 16 aa, 17 aa, 18 aa, 19, aa, 20 aa, 30 aa, 40 aa, 50 aa, 100 aa, 150 aa, 200 aa, 250 aa, 300 aa, 350 aa, 400 aa, 450 aa, 500 aa, 550 aa, 600 aa, 650 aa, 700 aa, 750 aa, 800 aa, 850 aa, or more, of a full-length animal ACE2 protein or a fragment or variant thereof. In some embodiments, the target-binding moiety comprises less than about 805 aa of a full-length animal ACE2 protein or a fragment or variant thereof, such as less than about n, where n is selected from 800 aa, 750 aa, 700 aa, 650 aa, 600 aa, 550 aa, 500 aa, 450 aa, 400 aa, 350 aa, 300 aa, 250 aa, 200 aa, 150 aa, 100 aa, 40 aa, 30 aa, 50 aa, 20 aa, 19aa, 18aa, 17aa, 16aa, 15 aa, 14 aa, 13 aa, 12 aa, or less, of a full-length animal ACE2 protein or a fragment or variant thereof. In some embodiments, the target-binding moiety comprises any of about 805 aa, about 722 aa, about 714 aa, about 596 aa, about 380 aa, about 342 aa, about 331 aa, about 182 aa, 19 aa, or about 12 aa, of a full-length animal ACE2 protein or a fragment or variant thereof.

In some embodiments, the target-binding moiety comprises a fragment that selectively recognizes an S1 subunit of the S protein and is capable of interfering with S1 binding to a full-length ACE2. In some embodiments, the target-binding moiety comprises amino acids 24-42 of a full-length ACE2 protein (e.g., a full-length hACE2 protein) or a variant thereof. In some embodiments, the target-binding moiety comprises between about 12 aa and about 19 aa, such as between about 12 aa and about 14 aa, between about 13 aa and about 15 aa, between about 14 aa and about 16 aa, between about 15 aa and about 17 aa, between about 16 aa and about 18 aa, between about 17 aa and about 19 aa, or between about 18 aa and about 19 aa of amino acids 24-42, of a full-length ACE2 protein or a variant thereof. In some embodiments, the target-binding moiety comprises at least about 12 aa, such as at least about n, where n is selected from 13 aa, 14 aa, 15 aa, 16 aa, 17 aa, and 18 aa, of SEQ ID NO: 8. In some embodiments, the target-binding moiety comprises greater than about 12 aa, such as greater than about n, where n is selected from 13 aa, 14 aa, 15 aa, 16 aa, 17 aa, and 18 aa, of SEQ ID NO: 8. In some embodiments, the target-binding moiety comprises less than about 20 aa, such as less than about n, where n is selected from 19 aa, 18 aa, 17 aa, 16 aa, 15 aa, 14 aa, 13 aa, 12 aa, or fewer, of SEQ ID NO: 8. In some embodiments, the target-binding moiety comprises about 19 aa of SEQ ID NO: 8. In some embodiments, the chimeric protein comprises a target-binding moiety comprising the amino acid sequence of SEQ ID NO: 8, or a variant thereof comprising at least about 90% (such as about n % sequence identity, where n % is selected from 91%, 92%, 93%, 94%, 95%, 96%, 97%, 98%, and 99%) sequence identity to the amino acid sequence of SEQ ID NO: 8.

In some embodiments, the target-binding moiety comprises amino acids 30-41 of a full-length ACE2 protein (e.g., a full-length hACE2 protein or a full-length animal ACE2 protein) or a variant thereof. In some embodiments, the chimeric protein comprises a target-binding moiety comprising the amino acid sequence of any one of SEQ ID NOs: 102, 111-120, and 122, or a variant thereof comprising at least about 90% (such as about n % sequence identity, where n % is selected from 91%, 92%, 93%, 94%, 95%, 96%, 97%, 98%, and 99%) sequence identity to any one of SEQ ID NOs: 102, 111-120, and 122. In some embodiments, the full-length ACE2 protein or a variant thereof is a hACE2 protein or variant thereof. In some embodiments, the full-length ACE2 protein or variant thereof is not a canine or a chicken full-length ACE2 protein or variant thereof.

In some embodiments, the target-binding moiety comprises amino acids 29-40 of a full-length ACE2 protein (e.g., a full-length animal ACE2 protein) or a variant thereof. In some embodiments, the chimeric protein comprises a target-binding moiety comprising the amino acid sequence of SEQ ID NO: 110 or 121, or a variant thereof comprising at least about 90% (such as about n % sequence identity, where n % is selected from 91%, 92%, 93%, 94%, 95%, 96%, 97%, 98%, and 99%) sequence identity to SEQ ID NO: 110 or 121. In some embodiments, the full-length ACE2 protein or variant thereof is a canine or a chicken ACE2 protein or a variant thereof.

In some embodiments, the target-binding moiety comprises at least about 90% sequence identity (such as about n % sequence identity, where n % is selected from 91%, 92%, 93%, 94%, 95%, 96%, 97%, 98%, and 99%) to amino acids 24-42 of a full-length hACE2 protein. In some embodiments, the target-binding moiety comprises amino acids 24-42 of a full-length hACE2 protein. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 8. In some embodiments, the target-binding moiety comprises the amino acid sequence of SEQ ID NO: 8. In some embodiments, the target-binding moiety comprises ACE19, as described in Table 3.

In some embodiments, the target-binding moiety comprises at least about 90% sequence identity (such as about n % sequence identity, where n % is selected from 91%, 92%, 93%, 94%, 95%, 96%, 97%, 98%, and 99%) to amino acids 30-41 of a full-length hACE2 protein. In some embodiments, the target-binding moiety comprises amino acids 30-41 of a full-length hACE2 protein. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 102. In some embodiments, the target-binding moiety comprises the amino acid sequence of SEQ ID NO: 102. In some embodiments, the target-binding moiety comprises ACE12, as described in Table 3.

In some embodiments, there is provided a chimeric protein comprising a target-binding moiety comprising an EBD of a hACE2 protein that specifically binds to an S protein, or a fragment thereof. Exemplary hACE2 proteins are provided in Table 3 above. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of any one of SEQ ID NOs: 1-7, 9-14, and 135. In some embodiments, the target-binding moiety comprises the amino acid sequence of any one of SEQ ID NOs: 1-7, 9-14, and 135.

In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 1. In some embodiments, the target-binding moiety comprises the amino acid sequence of SEQ ID NO: 1. In some embodiments, the target-binding moiety comprises a full-length hACE2 protein, as described in Table 3.

In some embodiments, the target-binding moiety comprises amino acids 19-614 of hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 2. In some embodiments, the target-binding moiety comprises the amino acid sequence of SEQ ID NO: 2. In some embodiments, the target-binding moiety comprises ACE614, as described in Table 3.

In some embodiments, the target-binding moiety comprises amino acids 19-360 of hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 3. In some embodiments, the target-binding moiety comprises the amino acid sequence of SEQ ID NO: 3. In some embodiments, the target-binding moiety comprises ACE360, as described in Table 3.

In some embodiments, the target-binding moiety comprises amino acids 30-360 of hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 4. In some embodiments, the target-binding moiety comprises the amino acid sequence of SEQ ID NO: 4. In some embodiments, the target-binding moiety comprises ACEΔ360, as described in Table 3.

In some embodiments, the target-binding moiety comprises amino acids 19-732 of hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 5. In some embodiments, the target-binding moiety comprises the amino acid sequence of SEQ ID NO: 5. In some embodiments, the target-binding moiety comprises ACE732, as described in Table 3.

In some embodiments, the target-binding moiety comprises amino acids 19-740 of hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 135. In some embodiments, the target-binding moiety comprises the amino acid sequence of SEQ ID NO: 135. In some embodiments, the target-binding moiety comprises ACE740, as described in Table 3.

In some embodiments, the target-binding moiety comprises amino acids 19-200 of hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 6. In some embodiments, the target-binding moiety comprises the amino acid sequence of SEQ ID NO: 6. In some embodiments, the target-binding moiety comprises ACE200, as described in Table 3.

In some embodiments, the target-binding moiety comprises amino acids 42-420 of hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 7. In some embodiments, the target-binding moiety comprises the amino acid sequence of SEQ ID NO: 7. In some embodiments, the target-binding moiety comprises ACEΔ420, as described in Table 3.

In some embodiments, the target-binding moiety comprises a K26R point mutation at amino acid 26 in hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 9. In some embodiments, the target-binding moiety comprises the amino acid sequence of SEQ ID NO: 9. In some embodiments, the target-binding moiety comprises ACE2 K26R, as described in Table 3.

In some embodiments, the target-binding moiety comprises an I468V point mutation at amino acid 468 in hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 10. In some embodiments, the target-binding moiety comprises the amino acid sequence of SEQ ID NO: 10. In some embodiments, the target-binding moiety comprises ACE2 1468V, as described in Table 3.

In some embodiments, the hACE2 protein or a fragment thereof comprises an hACE2 fusion fragment comprising a N638S point mutation at amino acid 638 in hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 11. In some embodiments, the target-binding moiety comprises the amino acid sequence of SEQ ID NO: 11. In some embodiments, the target-binding moiety comprises ACE2 N638S, as described in Table 3.

In some embodiments, the target-binding moiety comprises a N720D point mutation at amino acid 720 in hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 12. In some embodiments, the target-binding moiety comprises the amino acid sequence of SEQ ID NO: 12. In some embodiments, the target-binding moiety comprises ACE2 N720D, as described in Table 3.

In some embodiments, the target-binding moiety comprises a hACE2 fragment comprising a H374N point mutation at amino acid 374, and a H378N point mutation at amino acid 378 in hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 13. In some embodiments, the target-binding moiety comprises the amino acid sequence of SEQ ID NO: 13. In some embodiments, the target-binding moiety comprises ACE2 HN-HN, as described in Table 3.

In some embodiments, the target-binding moiety comprises a hACE2 fragment comprising a T27Y point mutation at amino acid 27, and a H34A point mutation at amino acid 34 in hACE2 (e.g., SEQ ID NO: 1). In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 14. In some embodiments, the target-binding moiety comprises the amino acid sequence of SEQ ID NO: 14. In some embodiments, the target-binding moiety comprises ACE2 TY-HA, as described in Table 3.

In some embodiments, there is provided a chimeric protein comprising a target-binding moiety comprising an EBD of an animal ACE2 protein that specifically binds to an S protein, or a fragment thereof. In some embodiments, the target-binding moiety comprising an animal ACE2 protein described herein is a murine, guinea pig, equine, ferret, macaque, chimpanzee, swine, canine, feline, bovine, rabbit, mink, or chicken ACE2 protein or a fragment or variant thereof. Exemplary animal ACE2 proteins and fragments thereof are provided in Table 4 above.

In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to amino acids 30-41 of a full-length animal ACE2 protein. In some embodiments, the target-binding moiety comprises amino acids 30-41 of a full-length animal ACE2 protein. In some embodiments, the full-length animal ACE2 protein is a murine, guinea pig, equine, ferret, macaque, chimpanzee, swine, feline, bovine, rabbit, or mink ACE2 protein. In some embodiments, the full-length animal ACE2 protein comprises an amino acid sequence having at least about 90% sequence identity (such as about n % sequence identity, where n % is selected from 91%, 92%, 93%, 94%, 95%, 96%, 97%, 98%, and 99%) to any one of SEQ ID NOs: 15-20 and 22-26. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to amino acids 30-41 of a full-length murine, guinea pig, equine, ferret, macaque, chimpanzee, swine, feline, bovine, rabbit, or mink ACE2 protein. In some embodiments, the target-binding moiety comprises the amino acid sequence of amino acids 30-41 of a full-length murine, guinea pig, equine, ferret, macaque, chimpanzee, swine, feline, bovine, rabbit, or mink ACE2 protein. In some embodiments, the target-binding moiety comprises the amino acid sequence of any one of SEQ ID NOs: 15-20 and 22-26. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to any one of SEQ ID NOs: 111-120 and 122. In some embodiments, the target-binding moiety comprises the amino acid sequence of any one of SEQ ID NOs: 111-120 and 122. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 111. In some embodiments, the target-binding moiety comprises the amino acid sequence of SEQ ID NO: 111. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 112. In some embodiments, the target-binding moiety comprises the amino acid sequence of SEQ ID NO: 112. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 113. In some embodiments, the target-binding moiety comprises the amino acid sequence of SEQ ID NO: 113. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 114. In some embodiments, the target-binding moiety comprises the amino acid sequence of SEQ ID NO: 114. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 115. In some embodiments, the target-binding moiety comprises the amino acid sequence of SEQ ID NO: 115. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 116. In some embodiments, the target-binding moiety comprises the amino acid sequence of SEQ ID NO: 116. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 117. In some embodiments, the target-binding moiety comprises the amino acid sequence of SEQ ID NO: 117. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 118. In some embodiments, the target-binding moiety comprises the amino acid sequence of SEQ ID NO: 118. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 119. In some embodiments, the target-binding moiety comprises the amino acid sequence of SEQ ID NO: 119. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 120. In some embodiments, the target-binding moiety comprises the amino acid sequence of SEQ ID NO: 120. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 122. In some embodiments, the target-binding moiety comprises the amino acid sequence of SEQ ID NO: 122. In some embodiments, the full-length animal ACE2 protein is not a chicken or canine ACE2 protein (e.g., SEQ ID NOs: 21 and 27).

In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to amino acids 29-40 of a full-length animal ACE2 protein. In some embodiments, the target-binding moiety comprises amino acids 29-40 of a full-length animal ACE2 protein. In some embodiments, the full-length animal ACE2 protein is a canine or chicken ACE2 protein. In some embodiments, the full-length animal ACE2 protein comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 21 or 27. In some embodiments, the full-length animal ACE2 protein comprises the amino acid sequence of SEQ ID NO: 21 or 27. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to amino acids 29-40 of a full-length canine or chicken ACE2 protein. In some embodiments, the target-binding moiety comprises the amino acid sequence of amino acids 29-40 of a full-length canine or chicken ACE2 protein. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 110 or 121. In some embodiments, the target-binding moiety comprises the amino acid sequence of SEQ ID NO: 110 or 121. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 110. In some embodiments, the target-binding moiety comprises the amino acid sequence of SEQ ID NO: 110. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to SEQ ID NO: 121. In some embodiments, the target-binding moiety comprises the amino acid sequence of SEQ ID NO: 121.

In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of any one of SEQ ID NOs: 15-27. In some embodiments, the target-binding moiety comprises the amino acid sequence of any one of SEQ ID NOs: 15-27. In some embodiments, the target-binding moiety comprises a mouse ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 15. In some embodiments, the target-binding moiety comprises the amino acid sequence of SEQ ID NO: 15. In some embodiments, the target-binding moiety comprises a guinea pig ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 16. In some embodiments, the target-binding moiety comprises the amino acid sequence of SEQ ID NO: 16. In some embodiments, the target-binding moiety comprises an equine ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 17. In some embodiments, the target-binding moiety comprises the amino acid sequence of SEQ ID NO: 17. In some embodiments, the target-binding moiety comprises a macaque ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 18. In some embodiments, the target-binding moiety comprises the amino acid sequence of SEQ ID NO: 18. In some embodiments, the target-binding moiety comprises a chimpanzee ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 19. In some embodiments, the target-binding moiety comprises the amino acid sequence of SEQ ID NO: 19. In some embodiments, the target-binding moiety comprises a swine ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 20. In some embodiments, the target-binding moiety comprises the amino acid sequence of SEQ ID NO: 20. In some embodiments, the target-binding moiety comprises a canine ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 21. In some embodiments, the target-binding moiety comprises the amino acid sequence of SEQ ID NO: 21. In some embodiments, the target-binding moiety comprises a feline ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 22. In some embodiments, the target-binding moiety comprises the amino acid sequence of SEQ ID NO: 22. In some embodiments, the target-binding moiety comprises a bovine ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 23. In some embodiments, the target-binding moiety comprises the amino acid sequence of SEQ ID NO: 23. In some embodiments, the target-binding moiety comprises a rabbit ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 24. In some embodiments, the target-binding moiety comprises the amino acid sequence of SEQ ID NO: 24. In some embodiments, the target-binding moiety comprises a ferret ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 25. In some embodiments, the target-binding moiety comprises the amino acid sequence of SEQ ID NO: 25. In some embodiments, the target-binding moiety comprises a mink ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 26. In some embodiments, the target-binding moiety comprises the amino acid sequence of SEQ ID NO: 26. In some embodiments, the target-binding moiety comprises a chicken ACE2 fusion fragment. In some embodiments, the target-binding moiety comprises an amino acid sequence having at least about 90% sequence identity (such as about n % sequence identity, where n % is selected from 91%, 92%, 93%, 94%, 95%, 96%, 97%, 98%, and 99%) to the amino acid sequence of SEQ ID NO: 27. In some embodiments, the target-binding moiety comprises the amino acid sequence of SEQ ID NO: 27.

Coronaviruses are a group of related viruses that cause diseases in mammals and birds. In humans, coronaviruses cause respiratory tract infections that can range from mild to lethal. Mild illnesses include some cases of the common cold (e.g., with symptoms such as fever, sore throat), while more lethal varieties can cause SARS and COVID-19. Coronaviruses can cause pneumonia (either direct viral pneumonia or secondary bacterial pneumonia) and bronchitis (cither direct viral bronchitis or secondary bacterial bronchitis).

Coronaviruses are large pleomorphic spherical particles with bulbous surface projections. The average diameter of the virus particles is around 120 nm (0.12 μm). The diameter of the envelope is ~80 nm (0.08 μm) and the spikes are ~20 nm (0.02 μm) long. The viral envelope consists of a lipid bilayer where the membrane (M), envelope (E) and spike(S) structural proteins are anchored. A subset of coronaviruses (specifically the members of betacoronavirus subgroup A) also have a shorter spike-like surface protein called hemagglutinin esterase (HE). Inside the envelope, there is the nucleocapsid, which is formed from multiple copies of the nucleocapsid (N) protein, which are bound to the positive-sense single-stranded RNA genome in a continuous beads-on-a-string type conformation. The lipid bilayer envelope, membrane proteins, and nucleocapsid protect the virus when it is outside the host cell.

Infection begins when the viral S glycoprotein attaches to its complementary host cell receptor. After attachment, a protease of the host cell cleaves and activates the receptor-attached spike protein. Depending on the host cell protease available, cleavage and activation allows the virus to enter the host cell by endocytosis or direct fusion of the viral envelope with the host membrane. On entry into the host cell, the virus particle is uncoated, and its genome enters the cell cytoplasm. The coronavirus RNA genome has a 5' methylated cap and a 3' polyadenylated tail, which allows the RNA to attach to the host cell's ribosome for translation. The host ribosome translates the initial overlapping open reading frame of the virus genome and forms a long polyprotein. The polyprotein has its own proteases, which cleave the polyprotein into multiple nonstructural proteins.

The coronaviruses can be classified into five genera: Alpha, Beta, Gamma, Delta, and Omicron CoVs (Woo et al., 2009). Previously identified human CoVs that cause human disease include the αCoVs hCoV-NL63 and hCoV-229E and the βCoVs HCoV-OC43, HKU1, Severe Acute Respiratory Syndrome CoV (SARS-CoV), Middle East respiratory syndrome coronavirus (MERS-CoV), and Severe Acute Respiratory Syndrome Coronavirus 2 (SARS-CoV-19; previously known as 2019-nCOV (Lu et al., 2015; Wevers and van der Hoek, 2009; Zhu et al., 2020). HCoV-OC43, HCoV-HKU1, HCoV-229E and HCoV-NL63 continually circulate in the human population and produce generally mild symptoms of the common cold in adults and children worldwide.

SARS-CoV is a zoonotic pathogen originating in animals. Detailed investigations indicate that SARS-CoV is transmitted from civet cats to humans (Azhar et al., 2014; Ge et al., 2013; Guan et al., 2003). Bats and birds, as warm-blooded flying vertebrates, are an ideal natural reservoir for the coronavirus gene pool (bats the reservoir for alphacoronavirus and betacoronavirus—and birds the reservoir for gammacoronavirus and deltacoronavirus). The large number of host bat and avian species, and their global range, has enabled extensive evolution and dissemination of coronaviruses.

SARS-CoV-2 is a betacoronavirus from Group 2B with approximately 70% genetic similarity to the SARS-CoV. The virus has a 96% similarity to a bat coronavirus (SARSr-CoV_RaTG13), so it is widely suspected to originate from bats as well.

Coronaviruses have been recognized as causing pathological conditions in veterinary medicine since the 1930s. Coronaviruses primarily infect the upper respiratory and gastrointestinal tract of mammals and birds. They also cause a range of diseases in farm animals and domesticated pets, some of which can be serious and are a threat to the farming industry. Exemplary coronaviruses that infect animals include the Infectious Bronchitis Virus (IBV) for chickens, porcine coronavirus (Transmissible Gastroenteritis Coronavirus, TGEV), Porcine Respiratory Coronavirus (PEDV), bovine coronavirus (BCoV), feline enteric coronavirus, Feline Infectious Peritonitis Virus (FIPV), ferret enteric coronavirus, ferret systemic coronavirus, Canine Coronavirus (CCoV), mouse hepatitis virus (MHV), Sialodacryoadenitis Virus (SDAV), and Swine Acute Diarrhea Syndrome Coronavirus (SADS-CoV).

A naturally occurring S protein of a coronavirus forms homotrimers protruding from the viral surface. The S protein comprises two functional subunits responsible for binding to the host cell receptor (S1 subunit), and fusion of the viral and cellular membranes (S2 subunit). For many CoVs, S is cleaved at the boundary between the S1 and S2 subunits, which remain non-covalently bound in the pre-fusion conformation of the CoV. The distal S1 subunit comprises the RBD(s) and contributes to stabilization of the prefusion state of the membrane-anchored S2 subunit that contains the fusion machinery. For all CoVs, S is further cleaved by host proteases at the so-called S2' site located immediately upstream of the fusion peptide. This cleavage has been proposed to activate the protein for membrane fusion via extensive irreversible conformational changes. As a result, coronavirus entry into susceptible cells is a complex process that requires the concerted action of receptor-binding and proteolytic processing of the S protein to promote virus-cell fusion. See, Walls et al., *Cell* 180, 281-292 (2020).

For example, the S protein of SARS-CoV could be cleaved by trypsin at two distinct sites, one located at the boundary of S1 and S2, the "classical" S1/S2 site (R667 P1 residue), and the S2' site (R797 P1 residue). Protease cleavage of SARS-CoV S is thought to be sequential, with the S1/S2 cleavage occurring first and enhancing subsequent cleavage at S2'. It is the second cleavage event, at S2', that is believed to be crucial for fusion activation of S. The S1/S2 cleavage appears dispensable for syncytia formation and virus-cell fusion. See, Millet, Virus Research 202:120-134 (2015).

The spike protein of SARS-CoV-2 can be cleaved by both furin at the S1/S2 site and the transmembrane protease/serine (TMPRSS) protease 2, TMPRSS2, at the S2' site. See, Hoffman et al., Cell 181, 271-280, 2020. The furin cleavage site of SARS-CoV-2 is located between amino acids 685 and 686 of the S protein. SARS-CoV-2 and SARS-CoV both use ACE2 as the receptor to enter human cells. See, Zhou et al., Nature 579:270 (2020).

S1 of the S protein can be further divided into an N-terminal domain (NTD) and a C-terminal domain (CTD), both of which can function as a receptor-binding entity (e.g., SARS-CoV utilizes the S1 CTD to recognize the receptor (also called receptor binding domain [RBD]) (Li et al., 2005; Lu et al., 2013).

Exemplary coronavirus S proteins and variants thereof are provided in Table 5.

TABLE 5

Exemplary coronavirus strains and sequences of their spike proteins' receptor binding domains

| Strain/ Reference | Receptor Binding Domain (aa319-541) | RBD mutations | SEQ ID NO |
|---|---|---|---|
| WIV4 ("wildtype" or "WT") P0DTC2 | RVQPTESIVRFPNITNLCPFGEVFNATRFASVYAWNRKRISNCVA DYSVLYNSASFSTFKCYGVSPTKLNDLCFTNVYADSFVIRGDEV RQIAPGQTGKIADYNYKLPDDFTGCVIAWNSNNLDSKVGGNYN YLYRLFRKSNLKPFERDISTEIYQAGSTPCNGVEGFNCYFPLQSY GFQPTNGVGYQPYRVVVLSFELLHAPATVCGPKKSTNLVKNKC VNF | | 96 |
| Alpha 7EKF_B | RVQPTESIVRFPNITNLCPFGEVFNATRFASVYAWNRKRISNCVA DYSVLYNSASFSTFKCYGVSPTKLNDLCFTNVYADSFVIRGDEV RQIAPGQTGKIADYNYKLPDDFTGCVIAWNSNNLDSKVGGNYN YLYRLFRKSNLKPFERDISTEIYQAGSTPCNGVEGFNCYFPLQSY GFQPTYGVGYQPYRVVVLSFELLHAPATVCGPKKSTNLVKNKC VNF | N501Y | 123 |
| Beta 7EKG_B | RVQPTESIVRFPNITNLCPFGEVFNATRFASVYAWNRKRISNCVA DYSVLYNSASFSTFKCYGVSPTKLNDLCFTNVYADSFVIRGDEV RQIAPGQTGKIADYNYKLPDDFTGCVIAWNSNNLDSKVGGNYN YLYRLFRKSNLKPFERDISTEIYQAGSTPCNGVEGFNCYFPLQSY GFQPTYGVGYQPYRVVVLSFELLHAPATVCGPKKSTNLVKNKC VNF | K417N, E484K | 124 |
| Delta QWK65230.1 | RVQPTESIVRFPNITNLCPFGEVFNATRFASVYAWNRKRISNCVA DYSVLYNSASFSTFKCYGVSPTKLNDLCFTNVYADSFVIRGDEV RQIAPGQTGKIADYNYKLPDDFTGCVIAWNSNNLDSKVGGNYN YRYRLFRKSNLKPFERDISTEIYQAGSKPCNGVEGFNCYFPLQSY GFQPTNGVGYQPYRVVVLSFELLHAPATVCGPKKSTNLVKNKC VNF | L452R T478K | 97 |

TABLE 5-continued

Exemplary coronavirus strains and sequences of their spike proteins' receptor binding domains

| Strain/<br>Reference | Receptor Binding Domain (aa319-541) | RBD<br>mutations | SEQ<br>ID<br>NO |
|---|---|---|---|
| Omicron<br>BA.1<br>UJT03851.1 | RVQPTESIVRFPNITNLCPFDEVFNATRFASVYAWNRKRISNCVA<br>DYSVLYNLAPFFTFKCYGVSPTKLNDLCFTNVYADSFVIRGDEV<br>RQIAPGQTGNIADYNYKLPDDFTGCVIAWNSNKLDSKVSGNYN<br>YLYRLFRKSNLKPFERDISTEIYQAGNKPCNGVAGFNCYFPLRSY<br>SFRPTYGVGHQPYRVVVLSFELLHAPATVCGPKKSTNLVKNKC<br>VNF | G339D,<br>S371L,<br>S373P,<br>S375F,<br>K417N,<br>N440K,<br>G446S,<br>S477N,<br>T478K,<br>E484A,<br>Q493R,<br>G496S,<br>N501Y,<br>Y505H | 98 |
| Omicron<br>BA.2<br>UMF62763.1 | RVQPTESIVRFPNITNLCPFDEVFNATRFASVYAWNRKRISNCVA<br>DYSVLYNFAPFFAFKCYGVSPTKLNDLCFTNVYADSFVIRGNEV<br>SQIAPGQTGNIADYNYKLPDDFTGCVIAWNSNKLDSKVGGNYN<br>YLYRLFRKSNLKPFERDISTEIYQAGNKPCNGVAGFNCYFPLRSY<br>GFRPTYGVGHQPYRVVVLSFELLHAPATVCGPKKSTNLVKNKC<br>VNF | S371F,<br>T376A,<br>D405N,<br>R408S,<br>S445G,<br>S495G | 99 |
| Bat<br>UAY13265.1 | RVLPSTEVVRFPNITNFCPFDKVFNATRFPNVYAWQRTKISDCIA<br>DYTVLYNSTSFSTFKCYGVSPSKLIDLCFTSVYADTFLIRFSEVRQ<br>IAPGETGVIADYNYKLPDDFTGCVLAWNTAQQDIGSYFYRSHRA<br>VKLKPFERDLSSDENGVRTLSTYDFNPNVPLDYQATRVVVLSFE<br>LLNAPATVCGPKLSTQLVKNRCVNF | | 100 |
| SARS-CoV<br>ABD75332.1 | VTPTQEVVRFPNITNRCPFDKVFNASRFPNVYAWERTKISDCVA<br>DYTVLYNSTSFSTFKCYGVSPSKLIDLCFTSVYADTFLIRSSEVRQ<br>VAPGETGVIADYNYKLPDDFTGCVIAWNTAQQDQGQYYYRSY<br>RKEKLKPFERDLSSDENGVYTLSTYDFYPSIPVEYQATRVVVLSF<br>ELLNAPATVCGPKLSTQLVKNQCVNF | | 103 |
| BA.5.1.1<br>WEF43315.1 | RVQPTESIVRFPNITNLCPFDEVFNATRFASVYAWNRKRISNCVA<br>DYSVLYNFAPFFAFKCYGVSPTKLNDLCFTNVYADSFVIRGNEV<br>SQIAPGQTGNIADYNYKLPDDFTGCVIAWNSNKLDSKVGGNYN<br>YRYRLFRKSNLKPFERDISTEIYQAGNKPCNGVAGVNCYFPLQS<br>YGFRPTYGVGHQPYRVVVLSFELLHAPATVCGPKKSTNLVKNK<br>CVNF | L452R,<br>F486V,<br>R496Q | 141 |
| BQ.1<br>WEJ42036.1 | RVQPTESIVRFPNITNLCPFDEVFNATTFASVYAWNRKRISNCVA<br>DYSVLYNFAPFFAFKCYGVSPTKLNDLCFTNVYADSFVIRGNEV<br>SQIAPGQTGNIADYNYKLPDDFTGCVIAWNSNKLDSTVGGNYN<br>YRYRLFRKSKLKPFERDISTEIYQAGNKPCNGVAGVNCYFPLQS<br>YGFRPTYGVGHQPYRVVVLSFELLHAPATVCGPKKSTNLVKNK<br>CVNF | R346T,<br>K444T | 142 |
| XBB.1.5<br>WEI68632.1 | RVQPTESIVRFPNITNLCPFHEVFNATTFASVYAWNRKRISNCVA<br>DYSVIYNFAPFFAFKCYGVSPTKLNDLCFTNVYADSFVIRGNEVS<br>QIAPGQTGNIADYNYKLPDDFTGCVIAWNSNKLDSKPSGNYNYL<br>YRLFRKSKLKPFERDISTEIYQAGNKPCNGVAGPNCYSPLQSYGF<br>RPTYGVGHQPYRVVVLSFELLHAPATVCGPKKSTNLVKNKCVN<br>F | F486P | 143 |

Provided herein are ACE2 chimeric proteins comprising a target-binding moiety that specifically binds to an S protein or a fragment thereof of a coronavirus or a variant thereof, such as those described in Table 5 (e.g., any one of SEQ ID NOs: 96-100, 103, 123-127, and 141-143, or a variant thereof comprising at least about 90% sequence identity (such as about n % sequence identity, where n % is selected from 91%, 92%, 93%, 94%, 95%, 96%, 97%, 98%, and 99%) to any one of SEQ ID NOs: 96-100, 103, 123-127, and 141-143). In some embodiments, the target-binding moiety specifically binds to a RBD of an S protein of a coronavirus or a variant thereof. In some embodiments, the RBD is from a SARS-CoV, SARS-CoV-2, or HCoV-NL63 coronavirus, or a variant thereof. In some embodiments, the RBD is from a reference SARS-CoV-2 (e.g., WIV4, i.e., hCoV-19/WIV04/2019 or BetaCoV/WIV04/2019; e.g., SEQ ID NO: 96) or a SARS-CoV-2 virus having substantially the same genomic sequence (e.g., fewer than any one of 200, 100, 50, 20, 10, 5, 4, 3, 2, or 1 mutations) and phenotypes as the reference SARS-CoV-2. In some embodiments, the SARS-CoV-2 is a variant, such as a variant of interest, a variant of concern, or a variant of high consequence. In some embodiments, the SARS-CoV-2 is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (also known as B.1.1.28.1) variant, an A.23.1 variant, a CAL.20C variant, a B.1.427 variant, a B.1.429 variant, a B.1.525 variant, a P.1.351, a BA.5.1.1, a BQ.1 variant, a XBB variant, a XBB.1.5 variant, and a XBB.1.16 variant. In some embodiments, the SARS-CoV-2 variant is a B.1.1.7 variant. In some embodiments, the SARS-CoV-2 variant is a B.1.351 variant. In some embodiments, the SARS-CoV-2 variant is a B.1.617.2 variant. In some embodiments, the RBD is from a Delta, Omicron BA.1, or Omicron BA.2 SARS-CoV-2 variant, as described in Table 5 (e.g., SEQ ID NOs: 97-100). In some embodiments, the RBD is from an animal coronavirus, such as a Bat coronavirus, as described in Table 5 (e.g., SEQ ID NO: 100). In some embodiments, the RBD is from a SARS-CoV coronavirus, as described in Table 5 (e.g., SEQ ID NO: 103). In some embodiments, the RBD comprises the amino acid sequence of any one of SEQ ID NOs: 96-100, 103, 123-127, and 141-143, as described in Table 5.

SARS-CoV-2

In some embodiments, the target-binding moiety specifically binds an S protein of SARS-CoV-2. In some embodiments, the target-binding moiety specifically binds an S1 subunit of the S protein. Exemplary ACE2 proteins or fragments thereof (e.g., hACE proteins or fragments thereof, and animal ACE2 proteins or fragments thereof) that specifically binds to the S1 subunit of the S protein are disclosed herein in Tables 3 and 4. In some embodiments, the target-binding moiety specifically binds an RBD of an S protein of SARS-CoV-2. Exemplary RBD sequences from S proteins of SARS-CoV-2 are shown in Table 5.

SARS-CoV-2 S protein includes a signaling peptide (amino acid residues 1-19), S1 region containing a N-terminal domain (NTD; amino acid residues 20-286) and a C-terminal domain (CTD; amino acid residues 319-541), a S2 region (amino acid residues 686-1213), a transmembrane region (amino acid residues 1214-1236), and a short cytoplasmic domain (amino acid residues 1237-1273). The CTD, in particular amino acid residues 333-527, play key roles in binding to ACE2. In particular, amino acid residues A475, K417, G446, Y449, G496, Q498, T500, G502, Y489, F486, and N487 contribute to binding of the SARS-CoV-2 CTD with hACE2. See, Wang et al., 2020, Cell 181, 1-11, which is incorporated herein by reference in its entirety.

In some embodiments, the target-binding moiety can recognize two or more isolates or clusters of SARS-CoV-2 (e.g., cluster A, B or C; or any one of the isolates as disclosed in Forster et al. *Proc Natl Acad Sci* (2020)). In some embodiments, the target-binding moiety specifically blocks binding of one or more variants of the S1 protein of SARS-CoV-2 to hACE2, including the SARS-CoV-2 S1 S protein variants of Table 5, such as an S1 protein comprising one or more mutations selected from the group consisting of D614G, V367F, N439K, A435S, V483A, K458R, G476S, R408I, V503F, A522V, Y508H, L452R, A520S, 1472V, T478I, F490S, and/or P384L.

In some embodiments, the target-binding moiety can recognize two or more variants of SARS-CoV-2. In some embodiments, the component is derived from a reference SARS-CoV-2. In some embodiments, the component is derived from a SARS-CoV-2 variant. In some embodiments, there is provided a composition comprising a plurality of chimeric proteins that are capable of recognizing a plurality of SARS-CoV-2 variant and reference viruses. In some embodiments, the plurality of chimeric proteins each contain the same target-binding moiety. In some embodiments, at least two of the plurality of chimeric proteins contain different target-binding moieties, which recognize different SARS-CoV-2 variants.

Exemplary SARS-CoV-2 variants and their properties are shown in the Table 6 below. The chimeric proteins and compositions described herein may be used for treating any one of the SARS-CoV-2 variants described herein. The SARS-CoV-2 variants described herein are named according to the Phylogenetic Assignment of Named Global Outbreak (PANGO) Lineages software. It is understood that the same variants may be referred to using different naming systems and algorithms in the art. SARS-CoV-2 variant classifications and definitions, as well as a list of known SARS-CoV-2 variants can be found at worldwide web.cdc.gov/coronavirus/2019-ncov/variants/variant-info.html.

TABLE 6

SARS-CoV-2 variants and properties.

| Name | Spike Protein Substitutions | Phenotypes |
|---|---|---|
| B.1.525 | Spike: A67V, 69del, 70del, 144del, E484K, D614G, Q677H, F888L | Potential reduction in neutralization by some Emergency Use Authorization (EUA) monoclonal antibody treatments. Potential reduction in neutralization by convalescent and post-vaccination sera. |
| B.1.526 | Spike: (L5F*), T95I, D253G, (S477N*), (E484K*), D614G, (A701V*) | Reduced susceptibility to the combination of bamlanivimab and etesevimab monoclonal antibody treatment; however, the clinical implications of this are not known. Alternative monoclonal antibody treatments are available. Reduced neutralization by convalescent and post-vaccination sera. |
| B.1.526.1 | Spike: D80G, 144del, F157S, L452R, D614G, (T791I*), (T859N*), D950H | Potential reduction in neutralization by some EUA monoclonal antibody treatments. Potential reduction in neutralization by convalescent and post-vaccination sera. |
| B.1.617 | Spike: L452R, E484Q, D614G | Potential reduction in neutralization by some EUA monoclonal antibody treatments Slightly reduced neutralization by post-vaccination sera. |
| B.1.617.1 | Spike: (T95I), G142D, E154K, L452R, E484Q, D614G, P681R, Q1071H | Potential reduction in neutralization by some EUA monoclonal antibody treatments. Potential reduction in neutralization by post-vaccination sera. |
| B.1.617.2 | Spike: T19R, (G142D), 156del, 157del, R158G, L452R, T478K, D614G, P681R, D950N | Potential reduction in neutralization by some EUA monoclonal antibody treatments. Potential reduction in neutralization by post-vaccination sera. |

TABLE 6-continued

SARS-CoV-2 variants and properties.

| Name | Spike Protein Substitutions | Phenotypes |
|---|---|---|
| B.1.617.3 | Spike: T19R, G142D, L452R, E484Q, D614G, P681R, D950N | Potential reduction in neutralization by some EUA monoclonal antibody treatments. Potential reduction in neutralization by post-vaccination sera. |
| P.2 | Spike: E484K, (F565L*), D614G, V1176F | Potential reduction in neutralization by some EUA monoclonal antibody treatments. Reduced neutralization by post-vaccination sera. |
| B.1.1.7 | 69del, 70del, 144del, (E484K*), (S494P*), N501Y, A570D, D614G, P681H, T716I, S982A, D1118H, (K1191N*) | ~50% increased transmission. Potential increased severity based on hospitalizations and case fatality rates. No impact on susceptibility to EUA monoclonal antibody treatments. Minimal impact on neutralization by convalescent and post-vaccination sera. |
| B.1.351 | D80A, D215G, 241del, 242del, 243del, K417N, E484K, N501Y, D614G, A701V | ~50% increased transmission. Significant decrease in susceptibility to the combination of bamlanivimab and etesevimab monoclonal antibody treatment, but other EUA monoclonal antibody treatments are available. Reduced neutralization by convalescent and post-vaccination sera. |
| B.1.427 | L452R, D614G | ~20% increased transmissibility. Modest decrease in susceptibility to the combination of bamlanivimab and etesevimab; however, the clinical implications of this decrease are not known. Alternative monoclonal antibody treatments are available. Reduced neutralization by convalescent and post-vaccination sera. |
| B.1.429 | S13I, W152C, L452R, D614G | ~20% increased transmissibility. Modest decrease in susceptibility to the combination of bamlanivimab and etesevimab; however, the clinical implications of this decrease are not known. Alternative monoclonal antibody treatments are available. Reduced neutralization by convalescent and post-vaccination sera. |
| P.1 | L18F, T20N, P26S, D138Y, R190S, K417T, E484K, N501Y, D614G, H655Y, T1027I | Significant decrease in susceptibility to the combination of bamlanivimab and etesevimab monoclonal antibody treatment, but other EUA monoclonal antibody treatments are available. Reduced neutralization by convalescent and post-vaccination sera. |
| BA.5.1.1 | T19I, del24-26, A27S, del69-70, G142D, V213G, R493Q, L452R, F486V, G339D, S371F, S373P, S375F, T276A, D405N, R408S, K417N, N440K, S477N, T478K, E484A, Q498R, N501Y, Y505H, D614G, H655Y, N679K, P681H, N764K, D796Y, Q954H, N969K | Increased transmissibility compared to wildtype (4X) and Delta (2X) strains. Significant decrease in susceptibility to the combination of bamlanivimab and etesevimab monoclonal antibody treatment, but other EUA monoclonal antibody treatments are available. Reduced neutralization by convalescent and post-vaccination sera. |
| BQ.1 | T19I, del24-26, A27S, del69-70, G142D, V213G, R493Q, L452R, F486V, G339D, S371F, S373P, S375F, T276A, D405N, R408S, K417N, N440K, S477N, T478K, E484A, Q498R, N501Y, Y505H, D614G, H655Y, N679K, P681H, N764K, D796Y, Q954H, N969K, K444T, N460K | Increased transmissibility compared to wildtype (4X) and Delta (2X) strains. Significant decrease in susceptibility to the combination of bamlanivimab and etesevimab monoclonal antibody treatment, but other EUA monoclonal antibody treatments are available. Reduced neutralization by convalescent and post-vaccination sera. |
| XBB | R346T, L368I, V445P, G446S, N460K, F486S, F490S, R493Q | Increased transmissibility compared to wildtype and Delta strains. Significant decrease in susceptibility to the combination of bamlanivimab and etesevimab monoclonal antibody treatment, but other EUA monoclonal antibody treatments are available. Reduced neutralization by convalescent and post-vaccination sera. |
| XBB.1.5 | G339H, R346T, L368I, V445P, G446S, N460K, F486P, F490S, R493Q | Increased transmissibility compared to wildtype (4X) and Delta (2X) strains. Significant decrease in susceptibility to the combination of bamlanivimab and etesevimab monoclonal antibody treatment, but other EUA monoclonal antibody treatments are available. Reduced neutralization by convalescent and post-vaccination sera. |
| XBB.1.16 | R346T, L368I, V445P, G446S, N460K, F486S, F486P, F490S, | Increased transmissibility compared to wildtype and Delta strains. |

TABLE 6-continued

| SARS-CoV-2 variants and properties. | | |
|---|---|---|
| Name | Spike Protein Substitutions | Phenotypes |
| | Q493R, E180V, F486P and K478R | Significant decrease in susceptibility to the combination of bamlanivimab and etesevimab monoclonal antibody treatment, but other EUA monoclonal antibody treatments are available. Reduced neutralization by convalescent and post-vaccination sera. |

SARS-CoV

In some embodiments, the target-binding moiety specifically binds an S protein of SARS-CoV. In some embodiments, the S protein is derived from a reference SARS-CoV. In some embodiments, the S protein is derived from a SARS-CoV variant. In some embodiments, target-binding moiety specifically binds an S1 subunit of the S protein of SARS-CoV. Sequences of SARS-CoV S1 proteins are known in the art, including, for example, UniProtKB ID: P59594, UniProt KB ID: P0DTC2, NCBI RefSeq ID: YP_009724390.1, GeneBank ID: AAP41037.1. In some embodiments, SARS-CoV S1 protein comprises the amino acid sequence of SEQ ID NO: 103, described in Table 5.

In some embodiments, the target-binding moiety is an EBD of an ACE2 protein or a fragment thereof that specifically binds to the S1 subunit of an S protein of SARS-CoV. In some embodiments, the target-binding moiety inhibits the binding of SARS-CoV S protein S1 to the cell surface. In some embodiments, the target-binding moiety binds within the RBD of the S1 protein of SARS-CoV, or an antigen-binding fragment thereof. In some embodiments, the target-binding moiety specifically binds to amino acid residues 319-510 of the S1 protein, wherein the numbering is based on SEQ ID NO: 103. In some embodiments, the target-binding moiety is able to cross-neutralize several SARS-CoV isolates. In some embodiments, the target-binding moiety binds to the different conformational epitopes of the RBD of the S1 protein. In some embodiments, SARS-CoV human isolates (e.g., Tor2, GD03T0013) or palm civet (*Paguma larvata*) isolate fusion proteins (e.g., Sz3 S1-Fc) may be used as immunogens to induce high titers of cross-neutralizing target-binding moieties.

In some embodiments, the target-binding moiety is a derivative of any one of the target-binding moieties against the S1 protein of SARS-CoV described herein.

The S protein of SARS-CoV mediates receptor binding and viral entry (i.e., viral infection) of host cells, and is therefore an attractive target for vaccine design. The S protein is a type I transmembrane glycoprotein possessing an S1 domain, comprising amino acid residues 1 to 672 of the S protein. A fragment located in the central region of the S1 domain, amino acid residues 318-510, is defined as the receptor-binding domain. The receptor-binding domain of the S1 protein is a major determinant of SARS-CoV neutralization. Antibodies targeting the S1 protein, and in particular the receptor binding domain, represent a large class of useful therapeutics for prevention and treatment of SARS-CoV infection.

B. Variants

In some embodiments, amino acid sequence variants of the target-binding moieties (e.g., amino acid sequence variants of an EBD of an ACE2 protein or a fragment thereof) of the chimeric proteins provided herein, are contemplated. For example, amino acid sequence variants of the ACE2 proteins or fragments thereof described herein (e.g., hACE2 and animal ACE2 proteins or fragments thereof, described in Tables 3 and 4, respectively), are contemplated. It may be desirable to improve the binding affinity and/or other biological properties of the target-binding moieties. Amino acid sequence variants of a target-binding moiety (e.g., an EBD of an ACE2 protein or a fragment thereof) may be prepared by introducing appropriate modifications into the nucleotide sequence encoding the target-binding moiety, or by peptide synthesis. Such modifications include, for example, deletions from, and/or insertions into and/or substitutions of residues within the amino acid sequences of the target-binding moiety (e.g., an EBD of an ACE2 protein or a fragment thereof). Any combination of deletion, insertion, and substitution can be made to arrive at the final construct, provided that the final construct possesses the desired characteristics, e.g., S protein (such as the S1 subunit of the S protein) binding.

In some embodiments, variants having one or more amino acid substitutions are provided. Amino acid substitutions may be introduced into a target-binding moiety of interest (e.g., an EBD of an ACE2 protein or a fragment thereof) and the products screened for a desired activity, e.g., retained/improved target-binding or decreased immunogenicity.

Conservative substitutions are shown in Table B below.

TABLE B

| Conservative amino acid substitutions | | |
|---|---|---|
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;

b. neutral hydrophilic: Cys, Ser, Thr, Asn, Gln;

c. acidic: Asp, Glu;

d. basic: His, Lys, Arg;

e. residues that influence chain orientation: Gly, Pro;

f. aromatic: Trp, Tyr, Phe.

Non-conservative substitutions will entail exchanging a member of one of these classes for another class.

In some embodiments, substitutions, insertions, or deletions may occur within the target-binding moiety so long as such alterations do not substantially reduce the ability of the target-binding moiety to bind antigen. For example, conservative alterations (e.g., conservative substitutions as provided herein) that do not substantially reduce binding affinity may be made. In some embodiments of the variant target-binding moieties, the target-binding moiety either is unaltered, or contains no more than one, two or three amino acid substitutions.

A useful method for identification of residues or regions of a target-binding moiety that may be targeted for mutagenesis is called "alanine scanning mutagenesis" as described by Cunningham and Wells *Science,* 244:1081-1085 (1989). In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the target-binding moiety with the S protein (e.g., the S1 subunit of the S protein) is affected. Further substitutions may be introduced at the amino acid locations demonstrating functional sensitivity to the initial substitutions. Alternatively, or additionally, a crystal structure of a target-binding moiety-S protein complex can be determined to identify contact points between the target-binding moiety and the S protein. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a target-binding moiety with an N-terminal methionyl residue. Other insertional variants of the target-binding moiety include the fusion to the N- or C-terminus of the target-binding moiety to an enzyme (e.g., for ADEPT) or a polypeptide which increases the serum half-life of the target-binding moiety.

C. Mucoadhesive Peptide Fragments

The chimeric proteins described herein comprise one or more (e.g., 1, 2, 3, 4, or more) mucoadhesive peptide fragments.

In some embodiments, the target-binding moiety comprises the same number of polypeptide chains as the number of mucoadhesive peptide fragment(s) in the chimeric protein. In some embodiments, the target-binding moiety comprises more polypeptide chains than the number of mucoadhesive peptide fragment(s) in the chimeric protein. In some embodiments, each polypeptide chain of the target-binding moiety is coupled to (e.g., fused to) a mucoadhesive peptide fragment. In some embodiments, the target-binding moiety comprises polypeptide chains that are not coupled (e.g., fused to) a mucoadhesive peptide fragment.

In some embodiments, the mucoadhesive peptide fragment is fused to any position in the target-binding moiety that does not interference with binding of the target-binding moiety to the S protein (e.g., the S1 subunit of the S protein). In some embodiments, the mucoadhesive peptide fragment is fused to a site that is distal from the target-binding site. In some embodiments, the mucoadhesive peptide fragment is fused to the C-terminus of the target-binding moiety.

In some embodiments, the chimeric protein comprises a single polypeptide chain comprising the target-binding moiety and a mucoadhesive peptide fragment.

In some embodiments, the mucoadhesive peptide fragment comprises about 10 to about 600 amino acid residues (e.g., positively charged amino acid residues plus non-positively charges amino acid residues). In some embodiments, the mucoadhesive peptide fragment comprises about 10 to about 20 amino acid residues. In some embodiments, the mucoadhesive peptide fragment comprises about 22 to about 30 amino acid residues. In some embodiments, the mucoadhesive peptide fragment comprises about 32 to about 40 amino acid residues. In some embodiments, the mucoadhesive peptide fragment comprises about 42 to about 50 amino acid residues. In some embodiments, the mucoadhesive peptide fragment comprises about 52 to about 60 amino acid residues. In some embodiments, the mucoadhesive peptide fragment comprises about 16 to about 50 amino acid residues. In some embodiments, the mucoadhesive peptide fragment comprises about 20 to about 44 amino acid residues. In some embodiments, the mucoadhesive peptide fragment comprises about 24 to about 40 amino acid residues. In some embodiments, the mucoadhesive peptide fragment comprises about 28 to about 36 amino acid residues. In some embodiments, the mucoadhesive peptide fragment comprises about n amino acid residues, where n is selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 120, 140, 160, 180, 200, 300, 400, 500, 600, or more. In some embodiments, the mucoadhesive peptide fragment comprises about any one of about n amino acid residues, where n is selected from 10-20, 21-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 301-310, 311-320, 321-330, 331-340, 341-350, 351-360, 361-370, 371-380, 381-390, 391-400, 401-410, 411-420, 421-430, 431-440, 441-450, 451-460, 461-470, 471-480, 481-490, 491-500, 501-510, 511-520, 521-530, 531-540, 541-550, 551-560, 561-570, 571-580, 581-590, 591-600, 10-30, 10-40, 10-50, 16-30, 16-40, 16-50, 20-40, 20-50, 24-40, 24-50, 30-50-30-60, 10-60, 12-60, and 10-100. In some embodiments, the mucoadhesive peptide fragment comprises at least about n amino acid residues, where n is selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 120, 140, 160, 180, 200, 300, 400, 500, 600, or more. In some embodiments, the mucoadhesive peptide fragment comprises no more than about n amino acid residues, where n is selected from 600, 500, 400, 300, 200, 180, 160, 140, 120, 100, 90, 80, 70, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, and 10.

In some embodiments, the mucoadhesive peptide fragment comprises about 5 to about 300 positively charged amino acid residues. In some embodiments, the mucoadhesive peptide fragment comprises about 5 to about 10 positively charged amino acid residues. In some embodiments, the mucoadhesive peptide fragment comprises about 11 to about 15 positively charged amino acid residues. In some embodiments, the mucoadhesive peptide fragment comprises about 16 to about 20 positively charged amino acid residues. In some embodiments, the mucoadhesive peptide fragment comprises about 21 to about 25 positively charged amino acid residues. In some embodiments, the mucoadhesive peptide fragment comprises about 26 to about 30 positively charged amino acid residues. In some embodiments, the mucoadhesive peptide fragment comprises about 8 to about 25 positively charged amino acid residues. In some embodiments, the mucoadhesive peptide fragment comprises about 10 to about 22 positively charged amino acid residues. In some embodiments, the mucoadhesive peptide fragment comprises about 12 to about 20 positively charged amino acid residues. In some embodiments, the mucoadhesive peptide fragment comprises about 14 to about 18 positively charged amino acid residues. In some embodiments, the mucoadhesive peptide fragment comprises any one of about n positively charged amino acid residues, where n is selected from 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, or more. In some embodiments, the mucoadhesive peptide fragment comprises about n positively charged amino acid residues, where n is selected from any one of about 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 5-15, 5-20, 5-25, 8-15, 8-20, 8-25, 10-20, 10-25, 12-20, 12-25, 15-25, 15-30, 5-30, 6-30, and 5-50. In some embodiments, the mucoadhesive peptide fragment comprises at least about n positively charged amino acid residues, where n is selected from 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, or more. In some embodiments, the mucoadhesive peptide fragment comprises no more than about n positively charged amino acid residues, where n is selected from 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, and 5.

In some embodiments, the mucoadhesive peptide fragment comprises at least about 5 positively charged amino acid residues (e.g., lysines, arginines, histidines, ornithines, and combinations thereof). In some embodiments, the mucoadhesive peptide fragment comprises at least about 5 positively charged amino acid residues (e.g., lysines, arginines, histidines, ornithines, and combinations thereof). In some embodiments, the mucoadhesive peptide fragment comprises about 5 to about 50 positively charged amino acid residues (e.g., lysines, arginines, histidines, ornithines, and combinations thereof). In some embodiments, the mucoadhesive peptide fragment comprises about 5 to about 30 positively charged amino acid residues (e.g., lysines, arginines, histidines, ornithines, and combinations thereof). In some embodiments, the mucoadhesive peptide fragment comprises about 5, 6, 12, 18, 24 or 30 positively charged amino acid residues (e.g., lysines, arginines, histidines, ornithines, and combinations thereof).

In some embodiments, the chimeric protein comprises two or more mucoadhesive peptide fragments. In some embodiments, each of the two or more mucoadhesive peptide fragments comprises about 5 to about 300 positively charged amino acid residues. In some embodiments, each of the two or more mucoadhesive peptide fragments comprises about 5 to about 10 positively charged amino acid residues. In some embodiments, each of the two or more mucoadhesive peptide fragments comprises about 11 to about 15 positively charged amino acid residues. In some embodiments, each of the two or more mucoadhesive peptide fragments comprises about 16 to about 20 positively charged amino acid residues. In some embodiments, each of the two or more mucoadhesive peptide fragments comprises about 21 to about 25 positively charged amino acid residues. In some embodiments, each of the two or more mucoadhesive peptide fragments comprises about 26 to about 30 positively charged amino acid residues. In some embodiments, each of the two or more mucoadhesive peptide fragments comprises about 8 to about 25 positively charged amino acid residues. In some embodiments, each of the two or more mucoadhesive peptide fragments comprises about 10 to about 22 positively charged amino acid residues. In some embodiments, each of the two or more mucoadhesive peptide fragments comprises about 12 to about 20 positively charged amino acid residues. In some embodiments, each of the two or more mucoadhesive peptide fragments comprises about 14 to about 18 positively charged amino acid residues. In some embodiments, each of the two or more mucoadhesive peptide fragments comprises about n positively charged amino acid residues, where n is selected from 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, or more. In some embodiments, each of the two or more mucoadhesive peptide fragments comprises about n amino acid residues, where n is selected from 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 5-15, 5-20, 5-25, 8-15, 8-20, 8-25, 10-20, 10-25, 12-20, 12-25, 15-25, 15-30, 5-30, 6-30, and 5-50. In some embodiments, each of the two or more mucoadhesive peptide fragments comprises at least about n positively charged amino acid residues, where n is selected from 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, or more. In some embodiments, each of the two or more mucoadhesive peptide fragments comprises no more than about n positively charged amino acid residues, where n is selected from 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, and 5.

In some embodiments, the total number of positively charged amino acid residues in the mucoadhesive peptide fragment(s) in the chimeric protein is about 5 to about 600. In some embodiments, the total number of positively charged amino acid residues in the mucoadhesive peptide fragment(s) in the chimeric protein is about 5 to about 20. In some embodiments, the total number of positively charged amino acid residues in the mucoadhesive peptide fragment(s) in the chimeric protein is about 11 to about 30. In some embodiments, the total number of positively charged amino acid residues in the mucoadhesive peptide fragment(s) in the chimeric protein is about 16 to about 40. In some embodiments, the total number of positively charged amino acid residues in the mucoadhesive peptide fragment(s) in the chimeric protein is about 21 to about 50. In some embodiments, the total number of positively charged amino acid residues in the mucoadhesive peptide fragment(s) in the chimeric protein is about 26 to about 60. In some embodiments, the total number of positively charged amino acid residues in the mucoadhesive peptide fragment(s) in the chimeric protein is about 8 to about 50. In some embodiments, the total number of positively charged amino acid residues in the mucoadhesive peptide fragment(s) in the chimeric protein is about 10 to about 44. In some embodiments, the total number of positively charged amino acid residues in the mucoadhesive peptide fragment(s) in the chimeric protein is about 12 to about 40. In some embodiments, the total number of positively charged amino acid residues in the mucoadhesive peptide fragment(s) in the chimeric protein is about 14 to about 36. In some embodiments, the total number of positively charged amino acid residues in the mucoadhesive peptide fragment(s) in the chimeric protein is about n positively charged amino acid residues, where n is selected from 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 550, 600, or more. In some embodiments, the total number of positively charged amino acid residues in the mucoadhesive peptide fragment(s) in the chimeric protein is about n positively charged amino acid residues, where n is selected from 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-240, 241-250, 251-160, 261-270, 271-280, 281-290, 291-300, 301-310, 311-320, 321-330, 331-340, 341-350, 351-360, 361-370, 371-380, 381-390, 391-400, 401-410, 411-420, 421-430, 431-440, 441-450, 451-460, 461-470, 471-480, 481-490, 491-500, 501-510, 511-520, 521-530, 531-540, 541-550, 551-560, 561-570, 571-580, 581-590, 591-600, 5-15, 5-20, 5-25, 8-15, 8-20, 8-25, 10-20, 10-25, 12-20, 12-25, 15-25, 15-30, 5-30, 6-30, and 5-50. In some embodiments, the total number of positively charged amino acid residues in the mucoadhesive peptide fragment(s) in the chimeric protein is at least about n positively charged amino acid residues, where n is selected from 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, or more. In some embodiments, the total number of positively charged amino acid residues in the mucoadhesive peptide fragment(s) in the chimeric protein is no more than about n positively charged amino acid residues, where n is selected from 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, and 5.

In some embodiments, the number of positively charged amino acid residues in the mucoadhesive peptide fragment(s) per target-binding moiety is about 5 to about 30. In some embodiments, the number of positively charged amino acid residues in the mucoadhesive peptide fragment(s) per target-binding moiety is about 8 to about 25. In some embodiments, the number of positively charged amino acid residues in the mucoadhesive peptide fragment(s) per target-binding moiety is about 10 to about 22. In some embodiments, the number of positively charged amino acid residues in the mucoadhesive peptide fragment(s) per target-binding moiety is about 12 to about 20. In some embodiments, the number of positively charged amino acid residues in the mucoadhesive peptide fragment(s) per target-binding moiety is about 14 to about 18. In some embodiments, the number of positively charged amino acid residues in the mucoadhesive peptide fragment(s) per target-binding moiety is about n positively charged amino acid residues, where n is selected from 5, 6, 7, 8, 9, 10, 11, 12, 13, 14, 15, 16, 17, 18, 19, 20, 21, 22, 23, 24, 25, 26, 27, 28, 29, 30, or more. In some embodiments, the number of positively charged amino acid residues in the mucoadhesive peptide fragment(s) per target-binding moiety is about n positively charged amino acid residues, where n is selected from 5-10, 11-15, 16-20, 21-25, 26-30, 5-15, 5-20, 5-25, 8-15, 8-20, 8-25, 10-20, 10-25, 12-20, 12-25, 15-25, 15-30, 5-30, and 6-30. In some embodiments, the number of positively charged amino acid residues in the mucoadhesive peptide fragment(s) per target-binding moiety is at least about n positively charged amino acid residues, where n is selected from 5, 6, 7, 8, 9, 10, 11, 12, 13, 14, 15, 16, 17, 18, 19, 20, 21, 22, 23, 24, 25, 30, or more. In some embodiments, the number of positively charged amino acid residues in the mucoadhesive peptide fragment(s) per target-binding moiety is no more than about n positively charged amino acid residues, where n is selected from 30, 29, 28, 27, 26, 25, 24, 23, 22, 21, 20, 19, 18, 17, 16, 15, 14, 13, 12, 10, 9, 8, 7, 6, and 5.

The mucoadhesive peptide fragment(s) may comprise any suitable positively charged amino acid residues at physiological pH of the mucosa, including naturally occurring and synthetic amino acid residues such as lysine, arginine, histidine, ornithine, and combinations thereof. In some embodiments, the mucoadhesive peptide fragment comprises lysines only. In some embodiments, the mucoadhesive peptide fragment comprises arginines only. In some embodiments, the mucoadhesive peptide fragment comprises histidines only. In some embodiments, the mucoadhesive peptide fragment comprises ornithines only.

In some embodiments, the mucoadhesive peptide fragment comprises both lysines and arginines. In some embodiments, the mucoadhesive peptide fragment comprises an equal number of lysines and arginines. In some embodiments, the mucoadhesive peptide fragment comprises unequal numbers of lysines and arginines. In some embodiments, the mucoadhesive peptide fragment comprises both lysines and histidines. In some embodiments, the mucoadhesive peptide fragment comprises an equal number of lysines and histidines. In some embodiments, the mucoadhesive peptide fragment comprises unequal numbers of lysines and histidines. In some embodiments, the mucoadhesive peptide fragment comprises both lysines and ornithines. In some embodiments, the mucoadhesive peptide fragment comprises an equal number of lysines and ornithines. In some embodiments, the mucoadhesive peptide fragment comprises unequal numbers of lysines and ornithines. In some embodiments, the mucoadhesive peptide fragment comprises both arginines and ornithines. In some embodiments, the mucoadhesive peptide fragment comprises an equal number of arginines and ornithines. In some embodiments, the mucoadhesive peptide fragment comprises an unequal number of arginines and ornithines. In some embodiments, the mucoadhesive peptide fragment comprises both arginines and histidines. In some embodiments, the mucoadhesive peptide fragment comprises an equal number of arginines and histidines. In some embodiments, the mucoadhesive peptide fragment comprises an unequal number of ornithines and histidines. In some embodiments, the mucoadhesive peptide fragment comprises both ornithines and histidines. In some embodiments, the mucoadhesive peptide fragment comprises an equal number of ornithines and histidines. In some embodiments, the mucoadhesive peptide fragment comprises an unequal number of ornithines and histidines. In some embodiments, the mucoadhesive peptide fragment comprises lysines, arginines, and ornithines. In some embodiments, the mucoadhesive peptide fragment comprises an equal number of lysines, arginines, and ornithines. In some embodiments, the mucoadhesive peptide fragment comprises unequal numbers of lysines, arginines, and ornithines. In some embodiments, the mucoadhesive peptide fragment comprises histidines, arginines, and ornithines. In some embodiments, the mucoadhesive peptide fragment comprises an equal number of histidines, arginines, and ornithines. In some embodiments, the mucoadhesive peptide fragment comprises unequal numbers of histidines, arginines, and ornithines. In some embodiments, the mucoadhesive peptide fragment comprises lysines, histidines, and ornithines. In some embodiments, the mucoadhesive peptide fragment comprises an equal number of lysines, histidines, and ornithines. In some embodiments, the mucoadhesive peptide fragment comprises unequal numbers of lysines, histidines, and ornithines. In some embodiments, the mucoadhesive peptide fragment comprises lysines, arginines, and histidines. In some embodiments, the mucoadhesive peptide fragment comprises an equal number of lysines, arginines, and histidines. In some embodiments, the mucoadhesive peptide fragment comprises unequal numbers of lysines, arginines, and histidines. In some embodiments, the mucoadhesive peptide fragment comprises lysines, arginines, histidines, and ornithines. In some embodiments, the mucoadhesive peptide fragment comprises an equal number of lysines, arginines, histidines, and ornithines. In some embodiments, the mucoadhesive peptide fragment comprises unequal numbers of lysines, arginines, histidines, and ornithines. In some embodiments, the mucoadhesive peptide fragment(s) comprises one or more non-naturally occurring amino acid residues that are positively charged at physiological pH of the mucosa.

In some embodiments, the mucoadhesive peptide fragment has an isoelectric point (pI) higher than the pH of the mucosa. The pH values of various mucosa in human are known. For example, the human nasal mucosa may have a pH range of about 5.5 to about 6.5, about 5.5 to about 6.6, about 6.44 to about 6.91, about 6.4 to about 7.9, or about 6.4 to about 6.5. In some examples, the human nasal mucosa may have a pH of about 6.6. In other examples, the human tracheal mucosa may have a pH range of about 6.1 to about 7.9, or a pH of about 6.71. In further examples, the human bronchial mucosa may have a pH range of about 5.7 to about 6.6 or about 7 to about 7.5. In some examples, the human bronchial mucosa may have a pH of about 6.7, about 7.1, about 6.25, about 6.78, or about 6.58. In some examples, the human mucosa may be diseased. In such examples, smokers may have a sputum mucosa pH of about 7.25 or about 6.82. In other examples, patients suffering with chronic bronchitis may have a sputum mucoid pH of about 7.59 and/or a sputum purulent pH of about 7.83. In other examples, patients suffering with rhinitis may have a nasal mucosa pH range of about 7.2 to about 8.3. In other examples still, patients suffering with the common cold may have a mucosa pH range of about 7.2 to about 8.3.

In some embodiments, at nasal pH (e.g., ~6.5), the various properties (e.g., pI, net charge, and molecular weight) of polycationic peptides described herein may be calculated. In some examples, at nasal pH (e.g., ~6.5), the equivalent of a 20-mer polypeptide may be calculated. The 20-mer polypeptide will be linear, and the size of each polypeptide will be proportional to the molecular weight. The pI and molecular weight of various exemplary 20-mer polypeptides at nasal pH were calculated and are listed in Table 7. The interactions between the positively charged polypeptides and mucosal cells or mucin may primarily occur by charge.

TABLE 7

Exemplary amino acid and corresponding 20-mer polypeptides properties at nasal pH

| Amino acid or polypeptide | pI | Net charge | Molecular weight (Da) |
|---|---|---|---|
| Lysine (K) | 8.8 | +1 | 146.2 |
| Arginine (R) | 10.0 | +1 | 174.2 |
| Histidine (H) | 7.2 | +0.5 | 155.2 |
| K-20 | 11.3 | +20 | 2581.5 |
| R-20 | 13.3 | +20 | 3141.8 |
| H-20 | 8.1 | +10 | 2760.8 |

In some embodiments, the pI range of the mucoadhesive peptide fragment is at least about n, where n is selected from 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.5, 12, 12.5, 13, or more. In some embodiments, the pI range of the mucoadhesive peptide fragment is about 8 to about 14. In some embodiments, the range of pI values of the mucoadhesive peptide fragment is about 8.8 to about 10.0. In some embodiments, the range of pI values of the mucoadhesive peptide fragment is about 11.3 to about 13.3. In some embodiments, the range of pI values of the chimeric protein is at least about n, where n is selected from 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.5, 12, 12.5, 13, or more, including, 8-8.3, 8.3-8.5, 8.5-8.7, 8.7-8.9, 8.9-9.1, 9.1-9.3, 9.3-9.4, 9.4-10, 8-10, 8-9, 9-10, 8-11, 8.5-9.5, 8.76-9.44, 8.77-9.61, and 8.32-9.33.

In some embodiments, the mucoadhesive peptide fragment is a polylysine peptide. In some embodiments, the mucoadhesive peptide fragment is a polylysine peptide having about n contiguous lysines, where n is selected from 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment is a polylysine peptide having about n contiguous lysines, where n is selected from 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, and 5-50.

In some embodiments, the mucoadhesive peptide fragment is a polyhistidine peptide. In some embodiments, the mucoadhesive peptide fragment is a polyhistidine peptide having about n contiguous histidines, where n is selected from 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment is a polyhistidine peptide having about n contiguous histidines, where n is selected from 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, and 5-50.

In some embodiments, the mucoadhesive peptide fragment is a polyarginine peptide. In some embodiments, the mucoadhesive peptide fragment is a polyarginine peptide having about n contiguous arginines, where n is selected from 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment is a polyarginine peptide having about n contiguous arginines, where n is selected from 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, and 5-50.

In some embodiments, the mucoadhesive peptide fragment is a polyornithine peptide. In some embodiments, the mucoadhesive peptide fragment is a polyornithine peptide having about n contiguous ornithines, where n is selected from 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment is a polyornithine peptide having about n contiguous ornithines, where n is selected from 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, and 5-50.

In some embodiments, the mucoadhesive peptide fragment comprises a continuous stretch of positively charged amino acid residues. In some embodiments, the mucoadhesive peptide fragment comprises about n contiguous positive amino acids, such as arginines, histidines, lysines, or ornithines, or combinations thereof, where n is selected from 2, 3, 4, 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment comprises about contiguous positive amino acids, such as arginines, histidines, lysines, or ornithines, or combinations thereof, where n is selected from 2-5, 5-10, 10-15, 15-20, 20-25, 25-30, 30-40, 40-50, 2-15, 2-20, 2-25, 8-15, 8-20, 8-25, 10-20, 10-25, 12-20, 12-25, 15-25, 15-30, 2-30, 6-30, and 2-50. In some embodiments, all positively charged amino acid residues are contiguous with respect to each other.

In some embodiments, the mucoadhesive peptide fragment comprises one or more non-positively charged amino acid residues. In some embodiments, the non-positively charged amino acid residues are non-polar amino acids or polar uncharged amino acids. In some embodiments, the mucoadhesive peptide fragment comprises isoleucine, valine, alanine, tryptophan, leucine, glycine, methionine, proline, phenylalanine, threonine, cysteine, tyrosine, glutamine, serine, asparagine, or combinations thereof. In some embodiments, the mucoadhesive peptide fragment comprises one or more alanine, threonine, cysteine, serine, glutamine, asparagine, or combinations thereof. In some embodiments, the mucoadhesive peptide fragment comprises a combination of one or more isoleucines, valines, alanines, tryptophans, leucines, glycines, methionines, prolines, phenylalanines, threonines, cysteiness, tyrosinse, glutamine, serines, or asparagines. In some embodiments, the mucoadhesive peptide fragment comprises a combination of one or more alanines, threonines, cysteines, serines, glutamines, or asparagines. In some embodiments, the mucoadhesive peptide fragment(s) comprises one or more non-naturally occurring amino acid residues that are non-positively charged at physiological pH of the mucosa.

In some embodiments, the positively charged amino acid residues are interspersed with non-positively charged amino acid residues. In some embodiments, the positively charged amino acid residues are present in every other position in the mucoadhesive peptide fragment. In some embodiments, the positively charged amino acid residues are present in every third position in the mucoadhesive peptide fragment. In some embodiments, the positively charged amino acid residues are present in every fourth position in the mucoadhesive peptide fragment. In some embodiments, the positively charged amino acid residues are randomly dispersed in the mucoadhesive peptide fragment. In some embodiments, the positive charged residues are present in one or more clusters within the mucoadhesive peptide fragment.

In some embodiments, at least about n % of the amino acid residues in the mucoadhesive peptide fragment are positively charged amino acid residues, where n % is selected from 10%, 20%, 30%, 40%, 50%, 60%, 70%, 80%, 90%, 95%, 99%, or more. In some embodiments, all amino acid residues in the mucoadhesive peptide fragment are positively charged. In some embodiments, no more than about n % of the amino acid residues in the mucoadhesive peptide fragment are positively charged amino acid residues, where n % is selected from 99%, 95%, 90%, 80%, 70%, 60%, 50%, 40%, 30%, 20%, and 10%. In some embodiments, about n % of the amino acid residues in the mucoadhesive peptide fragment are positively charged amino acid residues, where n % is selected from 10%-99%, 10%-20%, 20%-30%, 30%-40%, 40%-50%, 50%-60%, 60%-80%, 10%-100%, 10%-30%, 30%-60%, 60%-90%, 20%-50%, and 50%-100%. In some embodiments, at least 50% of the amino acid residues in the mucoadhesive peptide fragment are positively charged amino acid residues.

In some embodiments, at least about n % of the amino acid residues in the mucoadhesive peptide fragment are non-positively charged amino acid residues, where n % is selected from 1%, 2%, 3%, 4%, 5%, 6%, 7%, 8%, 9%, 10%, 20%, 30%, 40%, 50%, or more. In some embodiments, all amino acid residues in the mucoadhesive peptide fragment are positively charged. In some embodiments, no more than about n % of the amino acid residues in the mucoadhesive peptide fragment are non-positively charged amino acid residues, where n % is selected from 50%, 40%, 30%, 20%, 10%, 9%, 8%, 7%, 6%, 5%, 4%, 3%, 2%, and 1%. In some embodiments, about n % of the amino acid residues in the mucoadhesive peptide fragment are non-positively charged amino acid residues, where n % is selected from 1%-5%, 5%-10%, 10%-25%, 25%-50%, 1%-10%, 5%-15%, 10%-20%, 15%-25%, 20%-30%, 25%-35%, 30%-40%, 35%-45%, or 40%-50% of the amino acid residues in the mucoadhesive peptide fragment are positively charged amino acid residues. In some embodiments, no more than 50% of the amino acid residues in the mucoadhesive peptide fragment are non-positively charged amino acid residues.

In some embodiments, the mucoadhesive peptide fragment is no more than about 15 kD. In some embodiments, the mucoadhesive peptide fragment is about 0.5 kD to about 50 kD. In some embodiments, the mucoadhesive peptide fragment is about 0.5 kD to about 15 kD. In some embodiments, the mucoadhesive peptide fragment is about 2 kD to about 12 kD. In some embodiments, the mucoadhesive peptide fragment is about 4 kD to about 10 kD. In some embodiments, the mucoadhesive peptide fragment is about 6 kD to about 14 kD. In some embodiments, the mucoadhesive peptide fragment is about n, where n is selected from 0.5 kD, 1 kD, 2 kD, 3 kD, 4 kD, 5 kD, 6 kD, 7 kD, 8 kD, 9 kD, 10 kD, 11 kD, 12 kD, 13 kD, 14 kD, 15 kD, 20 kD, 25 kD, 30 kD, 35 kD, 40 kD, 45 kD, 50 kD, or more. In some embodiments, the mucoadhesive peptide fragment is about n, where n is selected from 0.5-1 kD, 1-2 kD, 2-3 kD, 4-5 kD, 5-6 kD, 6-7 kD, 8-9 kD, 9-10 kD, 10-11 kD, 11-12 kD, 12-13 kD, 13-14 kD, 14-15 kD, 15-20 kD, 20-25 kD, 25-30 kD, 30-35 kD, 35-40 kD, 40-45 kD, 45-50 kD, or more. In some embodiments, the mucoadhesive peptide fragment at least about n, where n is selected from 0.5 kD, 1 kD, 2 kD, 3 kD, 4 kD, 5 kD, 6 kD, 7 kD, 8 kD, 9 kD, 10 kD, 11 kD, 12 kD, 13 kD, 14 kD, 15 kD, 20 kD, 25 kD, 30 kD, 35 kD, 40 kD, 45 kD, 50 kD, or more. In some embodiments, the mucoadhesive peptide fragment is no more than about n, where n is selected from 50 kD, 45 kD, 40 kD, 35 kD, 30 kD, 25 kD, 20 kD, 15 kD, 14 kD, 13 kD, 12 kD, 11 kD, 10 kD, 9 kD, 8 kD, 7 kD, 6 kD, 5 kD, 4 kD, 3 kD, 2 kD, 1 kD, and 0.5 kD.

In some embodiments, the mucoadhesive peptide fragment does not facilitate penetration of the chimeric protein into a cell of the mucosa. In some embodiments, the mucoadhesive peptide fragment does not comprise a motif in a cell penetrating peptide. In some embodiments, the mucoadhesive peptide is not a cell penetrating peptide.

In some embodiments, the mucoadhesive peptide fragment is not a histidine tag. In some embodiments, the mucoadhesive peptide fragment is not a peptide consisting of, or consisting essentially of, six histidines.

In some embodiments, the mucoadhesive peptide fragment does not disrupt folding of the chimeric protein within a host cell expressing the chimeric protein. In some embodiments, at least about n % of chimeric protein expressed in a mammalian host cell is properly folded, where n % is selected from 20%, 30%, 40%, 50%, 60%, 70%, 80%, 90%, or more.

In some embodiments, the mucoadhesive peptide fragment does not block secretion of the chimeric protein from a host cell expressing the chimeric protein. In some embodiments, at least about n % of chimeric protein expressed in a mammalian host cell is secreted, where n % is selected from 20%, 30%, 40%, 50%, 60%, 70%, 80%, 90%, or more. Without being bound by any theory or hypothesis, proteins with positively charged fragments tend to be trapped in the Golgi apparatus of cells expressing the proteins. The chimeric proteins described herein are readily expressed and secreted by host cells, and do not get trapped in the Golgi apparatus.

In some embodiments, the mucoadhesive peptide fragment does not interfere with the specific binding between the target-binding moiety and the S protein (e.g., the S1 subunit of the S protein). In some embodiments, the mucoadhesive peptide fragment reduces binding between the target-binding moiety and the S protein (e.g., the S1 subunit of the S protein) by no more than about n %, where n % is selected from 50%, 40%, 30%, 20%, 10%, or less.

Exemplary mucoadhesive peptide fragments for incorporation into a chimeric protein of the present disclosure are provided herein and are shown in Table 8.

TABLE 8

Exemplary mucoadhesive peptide fragments

| Mucoadhesive Peptide Fragment | Percentage Positively Charged AA Residues | Sequence | SEQ ID NO |
|---|---|---|---|
| 5H | 100 | HHHHH | 128 |
| 6H | 100 | HHHHHH | 28 |
| 12H | 100 | HHHHHHHHHHHH | 29 |
| 30H | 100 | HHHHHHHHHHHHHHHHHHHHHHHHHHHHHH | 30 |
| 6K | 100 | KKKKKK | 31 |
| 12K | 100 | KKKKKKKKKKKK | 32 |
| 30K | 100 | KKKKKKKKKKKKKKKKKKKKKKKKKKKKKK | 33 |
| 6R | 100 | RRRRRR | 34 |
| 12R | 100 | RRRRRRRRRRRR | 35 |
| 30R | 100 | RRRRRRRRRRRRRRRRRRRRRRRRRRRRRR | 36 |
| 6O | 100 | OOOOOO | 37 |
| 12O | 100 | OOOOOOOOOOOO | 38 |
| 30O | 100 | OOOOOOOOOOOOOOOOOOOOOOOOOOOOOO | 39 |
| 6X-1 | 100 | HHKKOO | 40 |
| 6X-2 | 100 | HORKHR | 41 |
| 6X-3 | 83.3 | HKRSOH | 42 |
| 6X-4 | 83.3 | RRHTHR | 43 |
| 6X-7 | 100 | KKOORR | 44 |
| 6X-5 | 100 | KKHHRR | 45 |
| 6X-6 | 100 | OORRHH | 46 |

TABLE 8-continued

| Exemplary mucoadhesive peptide fragments | | | |
|---|---|---|---|
| Mucoadhesive Peptide Fragment | Percentage Positively Charged AA Residues | Sequence | SEQ ID NO |
| 7X-1 | 85.7 | KKKGKKK | 129 |
| 12X-1 | 100 | HHHKKKRRROOO | 47 |
| 12X-2 | 75 | HHOAKKRCOOQH | 48 |
| 12X-3 | 100 | HRKOORKHHRKK | 49 |
| 12X-4 | 75 | KRAHOKCORKSH | 50 |
| 12X-5 | 100 | KKRROOHHHRRR | 51 |
| 12X-6 | 100 | OOORRRKKKHHH | 52 |
| 12X-7 | 66.6 | KKAHHGKKAHHV | 130 |
| 12X-8 | 66.6 | KKARRGKKARRV | 131 |
| 12X-9 | 66.6 | KLIHKKARVRGK | 132 |
| 15X-1 | 66.6 | ILRRKAHHGKIKKVR | 133 |
| 15X-2 | 75 | GHRVKKAVRHIKRL | 134 |
| 30X-1 | 100 | HKROHKROHKROHKROHKROHKROHKROHK | 53 |
| 30X-2 | 80 | KOHRSOKRHTORHKAHORKCKROKQRKHOS | 54 |
| 30X-3 | 80 | KKROSRRHOTOOHHAROKHCKHROTRHKKS | 55 |
| 30X-4 | 80 | HRKQOHRSOOKTRRRAHROCHHHSRHOTHR | 56 |
| 35X-1 | 65.7 | GRHKAKNHIRRPKSRWKKWHKYRKVHRHKV HKGRR | 57 |
| 40X-2 | 57.5 | WRKVHHYKKQHKNRAHGKLKLRAKIHQRSR MHGKQKHYHR | 58 |
| 42X-1 | 71.4 | AHHKCRRGHKQKILHRRPHKFHRWKRVHKG RHGKKHRRHKHR | 59 |
| 45X-1 | 67 | QHRGKAKYHRTHHVKKQRHGRKNHKVHRHA RKFHKIRRLKCHKKH | 60 |
| 50X-1 | 70 | HNKRFKKGRHVRHSRHKSHRRTHKYHHWRH YRKVHRCKKAHKSHHRVHHK | 61 |
| 50X-2 | 60 | AHGRPHOFKROCKAHOVKHILKRTOSHOYK OVHQRNKOAOKMRKIRGGHK | 62 |

It should be understood that additional mucoadhesive peptide fragments comprising similar percentages of positively charged and/or non-positively charged amino acid residues are also within the scope of the invention.

In some embodiments, the mucoadhesive peptide fragment comprises an amino acid sequence having at least about 90% sequence identity (such as about n % sequence identity, where n % is selected from 91%, 92%, 93%, 94%, 95%, 96%, 97%, 98%, and 99%) to the amino acid sequence of any one of SEQ ID NOs: 28-62 and 128-134. In some embodiments, mucoadhesive peptide fragment comprises the amino acid sequence of any one of SEQ ID NOS: 28-62 and 128-134, or a variant thereof comprising about 1, 2, or 3 amino acid substitutions. In some embodiments, the mucoadhesive peptide fragment comprises the amino acid sequence of any one of SEQ ID NOs: 28-62 and 128-134.

D. Linkers

In some aspects, the target-binding moiety is linked to the mucoadhesive peptide fragment via a linker (such as a peptide linker, also referred herein as a connecting peptide). In some embodiments, the target-binding moiety is not covalently linked to the mucoadhesive peptide fragment. In some embodiments, the mucoadhesive peptide fragment is chemically conjugated to the target-binding moiety, i.e., via a chemical linker.

In some embodiments, the peptide linker is located between the target-binding moiety and the mucoadhesive peptide fragment of the chimeric protein. In some embodiments, the peptide linker is fused to a polypeptide chain of the target-binding moiety. In some embodiments, the linker is fused to the mucoadhesive peptide fragment.

In some embodiments, the mucoadhesive peptide fragment is fused to a polypeptide chain of the target-binding moiety via a peptide linker. In some embodiments, the linker is about 1 to about 20 amino acid residues. In some embodiments, the linker is a glycine-serine linker. In some embodiments, the linker has the amino acid sequence of GGGGS (SEQ ID NO: 79).

The length, the degree of flexibility and/or other properties of the linker may have some influence on properties, including but not limited to the affinity, specificity or avidity for one or more targets of the chimeric protein (e.g., bispecific immune cell engager or engineered receptor) described herein. For example, longer linkers may be selected to ensure that two adjacent binding moieties do not sterically interfere with one another. In some embodiments, a linker (such as peptide linker) comprises flexible residues (such as glycine and serine) so that the adjacent binding moieties are free to move relative to each other. For example, a glycine-serine doublet can be a suitable peptide linker. In some embodiments, the linker is a non-peptide linker. In some embodiments, the linker is a peptide linker. In some embodiments, the linker is a non-cleavable linker. In some embodiments, the linker is a cleavable linker.

Other linker considerations include the effect on physical or pharmacokinetic properties of the resulting chimeric protein (e.g., bispecific immune cell engager or engineered receptor), such as solubility, lipophilicity, hydrophilicity, hydrophobicity, stability (more or less stable as well as planned degradation), rigidity, flexibility, immunogenicity, modulation of target-binding moiety binding, the ability to be incorporated into a micelle or liposome, and the like.

Any one or all of the linkers described herein can be accomplished by any chemical reaction that will bind the two molecules so long as the components or fragments retain their respective activities. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents are useful in coupling protein molecules, such as an Fc fragment. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (see Killen and Lindstrom, *Jour. Immun.* 133:1335-2549 (1984); Jansen et al., Immunological Reviews 62:185-216 (1982); and Vitetta et al., *Science* 238:1098 (1987)).

Linkers that can be applied in the present application are described in the literature (see, for example, Ramakrishnan, S. et al., *Cancer Res.* 44:201-208 (1984) describing use of MBS (M-maleimidobenzoyl-N-hydroxysuccinimide ester)). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. #21558G); (iii) SPDP (succinimidyl-6 [3-(2-pyridyldithio) propionamido]hexanoate (Pierce Chem. Co., Cat. #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to chimeric proteins with different physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form chimeric proteins with increased stability. Disulfide linkages, are in general, less stable than other linkages because the disulfide linkage is cleaved in vitro, resulting in less chimeric protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Any one or all of the linkers described herein can be peptide linkers. The peptide linker may have a naturally occurring sequence, or a non-naturally occurring sequence. For example, a sequence derived from the hinge region of heavy chain only antibodies may be used as the linker. See, for example, WO1996/34103.

The peptide linker can be of any suitable length. In some embodiments, the peptide linker is at least about n amino acids (aa) long, where n is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, and 100. In some embodiments, the peptide linker is no more than about n aa long, where n is selected from 100, 75, 50, 40, 35, 30, 25, 20, 19, 18, 17, 16, 15, 14, 13, 12, 11, 10, 9, 8, 7, 6, 5, or fewer. In some embodiments, the length of the peptide linker is from 1 aa to about 10 aa, about 1 aa to about 20 aa, about 1 aa to about 30 aa, about 5 aa to about 15 aa, about 10 aa to about 25 aa, about 5 aa to about 30 aa, about 10 aa to about 30 aa, about 30 aa to about 50 aa, about 50 aa to about 100 aa, or about 1 aa to about 100 aa.

In some embodiments, the peptide linker is a stable linker, which is not cleavable by a protease. In some embodiments, the peptide linker is cleavable by a protease.

In some embodiments, the peptide linker tends not to adopt a rigid three-dimensional structure, but rather provide flexibility to a polypeptide. In some embodiments, the peptide linker is a flexible linker. Exemplary flexible linkers include glycine polymers $(G)_n$, where n≥1, glycine-serine polymers (including, for example, $GS(GS)_n$, where n≥0 (SEQ ID NO: 80), $(GSGGS)_n$, where n≥1 (SEQ ID NO: 81), $(GGGGS)_n$, where n≥1 (SEQ ID NO: 82), and $(GGGS)_n$, where n≥1 (SEQ ID NO: 83)), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine and is much less restricted than residues with longer side chains (see Scheraga, *Rev. Computational Chem.* 11 173-142 (1992)). The ordinarily skilled artisan will recognize that design of a chimeric protein can include linkers that are all or partially flexible, such that the linker can include a flexible linker portion as well as one or more portions that confer less flexible structure to provide a desired chimeric protein structure.

Natural linkers adopt various conformations in secondary structure, such as helical, β-strand, coil/bend and turns, to exert their functions. Linkers in an a-helix structure might serve as rigid spacers to effectively separate protein domains, thus reducing their unfavorable interactions. Non-helical linkers with Pro-rich sequence could increase the linker rigidity and function in reducing inter-domain interference.

Additional linkers may be used in the chimeric proteins of the present application for purposes of stability. For example, in some embodiments, the linker stabilizes the chimeric protein. In some embodiments, the linker increases, the serum half-life of the chimeric protein in vivo, the avidity of the chimeric protein to the S protein in vitro, the number of chimeric proteins in vitro, and/or the effective amount of the chimeric protein delivered to a nasal cavity in vivo. In some embodiments, the linker comprises an oligomerization or multimerization domain. In some embodiments, the oligomerization or multimerization domain is from a naturally occurring protein. In some embodiments, the oligomerization or multimerization domain is from a non-naturally occurring protein. Exemplary linkers (e.g., peptide linkers and domains to be included in linkers) are shown in Table 9.

TABLE 9

Exemplary peptide linkers and linker domains

| Linker or Multimerization Domain | Cluster | Exemplary Sequence | SEQ ID NO | Reference |
|---|---|---|---|---|
| Immunoglobulin Fc region ($CH_2CH_3$); "Fc1" | Dimer | TCPPCPAPELLGGPSVFLFPPKPKDTLMISRTP EVTCVVVDVSHEDPEVKFNWYVDGVEVHNA KTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSL SPGK | 63 | Lobner et al., *Immunol. Rev.*, 270(1)113-31 (2016) |
| Immunoglobulin Fc region ($CH_2CH_3CH_4$) | Dimer | PPKVSVFVPPRDGFFGNPRKSKLICQATGFSPR QIQVSWLREGKQVGSGVTTDQVQAEAKESGP TTYKVTSTLTIKESDWLSQSMFTCRVDHRGLT FQQNASSMCVPDQDTAIRVFAIPPSFASIFLTK STKLTCLVTDLTTYDSVTISWTRQNGEAVKT HTNISESHPNATFSAVGEASICEDDWNSGERF TCTVTHTDLPSPLKQTISRPKGVALHRPDVYL LPPAREQLNLRESATITCLVTGFSPADVFVQW MQRGQPLSPEKYVTSAPMPEPQAPGRYFAHSI LTVSEEEWNTGETYTCVVAHEALPNRVTERT VDKSTGKPTLYNVSLVMSDTAGTCY | 94 | pir\|\|S37768 |
| Immunoglobulin $C_L$ | Dimer (pairing with $CH_1$) | GQPKANPTVTLFPPSSEELQANKATLVCLISDF YPGAVTVAWKADGSPVKAGVETTKPSKQSN NKYAASSYLSLTPEQWKSHRSYSCQVTHEGS TVEKTVAPTECS | 64 | Lobner et al., *Immunol. Rev.*, 270(1)113-31 (2016) |
| Immunoglobulin $CH_1$ | Dimer (pairing with $C_L$) | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK RVEPKSC | 65 | Lobner et al., *Immunol. Rev.*, 270(1)113-31 (2016) |
| Immunoglobulin $CH_2$ | Dimer (pairing with $CH_2$) | TCPPCPAPELLGGPSVFLFPPKPKDTLMISRTP EVTCVVVDVSHEDPEVKFNWYVDGVEVHNA KTKPREEQYNSTYRVVSVLTVLHQDWLNGK EYKCKVSNKALPAPIEKTISKAKGQPRE | 66 | Lobner et al., *Immunol. Rev.*, 270(1)113-31 (2016) |
| Immunoglobulin $CH_3$ | Dimer (pairing with $CH_3$) | PQVYTLPPSRDELTKNQVSLTCLVKGFYPSDI AVEWESNGQPENNYKTTPPVLDSDGSFFLYS KLTVDKSRWQQGNVFSCSVMHEALHNHYTQ KSLSLSPGK | 67 | Lobner et al., *Immunol. Rev.*, 270(1)113-31 (2016) |
| Immunoglobulin $CH_4$ | Dimer (pairing with $CH_4$) | PDVYLLPPAREQLNLRESATITCLVTGFSPAD VFVQWMQRGQPLSPEKYVTSAPMPEPQAPGR YFAHSILTVSEEEWNTGETYTCVVAHEALPN RVTERTVDKSTGK | 68 | pir\|\|S37768 |
| Alkaline phosphatase | Dimer | MWWRLWWLLLLLLLLWGSSASAAIIPVEEEN PDFWNREAAEALGAAKKLQPAQTAAKNLIIF LGDGMGVSTVTAARILKGQKKDKLGPEIPLA MDRFPYVALSKTYNVDKHVPDSGATATAYL CGVKGNFQTIGLSAAARFNQCNTTRGNEVISV MNRAKKAGKSVGVVTTTRVQHASPAGTYAH TVNRNWYSDADVPASARQEGCQDIATQLISN MDIDVILGGGRKYMFRMGTPDPEYPDDYSQG GTRLDGKNLVQEWLAKRQGARYVWNRTEL | 69 | BBD75655.1 |

TABLE 9-continued

| Exemplary peptide linkers and linker domains | | | | |
|---|---|---|---|---|
| Linker or Multimerization Domain | Cluster | Exemplary Sequence | SEQ ID NO | Reference |
| | | MQASLDPSVTHLMGLFEPGDMKYEIHRDSTL DPSLMEMTEAALRLLSRNPRGFFLFVEGGRID HGHHESRAYRALTETIMFDDAIERAGQLTSEE DTLSLVTADHSHVFSFGGYPLRGSSIFGLAPG KARDRKAYTVLLYGNGPGYVLKDGARPDVT ESESGSPEYRQQSAVPLDEETHAGEDVAVFA RGPQAHLVHGVQEQTFIAHVMAFAAC LEPYTACDLAPPAGTTDAAHPGYSRVGAAGR FEQT | | |
| Glutathione-s-transferase (GST) | Dimer | MKLVGSYTSPFVRKLSILLLEKGITFEFINELP YNADNGVAQFNPLGKVPVLVTEEGECWFDSP IIAEYIELMNVAPAMLPRDPLESLRVRKIEALA DGIMDAGLVSVREQARPAAQQSEDELLRQRE KINRSLDVLEGYLVDGTLKTDTVNLATIAIAC AVGYLNFRRVAPGWCVDRPHLVKLVENLFS RESFARTEPPKA | 70 | WP_000779792 |
| bHLH-Leucine Zipper | Trimer | LENHSRRLEMTNKQLWLRIQEL | 71 | Napolitano and Ballabio, *J. Cell Sci.*, 129(13):2475-81 (2016) |
| Leucine/ Isoleucine Zipper (bIZIP) | Trimer | LSIIAICLGSLGLILIIILLSVVVWKLL | 72 | Branttie and Dutch, *J. Gen Virol.*, 101(5):467-472 (2020) |
| Collagen-like Peptide | Trimer | GPP(GPP)$_n$, where n ≥ 0 | 73 | Fan et al., *FASEB J.*, 22:3795-3804 (2008). |
| p53 Tetramerization Domain | Tetramer | EYFTLQIRGRERFEMFRELNEALELKDAQAG | 74 | Gencel-Augusto et al., *Genes Dev.*, 34(17-18):1128-1146 (2020) |
| Streptavidin (SA) | Tetramer | MAEAGITGTWYNQLGSTFIVTAGADGALTGT YESAVGNAEGDYVLTGRYDSAPATDGSGTAL GWTVAWKNNYRNAHSATTWSGQYVGGAEA RINTQWLLTSGTTEANAWKSTLVGHDTFTKV KPSAAS | 75 | Chivers et al., *Biochem J.*, 435(Pt1):55-63 (2011) |
| T4 Fibritin (T4F) | Trimer | GYIPEAPRDGQAYVRKDGEWVLLSTFL | 76 | Yang et al., *J. Virol.*, 76(9):4634-42 (2002) |
| COMP (cartilage oligomeric matrix protein) | Pentamer | GPQMLRELGETNAALQDVRELLRQQVREITF LKNTVMEBDAC | 77 | Holler et al., *J. Immunol. Methods*, 237:159-173 (2000) |
| Dextramers + SA | 3, 6 or 13 SA per Dextramer | Dextran polymer scaffold | N/A | Dolton et al., *Clin. Exp. Immunol.*, 177(1):47-63 (2014) |
| DMGS + SA | Octamers | Di-maleimide-di-glycine-serine | N/A | Guillaume et al., *J. Biol. Chem.*, 278:P4500-4509 (2003) |

TABLE 9-continued

| Exemplary peptide linkers and linker domains | | | | |
|---|---|---|---|---|
| Linker or Multimerization Domain | Cluster | Exemplary Sequence | SEQ ID NO | Reference |
| Linker A | N/A | SRGGGGSGGGGSGGGGSLEMA | 78 | N/A |
| Linker 1 | N/A | GGGGS | 79 | N/A |
| Linker 2 | N/A | GS(GS)$_n$, where n ≥ 0 | 80 | N/A |
| Linker 3 | N/A | (GSGGS)$_n$, where n ≥ 1 | 81 | N/A |
| Linker 4 | N/A | (GGGGS)$_n$, where n ≥ 1 | 82 | N/A |
| Linker 5 | N/A | (GGGS)$_n$, where n ≥ 1 | 83 | N/A |
| (GPP)$_{10}$ | N/A | GPPGPPGPPGPPGPPGPPGPPGPPGPPGPP | 109 | N/A |

Any of the linkers described in Table 9 are compatible with the chimeric proteins provided herein. In some embodiments, the mucoadhesive peptide fragment is fused to a polypeptide chain of the target-binding moiety via any of the linkers provided in Table 9, or variants thereof. In some embodiments, the mucoadhesive peptide fragment is fused to a polypeptide chain of the target-binding moiety via a linker comprising at least about 90% sequence identity (such as about n % sequence identity, where n % is selected from 91%, 92%, 93%, 94%, 95%, 96%, 97%, 98%, and 99%) to the amino acid sequence of any one of SEQ ID NOs: 63-83, 94, and 109. In some embodiments, the linker comprises the amino acid sequence of any one of SEQ ID NOs: 63-83, 94, and 109. It should be understood that the linkers provided in Table 9 are exemplary, and other linkers with similar properties would similarly be compatible with the chimeric proteins provided herein.

In some embodiments, the peptide linker comprises an enzymatic tag, such as a detectable enzymatic tag. In some embodiments, the enzymatic tag functions as a dimer. In some embodiments, the enzymatic tag is an alkaline phosphatase. In some embodiments, the enzymatic tag is a glutathione-s-transferase (GST).

Additional peptide linkers or useful domains to be included in linkers described herein may be used to facilitate stable protein: protein interactions in the chimeric proteins of the present invention. In some embodiments, the linker comprises a domain that facilitates protein: protein interactions. In some embodiments, the linker comprises one or more heptad repeats. The term "heptad repeat" as used herein refers to a structural motif that consists of a repeating pattern of seven amino acids. In some embodiments, the heptad repeat comprises the repeating pattern: "H PPHCPC", wherein "H" represents a hydrophobic amino acid residue, "C" typically represents a charged amino acid residue, and "P" represents a polar (hydrophilic) amino acid residue. In some embodiments, the linker comprises the heptad repeats of a basic helix-loop-helix leucine zipper (bZIP) domain. In some embodiments, the linker comprises the heptad repeats of a basic isoleucine bZIP domain. In some embodiments, the heptad repeat forms a protein trimer.

Glycine-X-Y repeats (e.g., GPP(GPP)$_n$, where n≥0 (SEQ ID NO: 73)) have been shown not to interfere with the functionality or safety profile of chimeric proteins. In some embodiments, the linker comprises one or more (GPP)$_n$, where n≥1, motifs. In some embodiments, the linker comprises a collagen-like protein. In some embodiments, the collagen-like protein forms a protein trimer.

Other, higher order, multimerization domains may be incorporated in the linkers provided herein. In some embodiments, the multimerization domains may form self-assembling complexes. In some embodiments, the linker comprises an affinity moiety. In some embodiments, the linker comprises a streptavidin (SA) protein. In some embodiments, the streptavidin protein forms a tetramer with biotin molecules. In some embodiments, the linker comprises a dextran scaffold domain. In some embodiments, the linker comprises a SA protein and a dextran scaffold domain. In some embodiments, the linker comprises one or more maleimide polymers (DMGS). In some embodiments, the linker comprises one or more malemide polymers and a SA protein. In some embodiments, the linker comprises a p53 tetramerization domain. In some embodiments, the linker comprises a bacteriophage T7 fibritin protein, or a portion thereof. In some embodiments, the linker comprises the C-terminal 27 amino acids of the bacteriophage T7 fibritin protein. In some embodiments, the C-terminal 27 amino acids of the bacteriophage T7 fibritin protein forms a trimeric complex. In some embodiments, the linker comprises one or more coiled-coil structural domains. In some embodiments, the linker comprises a cartilage oligomeric matrix protein (COMP), or a portion thereof. In some embodiments, the liner comprises a coiled-coil domain of the COMP. In some embodiments, the coiled-coil domain of the COMP forms a pentameric complex.

Antibody and Fc Region Linkers

In some embodiments, the peptide linker comprises a constant region of a full-length antibody, or a fragment thereof. The fragment thereof refers to a fragment of the constant region of a full-length antibody. In some embodiments, the peptide linker comprises the complete constant region of a full-length antibody. In some embodiments wherein the full-length antibody is IgG, IgA, or IgD, the peptide linker comprises the $CH_1$, $CH_2$, and $CH_3$ domains. In some embodiments wherein the full-length antibody is IgE or IgM, the peptide linker comprises the $CH_1$, $CH_2$, $CH_3$, and $CH_4$ domains. In some embodiments, the peptide linker comprises a fragment of a constant region of a full-length antibody. In some embodiments, the peptide linker comprises the constant region of a light chain of a full-length antibody or a fragment thereof. In some embodiments, the peptide linker comprises a $CH_1$ domain or a fragment thereof. In some embodiments, the peptide linker comprises a $CH_2$ domain or a fragment thereof. In some embodiments, the peptide linker comprises a $CH_3$ domain or a fragment thereof. In some embodiments, the peptide linker comprises a $CH_4$ domain or a fragment thereof. In some embodiments, the peptide linker comprises a $C_L$ domain or a fragment thereof. In some embodiments, the peptide linker further comprises an antibody hinge domain or a fragment thereof.

Fc regions, or fragments thereof, may be used as the peptide linker or a portion thereof. The term "Fc region," "Fc domain" or "Fc" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., *Sequences of Proteins of Immunological Interest,* 5th Ed. Public Health Service, National Institutes of Health, Bethesda, MD, 1991. The Fc region may facilitate dimerization and retain antibody-like properties, including physicochemical characteristics for expression, purification and storage, and long serum half-life in vivo. Such properties would be advantageous to the chimeric proteins provided herein. In some embodiments, the peptide linker comprises an Fc region or a fragment thereof. In some embodiments, the Fc region comprises a $CH_2$ and $CH_3$ domain. In some embodiments, the Fc region comprises a $CH_2$, $CH_3$, and $CH_4$ domain.

In some embodiments, the Fc fragment comprises an immunoglobulin IgG heavy chain constant region comprising a hinge region (starting at Cys226), an IgG $CH_2$ domain and $CH_3$ domain. The term "hinge region" or "hinge sequence" as used herein refers to the amino acid sequence located between the linker and the $CH_2$ domain. In some embodiments, the chimeric protein comprises an Fc fragment comprising a hinge region. In some embodiments, the chimeric protein comprises an Fc fragment that does not comprise the hinge region.

In some embodiments, the peptide linker comprises an Fc fragment selected from the group consisting of Fc fragments from IgG, IgA, IgD, IgE, IgM, and combinations and hybrids thereof. IgG's, IgA's and IgD's Fc fragments comprise $CH_2$ and $CH_3$, while IgE's and IgM's Fc fragments comprise $CH_2$, $CH_3$, and $CH_4$. In some embodiments, the Fc fragment is derived from a human IgG. In some embodiments, the Fc fragment comprises the Fc region of human $IgG_1$, $IgG_2$, $IgG_3$, $IgG_4$, or a combination or hybrid IgG. In some embodiments, the Fc fragment is an $IgG_1$ Fc fragment. In some embodiments, the Fc fragment comprises the $CH_2$ and $CH_3$ domains of $IgG_1$. In some embodiments, the Fc fragment is an $IgG_4$ Fc fragment. In some embodiments, the Fc fragment comprises the $CH_2$ and $CH_3$ domains of $IgG_4$. $IgG_4$ Fc is known to exhibit less effector activity than $IgG_1$ Fc, and thus may be desirable for some applications. In some embodiments, the Fc fragment is derived from of a mouse immunoglobulin.

In some embodiments, the IgG $CH_2$ domain starts at Ala231. In some embodiments, the $CH_3$ domain starts at Gly341. It is understood that the C-terminus Lys residue of human IgG can be optionally absent. It is also understood that conservative amino acid substitutions of the Fc region without affecting the desired structure and/or stability of Fc is contemplated within the scope of the invention.

In some embodiments of the chimeric proteins disclosed herein, especially the embodiments wherein the chimeric protein comprises an Fc region or a fragment thereof such as $CH_2$, the chimeric protein binds to or recruits a component of the complement system, known as the C1 complex (C1qC1r2Cls2). Such recruitment can initiate a cleavage cascade involving C2, C3, C4, and C5, and subsequently trigger microbial clearance. The microbial clearance can result from the so-called "classical complement pathway," which depends on further downstream complement components, e.g., the membrane attack complex (MAC), thereby killing the microbial targets, e.g., bacterial cells or enveloped viruses. See Mellors et al., 2020. Microbial clearance may also be achieved through a C1- and C4-dependent antiviral mechanism that is independent of downstream complement components. With assistance from C1, which is recruited by Fc or just $CH_2$ (a fragment of Fc), C4 directly inactivates the virus capsid and neutralizes viruses. See Bottermann et al., *Cell Host & Microbe,* 25:617-629 (2019). As used herein, the term "activation of the complement pathway" includes activation of the classical complement pathway and/or the C4-dependent antiviral pathway.

Additionally, peptide linkers comprising any of the Fc variants known in the art, or combinations thereof, are contemplated. In some embodiments, the Fc fragment comprises sequence that has been altered or otherwise changed so that it has enhanced C1 recruitment, complement dependent cytotoxicity (CDC), or antibody dependent cellular cytotoxicity (ADCC) effector function.

In some embodiments, each chain of the Fe fragment is fused to the same entity. In some embodiments, the chimeric protein comprises two identical target-binding moieties described herein (e.g., identical ACE2 proteins or fragments thereof), each fused with one chain of the Fc fragment. In some embodiments, the two chains of the Fc fragment are identical. In some embodiments, the chimeric comprising the Fc fragment is a homodimer.

In some embodiments, each chain of the Fc fragment is fused to a different entity. In some embodiments, the target-binding moiety comprises two different target-binding moieties (e.g., two different ACE2 proteins or fragments thereof), each fused to one chain of the Fc fragment. In some embodiments, the two target-binding moieties are different, but both specifically recognize an S protein (e.g., an S1 subunit of the S protein). In some embodiments, the target-binding is monovalent, i.e., only one target-binding moiety is fused to one chain of the Fc fragment, and the second chain of the Fc fragment is not fused to a target-binding moiety, respectively. In some embodiments, the target-binding moiety comprising the Fc fragment is a heterodimer.

Heterodimerization of non-identical polypeptides in the target-binding moiety can be facilitated by methods known in the art, including without limitation, heterodimerization by the knob-into-hole technology. The structure and assembly method of the knob-into-hole technology can be found in, e.g., U.S. Pat. Nos. 5,821,333, 7,642,228, US 2011/0287009, and PCT/US2012/059810, hereby incorporated by reference in their entireties. This technology was developed by introducing a "knob" (or a protuberance) by replacing a small amino acid residue with a large one in the $CH_3$ domain of one Fc and introducing a "hole" (or a cavity) in the $CH_3$ domain of the other Fc by replacing one or more large amino acid residues with smaller ones. In some embodiments, one chain of the Fc fragment in the chimeric protein comprises a knob, and the second chain of the Fc fragment comprises a hole.

The preferred residues for the formation of a knob are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the knob has a small side chain volume, such as alanine, asparagine, aspartic acid, glycine, serine, threonine or valine. Exemplary amino acid substitutions in the $CH_3$ domain for forming the knob include without limitation the T366W, T366Y or F405W substitution.

The preferred residues for the formation of a hole are usually naturally occurring amino acid residues and are preferably selected from alanine (A), serine(S), threonine (T) and valine (V). In one embodiment, the original residue for the formation of the hole has a large side chain volume, such as tyrosine, arginine, phenylalanine or tryptophan. Exemplary amino acid substitutions in the $CH_3$ domain for generating the hole include without limitation the T366S, L368A, F405A, Y407A, Y407T and Y407V substitutions. In certain embodiments, the knob comprises T366W substitution, and the hole comprises the T366S/L368A/Y407V substitutions. It is understood that other modifications to the Fc region known in the art that facilitate heterodimerization are also contemplated and encompassed by the instant application.

III. Methods of Prevention and Treatment, Methods of Killing a Virus, Methods of Neutralizing a Virus, Methods of Activating Complement Pathway The present application further provides methods of preventing or treating an infection caused by a coronavirus in an individual, comprising administering to the individual an effective amount of any one of the chimeric proteins described herein, or a cocktail composition of chimeric proteins described herein. In some embodiments, the method comprises administering to the individual a pharmaceutical composition, such as any of the pharmaceutical compositions provided herein, comprising an effective amount of any one of the chimeric proteins described herein, or a cocktail composition of chimeric proteins described herein. In some embodiments, the chimeric protein comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof. In some embodiments, the method is for preventing an infection caused by a coronavirus, such as SARS-CoV-2, including SARS-CoV-2 variants, in an individual. In some embodiments, the method is for treating an infection caused by a coronavirus, such as SARS-CoV-2, including SARS-CoV-2 variants, in an individual. In some embodiments, the method is for activation of complement pathway in an individual. In some embodiments, the method is an in vitro method for killing or neutralizing a coronavirus. In some embodiments, the method is for killing or neutralizing a coronavirus, such as SARS-CoV-2, including SARS-CoV-2 variants, in an individual. In some embodiments, the method of for preventing, treating, or reducing infection caused by a coronavirus in an individual, wherein at least one virus is killed or neutralized on the mucosa. Use of the chimeric proteins in prevention or treatment of an infection and use of the chimeric proteins in the preparation of a medicament for preventing or treating an infection, for activating the complement pathway, or for killing or neutralizing a virus, are also provided. Methods of veterinary use are also contemplated herein.

In some embodiments, there is provided a method of preventing or treating an infection caused by a coronavirus or variant thereof that infects through a mucosa in an individual, comprising administering to the individual an effective amount of a chimeric protein comprising: (a) a target-binding moiety comprising an EBD of an ACE2 protein or a fragment thereof that specifically binds to an S protein; and (b) a mucoadhesive peptide fragment comprising at least about 5 positively charged amino acid residues, wherein the mucoadhesive peptide fragment facilitates attachment of the chimeric protein to the mucosa.

In some embodiments, there is provided a method of activating the complement pathway in an individual infected with a coronavirus or variant thereof, comprising administering to the individual an effective amount of a chimeric protein comprising: (a) a target-binding moiety comprising an EBD of an ACE2 protein or a fragment thereof that specifically binds to an S protein; and (b) a mucoadhesive peptide fragment comprising at least about 5 positively charged amino acid residues, wherein the mucoadhesive peptide fragment facilitates attachment of the chimeric protein to a mucosa. In some embodiments, the chimeric protein comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof. In some embodiments, at least one coronavirus is killed or neutralized on the mucosa.

In some embodiments, there is provided a method of killing or neutralizing a coronavirus in an individual, comprising administering to the individual an effective amount of a chimeric protein comprising: (a) a target-binding moiety comprising an EBD of an ACE2 protein or a fragment thereof that specifically binds to an S protein; and (b) a mucoadhesive peptide fragment comprising at least about 5 positively charged amino acid residues, wherein the mucoadhesive peptide fragment facilitates attachment of the chimeric protein to a mucosa. In some embodiments, the chimeric protein comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof. In some embodiments, at least one coronavirus is killed or neutralized on the mucosa. In some embodiments, the killing or neutralization is via activation of the complement pathway.

In some embodiments, there is provided an in vitro method of killing or neutralizing a coronavirus, comprising contacting a coronavirus with a chimeric protein comprising: (a) a target-binding moiety comprising an EBD of an ACE2 protein or a fragment thereof that specifically binds to an S protein; and (b) a mucoadhesive peptide fragment comprising at least about 5 positively charged amino acid residues, wherein the mucoadhesive peptide fragment facilitates attachment of the chimeric protein to a mucosa, in the presence of at least one component of the complement system. In some embodiments, the at least one component of the complement system is C1, C4, or membrane attack complex (MAC). In some embodiments, the at least one component of the complement system is C1. In some embodiments, the at least one component of the complement system is C4. In some embodiments, the C4 is involved in the neutralization of the virus. In some embodiments, the at least one component of the complement system is MAC. In some embodiments, the MAC is involved in the killing of the virus. In some embodiments, the chimeric protein comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof. In some embodiments, at least one coronavirus is killed or neutralized on the mucosa. In some embodiments, the killing or neutralization is via activation of the complement pathway.

In some embodiments, there is provided a method of preventing, treating, or reducing infection caused by a coronavirus in an individual, comprising administering to the individual a chimeric protein comprising: (a) a target-binding moiety comprising an EBD of an ACE2 protein or a fragment thereof that specifically binds to an S protein; and (b) a mucoadhesive peptide fragment comprising at least about 5 positively charged amino acid residues, wherein the mucoadhesive peptide fragment facilitates attachment of the chimeric protein to a mucosa, wherein at least one coronavirus is killed or neutralized on the mucosa. In some embodiments, the chimeric protein comprises a peptide linker comprising an Fc region or a fragment thereof. In some embodiments, the peptide linker comprises a $CH_1$, $CH_2$, $CH_3$, $CH_4$, and/or $C_L$ domain or a fragment thereof. In some embodiments, the peptide linker comprises a $CH_2$ domain or a fragment thereof. In some embodiments, the peptide linker further comprises an antibody hinge domain or a fragment thereof. In some embodiments, the chimeric protein induces an immune response in the individual. In some embodiments, the chimeric protein activates the complement pathway in the individual. In some embodiments, the at least one coronavirus is killed or neutralized on the mucosa via activation of the complement pathway.

In some embodiments, the chimeric protein is administered to the individual before the individual is exposed to the coronavirus virus or variant thereof. In some embodiments, the chimeric protein is administered to the individual within about n hours from exposure of the individual to the coronavirus virus or variant thereof, where n is selected from 72, 48, 36, 24, 12, 6, 4, or less. In some embodiments, administration of the chimeric protein to the individual protects the individual from infection by the coronavirus for about n days, where n is selected from 1, 2, 3, 4, 5, 6, 7, 8, 9, 10, 11, 12, 13, 14, or more. In some embodiments, the chimeric protein is administered topically to the mucosa. In some embodiments, the chimeric protein is administered via a nasal spray, an inhaler, a nebulizer, or an eye drop. In some embodiments, the chimeric protein is administered to both nostrils of the individual. In some embodiments, the chimeric protein is administered once every two days, once daily, or twice daily.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about n years old, where n is selected from 50, 40, 30, 25, 20, 15, and 10). In some embodiments, the individual is about 60 years old or older (including for example older than about n years old, where n is selected from 70, 80, 90, and 100). In some embodiments, the individual has not been exposed to the coronavirus virus or variant thereof. In some embodiments, the individual is diagnosed with a coronavirus infection, such as a SARS-CoV-2 infection. In some embodiments, the individual is diagnosed with a SARS-CoV-2 variant infection, such as a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (B.1.1.28.1) variant, an A.23.1 variant, a CAL.20C variant, a B.1.427 variant, a B.1.429 variant, a B.1.525 variant, P.1.351 variant, a BA.5.1.1 variant, a BQ.1 variant, a XBB variant, a XBB.1.5 variant, and a XBB.1.16 variant. In some embodiments, the individual is at a risk of developing severe symptoms of the infection (e.g., coronavirus infection). In some embodiments, the individual has an underlying medical condition, such as cardiovascular disease, diabetes, chronic respiratory disease, and/or cancer.

In some embodiments, the method is for preventing or treating infection by one or more coronavirus variants (e.g., SARS-CoV-2 variants). In some embodiments, the method prevents or treats infection by a plurality (e.g., 2, 3, 4, 5, 6, 7, 8, 9, 10, or more) of coronavirus variants. In some embodiments, the method prevents or treats infection by a plurality (e.g., 2, 3, 4, 5, 6, 7, 8, 9, 10, or more) of SARS-CoV-2 variants. In some embodiments, the one or more SARS-CoV-2 variants are selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (B.1.1.28.1) variant, an A.23.1 variant, a CAL.20C variant, a B.1.427 variant, a B.1.429 variant, a B.1.525 variant, a P.1.351 variant, a BA.5.1.1 variant, a BQ.1 variant, a XBB variant, a XBB.1.5 variant, and a XBB.1.16 variant.

In some embodiments, there is provided a method of treating or preventing infection of an individual by a plurality of coronavirus variants (e.g., SARS-CoV-2 variants), comprising administering to the individual an effective amount of a pharmaceutical composition (e.g., a cocktail composition) comprising a plurality of chimeric proteins, wherein the plurality of chimeric proteins each comprises: (a) a target-binding moiety comprising an EBD of an ACE2 protein or a fragment thereof that specifically binds to an S protein; and (b) a mucoadhesive peptide fragment comprising at least about 5 positively charged amino acid residues, wherein the mucoadhesive peptide fragment facilitates attachment of the chimeric protein to a mucosa.

In some embodiments, the plurality of chimeric proteins each comprise a different target-binding moiety that specifically recognize different coronavirus variants (e.g., SARS-CoV-2 variants). For example, the pharmaceutical composition may comprise a cocktail of chimeric proteins each comprising a target-binding fragment derived from a different ACE2 protein or a fragment described herein or known in the art. In some embodiments, the mucoadhesive peptide fragment comprises at least 5 positively charged amino acid residues interspersed with one or more non-positively charged amino acid residues. In some embodiments, the chimeric protein is administered via a nasal spray. In some embodiments, the chimeric protein, e.g., any of the chimeric proteins comprising ACE2 peptides or a fragment thereof of the present application, is administered as a single agent, or in combination with a second, third, or fourth agent (including, e.g., anti-viral drugs, convalescent plasma, anti-inflammatory drugs etc.) to treat the infection, kill the virus, neutralize the virus, and/or activate the complement pathway.

Efficacy of the treatments can be evaluated, for example, by viral load (e.g., via detection of viral DNA), duration of survival, quality of life, viral protein expression and/or activity, detection of serological antibodies against the coronavirus or variant thereof, assessment of respiratory functions, and/or Computerized Tomography (CT) imaging.

IV. Nucleic Acids and Methods of Preparation

Nucleic acid molecules encoding the chimeric proteins (e.g., chimeric proteins comprising ACE2 or a fragment thereof) described herein are contemplated. In some embodiments, the nucleic acid molecules encode the chimeric proteins described herein. In some embodiments, there is provided a nucleic acid (such as an isolated nucleic acid) encoding any of the chimeric proteins described herein. In some embodiments, the nucleic acid (such as an isolated nucleic acid) encodes the complete amino acid sequence or sequences of any of the chimeric proteins described herein. In some embodiments, there is provided a set of nucleic acids (such as a set of isolated nucleic acids) encoding any of the chimeric proteins described herein. For example, different polypeptides of a chimeric protein, such as any of the chimeric proteins described herein, may be encoded by different nucleic acids (such as isolated nucleic acids) within the set of nucleic acids (such as a set of isolated nucleic acids). Nucleic acid molecules may be constructed using recombinant DNA techniques conventional in the art. In some embodiments, a nucleic acid molecule is an expression vector that is suitable for expression in a selected host cell.

Vectors comprising polynucleotides that encode the chimeric proteins described herein are also provided. In some embodiments, the vectors comprise polynucleotides encoding the chimeric proteins described herein. In some embodiments, the vectors comprise a nucleic acid encoding any of the chimeric proteins described herein. In some embodiments, a vector comprises a nucleic acid sequence encoding the complete amino acid sequence or sequences of any of the chimeric proteins described herein. In some embodiments, there is provided a set of vectors comprising different nucleic acids encoding different polypeptides of the chimeric proteins described herein. Such vectors include, but are not limited to, DNA vectors, phage vectors, viral vectors, retroviral vectors, etc.

In various embodiments, the chimeric proteins described herein may be expressed in prokaryotic cells, such as bacterial cells; or in eukaryotic cells, such as fungal cells (such as yeast cells), plant cells, insect cells, and mammalian cells. In some embodiments, the chimeric proteins described herein may be expressed in prokaryotic cells, such as bacterial cells; or in eukaryotic cells, such as fungal cells (such as yeast cells), plant cells, insect cells, and mammalian cells. In some embodiments, a nucleic acid encoding any of the chimeric proteins described herein may be expressed in prokaryotic cells, such as bacterial cells; or in eukaryotic cells, such as fungal cells (such as yeast cells), plant cells, insect cells, and mammalian cells. In some embodiments, a set of nucleic acids encoding any of the chimeric proteins described herein may be expressed in prokaryotic cells, such as bacterial cells; or in eukaryotic cells, such as fungal cells (such as yeast cells), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

The invention also provides host cells comprising any of the nucleic acids or vectors described herein. In some embodiments, the invention provides a host cell comprising a chimeric protein described herein. In some embodiments, the invention provides a host cell comprising a chimeric protein described herein. In some embodiments, the invention provides a host cell comprising a nucleic acid encoding any of the chimeric proteins described herein. In some embodiments, the nucleic acid encodes the complete amino acid sequence or sequences of any of the chimeric proteins described herein. In some embodiments, the invention provides a host cell comprising a set of nucleic acids encoding any of the chimeric proteins described herein. In some embodiments, the invention provides a host cell comprising a vector that contains a nucleic acid encoding any of the chimeric proteins described herein. In some embodiments, the vector comprises a nucleic acid sequence encoding the complete amino acid sequence or sequences of any of the chimeric proteins described herein. In some embodiments, the invention provides a host cell comprising a set of vectors comprising different nucleic acids encoding different polypeptides of any of the chimeric proteins described herein. Any host cells capable of over-expressing heterologous DNAs can be used for the purpose of isolating the genes encoding the polypeptide interest. Non-limiting examples of mammalian host cells include but not limited to COS, HeLa, and CHO cells. Suitable non-mammalian host cells include prokaryotes (such as *E. coli* or *B. subtilis*) and yeast (such as *S. cerevisiae, S. pombe*; or *K. lactis*).

The chimeric proteins described herein, the isolated nucleic acids encoding any of the chimeric proteins described herein, and/or the set of isolated nucleic acids encoding any of the chimeric proteins described herein may be purified by any suitable method. Such methods include, but are not limited to, the use of affinity matrices or hydrophobic interaction chromatography. Suitable affinity ligands include ligands that bind the target-binding moieties described herein. For example, a Protein A, Protein G, Protein A/G, or an affinity column may be used to bind the target-binding moiety and to purify a chimeric protein. Hydrophobic interactive chromatography, for example, a butyl or phenyl column, may also be suitable for purifying some polypeptides such as inhibitory polypeptides. Ion exchange chromatography (e.g., anion exchange chromatography and/or cation exchange chromatography) may be also suitable for purifying some polypeptides. Mixed-mode chromatography (e.g., reversed phase/anion exchange, reversed phase/cation exchange, hydrophilic interaction/anion exchange, hydrophilic interaction/cation exchange, etc.)

may also be suitable for purifying some polypeptides. Many methods of purifying polypeptides are known in the art.

V. Pharmaceutical compositions, Kits and articles of manufacture

A. Pharmaceutical Composition

One aspect of the present application provides compositions (e.g., pharmaceutical compositions) comprising any one of the chimeric proteins described herein. In some embodiments, the pharmaceutical composition is suitable for nasal administration. In some embodiments, the pharmaceutical composition is suitable for respiratory (e.g., upper respiratory airway) administration. In some embodiments, the pharmaceutical composition is suitable for administration by inhalation. In some embodiments, the pharmaceutical composition is a nasal spray formulation.

In some embodiments, the pharmaceutical composition comprises a pharmaceutically acceptable carrier. In some embodiments, the pharmaceutical composition comprises a citrate-buffered saline carrier. In some embodiments, the pharmaceutical composition comprises a stabilizing agent, a viscosity enhancing agent, a surfactant, and/or a preservative. In some embodiments, the pharmaceutical composition comprises 25 mM citrate buffer, pH 6.5, 100 mM NaCl, 0.1% methionine, 0.02% polysorbate 80, and 0.1% potassium sorbate. In some embodiments, the pharmaceutical composition comprises 25 mM citrate buffer, pH 6.5, 125 mM NaCl, 5% glycerin, 0.1% methionine, 0.02% polysorbate 80, and 0.1% potassium sorbate.

In some embodiments, the pharmaceutical composition comprises a single type of chimeric protein. In some embodiments, the pharmaceutical composition comprises at least two chimeric proteins, wherein the two chimeric proteins have different target-binding moieties. In some embodiments, the pharmaceutical composition comprises a plurality (e.g., 2, 3, 4, 5, 6, 7, 8, 9, 10, 15, 20, or more) of chimeric proteins, wherein the target-binding moieties of the chimeric proteins are different from each other. In some embodiments, the pharmaceutical composition comprises a cocktail of chimeric proteins that target different component of the same coronavirus and/or the same component of different variants (e.g., strains) of a coronavirus. In some embodiments, the chimeric proteins in the cocktail composition each comprise the same mucoadhesive peptide fragment(s). In some embodiments, the chimeric proteins in the cocktail composition each comprise different mucoadhesive peptide fragment(s).

In some embodiments, the pharmaceutical composition is formulated for topical administration to a mucosa, such as nasal mucosa, larynx mucosa, trachea mucosa, bronchi mucosa, lung mucosa, eye mucosa, and combinations thereof. In some embodiments, the pharmaceutical composition is formulated for administration via a nasal spray, an inhaler, a nebulizer, or an eye drop.

In some embodiments, there is provided a pharmaceutical composition comprising: (a) a chimeric protein comprising a target-binding moiety comprising an EBD of an ACE2 protein or a fragment thereof that specifically binds to an S protein, and a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa, (b) a stabilizing agent that maintains the weak reducing environment in nasal area, (c) a buffering agent, and (d) an osmolality adjusting agent, wherein the pharmaceutical composition has a pH of about 4.5 to about 7.5 (e.g., about 6.0 to about 7.0), and wherein the pharmaceutical composition has an osmolality of about 230 to about 330 Osm/kg (e.g., about 250 to about 300 Osm/kg). In some embodiments, the S protein is from a coronavirus (e.g., a SARS-CoV-2 virus). In some embodiments, the target-binding moiety specifically binds an S1 subunit of the S protein. In some embodiments, the target-binding moiety is any one of the target-binding moieties as described in Section II. In some embodiments, the chimeric protein is any one of the chimeric proteins described in Section II. In some embodiments, the positively charged amino acid residues are interspersed with one or more non-positively charged amino acid residues. In some embodiments, the pharmaceutical composition further comprises a viscosity-enhancing agent. In some embodiments, the pharmaceutical composition further comprises a surfactant. In some embodiments, the formulation further comprises a preservative.

In some embodiments, there is provided a pharmaceutical composition for nasal administration comprising: (a) a chimeric protein comprising a target-binding moiety comprising an EBD of an ACE2 protein or a fragment thereof that specifically binds to an S protein, and a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa, (b) a methionine, (c) a buffering agent, (d) an osmolality adjusting agent, (c) a viscosity enhancing agent, (f) a surfactant, and (g) a preservative, wherein the pharmaceutical composition has a pH of about 4.5 to about 7.5 (e.g., about 6.0 to about 7.0), and wherein the pharmaceutical composition has an osmolality of about 230 to about 330 Osm/kg (e.g., about 250 to about 300 Osm/kg). In some embodiments, the S protein is from a coronavirus (e.g., a SARS-CoV-2 virus). In some embodiments, the target-binding moiety specifically binds an S1 subunit of the S protein. In some embodiments, the target-binding moiety is any one of the target-binding moieties as described in Section II. In some embodiments, the chimeric protein is any one of the chimeric proteins described in Section II. In some embodiments, the positively charged amino acid residues are interspersed with one or more non-positively charged amino acid residues.

In some embodiments, there is provided a pharmaceutical composition for nasal administration comprising: (a) a chimeric protein comprising a target-binding moiety comprising an EBD of an ACE2 protein or a fragment thereof that specifically binds to an S protein, and a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa, (b) a methionine, (c) a citrate buffer, and (d) NaCl, wherein the pharmaceutical composition has a pH of about 4.5 to about 7.5 (e.g., about 6.0 to about 7.0), and wherein the pharmaceutical composition has an osmolality of about 230 to about 330 Osm/kg (e.g., about 250 to about 300 Osm/kg). In some embodiments, the S protein is from a coronavirus (e.g., a SARS-CoV-2 virus). In some embodiments, the target-binding moiety specifically binds an S1 subunit of the S protein. In some embodiments, the target-binding moiety is any one of the target-binding moieties as described in Section II. In some embodiments, the chimeric protein is any one of the chimeric proteins described in Section II. In some embodiments, the positively charged amino acid residues are interspersed with one or more non-positively charged amino acid residues. In some embodiments, the pharmaceutical composition further comprises a viscosity-enhancing agent (e.g., glycerin). In some embodiments, the pharmaceutical composition further comprises a surfactant (e.g., polysorbate 80). In some embodiments, the pharmaceutical composition further comprises a preservative (e.g., potassium sorbate).

In some embodiments, there is provided a pharmaceutical composition for nasal administration comprising: (a) a chimeric protein comprising a target-binding moiety comprising an EBD of an ACE2 protein or a fragment thereof that specifically binds to an S protein, and a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa at a concentration of about 0.6 mg/mL to about 1 mg/mL (e.g., about 1 mg/mL to about 3 mg/mL), (b) a methionine at about 0.05% to 0.2% (e.g., about 0.075% to about 0.125%) (w/w), (c) a citrate buffer at about 20 mM to about 50 mM (e.g., about 20 mM to about 30 mM), (d) NaCl at about 100 mM to about 150 mM (e.g., about 110 mM to about 130 mM), (c) glycerin at about 1% to about 10% (e.g., about 2.5% to about 7.5%) (w/w), (f) polysorbate 80 at about 0.01% to about 0.1% (e.g., about 0.01% to about 0.05%) (w/w), and (g) potassium polysorbate at about 0.05% to 0.2% (e.g., about 0.075% to about 0.125%) (w/w), wherein the pharmaceutical composition has a pH of about 4.5 to about 7.5 (e.g., about 6.0 to about 7.0). In some embodiments, the pharmaceutical composition comprises about 25 mM citrate at pH 6.5, about 125 mM NaCl, about 5% glycerin, about 0.1% methionine, about 0.02% polysorbate 80, and about 0.1% potassium sorbate. In some embodiments, the S protein is from a coronavirus (e.g., a SARS-CoV-2 virus). In some embodiments, the target-binding moiety specifically binds an S1 subunit of the S protein. In some embodiments, the target-binding moiety is any one of the target-binding moieties as described in Section II. In some embodiments, the chimeric protein is any one of the chimeric proteins described in Section II. In some embodiments, the positively charged amino acid residues are interspersed with one or more non-positively charged amino acid residues.

In some embodiments, the pharmaceutical composition described herein is for administration via a nasal spray. In some embodiments, the pharmaceutical composition is for prophylactic use. In some embodiments, the pharmaceutical composition maintains the stability (including physical and chemical stability) of the target-binding moiety at 37° C. for at least about n days, where n is selected from 1, 2, 3, 4, 5, 6, 7, 8, 9, 10, 11, 12, 13, 14, or more days, including any values and ranges in between these values. In some embodiments, the pharmaceutical composition promotes adhesion of the target-binding moiety to a mucosa, such as nasal mucosa. In some embodiments, the pharmaceutical composition prolongs the residence time of the target-binding moiety in nostrils and other upper respiratory tract areas, for example, by at least about n compared to the target-binding moiety in PBS, where n is selected from 12 hours, 24 hours, 2 days, 3 days, 4 days, 5 days, 6 days, 7 days, 8 days, 9 days, 10 days, or more. In some embodiments, the pharmaceutical composition is neutral and gentle to the nasal surfaces. In some embodiments, the pharmaceutical composition is a solution of the target-binding moiety. In some embodiments, the pharmaceutical composition is an aqueous solution.

Nasal spray pharmaceutical composition parameters and excipients have been described, for example, in Kulkami, C and Shaw, D, *Inhalation,* 10-11 (2021); Thorat, *Scholars Journal of Applied Medical Sciences* (*SJAMS*), 4 (8D): 2976-2985 (2016), which are incorporated by reference in their entirety. Commonly used excipients for nasal spray pharmaceutical composition include, but are not limited to, tonicity agent or osmolality adjustment agent, buffering agent, purging agent, preservative, surfactant, chelating agent, suspending agent, co-solvent, antioxidant, and humectant. Pharmaceutical compositions for various route of administration, including nasal pharmaceutical composition, have been described, for example, in Cui Y. et al., *Drug Development and Industrial Pharmacy,* 11:28 (2017), which is incorporated herein by reference. Any excipients compatible with the FDA guideline for nasal spray pharmaceutical composition and/or pharmaceutical composition may be used here.

In some embodiments, the pharmaceutical composition has a pH that is compatible with the nasal environment. The average baseline human nasal pH is about 6.3. The optimal pH of the pharmaceutical composition also depends on factors, including, for example, pI of the target-binding moiety (including positively charged mucoadhesive peptide), protein stability, net charge of the target-binding moiety, etc. In some embodiments, the pharmaceutical composition has a pH of about 4.5 to about 7.5, such about n, where n is selected from 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, and 7.5, including any values or ranges in between the values. In some embodiments, the pharmaceutical composition has a pH of about n, where n is selected from 4.5-5.0, 5.0-5.5, 5.5-6.0, 6.0-6.5, 4.5-5.5, 5.5-6.5, 5.0-6.5, 4.5-6.0, 6.5-7.0, 7.0-7.5, 6.0-7.5, 5.5-7, 6-7, and 6.5-7.5. In some embodiments, the pharmaceutical composition has a pH of about 6.5.

For adjusting and buffering pH value, physiologically acceptable acids, bases, salts, and combinations of these may be used. Suitable excipients for lowering the pH value or as acidic components of a buffer system are strong mineral acids, in particular, sulfuric acid and hydrochloric acid. Moreover, inorganic and organic acids of medium strength as well as acidic salts may be used, for example, phosphoric acid, citric acid, tartaric acid, succinic acid, fumaric acid, methionine, acidic hydrogen phosphates with sodium or potassium, lactic acid, glucuronic acid etc. Suitable for raising the pH value or as basic component for buffer system are, in particular, mineral bases such as sodium hydroxide or other alkali and alkaline earth hydroxides and oxides such as, in particular, magnesium hydroxide and calcium hydroxide, ammonium hydroxide and basic ammonium salts such as ammonium acetate, as well as basic amino acids such as lysine, carbonates such as sodium or magnesium carbonate, sodium hydrogen carbonate, citrates such as sodium citrate etc.

In some embodiments, the pharmaceutical composition comprises a citrate buffer. In some embodiments, the citrate buffer contains citric acid and sodium citrate. The citrate buffer has a pKa of about 6.4. In some embodiments, the citrate buffer is present a concentration of about 20 mM to about 50 mM, such as about n mM, where n is selected from 20, 25, 30, 35, 40, 45, and 50, including any values or ranges in between these values. In some embodiments, the citrate buffer is present a concentration of about n mM, where n is selected from 20-30, 30-40, 40-50, 25-50, 25-35, and 25-40. In some embodiments, the pharmaceutical composition comprises a citrate buffer at about 25 mM.

In some embodiments, the pharmaceutical composition comprises a phosphate buffer. The phosphate buffer has a pKa of about 7.2.

In some embodiments, the pharmaceutical composition has an osmolality that is close to the nasal environment. In some embodiments, the pharmaceutical composition has an osmolality that facilitates adhesion of the target-binding moiety to a mucosa (e.g., nasal mucosa). In some embodiments, the pharmaceutical composition minimizes penetration of the target-binding moiety into blood stream. In some embodiments, the pharmaceutical composition has an osmolality of about 230 Osm/kg to about 330 Osm/kg, such as about n Osm/kg, where n is selected from 230, 240, 250, 260, 270, 280, 290, 300, 310, 320, and 330, including any values or ranges in between these values. In some embodiments, the pharmaceutical composition has an osmolality of about n Osm/kg, where n is selected from 230-250, 250-270, 270-290, 290-310, 310-330, 230-275, 275-300, 300-330, 230-280, 280-330, or 260-320. In some embodiments, the pharmaceutical composition has an osmolality of about 280 Osm/kg. A skilled person in the art could readily convert these osmolality values to osmolality.

In some embodiments, the pharmaceutical composition comprises an osmolality adjusting agent. Exemplary osmolality adjusting agents or tonicity agents include, but are not limited to, sodium, calcium or magnesium chloride, sulfate or phosphate. In some embodiments, the osmolality adjusting agent is sodium chloride. Calcium and magnesium salts may have a positive or auxiliary influence in the inhalation of active agent solutions, possibly because they themselves counteract the local irritations caused by the administration. Alternatively, physiologically safe organic compounds may be used as the osmolality adjusting agent. Particularly suitable are water-soluble substances with a relatively low molecular weight, for example, with a molecular weight of less than 300 or, better still, less than 200 and with a correspondingly high osmotic activity. Examples for such excipients are sugars and sugar alcohols, in particular, trehalose, mannitol, sorbitol and isomalt.

In some embodiments, the pharmaceutical composition comprises about 100 mM to about 150 mM NaCl, such as about n mM NaCl, where n is selected from 100, 105, 110, 115, 120, 125, 130, 135, 140, 145, and 150, including any values or ranges in between these values. In some embodiments, the pharmaceutical composition comprises about n mM NaCl, where n is selected from 100-120, 120-140, 100-125, 125-150, 130-150, and 110-130. In some embodiments, the pharmaceutical composition comprises about 125 mM NaCl.

In some embodiments, the pharmaceutical composition comprises one or more stabilizing agents. In some embodiments, the stabilizing agent maintains the weak reducing environment in nasal areas. In some embodiments, the one or more stabilizing agents comprises methionine. In some embodiments, the one or more stabilizing agents comprise glycerin. In some embodiments, the one or more stabilizing agents comprise trehalose, e.g., 10% trehalose. In some embodiments, the pharmaceutical composition comprises about 0.05% to about 0.2% (w/w) methionine, such as about n (w/w) methionine, where n is selected from 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, and 0.2%, including any values or ranges in between these values. In some embodiments, the pharmaceutical composition comprises about n (w/w) methionine, where n is selected from 0.05%-0.1%, 0.75%-1.25%, 0.1%-0.15%, 0.15%-0.2%, 0.1%-0.2%, 0.125-0.175%, 0.8%-1.6%, and 0.5%-0.15%. In some embodiments, the pharmaceutical composition comprises about 0.1% methionine.

In some embodiments, the pharmaceutical composition comprises a viscosity-enhancing agent. In some embodiments, the viscosity-enhancing agent is selected from the group consisting of glycerin, dextran and hydroxyethylcellulose. In some embodiments, the viscosity-enhancing agent is glycerin. In some embodiments, the pharmaceutical composition comprises about 1% to about 10% (w/w) glycerin, such as about n (w/w) glycerin, where n is selected from 1%, 2%, 3%, 3%, 4%, 5%, 6%, 7%, 8%, 9%, and 10%, including any values or ranges in between these values. In some embodiments, the pharmaceutical composition comprises about n (w/w) glycerin, where n is selected from 1%-4%, 2%-6%, 3%-7%, 5%-8%, 7%-10%, 2.5%-7.5%, 4%-6%, 1%-2.5%, 2.5%-5%, 5%-7.5%, and 7.5%-10%. In some embodiments, the pharmaceutical composition comprises about 5% glycerin.

In some embodiments, the pharmaceutical composition comprises surfactant. In some embodiments, the surfactant allows the target-binding moiety to cross a mucosa (e.g., nasal mucosa) and/or allows absorption of the target-binding moiety across the mucosa. Suitable surfactants include, in particular, those that are to be considered safe for oral or nasal inhalation or mucosal administration. Examples of surfactants with particularly good physiological compatibility include tyloxapol, polysorbates (such as polysorbate 20, polysorbate 80), PEG400, PEG3500, polyoxyl 400 stearate, vitamin E-TPGS, and macrogol hydroxystearates such as macrogol-15-hydroxystearate. In some embodiments, the surfactant is polysorbate 80. In some embodiments, the pharmaceutical composition comprises about 0.01% to about 0.1% (w/w) polysorbate 80, such as about n (w/w) polysorbate 80, where n is selected from 0.01%, 0.02%, 0.03%, 0.04%, 0.05%, 0.06%, 0.07%, 0.08%, 0.09%, and 0.1%, including any values or ranges in between these values. In some embodiments, the pharmaceutical composition about n (w/w) polysorbate 80, where n is selected from 0.01%-0.02%, 0.02%-0.05%, 0.05%-0.1%, 0.01%-0.05%, 0.02%-0.04%, 0.04%-0.08%, 0.02%-0.08%, and 0.02%-0.1%. In some embodiments, the pharmaceutical composition comprises about 0.02% polysorbate.

In some embodiments, the pharmaceutical composition comprises a preservative. In some embodiments, the preservative maintains sterility of the pharmaceutical composition. Exemplary preservatives include, but are not limited to, benzyl alcohol, benzalkonium chloride, chlorobutanol, methylparaben, phenylethyl alcohol, propylparaben, and potassium sorbate. In some embodiments, the preservative is potassium sorbate. In some embodiments, the pharmaceutical composition comprises about 0.05% to about 0.2% (w/w) potassium polysorbate, such as about n (w/w) potassium polysorbate, where n is selected from 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, and 0.2% (w/w), including any values or ranges in between these values. In some embodiments, the pharmaceutical composition comprises about n (w/w) potassium sorbate, where n is selected from 0.05%-0.1%, 0.75%-1.25%, 0.1%-0.15%, 0.15%-0.2%, 0.1%-0.2%, 0.125-0.175%, 0.8%-1.6%, and 0.5%-0.15%. In some embodiments, the pharmaceutical composition comprises about 0.1% potassium sorbate.

In some embodiments, the target-binding moiety is present in the pharmaceutical composition at a concentration of about 0.6 mg/mL to about 6 mg/mL, such as about n mg/mL, where n is selected from 0.6, 0.8, 1, 1.5, 2, 2.5, 3, 3.5, 4, 4.5, 5, 5.5, and 6, including about any values or ranges in between these values. In some embodiments, the target-binding moiety is present in the pharmaceutical composition at a concentration of about n mg/mL, where n is selected from 0.6-1, 1-2, 2-3, 3-4, 4-5, 5-6, 0.6-2.5, 2.5-5, 2-4, 4-6, 0.6-3, 3-6, and 2-5.

A nasal spray containing inhibitory polypeptides (e.g., ACE2 protein or a fragment thereof) can be used as a complement to vaccines, therapeutics and other preventive measures against the spread of coronavirus (e.g., SARS-CoV-2). Nasal sprays have many advantages. One advantage of using chimeric in a prophylaxis nasal spray is the well-established manufacturing process and scale-up capacity. An inhibitory polypeptide in a nasal spray application also has the advantage of a much lower dosage requirement (approximately 10,000 times lower) than a therapeutic. This will significantly lower the cost and make it affordable for wider use. Furthermore, use of a human ACE2 inhibitory polypeptide significantly reduces the risk of immunogenicity, which is an important consideration for a prophylactic nasal spray pharmaceutical composition subject to long-term repeated use. The long-term stability of the modified inhibitory polypeptide at room temperature in the nasal spray pharmaceutical composition makes it easy for daily use and storage.

In some embodiments, the pharmaceutical composition (e.g., nasal spray pharmaceutical composition or eye drop pharmaceutical composition) is administered at a dosage of about 0.1 mg to about 1 mg of the target-binding moiety, e.g., per nostril or per eye. In some embodiments, about 100 μL of the pharmaceutical composition (e.g., nasal spray pharmaceutical composition or eye drop pharmaceutical composition) is administered at a time, e.g., to both nostrils of an individual (e.g., 100 μL per nostril or 100 μL per eye).

Suitable pharmaceutical compositions are obtained by mixing the chimeric protein(s) described herein having the desired degree of purity with optional pharmaceutically acceptable carriers, excipients or stabilizers (*Remington's Pharmaceutical Sciences* 23rd edition, Adejare, A. Ed. (2020)), in the form of lyophilized pharmaceutical compositions or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™, or polyethylene glycol (PEG).

The pharmaceutical composition herein may also contain one or more active compounds in addition to the compositions described herein as necessary for the infection being treated, preferably those with complementary activities that do not adversely affect each other. Such molecules are suitably present in combination in amounts that are effective for the purpose intended. The effective amount of such other agents depends on the amount of the composition described herein present in the pharmaceutical composition, the type and severity of infection in the treatment, and other factors discussed above. These are generally used in the same dosages and with administration routes as described herein or from about 1% to about 99% of the heretofore employed dosages.

The pharmaceutical compositions to be used for in vivo administration must be sterile. This is readily accomplished by, e.g., filtration through sterile filtration membranes.

Further provided are methods and use of the pharmaceutical compositions described herein for preventing or treating an infection, e.g., coronavirus infection.

B. Kits and Articles of Manufacture

In some embodiments, there is provided an article of manufacture comprising materials useful for the prevention or treatment of a microbial infection (e.g., infection by a coronavirus or variant thereof, e.g., a SARS-CoV-2 infection or variant thereof). The article of manufacture can comprise a container and a label or package insert on or associated with the container. Suitable containers include, for example, bottles, vials, syringes, etc. The containers may be formed from a variety of materials such as glass or plastic. Generally, the container holds a composition, which is effective for treating a microbial infection, described herein, and may have a sterile access port. In some embodiments, the article of manufacture is a nasal spray, an inhaler, a nebulizer, or an eye drop. Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a microbial infection. The label or package insert may further comprise instructions for administering the composition to a patient.

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, there is provided an article of manufacture (e.g., a nasal spray) comprising a pharmaceutical composition comprising any one of the chimeric proteins described herein, and a spray device for applying the formulation to a nostril of a subject. In some embodiments, the nasal spray provides a uniform plume with droplets having a diameter of 10 μm or more. In some embodiments, the device sprays a volume of about 100 μL at a time. In some embodiments, the spray device is for an adult patient. In some embodiments, the spray device is for a pediatric patient. In some embodiments, the article of manufacture comprises a single dose of the active agent. In some embodiments, the article of manufacture comprises at least about n doses of the active agent, where n is selected from 2, 5, 10, 20, 30, 40, 50, or more.

Kits are also provided that are useful for various purposes, e.g., for prevention or treatment of a microbial infection described herein, optionally in combination with the articles of manufacture. Kits of the invention include one or more containers comprising any one of the compositions described herein (or unit dosage form and/or article of manufacture). In some embodiments, the kit further comprises other agents and/or instructions for use in accordance with any of the methods described herein. The kit may further comprise a description of selection of individuals suitable for prevention or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a chimeric protein comprising: (a) a target-binding moiety comprising an EBD of an ACE2 protein or a fragment thereof that specifically binds to an S protein; and (b) a mucoadhesive peptide fragment comprising at least about 5 (e.g., about 5 to about 30, such as about 12) positively charged amino acid residues (e.g., lysine, histidine, arginine, ornithine, or combinations thereof), wherein the mucoadhesive peptide fragment facilitates attachment of the chimeric protein to a mucosa. In some embodiments, the S protein is from a coronavirus. In some embodiments, the target-binding moiety specifically binds an S1 subunit of an S protein.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The containers may be unit doses, bulk packages (e.g., multi-dose packages) or sub-unit doses. Kits may also include multiple unit doses of the pharmaceutical compositions and instructions for use and packaged in quantities sufficient for storage and use in pharmacies, for example, hospital pharmacies and compounding pharmacies.

EXEMPLARY EMBODIMENTS

The following exemplary embodiments are provided herein:

Embodiment 1. A chimeric protein comprising:

(a) a target-binding moiety comprising an extracellular binding domain (EBD) of an angiotensin-converting enzyme 2 (ACE2) protein or a fragment thereof that specifically binds to a spike(S) protein; and (b) a mucoadhesive peptide fragment comprising at least about 5 positively charged amino acid residues, wherein the mucoadhesive peptide fragment facilitates attachment of the chimeric protein to a mucosa.

Embodiment 2. The chimeric protein of embodiment 1, comprising a single polypeptide chain.

Embodiment 3. The chimeric protein of embodiment 1, comprising two or more polypeptide chains.

Embodiment 4. The chimeric protein of embodiment 3, wherein the chimeric protein comprises two or more mucoadhesive peptide fragments.

Embodiment 5. The chimeric protein of embodiment 4, wherein each of the two or more mucoadhesive peptide fragments comprises at least about 5 positively charged amino acid residues.

Embodiment 6. The chimeric protein of any one of embodiments 1-5, wherein the mucoadhesive peptide fragment comprises at least about 6 positively charged amino acid residues.

Embodiment 7. The chimeric protein of any one of embodiments 1-6, wherein the positively charged amino acid residues are selected from the group consisting of lysine, arginine, histidine, ornithine, and combinations thereof.

Embodiment 8. The chimeric protein of embodiment 7, wherein the positively charged amino acid residues comprise lysines.

Embodiment 9. The chimeric protein of embodiment 8, wherein the mucoadhesive peptide fragment comprises about 5, about 6, about 12, or about 30 lysines.

Embodiment 10. The chimeric protein of embodiment 7, wherein the positively charged amino acid residues comprise arginines.

Embodiment 11. The chimeric protein of embodiment 10, wherein the mucoadhesive peptide fragment comprises about 5, about 6, about 12, or about 30 arginines.

Embodiment 12. The chimeric protein of embodiment 7, wherein the positively charged amino acid residues comprise histidines.

Embodiment 13. The chimeric protein of embodiment 12, wherein the mucoadhesive peptide fragment comprises about 5, about 6, about 12, or about 30 histidines.

Embodiment 14. The chimeric protein of embodiment 7, wherein the positively charged amino acid residues comprise ornithines.

Embodiment 15. The chimeric protein of embodiment 14, wherein the mucoadhesive peptide fragment comprises about 5, about 6, about 12, or about 30 ornithines.

Embodiment 16. The chimeric protein of any one of embodiments 1-15, wherein the mucoadhesive peptide fragment comprises at least 5 contiguous positively charged amino acids.

Embodiment 17. The chimeric protein of any one of embodiments 1-15, wherein the positively charged amino acid residues are interspersed with one or more non-positively charged amino acid residues.

Embodiment 18. The chimeric protein of embodiment 17, wherein the non-positively charged amino acid residues are non-polar amino acids or polar uncharged amino acids.

Embodiment 19. The chimeric protein of embodiment 17 or 18, wherein the non-positively charged amino acid residues are selected from the group consisting of isoleucine, valine, alanine, tryptophan, leucine, glycine, methionine, proline, phenylalanine, threonine, cysteine, tyrosine, glutamine, serine, and asparagine, and combinations thereof.

Embodiment 20. The chimeric protein of any one of embodiments 17-19, wherein at least 50% of the amino acid residues in the mucoadhesive peptide fragment are positively charged amino acid residues.

Embodiment 21. The chimeric protein of any one of embodiments 1-20, wherein the mucoadhesive peptide fragment is no more than about 15 kD.

Embodiment 22. The chimeric protein of any one of embodiments 1-21, wherein the mucoadhesive peptide fragment has an isoelectric point (pI) higher than the pH of the mucosa.

Embodiment 23. The chimeric protein of any one of embodiments 1-22, wherein the half-life of the chimeric protein on the mucosa is at least 12 hours.

Embodiment 24. The chimeric protein of any one of embodiments 1-23, wherein the mucoadhesive peptide fragment does not facilitate penetration of the chimeric protein into a cell of the mucosa.

Embodiment 25. The chimeric protein of any one of embodiments 1-24, wherein the mucoadhesive peptide fragment does not disrupt folding of the chimeric protein within a host cell expressing the chimeric protein.

Embodiment 26. The chimeric protein of any one of embodiments 1-25, wherein the mucoadhesive peptide fragment does not block secretion of the chimeric protein from a host cell expressing the chimeric protein.

Embodiment 27. The chimeric protein of any one of embodiments 1-26, wherein the mucoadhesive peptide fragment does not interfere with the binding between the target-binding moiety and the S protein.

Embodiment 28. The chimeric protein of any one of embodiments 1-27, wherein the mucoadhesive peptide fragment comprises an amino acid sequence of any one of SEQ ID NOS: 28-62 and 128-134, or a variant thereof comprising at least about 90% sequence identity to the amino acid sequence of any one of SEQ ID NOs: 28-62 and 128-134.

Embodiment 29. The chimeric protein of any one of embodiments 1-28, wherein the mucoadhesive peptide fragment is fused to the target-binding moiety via a bond.

Embodiment 30. The chimeric protein of any one of embodiments 1-28, wherein the mucoadhesive peptide fragment is fused to the target-binding moiety via a peptide linker.

Embodiment 31. The chimeric protein of embodiment 30, wherein the peptide linker comprises one or more oligomerization and/or multimerization domains.

Embodiment 32. The chimeric protein of embodiment 30 or 31, wherein the peptide linker comprises the constant region of a heavy chain of a full-length antibody or a fragment thereof, or the constant region of a light chain of a full-length antibody or a fragment thereof.

Embodiment 33. The chimeric protein of any one of embodiments 30-32, wherein the peptide linker comprises an Fc region or a fragment thereof.

Embodiment 34. The chimeric protein of any one of embodiments 30-33, wherein the peptide linker comprises a $CH_1$, $CH_2$, $CH_3$, $CH_4$, and/or $C_L$ domain or a fragment thereof.

Embodiment 35. The chimeric protein of any one of embodiments 30-34, wherein the peptide linker comprises a $CH_2$ domain or a fragment thereof.

Embodiment 36. The chimeric protein of any one of embodiments 30-35, wherein the peptide linker further comprises an antibody hinge domain or a fragment thereof.

Embodiment 37. The chimeric protein of any one of embodiments 30-35, wherein the peptide linker comprises a detectable enzymatic tag, optionally wherein the enzymatic tag is an alkaline phosphatase and/or a glutathione-s-transferase.

Embodiment 38. The chimeric protein of any one of embodiments 30-37, wherein the peptide linker comprises:

(i) a basic helix-loop-helix leucine zipper (bZIP) domain, bZIP isoleucine zipper domain, and/or bZIP-leucine/isoleucine zipper domain;

(ii) a collagen-like peptide;

(iii) a p53 tetramerization domain;

(iv) a streptavidin (SA) protein, optionally wherein the peptide linker further comprises a dextran scaffold or one or more maleimide polymers (DMGS);

(v) a bacteriophage T7 fibritin protein or a portion thereof; and/or (vi) a cartilage oligomeric matrix protein (COMP) protein.

Embodiment 39. The chimeric protein of any one of embodiments 1-38, wherein the mucoadhesive peptide fragment is fused to a C-terminus of the target-binding moiety.

Embodiment 40. The chimeric protein of any one of embodiments 1-39, wherein the target-binding moiety comprises the EBD of a human ACE2 (hACE2) protein or a fragment or variant thereof.

Embodiment 41. The chimeric protein of any one of embodiments 1-40, wherein the target-binding moiety comprises amino acids 30-41 of a full-length hACE2 protein, or a variant thereof comprising at least about 90% sequence identity to amino acids 30-41 of a full-length hACE2 protein.

Embodiment 42. The chimeric protein of any one of embodiments 1-40, wherein the target-binding moiety comprises the amino acid sequence of SEQ ID NO: 102, or a variant thereof comprising at least about 90% sequence identity to the amino acid sequence of SEQ ID NO: 102.

Embodiment 43. The chimeric protein of any one of embodiments 1-42, wherein the target-binding moiety comprises amino acids 24-42 of a full-length hACE2 protein, or a variant thereof comprising at least about 90% sequence identity to amino acids 24-42 of a full-length hACE2 protein.

Embodiment 44. The chimeric protein of any one of embodiments 1-43, wherein the target-binding moiety comprises the amino acid sequence of SEQ ID NO: 8, or a variant thereof comprising at least about 90% sequence identity to the amino acid sequence of SEQ ID NO: 8.

Embodiment 45. The chimeric protein of any one of embodiments 1-44, wherein the target-binding moiety comprises the amino acid sequence of any one of SEQ ID NOs: 1-7, 9-14, and 135, or a variant thereof comprising at least about 90% sequence identity the amino acid sequence of any one of SEQ ID NOs: 1-7, 9-14, and 135.

Embodiment 46. The chimeric protein of embodiment 40, comprising the amino acid sequence of any one of SEQ ID NOs: 84-88 and 136-140, or a variant thereof comprising at least about 90% sequence identity to the amino acid sequence of any one of SEQ ID NOs: 84-88 and 136-140.

Embodiment 47. The chimeric protein of any one of embodiments 1-39, wherein the target-binding moiety comprises the EBD of an animal ACE2 protein or a fragment or variant thereof.

Embodiment 48. The chimeric protein of embodiment 47, wherein the animal ACE2 protein is a murine, guinea pig, equine, ferret, macaque, chimpanzee, swine, canine, feline, bovine, rabbit, mink, or chicken ACE2 protein or a fragment or variant thereof.

Embodiment 49. The chimeric protein of any one of embodiments 1-39, 47, and 48, wherein the target-binding moiety comprises amino acids 30-41 of a full-length animal ACE2 protein, or a variant thereof comprising at least about 90% sequence identity to amino acids 30-41 of a full-length animal ACE2 protein, wherein the full-length animal ACE2 protein is not a chicken or canine ACE2 protein.

Embodiment 50. The chimeric protein of any one of embodiments 1-39, 47, and 48, wherein the target-binding moiety comprises amino acids 29-40 of a full-length animal ACE2 protein, or a variant thereof comprising at least about 90% sequence identity to amino acids 29-40 of a full-length animal ACE2 protein, wherein the full-length animal ACE2 protein is a chicken or canine ACE2 protein.

Embodiment 51. The chimeric protein of any one of embodiments 1-39 and 47-50, wherein the target-binding moiety comprises the amino acid sequence of any one of SEQ ID NOS: 110-122, or a variant thereof comprising at least about 90% sequence identity to any one of SEQ ID NOS: 110-122.

Embodiment 52. The chimeric protein of any one of embodiments 1-39 and 47-51, wherein the target-binding moiety comprises the amino acid sequence of any one of SEQ ID NOs: 15-27, or a variant thereof comprising at least about 90% sequence identity to the amino acid sequence of any one of SEQ ID NOs: 15-27.

Embodiment 53. The chimeric protein of any one of embodiments 47-52, comprising the amino acid sequence of any one of SEQ ID NOs: 89-93, or a variant thereof comprising at least about 90% sequence identity to the amino acid sequence of any one of SEQ ID NOs: 89-93.

Embodiment 54. The chimeric protein of any one of embodiments 1-53, wherein the mucosa is selected from the group consisting of nasal mucosa, larynx mucosa, trachea mucosa, bronchi mucosa, lung mucosa, eye mucosa, and combinations thereof.

Embodiment 55. A pharmaceutical composition comprising the chimeric protein of any one of embodiments 1-54, and a pharmaceutically acceptable carrier.

Embodiment 56. The pharmaceutical composition of embodiment 55, wherein the pharmaceutical composition comprises a plurality of the chimeric proteins, and wherein at least two of the plurality of the chimeric proteins are different from each other.

Embodiment 57. The pharmaceutical composition of embodiment 55 or 56, wherein the pharmaceutically acceptable carrier:

(i) comprises about 0.05% to about 0.2% (w/w) methionine;

(ii) has a pH of about 4.5 to about 7.5;

(iii) comprises about 20 mM to about 50 mM citrate;

(iv) comprises about 100 mM to about 150 mM NaCl;

(v) comprises about 0.01% to about 0.1% (w/w) polysorbate 80;

(vi) comprises about 1% to about 10% (w/w) glycerin; and/or (vii) comprises about 0.05% to about 0.2% (w/w) potassium sorbate.

Embodiment 58. The pharmaceutical composition of any one of embodiments 55-57, wherein the pharmaceutical composition is formulated for intranasal administration, intraocular administration, and/or intrabronchial administration.

Embodiment 59. An isolated nucleic acid or a set of isolated nucleic acids encoding the chimeric protein of any one of embodiments 1-54.

Embodiment 60. A vector or a set of vectors comprising the nucleic acid or the set of nucleic acids of embodiment 59.

Embodiment 61. A host cell comprising the chimeric protein of any one of embodiments 1-54, the nucleic acid or set of nucleic acids of embodiment 50, the vector or set of vectors of embodiment 60.

Embodiment 62. A method of preparing a chimeric protein, comprising:

(a) culturing a host cell of embodiment 61 under a condition effective to express the chimeric protein; and (b) obtaining the expressed chimeric protein from the host cell.

Embodiment 63. A method of preventing or treating an infection caused by a virus in an individual, comprising administering to the individual an effective amount of the chimeric protein of any one of embodiments 1-54, or the pharmaceutical composition of any one of embodiments 55-58.

Embodiment 64. The method of embodiment 63, wherein the chimeric protein or the pharmaceutical composition is administered to the individual before the individual is exposed to the virus.

Embodiment 65. The method of embodiment 63, wherein the chimeric protein or the pharmaceutical composition is administered to the individual within about 72 hours after the individual is exposed to the virus.

Embodiment 66. The method of any one of embodiments 63-65, wherein the chimeric protein or the pharmaceutical composition is administered topically onto the mucosa.

Embodiment 67. The method of embodiment 66, wherein the chimeric protein or the pharmaceutical composition is administered via a nasal spray, an inhaler, a nebulizer, or an eye drop.

Embodiment 68. The method of any one of embodiments 63-67, wherein the chimeric protein or the pharmaceutical composition is administered once daily.

Embodiment 69. An in vitro method of killing or neutralizing a virus, comprising contacting a virus with the chimeric protein of any one of embodiments 1-54 in the presence of at least one component of the complement system.

Embodiment 70. The method of embodiment 69, wherein the virus is contacted with the chimeric protein of any one of embodiments 33-36.

Embodiment 71. The method of embodiment 69, wherein the at least one component of the complement system is C1, C4, or membrane attack complex (MAC).

Embodiment 72. The method of embodiment 71, wherein the at least one component of the complement system is C1.

Embodiment 73. The method of embodiment 71, wherein the at least one component of the complement system is C4.

Embodiment 74. The method of embodiment 71, wherein the at least one component of the complement system is MAC.

Embodiment 75. A method of killing or neutralizing a virus in an individual, comprising administering to the individual an effective amount of the chimeric protein of any one of embodiments 1-54, or the pharmaceutical composition of any one of embodiments 55-58.

Embodiment 76. The method of embodiment 75, wherein an effective amount of the chimeric protein of any one of embodiments 33-36, or a pharmaceutical composition comprising the chimeric protein of any one of embodiments 33-36 and a pharmaceutically acceptable carrier, is administered to the individual.

Embodiment 77. A method of activating the complement pathway in an individual, comprising administering to the individual an effective amount of the chimeric protein of any one of embodiments 1-54, or the pharmaceutical composition of any one of embodiments 55-58.

Embodiment 78. The method of embodiment 77, wherein an effective amount of the chimeric protein of any one of embodiments 33-36, or a pharmaceutical composition comprising the chimeric protein of any one of embodiments 33-36 and a pharmaceutically acceptable carrier, is administered to the individual.

Embodiment 79. The method of any one of embodiments 69-78, wherein at least one virus is killed or neutralized on the mucosa.

Embodiment 80. A method of preventing, treating, or reducing infection caused by a virus in an individual, comprising administering to the individual an effective amount of the chimeric protein of any one of embodiments 1-54, or the pharmaceutical composition of any one of embodiments 55-58, wherein at least one virus is killed or neutralized on the mucosa.

Embodiment 81. The method of embodiment 80, wherein an effective amount of the chimeric protein of any one of embodiments 33-36, or a pharmaceutical composition comprising the chimeric protein of any one of embodiments 33-36 and a pharmaceutically acceptable carrier, is administered to the individual.

Embodiment 82. The method of any one of embodiments 69-81, wherein the chimeric protein activates the complement pathway in the individual.

Embodiment 83. The method of any one of embodiments 69-77 and 79-82, wherein the killing or neutralization is via activation of the complement pathway.

Embodiment 84. The method of any one of embodiments 63-83, wherein the virus is a coronavirus.

Embodiment 85. The method of embodiment 84, wherein the virus is selected from the group consisting of SARS-CoV, SARS-CoV-2, and HCoV-NL63.

Embodiment 86. The method of any one of embodiments 63-85, wherein the S protein comprises the amino acid sequence of any one of SEQ ID NOs: 96-100, 103, 123-127, and 141-143, or a variant thereof comprising at least about 90% sequence identity to the amino acid sequence of any one of SEQ ID NOs: 96-100, 103, 123-127, and 141-143.

Embodiment 87. The chimeric protein of any one of embodiments 1-54, or the pharmaceutical composition of any one of embodiments 55-58, for use in a method of preventing or treating an infection caused by a virus in an individual, the method comprising administering to the individual an effective amount of the chimeric protein or pharmaceutical composition.

Embodiment 88. The chimeric protein or pharmaceutical composition for use of embodiment 87, wherein the chimeric protein or the pharmaceutical composition is administered to the individual before the individual is exposed to the virus.

Embodiment 89. The chimeric protein or pharmaceutical composition for use of embodiment 87, wherein the chimeric protein or the pharmaceutical composition is administered to the individual within about 72 hours after the individual is exposed to the virus.

Embodiment 90. The chimeric protein or pharmaceutical composition for use of any one of embodiments 87-89, wherein the chimeric protein or the pharmaceutical composition is administered topically onto the mucosa.

Embodiment 91. The chimeric protein or pharmaceutical composition for use of embodiment 90, wherein the chimeric protein or the pharmaceutical composition is administered via a nasal spray, an inhaler, a nebulizer, or an eye drop.

Embodiment 92. The chimeric protein or pharmaceutical composition of any one of embodiments 87-91, wherein the chimeric protein or the pharmaceutical composition is administered once daily.

Embodiment 93. The chimeric protein of any one of embodiments 1-54, or the pharmaceutical composition of any one of embodiments 55-58, for use in a method of killing or neutralizing a virus in an individual, the method comprising administering to the individual an effective amount of the chimeric protein or pharmaceutical composition.

Embodiment 94. The chimeric protein of any one of embodiments 1-54, or the pharmaceutical composition of any one of embodiments 55-58, for use in a method of activating the complement pathway in an individual, the method comprising administering to the individual an effective amount of the chimeric protein or pharmaceutical composition.

Embodiment 95. The chimeric protein or pharmaceutical composition for use of embodiment 93 or 94, wherein at least one virus is killed or neutralized on the mucosa.

Embodiment 96. The chimeric protein of any one of embodiments 1-54, or the pharmaceutical composition of any one of embodiments 55-58, for use in a method of preventing, treating, or reducing infection caused by a virus in an individual, the method comprising administering to the individual an effective amount of the protein or composition.

Embodiment 97. The chimeric protein or pharmaceutical composition for use of any one of embodiments 93-96, wherein the chimeric protein activates the complement pathway in the individual.

Embodiment 98. The chimeric protein or pharmaceutical composition for use of any one of embodiments 93 and 95-97, wherein the killing or neutralization is via activation of the complement pathway.

Embodiment 99. The chimeric protein or pharmaceutical composition for use of any one of embodiments 87-98, wherein the virus is a coronavirus.

Embodiment 100. The chimeric protein or pharmaceutical composition for use of embodiment 99, wherein the virus is selected from the group consisting of SARS-CoV, SARS-CoV-2, and HCoV-NL63.

Embodiment 101. The chimeric protein or pharmaceutical composition for use of any one of embodiments 87-101, wherein the S protein comprises the amino acid sequence of any one of SEQ ID NOs: 96-100, 103, 123-127, and 141-143, or a variant thereof comprising at least about 90% sequence identity to the amino acid sequence of any one of SEQ ID NOs: 96-100, 103, 123-127, and 141-143.

Embodiment 102. The chimeric protein of any one of embodiments 1-54, or the pharmaceutical composition of any one of embodiments 55-58, for use in a method of:

(a) preventing or treating an infection caused by a virus in an individual, (b) killing or neutralizing a virus in an individual, (c) activating the complement pathway in an individual, and/or (d) preventing, treating, or reducing infection caused by a virus in an individual, wherein at least one virus is killed or neutralized on the mucosa, the method comprising administering to the individual an effective amount of the protein or composition.

Embodiment 103. The use of a chimeric protein of any one of embodiments 1-54, or the pharmaceutical composition of any one of embodiments 55-58, in the manufacture of a medicament for preventing or treating an infection caused by a virus in an individual.

Embodiment 104. The use according to embodiment 103, wherein the chimeric protein or the pharmaceutical composition is administered to the individual before the individual is exposed to the virus.

Embodiment 105. The use according to embodiment 103, wherein the chimeric protein or the pharmaceutical composition is administered to the individual within about 72 hours after the individual is exposed to the virus.

Embodiment 106. The use according to any one of embodiments 103-105, wherein the chimeric protein or the pharmaceutical composition is administered topically onto the mucosa.

Embodiment 107. The use according to embodiment 106, wherein the chimeric protein or the pharmaceutical composition is administered via a nasal spray, an inhaler, a nebulizer, or an eye drop.

Embodiment 108. The use according to any one of embodiments 103-107, wherein the chimeric protein or the pharmaceutical composition is administered once daily.

Embodiment 109. The use of a chimeric protein of any one of embodiments 1-54, or the pharmaceutical composition of any one of embodiments 55-58, in the manufacture of a medicament for killing or neutralizing a virus in an individual.

Embodiment 110. The use of a chimeric protein of any one of embodiments 1-54, or the pharmaceutical composition of any one of embodiments 55-58, in the manufacture of a medicament for activating the complement pathway in an individual.

Embodiment 111. The use according to embodiment 109 or 110, wherein administration of the medicament leads to at least one virus being killed or neutralized on the mucosa.

Embodiment 112. The use of a chimeric protein of any one of embodiments 1-54, or the pharmaceutical composition of any one of embodiments 55-58, in the manufacture of a medicament for preventing, treating, or reducing infection caused by a virus in an individual, wherein administration of the medicament leads to at least one virus being killed or neutralized on the mucosa.

Embodiment 113. The use according to any one of embodiments 109-112, wherein the chimeric protein activates the complement pathway in the individual.

Embodiment 114. The use according to any one of embodiments 103-109 and 111, wherein the killing or neutralization is via activation of the complement pathway.

Embodiment 115. The use according to any one of embodiments 103-114, wherein the virus is a coronavirus, optionally wherein the coronavirus is selected from the group consisting of SARS-CoV, SARS-CoV-2, and HCoV-NL63.

Embodiment 116. The use according to any one of embodiments 103-115, wherein the S protein comprises the amino acid sequence of any one of SEQ ID NOs: 96-100, 103, 123-127, and 141-143, or a variant thereof comprising at least about 90% sequence identity to the amino acid sequence of any one of SEQ ID NOs: 96-100, 103, 123-127, and 141-143.

Embodiment 117. The use of a chimeric protein of any one of embodiments 1-54, or the pharmaceutical composition of any one of embodiments 55-58, in the manufacture of a medicament for:

(a) preventing or treating an infection caused by a virus in an individual, (b) killing or neutralizing a virus in an individual, (c) activating the complement pathway in an individual, and/or (d) preventing, treating, or reducing infection caused by a virus in an individual, wherein at least one virus is killed or neutralized on the mucosa.

Embodiment 118. A chimeric protein comprising:

(a) a target-binding moiety comprising an extracellular binding domain (EBD) of an angiotensin-converting enzyme 2 (ACE2) protein or a fragment thereof that specifically binds to a spike(S) protein; and (b) a mucoadhesive peptide fragment comprising at least about 5 positively charged amino acid residues, wherein the mucoadhesive peptide fragment facilitates attachment of the chimeric protein to a mucosa.

Embodiment 119. The chimeric protein of embodiment 118, comprising:

(i) a single polypeptide chain; or (ii) two or more polypeptide chains, wherein the chimeric protein comprises two or more mucoadhesive peptide fragments, optionally wherein each of the two or more mucoadhesive peptide fragments comprises at least about 5 positively charged amino acid residues.

Embodiment 120. The chimeric protein of embodiment 118 or 119, wherein the mucoadhesive peptide fragment comprises at least about 6 positively charged amino acid residues.

Embodiment 121. The chimeric protein of any one of embodiments 118-120, wherein the positively charged amino acid residues are selected from the group consisting of lysine, arginine, histidine, ornithine, and combinations thereof.

Embodiment 122. The chimeric protein of any one of embodiments 118-121, wherein:

(i) the mucoadhesive peptide fragment comprises at least 5 contiguous positively charged amino acids; and/or (ii) the positively charged amino acid residues are interspersed with one or more non-positively charged amino acid residues, optionally wherein at least about 50% of the amino acid residues in the mucoadhesive peptide fragment are positively charged amino acid residues.

Embodiment 123. The chimeric protein of any one of embodiments 118-122, wherein the mucoadhesive peptide fragment:

(i) is no more than about 15 kD;

(ii) has an isoelectric point (pI) higher than the pH of the mucosa;

(iii) does not facilitate penetration of the chimeric protein into a cell of the mucosa;

(iv) does not disrupt folding of the chimeric protein within a host cell expressing the chimeric protein;

(v) does not block secretion of the chimeric protein from a host cell expressing the chimeric protein; and/or (vi) does not interfere with the binding between the target-binding moiety and the S protein.

Embodiment 124. The chimeric protein of any one of embodiments 118-123, wherein the mucoadhesive peptide fragment comprises an amino acid sequence of any one of SEQ ID NOs: 28-62 and 128-134, or a variant thereof comprising at least about 90% sequence identity to the amino acid sequence of any one of SEQ ID NOs: 28-62 and 128-134.

Embodiment 125. The chimeric protein of any one of embodiments 118-124, wherein the mucoadhesive peptide fragment is fused to the target-binding moiety via a peptide linker.

Embodiment 126. The chimeric protein of embodiment 125, wherein the peptide linker comprises:

(i) one or more oligomerization and/or multimerization domains;

(ii) the constant region of a heavy chain of a full-length antibody or a fragment thereof, or the constant region of a light chain of a full-length antibody or a fragment thereof;

(iii) an Fc region or a fragment thereof;

(iv) a $CH_1$, $CH_2$, $CH_3$, $CH_4$, and/or $C_L$ domain or a fragment thereof;

(v) an antibody hinge domain or a fragment thereof;

(vi) a detectable enzymatic tag, optionally wherein the enzymatic tag is an alkaline phosphatase and/or a glutathione-s-transferase;

(vii) a basic helix-loop-helix leucine zipper (bZip) domain, bZip isoleucine zipper domain, and/or bZip-leucine/isoleucine zipper domain;

(viii) a collagen-like peptide;

(ix) a p53 tetramerization domain;
(x) a streptavidin (SA) protein, optionally wherein the peptide linker further comprises a dextran scaffold or one or more maleimide polymers (DMGS);
(xi) a bacteriophage T7 fibritin protein or a portion thereof; and/or
(xii) a cartilage oligomeric matrix protein (COMP) protein.

Embodiment 127. The chimeric protein of any one of embodiments 118-126, wherein the mucoadhesive peptide fragment is fused to a C-terminus of the target-binding moiety.

Embodiment 128. The chimeric protein of any one of embodiments 118-127, wherein the target-binding moiety comprises the EBD of a human ACE2 (hACE2) protein or a fragment or variant thereof.

Embodiment 129. The chimeric protein of any one of embodiments 118-128, wherein the target-binding moiety comprises:
(i) amino acids 30-41 of a full-length hACE2 protein, or a variant thereof comprising at least about 90% sequence identity to amino acids 30-41 of a full-length hACE2 protein; and/or,
(ii) the amino acid sequence of SEQ ID NO: 102, or a variant thereof comprising at least about 90% sequence identity to the amino acid sequence of SEQ ID NO: 102.

Embodiment 130. The chimeric protein of any one of embodiments 118-129, wherein the target-binding moiety comprises:
(i) amino acids 24-42 of a full-length hACE2 protein, or a variant thereof comprising at least about 90% sequence identity to amino acids 24-42 of a full-length hACE2 protein; and/or
(ii) the amino acid sequence of SEQ ID NO: 8, or a variant thereof comprising at least about 90% sequence identity to the amino acid sequence of SEQ ID NO: 8.

Embodiment 131. The chimeric protein of any one of embodiments 118-130, wherein the target-binding moiety comprises the amino acid sequence of any one of SEQ ID NOs: 1-7, 9-14, and 135, or a variant thereof comprising at least about 90% sequence identity the amino acid sequence of any one of SEQ ID NOs: 1-7, 9-14, and 135.

Embodiment 132. The chimeric protein of embodiment 128, comprising the amino acid sequence of any one of SEQ ID NOs: 84-88 and 136-140, or a variant thereof comprising at least about 90% sequence identity to the amino acid sequence of any one of SEQ ID NOs: 84-88 and 136-140.

Embodiment 133. The chimeric protein of any one of embodiments 118-127, wherein the target-binding moiety comprises the EBD of an animal ACE2 protein or a fragment or variant thereof, optionally wherein the animal ACE2 protein is a murine, guinea pig, equine, ferret, macaque, chimpanzee, swine, canine, feline, bovine, rabbit, mink, or chicken ACE2 protein or a fragment or variant thereof.

Embodiment 134. The chimeric protein of any one of embodiments 118-127 and 133, wherein the target-binding moiety comprises:
(i) amino acids 30-41 of a full-length animal ACE2 protein, or a variant thereof comprising at least about 90% sequence identity to amino acids 30-41 of a full-length animal ACE2 protein, wherein the full-length animal ACE2 protein is not a chicken or canine ACE2 protein: or,
(ii) amino acids 29-40 of a full-length animal ACE2 protein, or a variant thereof comprising at least about 90% sequence identity to amino acids 29-40 of a full-length animal ACE2 protein, wherein the full-length animal ACE2 protein is a chicken or canine ACE2 protein.

Embodiment 135. The chimeric protein of any one of embodiments 118-127, 133, and 134, wherein the target-binding moiety comprises the amino acid sequence of any one of SEQ ID NOs: 15-27 and 110-122, or a variant thereof comprising at least about 90% sequence identity to any one of SEQ ID NOs: 15-27 and 110-122.

Embodiment 136. The chimeric protein of any one of embodiments 133-135, comprising the amino acid sequence of any one of SEQ ID NOs: 89-93, or a variant thereof comprising at least about 90% sequence identity to the amino acid sequence of any one of SEQ ID NOs: 89-93.

Embodiment 137. A pharmaceutical composition comprising the chimeric protein of any one of embodiments 118-136, and a pharmaceutically acceptable carrier.

Embodiment 138. The pharmaceutical composition of embodiment 137, wherein the pharmaceutical composition comprises a plurality of the chimeric proteins, and wherein at least two of the plurality of the chimeric proteins are different from each other.

Embodiment 139. The pharmaceutical composition of embodiment 136 or 137, wherein the pharmaceutical composition is formulated for intranasal administration, intraocular administration, and/or intrabronchial administration.

Embodiment 140. An isolated nucleic acid or a set of isolated nucleic acids encoding the chimeric protein of any one of embodiments 118-136.

Embodiment 141. A vector or a set of vectors comprising the nucleic acid or the set of nucleic acids of embodiment 2.

Embodiment 142. A host cell comprising the chimeric protein of any one of embodiments 118-136 the nucleic acid or set of nucleic acids of embodiment 140, the vector or set of vectors of embodiment 141.

Embodiment 143. A method of preparing a chimeric protein, comprising:
(a) culturing a host cell of embodiment 142 under a condition effective to express the chimeric protein; and
(b) obtaining the expressed chimeric protein from the host cell.

Embodiment 144. A method of preventing or treating an infection caused by a virus in an individual, comprising administering to the individual an effective amount of the chimeric protein of any one of embodiments 118-136, or the pharmaceutical composition of any one of embodiments 137-139.

Embodiment 145. An in vitro method of killing or neutralizing a virus, comprising contacting a virus with the chimeric protein of any one of embodiments 118-136 in the presence of at least one component of the complement system, optionally wherein the at least one component of the complement system is C1, C4, or membrane attack complex (MAC).

Embodiment 146. A method of killing or neutralizing a virus in an individual, comprising administering to the individual an effective amount of the chimeric protein of any one of embodiments 118-136, or the pharmaceutical composition of any one of embodiments 137-139.

Embodiment 147. A method of activating the complement pathway in an individual, comprising administering to the individual an effective amount of the chimeric protein of any one of embodiments 118-136, or the pharmaceutical composition of any one of embodiments 137-139.

Embodiment 148. The method of any one of embodiments 28-30, wherein at least one virus is killed or neutralized on the mucosa.

Embodiment 149. A method of preventing, treating, or reducing infection caused by a virus in an individual, comprising administering to the individual an effective amount of the chimeric protein of any one of embodiments 118-136, or the pharmaceutical composition of any one of embodiments 137-139, wherein at least one virus is killed or neutralized on the mucosa.

Embodiment 150. The method of any one of embodiments x, wherein:

(i) the chimeric protein activates the complement pathway in the individual; and/or (ii) the killing or neutralization is via activation of the complement pathway.

Embodiment 151. The method of any one of embodiments x, wherein the virus is a coronavirus, optionally wherein the coronavirus is selected from the group consisting of SARS-CoV, SARS-CoV-2, and HCoV-NL63.

Embodiment 152. The method of any one of embodiments x, wherein the S protein comprises the amino acid sequence of any one of SEQ ID NOs: 96-100, 103, 123-127, and 141-143, or a variant thereof comprising at least about 90% sequence identity to the amino acid sequence of any one of SEQ ID NOs: 96-100, 103, 123-127, and 141-143.

Embodiment 153. The chimeric protein of any one of embodiments 118-136, or the pharmaceutical composition of any one of embodiments 137-139, for use in a method of preventing or treating an infection caused by a virus in an individual, the method comprising administering to the individual an effective amount of the protein or composition.

Embodiment 154. The chimeric protein of any one of embodiments 118-136, or the pharmaceutical composition of any one of embodiments 137-139, for use in a method of killing or neutralizing a virus in an individual, the method comprising administering to the individual an effective amount of the protein or composition.

Embodiment 155. The chimeric protein of any one of embodiments 118-136, or the pharmaceutical composition of any one of embodiments 137-139, for use in a method of activating the complement pathway in an individual, the method comprising administering to the individual an effective amount of the protein or composition.

Embodiment 156. The protein or composition for use according to embodiments 154 or 155, wherein at least one virus is killed or neutralized on the mucosa.

Embodiment 157. The chimeric protein of any one of embodiments 118-136, or the pharmaceutical composition of any one of embodiments 137-139, for use in a method of preventing, treating, or reducing infection caused by a virus in an individual, the method comprising administering to the individual an effective amount of the protein or composition, wherein at least one virus is killed or neutralized on the mucosa.

Embodiment 158. The protein or composition for use according to any one of embodiments 154-157, wherein:

(i) the chimeric protein activates the complement pathway in the individual; and/or (ii) the killing or neutralization is via activation of the complement pathway.

Embodiment 159. The protein or composition for use according to any one of embodiments 153-158, wherein the virus is a coronavirus, optionally wherein the coronavirus is selected from the group consisting of SARS-CoV, SARS-CoV-2, and HCoV-NL63.

Embodiment 160. The protein or composition for use according to any one of embodiments 153-159, wherein the S protein comprises the amino acid sequence of any one of SEQ ID NOs: 96-100, 103, 123-127, and 141-143, or a variant thereof comprising at least about 90% sequence identity to the amino acid sequence of any one of SEQ ID NOs: 96-100, 103, 123-127, and 141-143.

Embodiment 161. The chimeric protein of any one of embodiments 118-136, or the pharmaceutical composition of any one of embodiments 137-139, for use in a method of:

(a) preventing or treating an infection caused by a virus in an individual, (b) killing or neutralizing a virus in an individual, (c) activating the complement pathway in an individual, and/or (d) preventing, treating, or reducing infection caused by a virus in an individual, wherein at least one virus is killed or neutralized on the mucosa, the method comprising administering to the individual an effective amount of the protein or composition.

Embodiment 162. The use of a chimeric protein of any one of embodiments 118-136, or the pharmaceutical composition of any one of embodiments 137-139, in the manufacture of a medicament for preventing or treating an infection caused by a virus in an individual.

Embodiment 163. The use of a chimeric protein of any one of embodiments 118-136, or the pharmaceutical composition of any one of embodiments 137-139, in the manufacture of a medicament for killing or neutralizing a virus in an individual.

Embodiment 164. The use of a chimeric protein of any one of embodiments 118-136, or the pharmaceutical composition of any one of embodiments 137-139, in the manufacture of a medicament for activating the complement pathway in an individual.

Embodiment 165. The use according to embodiment 163 or 164, wherein administration of the medicament leads to at least one virus being killed or neutralized on the mucosa.

Embodiment 166. The use of a chimeric protein of any one of embodiments 118-136, or the pharmaceutical composition of any one of embodiments 137-139, in the manufacture of a medicament for preventing, treating, or reducing infection caused by a virus in an individual, wherein administration of the medicament leads to at least one virus being killed or neutralized on the mucosa.

Embodiment 167. The use according to any one of embodiments 163-166, wherein:

(i) the chimeric protein activates the complement pathway in the individual; and/or (ii) the killing or neutralization is via activation of the complement pathway.

Embodiment 168. The use according to any one of embodiments 162-167, wherein the virus is a coronavirus, optionally wherein the coronavirus is selected from the group consisting of SARS-CoV, SARS-CoV-2, and HCoV-NL63.

Embodiment 169. The use according to any one of embodiments 162-168, wherein the S protein comprises the amino acid sequence of any one of SEQ ID NOs: 96-100, 103, 123-127, and 141-143, or a variant thereof comprising at least about 90% sequence identity to the amino acid sequence of any one of SEQ ID NOs: 96-100, 103, 123-127, and 141-143.

Embodiment 170. The use of a chimeric protein of any one of embodiments 118-136, or the pharmaceutical composition of any one of embodiments 137-139, in the manufacture of a medicament for:

(a) preventing or treating an infection caused by a virus in an individual, (b) killing or neutralizing a virus in an individual, (c) activating the complement pathway in an individual, and/or (d) preventing, treating, or reducing infection caused by a virus in an individual, wherein at least one virus is killed or neutralized on the mucosa.

EXAMPLES

The invention will be more fully understood by reference to the following Examples. They should not, however, be construed as limiting the scope of the invention. It is understood that the Examples and embodiments described herein are for illustrative purposes only and that various modifications or changes in light thereof will be suggested to persons skilled in the art and are to be included within the spirit and purview of this application and scope of the appended claims.

Example 1. ACE2 Proteins and Fragments Useful for Generating ACE2 Mucoadhesive Chimeric Proteins Angiotensin converting enzyme II (ACE2) is the cellular receptor for several coronavirus species (e.g., SARS-CoV, SARS-CoV-2, and HCoV-NL63) and mediates binding of the viral spike protein present on the surface of viral particles, enabling viral entry into susceptible ACE2-positive cells of the respiratory tract. ACE2 is a metallocarboxyl peptidase of 805 amino acids comprised of an extracellular catalytic domain, a transmembrane region, and a short intracellular domain and is highly conserved among vertebrates. A catalytically active fragment of ACE2 membrane-bound protein can be released from its membrane tether by the action of the ADAM10/ADAM17 metalloproteinases or cleaved by the transmembrane protease TMPRSS2 at the cell membrane. ADAM17 and TMPRSS2 are expressed in ACE2-positive cells in the lung and play an important role in SARS-CoV-2 entry into those cells. ACE2 and TMPRSS2 are co-expressed in many tissues throughout the body and can be easily detected in the respiratory system; expression occurs in type II pneumocytes and enterocytes, alveolar cells, bronchial transient epithelial secretory cells, respiratory epithelial cells, and in the oral cavity and tongue (Beyerstedt et al. *Eur J Clin Microbiol Infect Dis* (2021) 40:905-919; Heurich et al. J Virol. (2014) January; 88 (2): 1293-307). In cells of the nasal epithelium, ACE2 is highly expressed in adults with lower expression in children, which may explain, in part, the lack of respiratory SARS-CoV-2 symptoms in younger patients.

The sites of proteolytic cleavage in the ACE2 protein are shown in FIG. 1, as is the location of the ACE12 region which is a binding site for the spike(S) protein S1 subunit. Other important features, such as the substrate attachment site, the catalytic domain (e.g., peptidase M2 region), membrane domain, and intracellular domain, are also labeled in FIG. 1.

For the experiments described in the following Examples, we have used human ACE2 (hACE2) proteins and protein fragments (described in Table 3) fused to various polycationic mucoadhesive peptide fragments, either directly or through a peptide linker (e.g., the Fc region of human immunoglobulin $IgG_1$, "Fc1", disclosed in Table 9) and expressed them as cationic, mucoadhesive chimeric proteins capable of adhering to the respiratory epithelium. Table 3 disclosed full-length hACE2, the extracellular domain of the hACE2 receptor ("ACE614", "ACE732"), further truncated forms or fragments of hACE2 that we designed ("ACE360", "ACEΔ360", "ACE200", "ACE420", "ACE19", and "ACE12"), as well as "ACE614" proteins with point mutations that have been shown to affect susceptibility or severity of disease ("720D"; Shikov et al. *Front Genet.* 11:551220 (2020)), inhibit enzyme activity ("HN-HN", Tanaka et al. *Nature* 11:12740-12753 (2021)), and alter the binding properties ("K26R" and "I468V"; Li et al. *Mol Genet Genomic Med.* 8 (8): e1344 (2020)) or affect the binding affinity to S1 (Tanaka et al., 2021).

Using molecular dynamics modeling, Mohebbi et al. found an S1-binding site on ACE2 to comprise the short peptide of aa 30-41 (DKFNHEAEDLFY, named as "ACE12" by the Applicants, SEQ ID NO: 102 in Table 3) (Mohebbi et al., *Future Virol.* 10:2217-2235 (2020)). Recently, Kunetsov et al., also using molecular dynamics modeling, found that a 19-amino-acid ACE2 fragment QAKTFLDKFNHEAEDLFYQ (named as "ACE19" by the Applicants, SEQ ID NO: 8 in Table 3), comprising the S1 binding site DKFNHEAEDLFY, selectively recognized the SARS-CoV-2 virus S protein S1 subunit and interfered with S1 binding (Kunetsov et al., *Int J Pept Res Ther,* 28:7 (2022)).

Additionally, the ACE2 proteins of domestic or farmed animals or fragments of these animal ACE2 proteins that are disclosed in Table 4 can be used to make chimeric proteins as discussed above for use in a veterinary setting. These animals reside in close contact with the human population and have served as vectors for SARS-CoV-2 or have become infected through interactions with other animals or humans. They are candidates for the prophylactic use of mucoadhesive chimeric proteins to prevent SARS-CoV-2 infections in animals living alongside humans and may help to reduce the incidence of animal-born transmission of the virus, reducing the incidence of SARS-CoV-2 infections world-wide. FIG. 2 illustrates an alignment of multiple hACE2 and animal ACE2 sequences, performed using CLUSTAL Omega multiple sequence alignment software. Asterisks indicate conserved amino acid residues, and the S1 binding site ACE12 in hACE2 is underlined.

Using the ACE2 proteins or protein fragments disclosed in Table 3 or 4 to fuse with the exemplary mucoadhesive peptide fragments of Table 8, optionally with exemplary linkers of Table 9, both human and animal mucoadhesive chimeric proteins can be made and may be used to block viral infections originating in the respiratory tract.

These Examples illustrate a means to block the entry of coronaviruses (e.g., SARS-CoV-2) into susceptible cells and tissues by providing an ACE2 receptor protein trap; we seek to prevent S1 from binding to its natural, cell membrane-bound receptor when the mucoadhesive chimeric proteins are administered to the nasal cavity of human and animal populations.

Example 2. Design and Expression of ACE2 Mucoadhesive Chimeric Proteins

This Example describes a variety of ACE2 mucoadhesive chimeric proteins that can be used to prevent or treat coronavirus (e.g., SARS-CoV-2) infection; all comprise an ACE2 protein fragment and a mucoadhesive protein fragment. These exemplary ACE2 mucoadhesive chimeric proteins include hACE2 chimeric proteins and animal ACE2 chimeric proteins, chimeric proteins comprising full-length ACE2 or partial ACE2 fragments (both categorized as "ACE2 protein fragments"), and chimeric proteins comprising ACE2 protein fragments fused directly to mucoadhesive protein fragments or chimeric proteins comprising ACE2 protein fragments fused indirectly through linker fragments.

Example 2A. ACE2 Chimeric Proteins Comprising Various Linkers

In some exemplary ACE2 chimeric proteins (e.g., ACE2 chimeric proteins comprising hACE2 or animal ACE2 proteins or fragments thereof), the ACE2 protein fragments are fused directly to mucoadhesive protein fragments. The ACE2 protein fragments can be from a human or an animal, full-length ACE2, or partial ACE2 fragments, including those described in Example 1, Table 3, and/or Table 4. Exemplary chimeric proteins of the present invention are described in Table 1.

In some instances, it may be necessary to stabilize the ACE2 chimeric proteins with the inclusion of linker peptide fragments, to increase the protein half-life, increase the avidity or number of mucoadhesive chimeric proteins in vitro in order to more easily detect or measure a signal; or to increase the avidity or number of mucoadhesive chimeric proteins in vivo to raise the effective amount of material being delivered to the nasal cavity in a single dose. For this purpose, various types of linker peptide fragments, including oligomerization or multimerization domains from natural proteins, are used in various embodiments. In the primary embodiment, the extracellular domain of hACE2 or the hACE2 protein fragments of Table 3 are fused to a human immunoglobulin Fc region, also referred to as an Fc linker. The Fc linker moiety is composed of heavy chain $CH_2$ and $CH_3$ domains of an IgG, IgA, or IgD antibody, or $CH_2$, $CH_3$, and $CH_4$ if the antibody is an IgM or IgE. In other embodiments of mucoadhesive chimeric proteins, the peptide linker fragments can comprise only parts of the constant region of a full-length antibody's heavy chain or a part of the constant region of an antibody's light chain, e.g., $CH_1$, $CH_2$, $CH_3$, and $CH_4$, and/or $C_L$. Some exemplary chimeric proteins comprise Immunoglobulin Fc regions as the peptide linker fragments or a part of the peptide linker fragments, which are comprised of $CH_2$ and $CH_3$ domains or $CH_2$, $CH_3$, and $CH_4$ domains. Fc regions act as dimerizing agents and retain some antibody-like properties, such as good physicochemical characteristics for expression, purification and storage, and long serum half-life in vivo, see Lobner et al., *Immunol. Rev.,* 270 (1) 113-31 (2016). Exemplary sequences of Fc as well as $CH_1$, $CH_2$, $CH_3$, and $CH_4$, and $C_L$ are shown in Table 9.

One ACE2 chimeric protein comprising ACE614 (Table 3), the ACE2 fragment with the sequence of SEQ ID NO: 2, and an immunoglobulin Fc region linker ($CH_2CH_3$), i.e., "Fc1" (Table 9), the immunoglobulin Fc linker with the sequence of SEQ ID NO: 63, was generated.

Other possible linker peptides or useful domains are considered herein, which are able to induce stable protein interactions when fused with the ACE2 proteins or protein fragments of Table 3. These include the detectable enzymatic tags alkaline phosphatase and glutathione-s-transferase (GST), both functioning as dimers. In particular, alkaline phosphatase (513 amino acids (aa)) dimerization contacts are formed by patches of discrete aa sequences from at N-terminus: aa27-42, aa68-76, aa83-85, aa94-98 and aa 103-105; and the C-terminus: 382-391 and 397-410. GST (217aa) homodimerizes as two monomers: monomer 1 (aa1-84): monomer 2 (aa85-217). Alkaline phosphate and GST chimeric proteins are highly soluble, easily detected using their enzymatic functions, and do not seem to interfere with the fusion partner's activity.

Exemplary full-length linker peptides or protein: protein interaction domains able to induce multimerization in their fusion partners and also increase the overall strength or avidity of binding are outlined in Table 9. Included are the often-used heptad repeats of the basic helix-loop-helix leucine zipper domains (bLZIP) or isoleucine zipper domains (bIZIP) found in transcription factors, which form stable protein trimers (see, Napolitano and Ballabio, *J. Cell Sci.,* 129 (13): 2475-81 (2016); and Branttie and Dutch, *J. Gen Virol.,* 101 (5): 467-472 (2020)). Collagen-like proteins (GPP) form trimers of great binding strength due to the presence of repeated Glycine-X-Y repeats $(GPP)_n$, where $n \geq 1$, and have been shown not to interfere with the chimeric protein's functionality or safety profile (Fan et al., *FASEB J.,* 22:3795-3804 (2008)). Higher order multimerization domains have been used extensively as well; the streptavidin protein (SA) is able to tightly bind biotin molecules forming tetrameric units that are easily detectable (Chivers et al., *Biochem J.,* 435 (Pt 1): 55-63 (2011)). Smaller and less bulky linkers are also considered; the p53 tetramerization domain (p53) is only 31 amino acids long (Gencel-Augusto et al., *Genes Dev.,* 34 (17-18): 1128-1146 (2020)); the C-terminal 27 amino acids of the bacteriophage T7 fibritin protein (T7F, also called folden; Yang et al., *J. Virol.,* 76 (9): 4634-42 (2002)) forms stable soluble trimeric complexes. The coiled-coil domain of the cartilage oligomeric matrix protein (COMP) (Holler et al., *J. Immunol. Methods,* 237: 159-173 (2000)) is able to form self-assembling pentameric complexes. Further protein-protein interaction domains can be found in the literature and higher-order complexes can be formed using dextran scaffolds (DxSA) or maleimide polymers (DMGS, DMSA) (see Dolton et al., *Clin. Exp. Immunol.,* 177 (1): 47-63 (2014); and Guillaume et al., *J. Biol. Chem.,* 278: P4500-4509 (2003).

Using the animal ACE2 protein sequences disclosed in Table 4 and fragments thereof corresponding to the various partial hACE2 fragments disclosed in Table 3 (fragments with equivalent sequence boundaries and lengths), exemplary animal-derived ACE2 proteins and protein fragments are joined to the Fc1 linker, or any other exemplary linkers disclosed in Table 9, resulting in various animal ACE2 chimeric proteins comprising the linker fragments.

Example 2B. ACE2 Chimeric Proteins Comprising Polylysine and Polyhistidine Peptides The ACE2 full-length proteins and partial fragments disclosed in Tables 3 and 4, as well as additional ACE2 protein fragments derived from them (e.g., animal ACE2 fragments described above) are each used to create mucoadhesive chimeric proteins by the addition of cationic moieties (i.e., polycationic peptides, also called "mucoadhesive peptide fragments") which are designed herein to adhere to the respiratory mucosa and provide a protein "trap", capturing SARS-CoV-2 virus via binding to the spike proteins arrayed on the viral particle. One type of exemplary mucoadhesive peptide fragment is polylysine, and another type of exemplary mucoadhesive peptide fragment is polyhistidine.

In some embodiments, mucoadhesive chimeric proteins comprising full-length ACE2 proteins or partial ACE2 fragments directly fused to various lengths of polylysine or polyhistidine peptide fragments are generated.

In other embodiments, mucoadhesive chimeric proteins are generated with an ACE2 protein fragment (such as any disclosed in previous Examples) fused to a linker (such as any linker disclosed in Table 9), which in turn is fused to a polylysine or a polyhistidine peptide fragment, or any other mucoadhesive peptide fragment (such as any fragment disclosed in Table 8).

In one experiment, a DNA fragment encoding a polylysine-modified ACE614-Fc1, the hACE2 extracellular domain with an Fc1 linker (i.e., ACE614-Fc1-12K), was cloned into a mammalian expression vector and then used to transfect HEK293F cells which then expressed the mucoadhesive chimeric protein ACE614-Fc1-12K, comprising 12 C-terminal lysine residues. After 7 days of culturing the transfected HEK293F cells at 37° C., the culture medium was harvested, and the chimeric protein was isolated and purified from culture supernatants using a HiTrap® Protein A HP column (Cytiva) on an ÄKTA FPLC system (GE Healthcare). Similar experiments are conducted for a DNA fragment encoding a polyhistidine-modified ACE614-Fc1, the hACE2 extracellular domain with an Fc1 linker (i.e., ACE614-Fc1-12H), according to the above methods.

In other experiments, DNA fragments encoding ACE614 or ACE614-Fc1 comprising different lengths of polylysine (e.g., 6K, 30K, etc.) or polyhistidine (e.g., 5H, 6H, 30H, etc.) are cloned into the same mammalian expression vector and then used to transfect HEK293F cells.

In yet other experiments, DNA fragments encoding the other exemplary ACE2 protein fragments (the hACE2 proteins or protein fragments other than ACE614 disclosed in Table 3, or the animal ACE proteins disclosed in Table 4, or fragments thereof as described in Example 1) fused directly to various lengths of polylysine (e.g., 6K, 12K, 30K, etc.) or polyhistidine (e.g., 6K, 30K, etc.) are cloned into the same mammalian expression vector and used to transfect HEK293F cells.

In other further experiments, DNA fragments encoding exemplary chimeric proteins comprising various linkers as described in Example 2A fused directly to various lengths of polylysine (e.g., 6K, 12K, 30K, etc.) or polyhistidine (e.g., 5H, 6H, 30H, etc.) are cloned into the same mammalian expression vector and then used to transfect host HEK293F cells.

After 7 days of culturing the transfected HEK293F cells at 37° C., culture medium from the above-described experiments is harvested, and the chimeric proteins are isolated and purified from culture supernatants using the methods as described above.

These polylysine and polyhistidine peptides are examples of mucoadhesive peptide fragments which facilitate the attachment of the exemplary chimeric proteins to the upper respiratory mucosa in vivo. In addition to lysine and histidine residues, other cationic amino acids can be used to provide mucoadhesive properties and are described in the next Example.

Example 2C. ACE2 Chimeric Proteins Comprising Other Mucoadhesive Polycationic Peptides Additional mucoadhesive chimeric proteins comprising any full-length ACE2 or partial ACE2 fragments described above, fused to other cationic (positively charged) peptides (polycationic peptides or mucoadhesive peptide fragments) directly or indirectly (e.g., via a linker as described in previous Examples), are produced using the cationic amino acids arginine (R) and/or ornithine (O). The mucoadhesive chimeric proteins with ornithine-containing peptides are produced by a method described in Mordhorst et al. *Angewandte Chemie* 59:21442-21447 (2020).

The polycationic peptides (mucoadhesive peptide fragments) may contain only cationic amino acids, or contain cationic amino acids interspersed with neutral amino acids (amino acids that do not carry a negative charge, i.e., non-positively charged amino acid residues), as shown in Table 8. The exemplary polycationic peptides listed in Table 8 include peptides consisting of only K, only H, only R, or only O, ranging from 6 to 45 amino acids or more, mixed cationic peptides consisting of mixtures of K, H, R, and O, ranging from 6 to 45 amino acids or more, and cationic plus neutral amino acid peptides ranging from 6 to 45 amino acids or more. Selected examples of various ACE2 mucoadhesive chimeric proteins are listed in Table 1. Other exemplary ACE2 chimeric proteins are generated using various ACE2 protein fragments disclosed in Example 1 or ACE2-linker protein fragments (such as ACE614-Fc1) disclosed in Example 2 fused with any of the exemplary cationic peptides disclosed in Table 8. Such ACE2 mucoadhesive chimeric proteins are expressed in HEK293F cells and purified as described above. The chimeric proteins described in this Example can be used in the in vitro and an in vivo Examples which follow.

Example 3. In Vitro Characterization of Human and Animal ACE2 Mucoadhesive Chimeric Proteins

Figure 3A:
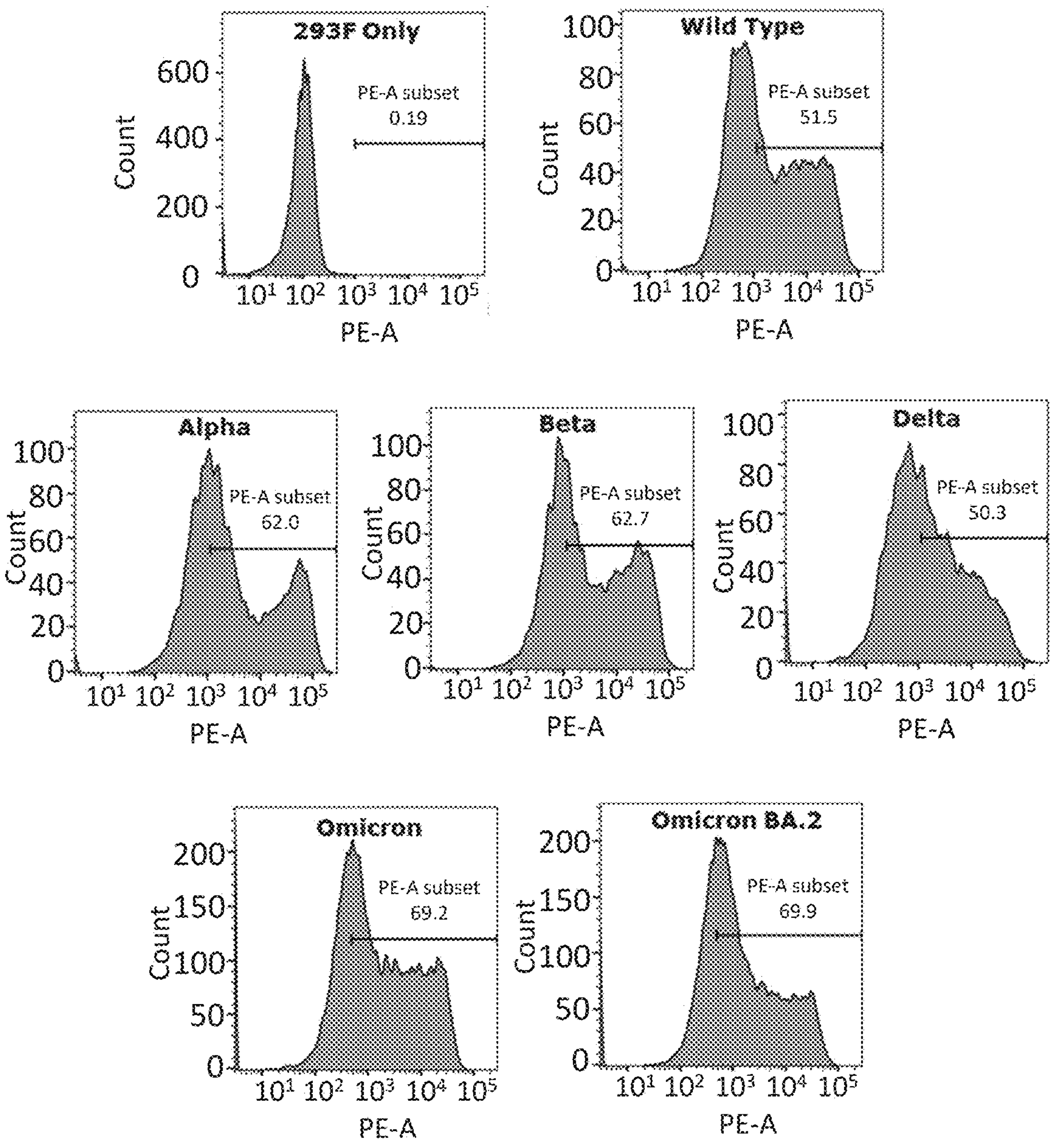
FIG. 3A shows that the exemplary ACE2-Fc1-12K chimeric protein binds to spike protein S1 subunit protein. Spike protein S1 subunit proteins from the SARS-CoV-2 WT, Alpha, Beta, Delta and Omicron variants BA.1 and BA.2 were transiently expressed in HEK293F cells. Cells were incubated first with ACE2-Fc1-12K followed by PE-Fc secondary antibody, then sorted using fluorescence-activated cell sorting (FACS).

Example 3A. Binding Specificity of ACE614-Fc1-12K Chimeric Protein to the Spike Proteins HEK293F cells (FreeStyle™ 293-F Cells, ThermoFisher Scientific) were transiently transfected with an expression vector carrying the SARS-CoV-2 variant Omicron S1 gene or the BA.2 S1 gene. The transfected cells were pooled and cultured for another 48 hours (h), and tested for Omicron and/or BA.2 S1 expression. S1-gene-transfected HEK293F and non-transfected HEK293F cells (negative control) were harvested and washed with 1% ice-cold bovine serum albumin (BSA) in phosphate buffered saline (PBS). The cells (100,000 cells for each concentration) were stained for 30 min using 5 μg/mL ACE2-hFc-12K at in the dark at room temperature (RT). The cells were then washed three times in 1% ice-cold BSA in PBS and incubated with PE-anti-human Fc secondary antibody (1:200, Jackson ImmunoResearch Laboratories) for 30 min at RT in the dark. The cells were washed three times with 1% ice-cold BSA in PBS and resuspended in 100 μL of washing buffer for flow cytometry analysis. Flow cytometry data were collected and analyzed using the BD FACSCanto™ II system and FlowJo™ v10.6.1 software package. ACE614-Fc1-12K was able to bind both Omicron and BA.2 S1 proteins expressed on the surface of HEK293F transfected cells as shown in the middle and right panels of FIG. 3A, while not binding to untransfected cells (left panel of FIG. 3A, "293F Only").

Example 3B. Binding of Mucoadhesive hIgG Chimeric Proteins to the Spike Protein S1 Subunit The binding affinity of the ACE2-Fc1-12K mucoadhesive chimeric protein to SARS-CoV-2 spike proteins (S1 subunit) was measured by Surface Plasmon Resonance using a BiaCore™ MX-100 instrument (Cytiva). The binding parameters between ACE2-Fc-12K and spike proteins from SARS-CoV-2 wild-type or variants Alpha, Beta, Delta, Omicron, or Omicron BA.2 were measured using a Protein G Sensor Chip (Cytiva) according to the manufacturer's protocol for Multi-Cycle Kinetics (MCK) analysis.

Figure 8:
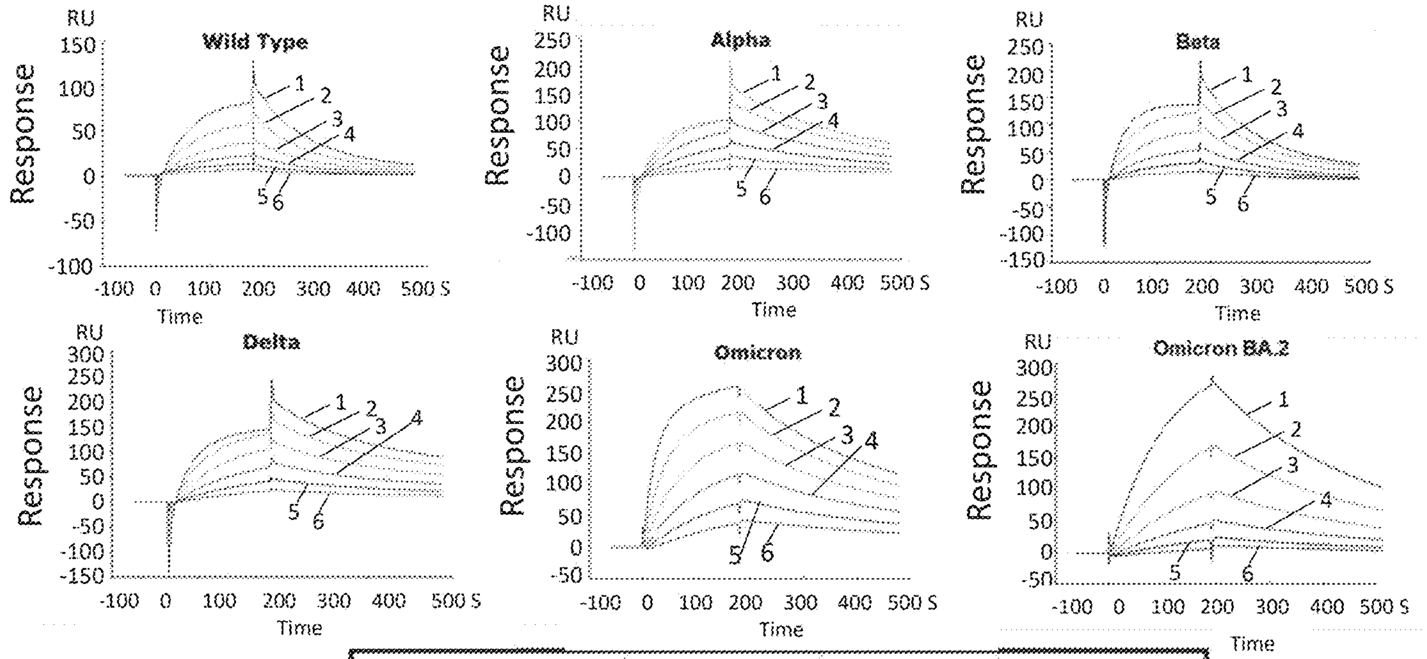
FIG. 8. The binding affinity of the ACE2-Fc1-12K mucoadhesive chimeric protein to SARS-CoV-2 spike proteins (S1 subunit) of various concentrations (90.91 nM ("1" in FIG. 8), 45.45 nM ("2" in FIG. 8), 22.73 nM ("3" in FIG. 8), 11.36 nM ("4" in FIG. 8), 5.682 nM ("5" in FIG. 8), and 2.841 nM ("6" in FIG. 8)) was measured by Surface Plasmon Resonance (upper panel). All SARS-CoV-2 variants tested show high affinity for the S1 subunit, demonstrated by $K_D$ values in the nanomolar range (lower panel).

ACE2-Fc1-12K was loaded onto the Sensor Chip on at 10 μg/mL. The spike protein from wild-type SARS-CoV-2 and each variant, in independent analyses, was added to the sensor chip at different concentrations (90.91, 45.45, 22.73, 11.36, 5.682, 2.841 nM). The data were analyzed using a 1:1 binding site mode using BiaCore X-100 evaluation software. The binding parameters, association (on-rate) constant $k_a$, dissociation (off-rate) constant $k_d$, and equilibrium dissociation constant $K_d$ were calculated using at least 3 replicates of each sample. As shown in FIG. 8, all SARS-CoV-2 variants displayed high affinity (all $K_D$ values are in the nM range) for the spike protein (S1 subunit).

Figure 3B:
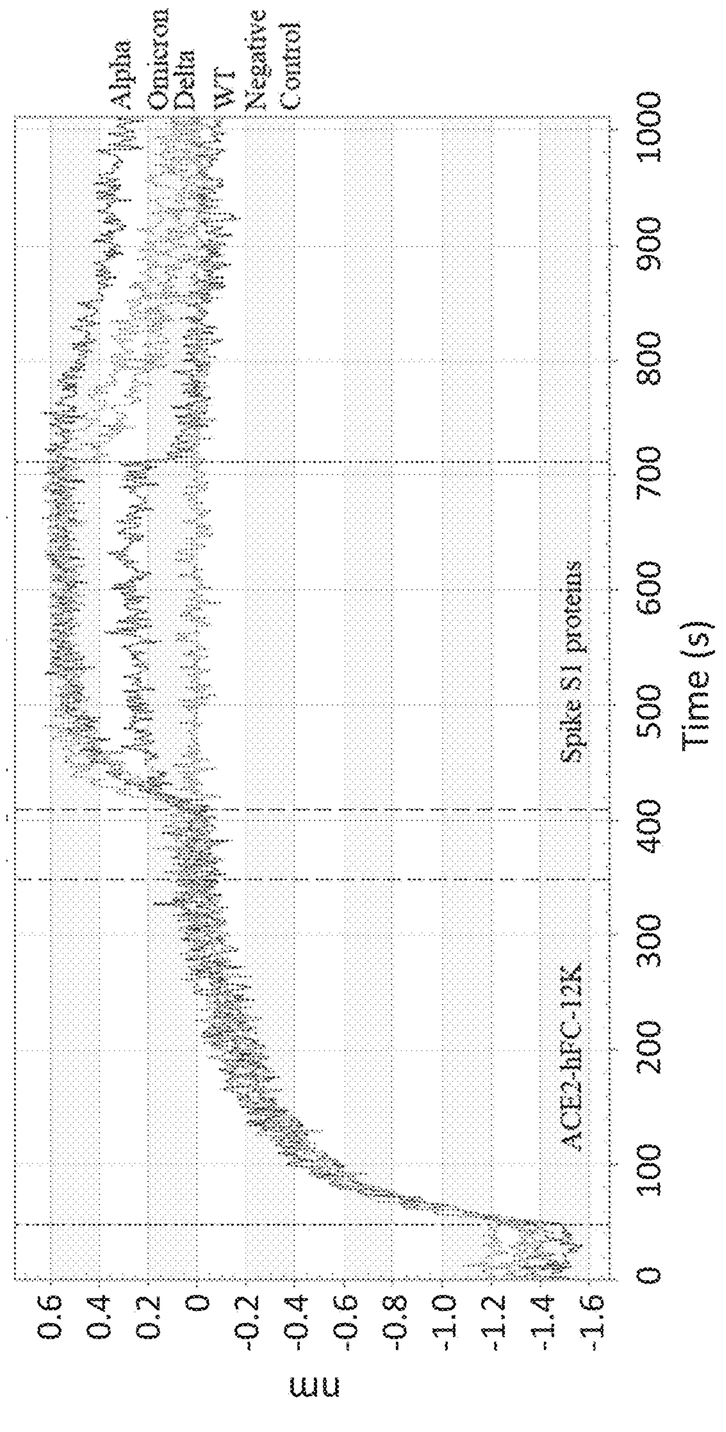
FIG. 3B shows that the exemplary ACE2-Fc1-12K chimeric protein (20 μg/mL) binds well to spike protein S1 subunit protein (10 μg/mL) from the Alpha, Delta, and Omicron variants of SARS-CoV-2, and is unaffected by the presence of the polycationic moiety. Bio-Layer Interferometry with a streptavidin sensor was used to measure the interactions; all steps were aligned by step Baseline 2 (sensor location). The negative control, lacking the C-terminal polycationic peptide, was a HIS-tagged hACE2 protein.

To determine whether the binding of ACE614-Fc1-12K chimeric protein to purified spike S1 protein was unaffected by the mucoadhesive cationic peptide modification, association of the chimeric protein to the S1 protein was examined by Bio-Layer Interferometry (BLI). The assay was conducted on a ForteBio Octet® KQ with a Sensor Chip CAP in 8 channel/96 well plate mode at 1,000 rpm. Binding of the ACE614-Fc1-12K chimeric protein was measured using the following protocol: 20 μg/mL biotinylated target ACE614-Fc1-12K protein in kinetics buffer (10 mM HEPES pH 7.4, 150 mM NaCl, 3 mM EDTA, 0.05% (v/v) Surfactant P20) was loaded onto a streptavidin (SA) biosensor. After washing off excess antibody, the spike S1 protein from the wildtype SARS-CoV-2 (WIV4, YP_009724390.1) isolate was added at 10 μg/mL in kinetics buffer for a 300 s period of association and a 300 s period of dissociation. FIG. 3B shows that the mucoadhesive ACE614-Fc1-12K chimeric proteins bind well to the S1 protein, with binding unaffected by the presence of the polycationic moiety. A negative control protein (i.e., hACE2-HIS tag) was also tested, but showed no binding to the ACE614-Fc1-12K mucoadhesive target under the same conditions. Additionally, the ACE614-Fc1-12K mucoadhesive chimeric protein was used to capture S1 proteins from the Alpha, Delta, and Omicron variants of SARS-CoV-2; all assays were done under identical conditions and show similar dissociation profiles.

Example 3C. Ability of ACE2 Mucoadhesive Chimeric Proteins to Block Full-Length ACE2 Binding to SARS-CoV-2 Spike Proteins This Example demonstrates that ACE614-Fc1 modified chimeric proteins (e.g., ACE614-Fc1-12K and ACE614-Fc1-12H) are able to block full-length ACE2 binding to SARS-CoV-2 S proteins. Briefly, SARS-CoV-2 spike protein with a murine Fc tag is coated onto high-binding 96-well plates at 2 μg/mL in PBS overnight. The coating solution is removed, and the plate is blocked with 3% BSA in TBST for 1 h at RT. ACE614-Fc1 or ACE614-Fc1-12K is incubated with SARS-CoV-2 S protein at 10 μg/mL for 30 minutes (min). The plate is washed by PBST three times. Full length hACE2 with a HIS tag (hACE2-HIS) is added to each well at a series of concentrations for 30 min and the plate is washed in PBST three times. Anti-His HRP secondary antibody is added to each well for 30 min and the plate is washed in PBST another three times. The substrate, 3,3',5,5'-tetramethylbenzidine (TMB), is added, the reaction is stopped with an equal volume of 2N H2SO4 and the optical density (OD, absorbance) at 450 nm is recorded by a standard plate reader. The readout demonstrates the ability of mucoadhesive chimeric proteins comprising hACE2-Fc to block ACE2 binding to the SARS-CoV-2 spike protein in vitro.

Example 3D. ACE614-Fc1-12K Blocks Pseudovirus Infection In Vitro

Pseudotyped viruses expressing the original or wildtype (WIV-4) SARS-CoV-2 S protein S1 subunit or the spike protein S1 subunit of one of four important SARS-CoV-2 isolates or variants (Alpha, Beta, Delta, and Omicron BA.1 and BA.2) were isolated from the cell culture supernatants of HEK293F cells expressing the variant spike proteins using the lentiviral expression vector pCDH-EF1-MCS (System Biosciences) along with helper plasmids encoding the proteins required in trans for the production of infectious pseudotyped virus.

To assess whether ACE614-Fc1-12K could block infection by SARS-CoV-2 viruses, a series of pseudoviruses were created and tested in a cell-based in vitro neutralization assay using luciferase as a reporter.

Figure 3C:
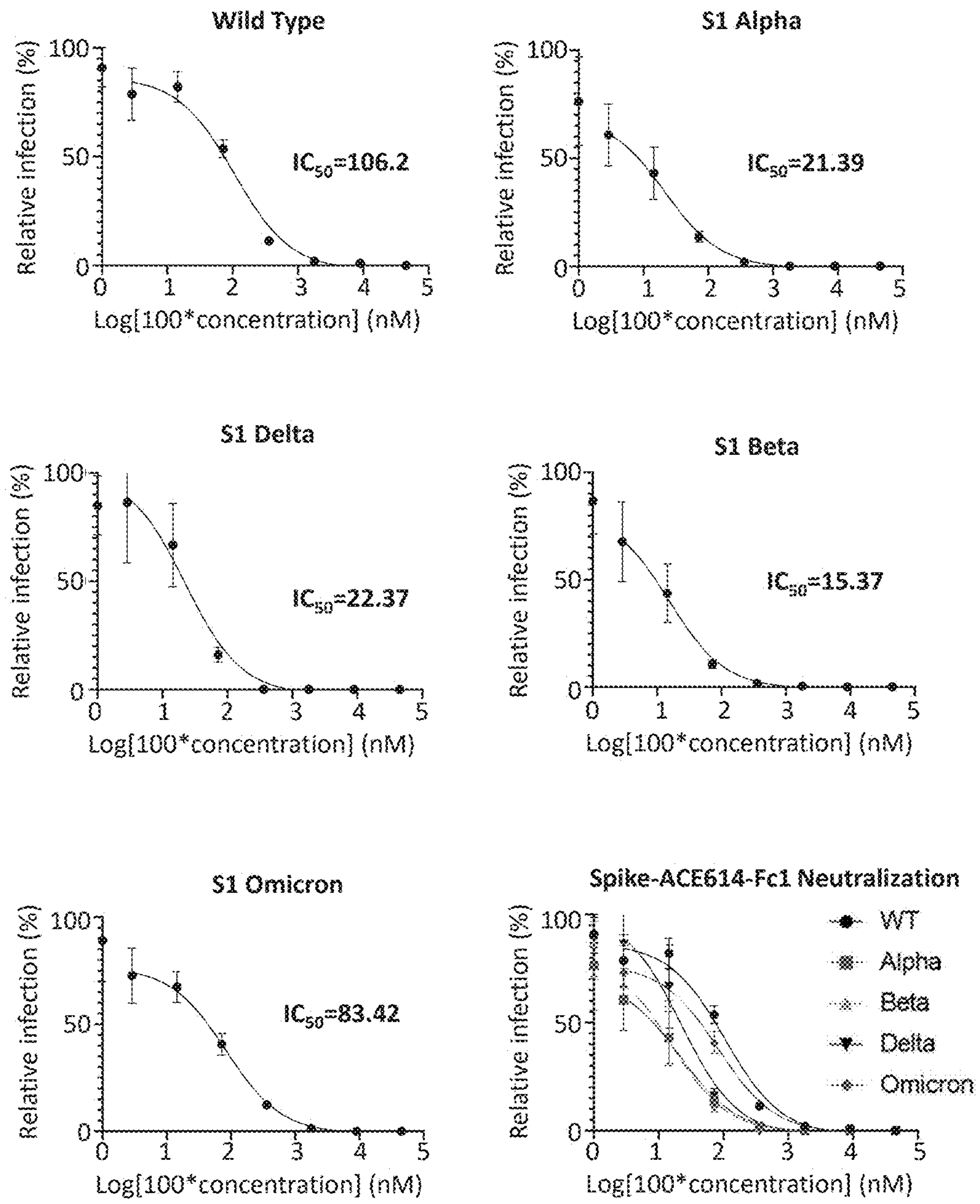
FIG. 3C shows that the exemplary ACE614-Fc1-12K chimeric protein blocks SARS-CoV-2 pseudovirus infection of HEK293F cells expressing ACE2 ("HEK293F-ACE2 cells"). ACE614-Fc1-12K chimeric protein was incubated with pseudotyped lentivirus containing an EF1-α-driven luciferase and GFP reporter genes separated by a P2A self-cleaving peptide and then added to the HEK293F-ACE2 cells. Infection was determined by detecting the luciferase level or by detecting GFP in infected cells.
Figure 3D:
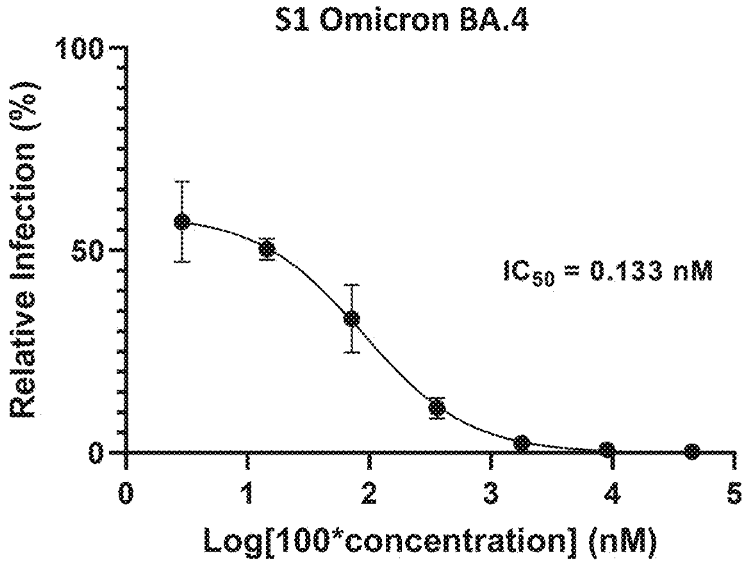
FIG. 3D shows that the ACE614-Fc1-12K chimeric protein is able to block pseudovirus prepared from the recently prevalent (2021 and 2022) Omicron BA.4 variant of SARS-CoV-2 from infection of HEK293F cells expressing ACE2 (using the method as in FIG. 3C).
Figure 3E:
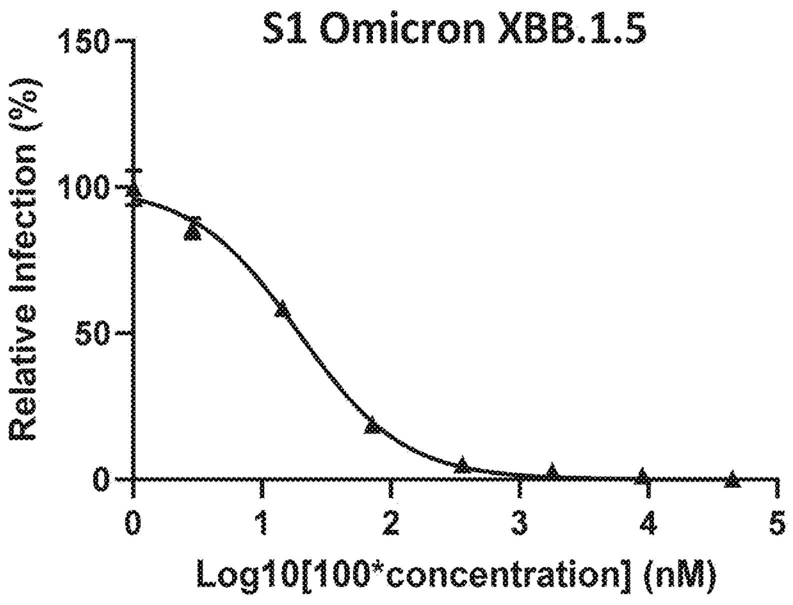
FIG. 3E shows that the ACE614-Fc1-12K chimeric protein is able to block pseudovirus prepared from the recently prevalent (2022-2023) Omicron XBB.1.5 variant of SARS-CoV-2 from infection of HEK293F cells expressing ACE2 (using the method as in FIG. 3C).

To generate the pseudotyped viruses, the pCDH lentiviral vector encoding an E1A-a-driven luciferase gene and the spike protein genes (S1 subunit) of either wild-type SARS-CoV-2 or a variant (Alpha, Beta, Delta, Omicron, or Omicron BA.2, BA.4, and XBB 1.5) were produced and transfected into HEK293F cells to generate each pseudotyped lentivirus. The lentivirus-containing cell culture supernatants were purified and concentrated and then incubated with a range of concentrations of ACE614-Fc1-12K chimeric protein for 30 min at RT. Thereafter, the pseudotyped lentivirus/mucoadhesive protein solution was added to engineered HEK293F-hACE2 cells (1 μl of ~$1\times10^7$ IU/mL virus per $5\times10^4$ cells) and cultured in 5% $CO_2$ at 37° C. for 48 h. The degree of cellular infection generated by the pseudotyped lentivirus was determined by detecting the level of luciferase produced by the infected cells using a luciferase assay system (Promega). The maximum bioluminescent value of the negative control group (untransduced HEK293F-hACE2 cells) was normalized to 100% and the $IC_{50}$ was calculated using a nonlinear fitting method using GraphPad Prism Version 8 software on at least 3 replicates per assay. For XBB.1.5, the $IC_{90}$ was also measured. In a separate experiment, ACE614-Fc1-12K was also able to bind Omicron BA.4 with high affinity (FIGS. 3C-3E). It is worth noting that the mutations in the S1 subunit of the spike protein of Omicron BA.4 are identical to those of BA.5, another recent SARS-CoV-2 variant.

As shown in FIGS. 3C-3E, low quantities of ACE614-Fc1-12K chimeric protein were a sufficient concentration to completely block the infection of HEK293F-ACE2 cells by pseudoviruses expressing S1 of any of the seven SARS-CoV-2 strains or substrains tested (wildtype, Alpha, Beta, Delta, and Omicron strains BA.2, BA.4, and XBB 1.5 variants/subvariants).

Example 3E. In Vitro Characterization of Other hACE2 and Animal ACE2 Mucoadhesive Chimeric Proteins Additional mucoadhesive chimeric proteins are designed and generated as described in Example 2, using any of the hACE2 protein fragments disclosed in Table 3 and corresponding animal ACE2 protein fragments (fragments of the full-length ACE2 proteins disclosed in Table 4 that correspond to the various partial hACE2 fragments disclosed in Table 3, including the animal ACE12 fragments disclosed in Table 4), fused to any polycationic peptides disclosed in Table 8 (e.g., polylysine or polyhistidine peptides), optionally with any of the exemplary peptide linkers disclosed in Table 9. These mucoadhesive chimeric proteins are tested for various functions using the methods described in Examples 3A-3D: binding specificity of the ACE2 chimeric proteins with the SARS-CoV-2 S protein S1 subunit, association and dissociation by BLI, blocking of full-length ACE2 binding to the S1 protein, and blocking of pseudoviral infection of HEK293-ACE2 cells. Each of the other human and animal mucoadhesive chimeric proteins are tested for their ability bind to SARS-CoV-2 S1 protein, block full-length ACE2 binding to the S1 protein, and block pseudoviral infection of HEK293-ACE2 cells.

Example 4. In Vitro Mucin Binding by ACE2 Mucoadhesive Chimeric Proteins

Example 4A. ACE2 Mucoadhesive Chimeric Proteins Bind Mucin In Vitro

Various cationic-modified forms (Table 8) of hACE614-Fc1 proteins, as described in Example 2 and disclosed in Table 1, including the 12K and 12H-modified forms, are tested for their ability to bind mucin. 96-well plates are coated with 50 μg/mL mucin (Sigma, M3895) for 2 h at room temperature. The plates are blocked with 3% BSA overnight at 4° C. 0.5 μg/well of ACE614-Fc1-12K protein or hACE2-Fc1 lacking the mucin interaction component are added to the plate and incubated for 1 h at RT. Thereafter, the plates are washed with washing buffer (25 mM HEPES, 50 nM NaCl, pH 6.5), stained with HRP-conjugated goat anti human IgG, and developed using 3,3',5,5'-Tetramethylbenzidine (TMB). The reaction is stopped with 100 μL of 2N sulfuric acid, and absorbance at $OD_{450}$ is measured. The hACE614-Fc1 chimeric proteins, which comprise various numbers of polycationic residues C-terminal to the Fc1 domain, have increased binding to mucin compared to unmodified hACE2-Fc1 proteins, and these modifications (addition of the polycationic peptide fragments) do not disrupt the ACE2 protein fragments' binding to a SARS-CoV-2 pseudovirus.

In addition to the mucoadhesive variants of hACE614-Fc1, the ability to bind mucin in vitro is tested using other exemplary hACE2 chimeric proteins and exemplary animal ACE2 chimeric proteins as described in Example 2 and Example 3E. The results of exemplary ACE2 modified chimeric proteins binding to mucin are presented. These other hACE2 chimeric proteins and the animal ACE2 chimeric proteins have increased binding to mucin compared to their corresponding unmodified ACE2 protein fragments (not fused to any cationic peptide fragments), and these modifications (addition of the cationic peptide fragments) do not disrupt the ACE2 protein fragments' binding to a SARS-CoV-2 pseudovirus.

The polycationic modifications in all the ACE2 chimeric proteins significantly increase binding of the proteins to mucin in vitro compared to unmodified ACE2 protein fragments, with or without linker peptides as a part of the chimeric proteins. Mucin glycoproteins produced by mucus-producing cells in the epithelium or submucosal glands are the major macromolecular constituent of mucus. Binding to mucin can potentially extend the retention time of a protein in the mucus of the respiratory tract. Therefore, the mucoadhesive ACE2 chimeric proteins can reside for an extended period of time in the mucus of respiratory tracts of the subjects who are administered the chimeric proteins.

Example 4B. ACE614-Fc1-12K Binds Mucin In Vitro

Figure 6:
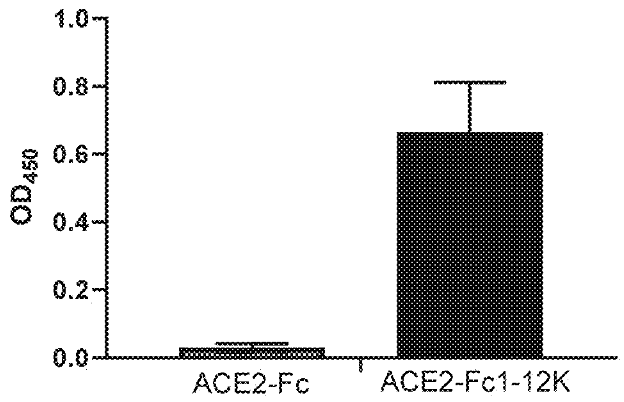
FIG. 6 demonstrates that the presence of the polylysine peptide significantly increases the attraction of ACE2-Fc1-12K chimeric protein to mucin proteins compared to that of ACE2-Fc1 which lacks the C-terminal polylysine peptide modification. An ELISA assay using mucin-coated plates was used to compare the binding of ACE2-Fc1-12K to that of ACE2 Fc1, which lacks the cationic modification (12 lysines). Binding was detected using horseradish peroxidase (HRP)-conjugated goat anti-human IgG and staining was detected at $OD_{450}$.

To simulate the retention of ACE614-Fc1-12K protein in the nasal mucosa, the affinity of ACE614-Fc1-12K and hACE2-Fc (no lysine modification) to mucin was assessed by ELISA. 96-well plates were coated with 50 μg/mL mucin (Sigma, M3895) for 2 h at room temperature. The plates were blocked with 3% BSA overnight at 4° C. 5 μg/mL antibody in 25 mM HEPES (pH 6.5) was added to the plates and incubated for 1 h at RT. The plates were washed 3 times in wash buffer (25 mM HEPES, pH 6.5), and 0.5 g/well of ACE614-Fc1-12K or hACE2-Fc1 (lacking the polylysine modification) was added to the plate and incubated for 1 hour at RT. The plates were washed 3 times in wash buffer for 1 min each, stained with HRP-conjugated goat anti-human IgG, washed 3 more times in wash buffer and developed using 3,3', 5,5'-Tetramethylbenzidine (TMB). The reaction was stopped with 100 μL of 2N sulfuric acid, and absorbance at OD450 was measured. As shown in FIG. 6, the hACE614-Fc1-12K chimeric protein, which comprises polycationic residues (12 lysines) C-terminal to the Fc1 domain, displayed a significant increase in binding to mucin as compared to unmodified hACE614-Fc1 protein. This modification (addition of the polycationic peptide fragment), as demonstrated in Example 3D, did not disrupt the hACE614-Fc1-12K protein fragments' binding to a SARS-CoV-2 pseudovirus.

Example 5. In Vitro Characterization of ACE2 Mucoadhesive Chimeric Proteins in a Nasal Spray Formulation Exemplary ACE614-Fc1 mucoadhesive chimeric proteins from Example 4 are prepared in a nasal spray formulation comprising the following formulation buffer ("nasal spray buffer" or "NS buffer"): 25 mM citrate buffer, pH 6.5, 125 mM NaCl, 5% glycerin, 0.1% methionine, 0.02% polysorbate 80, and 0.1% potassium sorbate. Stability and activity of the human and animal mucoadhesive ACE2-Fc1 chimeric proteins in the NS buffer are assessed in this Example.

Example 5A. ACE2-Fc1-12K Proteins, ACE2-Fc1-12H Proteins, and Other ACE2 Chimeric Proteins Stored in NS Buffer Maintain Binding Affinity to the Spike Protein S1 Subunit To confirm that the formulation buffer does not affect the binding ability of the ACE614-Fc1-12K protein, ACE614-Fc1-12H protein, or other cationic forms of ACE614-Fc1 (ACE2-Fc1 proteins with various lengths and compositions of cationic peptides) to the SARS COV-2 S protein S1 subunit, an accelerated stability assay is performed. Briefly, binding of the ACE2 protein is determined by employing a ForteBio Octet® instrument with SA sensor tips using Octet® Data Acquisition software 9.0, as described in previous Examples. The binding curves of various ACE2-Fc1 samples of the protein in NS buffer, maintained at 37° C. over a maximum period of 14 days, equivalent to about 1.5 years at 4° C., is compared to the binding curve of a sample of the unmodified ACE2-Fc1 protein stored in PBS at 4° C. Highly comparable binding (association and dissociation) of the hACE2-Fc1-12K, hACE2-Fc1-12H, and other mucoadhesive ACE2 proteins to biotinylated S1 protein is observed after storage in the nasal spray formulation for 0, 1, 3, 5, 7 or 14 days. Comparable binding of exemplary ACE2 mucoadhesive chimeric proteins and fragments from Tables 3 and 4, bearing exemplary linkers (Table 9), and exemplary cationic peptides (Table 8), are assessed.

No aggregation of the ACE2-Fc1-12K or hACE2-Fc1-12H proteins in NS buffer is detected, as assayed using size exclusion chromatography (SEC). The accelerated antibody stability test at 37° C. shows that the antibody is stable in the formulation over time. Similar experiments are performed, and similar results are obtained, with the other exemplary ACE2 chimeric proteins as described in Example 2 and Example 3E, including other exemplary human and animal ACE2 chimeric proteins. Each of the other exemplary ACE2 chimeric proteins (e.g., those disclosed in Table 1) exhibit highly comparable binding (association and dissociation) to biotinylated S1 protein after storage in the nasal spray formulation.

Example 5B. ACE614-Fc1 Chimeric Proteins Stored in NS Buffer Maintain the Ability to Bloc ACE2 Binding to S1

Enzyme-linked immunoassay (ELISA) plates are coated with 2 μg/mL ACE614-Fc1 protein in 100 μL PBS, at 4° C. overnight. The plates are then blocked with 3% blocking buffer, at 4° C. overnight. Serial dilutions of ACE614-Fc1-12K, ACE614-Fc1-30K, ACE614-Fc1-12H, ACE614-Fc1-30H, or ACE614-Fc1 without a polycationic peptide fragment, which have been stored in NS buffer at 37° C. for 0, 1, 3, 5, 7, or 14 days, are incubated with SARS-CoV-2-S1-HIS (2 μg/mL) for 1 h at RT. The incubated mixtures are subsequently added to an ELISA plate, developed for 1 h, and the plates are washed with PBST three times. HRP-Anti-HIS antibody (R&D Systems) is added, incubated for 1 h at RT, and then washed with PBST three times. TMB substrate (100 μL) is added, and the reaction is quenched with 100 μL of 2N $H_2SO_4$. The absorbance is measured at 450 nm ($OD_{450}$). Each of ACE614-Fc1-12K, ACE614-Fc1-30K, ACE614-Fc1-12H, and ACE614-Fc1-30H block SARS-CoV-2 S1 binding to hACE2 in a dose dependent manner.

Similar experiments are performed, and similar results are obtained, with the other exemplary ACE2 chimeric proteins as described in Example 2 and Example 3E, including other exemplary human and animal ACE2 chimeric proteins. Each of the other exemplary ACE2 chimeric proteins (e.g., those in Table 1) also retain the ability to block the SARS COV-2 S1 protein binding to their respective ACE2 receptors in vitro.

Example 5C. ACE2-Fc1 Chimeric Proteins Stored in NS Buffer Maintain the Ability to Block SARS CoV-2 Pseudovirus Infection of 293F-ACE2 Cells ACE614-Fc1-12K, ACE614-Fc1-12H, and exemplary animal ACE2-Fc1-12K or ACE2-Fc1-12H, are purified as described in Example 2 and stored in NS buffer at 37° C. for 0, 1, 3, 5, 7, or 14 days. Varying concentrations of these chimeric proteins, along with unmodified versions of these proteins (ACE614-Fc1 and exemplary animal ACE2-Fc1 without any polycationic peptide fragment, also stored in NS buffer at 37° C. for up to 14 days), are incubated with SARS-CoV-2 S-pseudotyped lentivirus containing the CMV-driven luciferase and GFP reporter genes, separated by a P2A self-cleaving peptide. Following a 30 min incubation, the SARS-CoV-2 pseudovirus is added to HEK293-ACE2 cells and cultured in 5% $CO_2$ at 37° C. for 48 h. The degree of cellular infection with the pseudotyped virus is determined by detecting the luciferase level of the infected cells (Promega). The SARS-CoV-2 pseudovirus infection is effectively blocked by each protein, ACE614-Fc1-12K, ACE614-Fc1-12H, animal ACE2-Fc1-12K, ACE2-Fc1-12H, or unmodified ACE614-Fc1 or animal ACE2-Fc1, in a dose dependent manner, after storage in the NS buffer. Similar experiments are performed, and similar results are obtained with the other exemplary ACE2 chimeric proteins as described in Example 2 and Example 3E, including other exemplary human and animal ACE2 chimeric proteins. Each of the other exemplary ACE2 chimeric proteins (e.g., those in Table 1) also retain the ability to block SARS-CoV-2 pseudovirus infection in vitro after storage in the NS buffer.

Example 6. ACE2 Mucoadhesive Chimeric Proteins in a Mouse Model of Infection

Example 6A1. ACE2 Mucoadhesive Chimeric Proteins Stored in NS Buffer Prevent SARS COV-2 Pseudovirus Infection in a Mouse Model ACE614-Fc1-12K and ACE614-Fc1-12H are stored in NS buffer at 4° C. to 37° C. for up to 7 days. Female transgenic mice expressing the hACE2 receptor are pre-treated with ACE614-Fc1-12K or ACE614-Fc1-12H nasally (20 μL instilled per nostril), for a total dose of 200 μg per nostril per mouse. 10 h after administration of the chimeric proteins, SARS-CoV-2 (isolate 2019-nCOV, i.e., WIV4, "YP_009724390.1") S-pseudotyped lentivirus is administered to mice intranasally (20 μL instilled per nostril which contains about 107 pseudovirus particles). Animals are closely monitored after nasal administration of the pseudovirus on day 3, day 5, and day 7 following pseudoviral administration. Bioluminescence and body weight are measured for each mouse. After the final measurement, the lungs are dissected and imaged. The degree of infection in the mice pre-treated with ACE2 mucoadhesive chimeric proteins is compared to mice that are i) not pre-treated with any ACE2 proteins, or ii) pre-treated with ACE614-Fc1 lacking mucoadhesive peptide fragments ("unmodified ACE614-Fc1").

The luciferase signal from hACE2-expressing mice is measured to detect the potential effect of ACE614-Fc1-12K, ACE614-Fc1-12H, or unmodified ACE614-Fc1 on SARS-CoV-2 pseudovirus infection in hACE2-expressing mice. The mice that are not pre-treated with ACE2 mucoadhesive chimeric proteins, including those that are pre-treated with unmodified ACE614-Fc1, show signs of infection, visualized as a strong luciferase signal in the nasal cavity in the days after the viral dosage, and in both nose and lung areas several days after that. In mice pre-treated with ACE614-Fc1-12K or ACE614-Fc1-12H, a luciferase signal is not detected following pseudovirus dosage. In these mice, ACE2-Fc-12K and ACE2-Fc-12H provide at least 10 h of protection against pseudoviral infection. Neither the nasal cavity nor lung areas show signs of infection in ACE2-Fc-12K- or ACE2-Fc-12H-treated mice after the viral dosage. The unmodified ACE614-Fc1, while being able to block pseudoviral infection in vitro, is not able to block pseudoviral infection in vivo. Therefore, the surprising effect of ACE614-Fc1-12K and ACE614-Fc1-12H in blocking pseudoviral infection in vivo is largely due to the inclusion of the polycationic peptide fragments.

It has been estimated that the concentration of SARS-CoV-2 virus in droplets in a room with an individual who is coughing frequently can be as high as 7.44 million copies/meter $(m)^3$ from an individual who is a high emitter of virus. Regular breathing from an individual who is a high emitter was modeled to result in lower room concentrations of up to 1,248 copies/$m^3$. See, Riediker M. and Tsai D., *JAMA Netw Open.*, 3 (7): c2013807 (2020). In the experiments described here, we protect mice from SARS-CoV-2 pseudovirus infection of about 107 pseudoviral particles by directly dropping 200 μg of ACE2 mucoadhesive chimeric proteins into each nostril of mice expressing hACE2. Inhibition of viral infection by pre-administration of ACE614-Fc1-12K or ACE614-Fc1-12H against this high viral titer, as demonstrated, shows the promise of nasal spray protection even in a worst-case scenario, and could provide a large cushion of protection in most common situations of a healthy person encountering an infected individual.

Example 6A2. ACE614-Fc1-12K Stored in NS Buffer Prevented SARS COV-2 Pseudovirus Infection in a Mouse Model ACE614-Fc1-12K was stored in NS buffer at 4° C. to 37° C. for up to 7 days. Female transgenic mice expressing the hACE2 receptor (B6.Cg-Tg (K18-ACE2) 2Prlmn/J, Zheng *Nature,* 2021, 589:603-607) were pre-treated with ACE614-Fc1-12K nasally (20 μL instilled per nostril), for a total dose of 200 μg per mouse. 10 h after administration of the chimeric proteins, SARS-CoV-2 (Delta and Omicron BA.2 isolates) S-pseudotyped lentivirus was administered to mice intranasally (20 μL instilled per nostril, containing about $1.5\times10^5$ or $2\times10^5$ functional pseudovirus particles, respectively). Animals were closely monitored after nasal administration of the pseudovirus in the days following pseudoviral administration. Body weight (not shown) and bioluminescence (BLI) were measured for each mouse before pseudoviral administration and on days 3, 5 and 7 post administration; BLI was measured using an IVIS® Spectrum in vivo imaging system (Perkin-Elmer). The degree of infection in the mice pre-treated with ACE2 mucoadhesive chimeric proteins is compared to mice that were not pre-treated with any ACE2 proteins (vehicle, nasal formulation only).

Figure 7B:
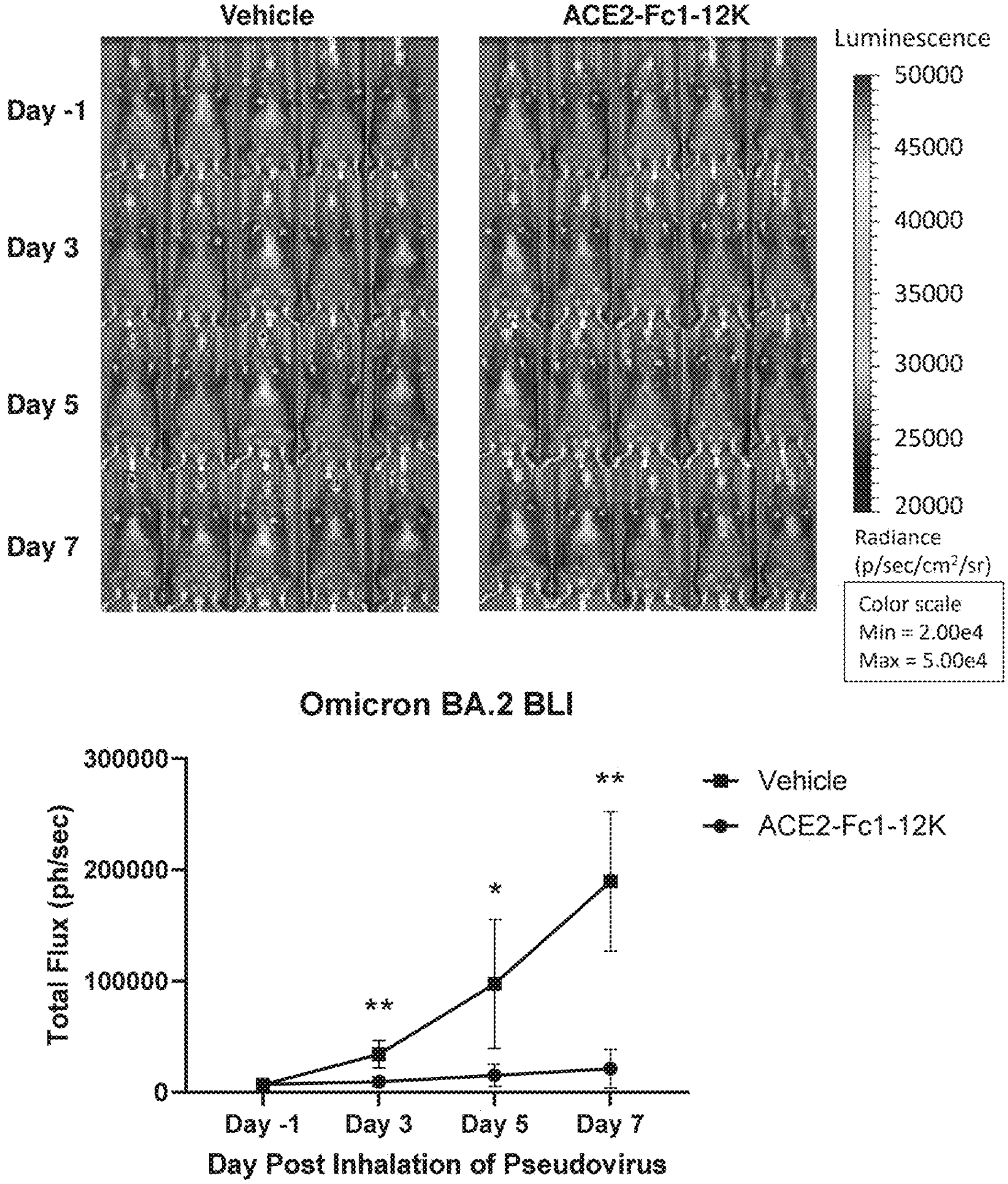
FIG. 7B. Bioluminescent images of hACE2 transgenic mice administered with SARS-CoV-2 Omicron BA.2 variant pseudoviruses using the same method as described herein for the data shown in FIG. 7A, demonstrating the ability of ACE2-Fc1-12K chimeric protein to protect mice from SARS-CoV-2 Omicron BA.2 variant pseudoviral infection.

The luciferase signal from hACE2-expressing mice was measured to detect the potential effect of ACE614-Fc1-12K on SARS-CoV-2 pseudovirus infection in hACE2-expressing mice compared to those receiving the vehicle only. The luciferase signal from hACE2-expressing mice was measured to detect the potential effect of ACE614-Fc1-12K versus vehicle on SARS-CoV-2 pseudovirus infection in hACE2-expressing mice, shown in FIG. 7A and FIG. 7B. The mice that were not pre-treated with ACE2 mucoadhesive chimeric proteins (left panels) show signs of infection, visualized as a strong luciferase signal (BLI) in the nasal cavity in the days following the pseudoviral dosage when inoculated with either the Delta (FIG. 7A) or Omicron BA.2 (FIG. 7B) variant of SARS-CoV-2. In mice pre-treated with ACE614-Fc1-12K (right panels), a luciferase signal was not detected following the dosage of either the Delta (FIG. 7A) or the Omicron BA.2 (FIG. 7B) pseudoviruses for up to 7 days. In these mice, ACE2-Fc-12K provided at least 10 h of protection against pseudoviral infection. It was estimated that $1.5\times10^5$ functional Delta pseudotyped virus or $2\times10^5$ functional omicron BA.2 pseudotyped virus equates to $10^7$-$10^9$ physical pseudotyped viral particles.

Figure 7C:
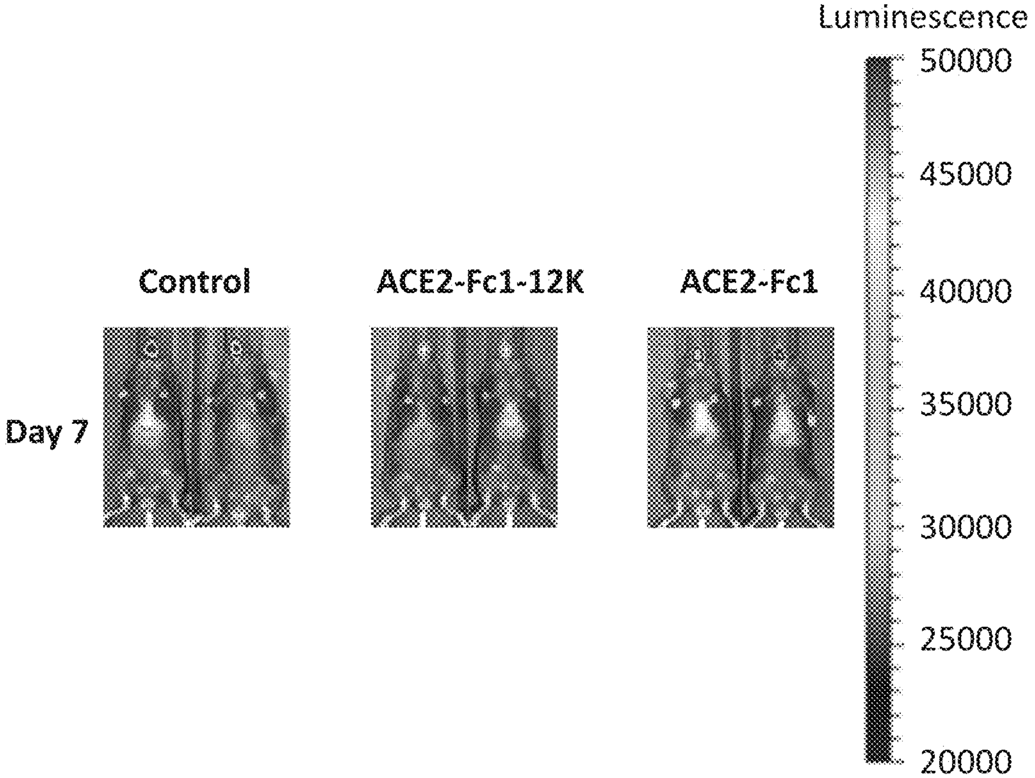
FIG. 7C. Bioluminescent images demonstrate the role of the mucoadhesive modification of ACE2-Fc1-12K chimeric proteins in protecting hACE2 transgenic mice from pseudoviral infection. Luciferase emission from mice pretreated with ACE2-Fc1-12K chimeric protein which has the polylysine mucoadhesive modification (center panel) was compared to mice pretreated with ACE2-Fc1 which lacks the polylysine mucoadhesive modification (right panel) 7 days following inoculation with SARS-CoV-2 variant Delta-pseudotyped lentiviruses. Pretreatment with vehicle only is shown in the left panel.

In a separate experiment, using the protocol described above, mice were pretreated with ACE2-Fc1-12K or with ACE2-Fc1 lacking the mucoadhesive component and administered Delta-pseudotyped lentivirus 10 hours later. As shown in FIG. 7C, on day 7 following pseudoviral administration, signs of infection are apparent in mice that are not pretreated (vehicle only, left panel) and in mice pretreated with ACE2-Fc1 lacking the polylysine modification (ACE2-Fc1, right panel). In contrast, the mice pretreated with ACE2-Fc1-12K show no sign of infection on day 7, demonstrating the importance of the mucoadhesive moiety in the mechanism of ACE2-Fc1-12K-mediated protection from infection by SARS-CoV-2.

In the experiments described in this Example, mice were protected from SARS-CoV-2 pseudovirus infection of up to $2\times10^5$ pseudoviral particles, very high viral titers, by directly dropping 200 μg total dose of ACE2 mucoadhesive chimeric proteins into mice expressing hACE2. Inhibition of viral infection by pre-administration of ACE614-Fc1-12K against such high viral titers, as demonstrated, shows the promise of nasal spray protection, and could provide a large cushion of protection in most common situations of a healthy person encountering an infected individual.

Example 6B. Blocking of SARS-CoV-2 Pseudovirus Infection by Other Exemplary ACE2 Mucoadhesive Chimeric Proteins in a Transgenic Mouse Model To assess whether protection from pseudoviral infection can be effective using other exemplary mucoadhesive chimeric proteins, the mouse pseudoviral infection experiments as described in Example 6A are performed with other exemplary mucoadhesive chimeric proteins as described in Example 2 and Example 3E (e.g., those disclosed in Table 1). Each of the other ACE2 mucoadhesive chimeric proteins blocks SARS-CoV-2 pseudovirus infection in ACE2-expressing mice.

Example 6C. Blocking of SARS-CoV-2 Pseudovirus Displaying Spike Protein S1 Subunit Protein from Prevalent Virus Strains in a Mouse Model of Infection New SARS-CoV-2 variants pose a challenge to the efforts to contain this pandemic, despite the availability of effective vaccines against the WT virus. There are reports of many new variants around the world, which are driving the rise of new COVID-19 cases in many counties. In 2020, there were troubling signs that B.1.1.7, B.1.351, and B.1.617.2 variants would evade protection from the vaccines. While efforts of getting as many people vaccinated as possible and developing next-generation vaccines against the variants are underway, there is an urgent need to explore additional approaches to slow down the spread of the variants.

In this experiment, we administer the same mucoadhesive chimeric proteins comprising ACE614-Fc1 as previously described directly into nostrils of mice which are later challenged with pseudotyped virions expressing the currently prevalent SARS-CoV-2 variants, Omicron and Omicron BA.2, and compare their ability to protect against the Delta strain, previously prevalent in human populations (see, Table 5).

The Delta variant is characterized by the S protein mutations in the receptor binding domain (RBD), L245R and T478K. The Omicron variant has many further mutations (i.e., 14) in this region: G339D, S371L, S373P, S375F, K417N, N440K, G446S, S477N, T478K, E484A, Q493R, G496S, N501Y, and Y505H. The BA.2 variant of Omicron has novel mutations (compared to the BA. 1 receptor binding domain) at S371F, T376A, D405N, R408S, S445G, and S495S. The Omicron variants are characterized by increased transmissibility and/or immune evasion; BA.1 mutations in the RBD also enhance binding to the ACE2 receptor (Viana et. al, *Nature* 603:679-686 (2022) and BA.2, dubbed the "Stealth Variant", appears to be more contagious than BA.1, suggesting a further enhancement of transmissibility. Compared to BA.2, the spike proteins of BA.4 and BA.5 have a number of differentiating mutations, including 469-70, L452R, F486V, and R493Q. It appears that BA.4/5 are more infectious than BA.2. Additionally, BA.4/5 shows reduced neutralization by serum from vaccinated individuals immunized against the BA.1 and BA.2 variants (Tuekprakhon et al. *Cell* 185 (14): 2422-2433 (2022). More recent variants BQ (K444T, N460K) and XBB (nicknamed "Kracken", K444T, N460K, F490F) show greater transmissibility, increased antibody evasion properties, and are resistant to neutralization by serum from fully vaccinated individuals (Wang et al. Cell 186:279-286 (2023).

The methods used are the same as those described in Example 6A1 and Example 6A2 but using virus pseudotyped with the S proteins of the Delta (B.1.617.2), Omicron (B.1.1.529), and Omicron BA.2 strains. Bioluminescence imaging is used to assess the degree of infection on day 7 after the mice are treated with the NS-buffer-stored mucoadhesive chimeric proteins comprising ACE614-Fc1. After measurement, the lungs are dissected and imaged. The ability to protect hACE2 transgenic mice by mucoadhesive ACE2 chimeric proteins stored in NS buffer is quantified.

Each of the ACE2 mucoadhesive chimeric proteins described in Example 2 and Example 3E is effective in protecting mice from infection by the three SARS-CoV-2 variants. These findings suggest an affordable, convenient, and effective prophylactic product to protect people from being infected by SARS-CoV-2 viruses in the air, in particular against the new variants Omicron and Omicron BA.2 for which the immune responses induced by currently approved vaccines are not effective in preventing infection.

Example 6D. Blocking of SARS-CoV-2 Pseudovirus Displaying S1 Proteins from an Animal Strain in a Mouse Model of Infection Using animal-derived mucoadhesive chimeric proteins shown in Table 4, we further test the ability to protect from pseudoviral infection using exemplary mucoadhesive chimeric proteins derived from animal ACE2 proteins (e.g., those disclosed in Table 1). The mouse pseudoviral infection assay is performed as described in Example 6A with an exemplary animal mucoadhesive chimeric protein, using the variant S protein derived from a Bat coronavirus, a potential reservoir for SARS-CoV-2 (Temmam, S. et al. *Nature* 604: 330-336 (2022)), which is infectious in human cells. These experiments are also performed using other ACE2 proteins tested, such as those disclosed in Table 4, designed using the ACE2 proteins or protein fragments disclosed in Table 3, and the mucoadhesive peptide fragments and linkers disclosed in Tables 9 and 8, respectively.

Example 7. Capability of ACE2 Mucoadhesive Chimeric Proteins to Neutralize Live SARS-CoV-2 Virus The ability of the mucoadhesive chimeric proteins ACE614-Fc1-12K and ACE614-Fc1-12H to neutralize live SARS-CoV-2 viruses is determined. Live SARS-CoV-2 virus (including those disclosed in Table 6) is pre-incubated with varying concentrations of ACE614-Fc1-12K, ACE614-Fc1-12H, or unmodified ACE614-Fc1 for 1 h at RT, prior to the addition of Vero E6 cells. Viral cytopathic effect (CPE) is determined by detecting the ATP levels of infected cells with Promega Viral ToxGlo™. ACE614-Fc1-12K and ACE614-Fc1-12H are able to neutralize live SARS-CoV-2 viruses, including all of the strains disclosed in Table 5. The inclusion of the polylysine fragment in ACE614-Fc1-12K and polyhistidine in ACE614-Fc1-12H improves the $IC_{50}$ (half maximal inhibitory concentration) when compared to unmodified ACE614-Fc1 in the ability to block infection by live SARS-CoV-2 virus in vitro.

The ability to neutralize live SARS-CoV-2 is also tested using other ACE2 mucoadhesive chimeric proteins or their unmodified counterparts (as described in Example 1 and Example 2). Some of these mucoadhesive chimeric proteins comprise the ACE2 proteins or fragments disclosed Tables 3 and 4, the linker fragments disclosed in Table 9, and the mucoadhesive peptide fragments of Table 8. Using these exemplary ACE2 mucoadhesive chimeric proteins, including those disclosed in Table 1, the CPE in infected Vero E6 cells is measured and compared to that of the unmodified counterparts and $IC_{50}$ values are calculated. Each of the ACE2 mucoadhesive chimeric proteins is able to neutralize live SARS-CoV-2 viruses, including all of the strains disclosed in Table 5. The inclusion of the polycationic peptide fragment in each of the ACE2 mucoadhesive chimeric proteins improves the $IC_{50}$ when compared to its unmodified counterpart in the ability to block infection by live SARS-CoV-2 virus in vitro.

Example 8. ACE2 Mucoadhesive Chimeric Proteins in NS Buffer Prevent SARS-CoV-2 Infection in Humans

Example 8A. Protection from SARS-CoV-2 Infection in Healthy Adults

The safety and efficacy of daily nasal spray administration of ACE614-Fc1-12K or ACE614-Fc1-12H are tested in human subjects as compared with a placebo.

The ACE614-Fc1-12K or ACE614-Fc1-12H mucoadhesive chimeric proteins are formulated in NS buffer as described in Example 6. The protein formulation is administered directly into nostrils of the human subjects at between 25 and 300 μg per dose. The protein concentration in a NS bottle is 0.125 mg/mL (e.g., 2.5 mg total ACE614-Fc1-12K or ACE614-Fc1-12H protein in a 20 ml bottle volume). Each spray is about 0.1 mL. Each human subject receives one dose per day, or about 4 sprays per day. In the placebo group, each human subject receives an equivalent amount of NS buffer that does not contain ACE614-Fc1-12K or ACE614-Fc1-12H mucoadhesive chimeric proteins. The duration of the study is 1 month or more.

Human subjects 5 years of age or older who are healthy or have stable chronic medical conditions are eligible for participation in the trial. Exclusion criteria include a medical history of COVID-19, treatment with immunosuppressive therapy, or diagnosis with an immunocompromising condition.

The safety endpoints include solicited, specific local or systemic adverse events, as prompted by and recorded in an electronic diary in a subset of participants, and unsolicited adverse events (those reported by the participants without prompts from the electronic diary).

The primary endpoints for efficacy include rate of confirmed COVID-19 with onset during the testing period and at least 7 days after the last dose. Confirmed COVID-19 is defined as the presence of at least one of the following symptoms: fever, new, or increased cough, new or increased shortness of breath, chills, new or increased muscle pain, new loss of taste or smell, sore throat, diarrhea, or vomiting, combined with a respiratory specimen obtained during the symptomatic period or within 4 days before or after it that was positive for SARS-CoV-2 by nucleic acid amplification-based testing, either at the central laboratory or at a local testing facility. Secondary endpoints include efficacy of the ACE614-Fc1-12K or ACE614-Fc1-12H mucoadhesive chimeric proteins against severe COVID-19. Severe COVID-19 is defined as confirmed COVID-19 with one of the following additional features: clinical signs at rest that are indicative of severe systemic illness; respiratory failure; evidence of shock; significant acute renal, hepatic, or neurologic dysfunction; admission to an intensive care unit; or death. Details are provided in the protocol. Additionally, efficacy of ACE614-Fc1-12K or ACE614-Fc1-12H against infection by SARS-CoV-2 variants, such as the Delta variant and Omicron variants BA.1 and BA.2, is assessed.

Example 8B. Protection from SARS-CoV-2 Infection in Animal Species in a Veterinary Setting To evaluate the safety, tolerability, and immunogenicity of recombinant canine cACE614-Fc1-12H and ACE614-Fc1-12H or cACE614-Fc1-12K and ACE614-Fc1-12K in a domestic dog population in a veterinary setting, protection from a zoonotic strain of SARS-CoV-2 (Temmam, S. et al., 2022) using the applicable methods described in Example 8A. The trial for each subject lasts for approximately 1 month. The protein formulation is administered directly into nostrils of the animal subjects at between 25 and 300 μg per dose as in Example 8A. At the end of the trial period, ACE614-Fc1-12K and ACE614-Fc1-12H in a nasal spray formulation are shown to provide protection from SARS-CoV-2 infection compared to placebo in animal populations.

The efficacy of ACE614-Fc1-12K or ACE614-Fc1-12KH against infection by the SARS-CoV-2 variant identified in bats is considered an important vector for SARS-CoV-2 spread in animal and human populations. The efficacy of canine ACE2 mucoadhesive chimeric proteins in animals from the human SARS-CoV-2 variants, such as the Delta variant and Omicron variants BA.1 and BA.2, are also assessed. The utility of nasal administration of mucoadhesive ACE2 chimeric proteins in other animal populations, such as those disclosed in Table 4, using mucoadhesive peptide fragments disclosed in Table 8, and optionally linkers disclosed in Tables 9, are shown to be similarly effective in a veterinary setting.

Example 9. ACE2 Mucoadhesive Chimeric Proteins Bind Spike Protein S1 and Activate Complement Pathway to Induce Virolysis

Example 9A. ACE2 Mucoadhesive Chimeric Proteins Activate Complement Pathway

The complement pathway is an important aspect of innate immunity. Activation of the complement pathway induces vital host responses to protect against acute, chronic, and recurrent viral infections (Huber et al., 2006; Mellors et al, 2020). Virus opsonization can be induced by complement pathway activation, wherein the opsonization of the viral surface can lead to the aggregation of the viruses, as well as phagocytosis of these viruses (due to complement receptors on phagocytic cells) and virolysis. (Mellors et al., 2020). Therefore, ACE2 mucoadhesive chimeric proteins were tested for their ability to activate the complement pathway, and subsequently kill SARS-CoV-2 pseudovirus. This Example demonstrates that ACE2 mucoadhesive chimeric proteins bind spike protein S1 and trigger the complement pathway.

Briefly, a complement pathway assay was performed (using a CH50 Functional Test Kit; CTK-907, Creative Biolabs) with some modifications. Plasma with normal complement activity was used as a positive control, and plasma with low complement activity was used as a negative control. In this assay, complement in serum samples and control samples is first activated. ACE2-Fc1-12K was incubated with the S1 spike protein of the SARS-CoV-2 Delta strain and complement immunoassay reagents including antibody to TCC (terminal complement complexes) and purified human complement proteins (Cat. #A3724; Quidel). Following a 5 min incubation, erythrocytes were added to the ACE2-Fc1-12K protein, complement, and S1 spike protein mixture, and were further incubated at 37° C. for 25 min, then centrifuged at 400×g for 5 min. The supernatant was analyzed at $OD_{415}$ to detect hemoglobin release.

Figure 4:
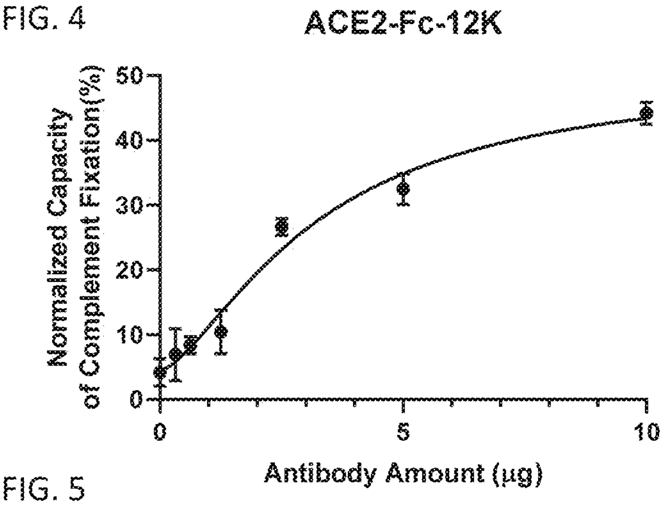
FIG. 4 shows that ACE2-Fc1-12K chimeric protein activates the complement pathway. ACE2-Fc1-12K chimeric protein was mixed with spike protein S1 subunit protein from SARS-CoV-2 (Delta) and complement immunoassay reagents using the Creative Biolabs CH50 Functional Test Kit with a human complement control (Quidel) and incubated with erythrocytes. Complement fixation pathway activity, or classical complement pathway activity, was determined by detecting the degree of hemolysis.

As shown in FIG. 4, ACE2-Fc1-12K chimeric protein activated the complement pathway. The results demonstrate the ability of ACE2 mucoadhesive chimeric proteins to bind the SARS-CoV-2 S1 subunit spike protein in vitro and induce complement pathway activation.

Example 9B. ACE2 Mucoadhesive Chimeric Protein Kill SARS-CoV-2 Pseudovirus Via Complement Pathway Activation This Example demonstrates that ACE2-Fc1-12K chimeric protein kills SARS-CoV-2 pseudovirus by activating the complement pathway.

Figure 5:
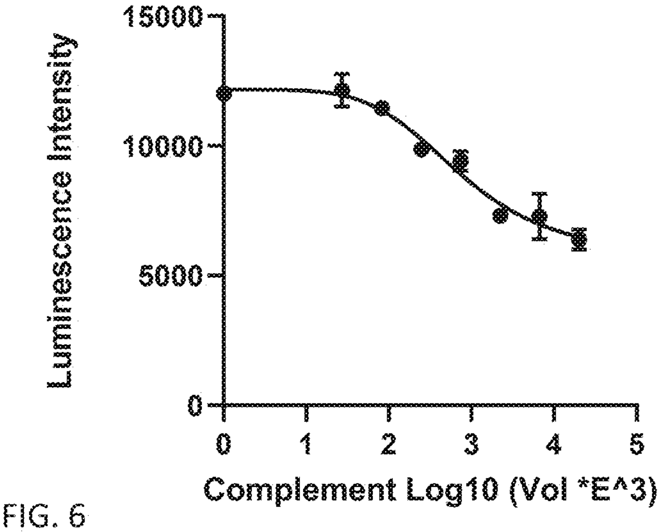
FIG. 5 shows that ACE2-Fc1-12K chimeric protein prevents SARS-CoV-2 pseudovirus infection of HEK293F cells expressing ACE2 by activating the complement pathway, thereby killing the SARS-CoV-2 pseudovirus and reducing the amount of SARS-CoV-2 pseudovirus available for infection. ACE2-Fc1-12K chimeric protein was mixed with pseudotyped lentivirus containing an EF1-α-driven luciferase reporter gene and then added to HEK293F-ACE2 cells and incubated with human complement IgG/IgM. Infection was determined by detecting the luciferase level.

Briefly, ACE2-Fc1-12K chimeric protein was incubated with pseudotyped lentivirus expressing the S1 spike protein of the SARS-CoV-2 Delta strain, and serially diluted human complement IgG/IgM (Cat. #340105, Pel Freez Biologicals). The pseudotyped virus contained the EF1-α-driven luciferase reporter gene. Following a 3 h incubation of ACE2-Fc1-12K chimeric protein with pseudotyped lentivirus and complement, the incubated solution was added to HEK293F-ACE2 cells. Cells were cultured in 5% $CO_2$ at 37° C. for 48 h. The degree of cellular infection with the pseudotyped virus was determined by detecting the luciferase level of the infected cells (Promega Luciferase Assay). As shown in FIG. 5, ACE2-Fc1-12K chimeric protein activated the complement pathway, thereby killing pseudovirus expressing S1 spike protein of the SARS-CoV-2 Omicron strain and leading to lower pseudoviral infection of HEK293F-ACE2 cells.

Taken together, these results show that ACE2 mucoadhesive chimeric proteins activate the complement pathway and induce virolysis of SARS-CoV-2 pseudovirus.

Example 10. ACE2 Mucoadhesive Chimeric Peptides Kill SARS-CoV-2 Virus in Plasma ACE2 mucoadhesive chimeric proteins are evaluated to assess whether they can bind and kill SARS-CoV-2 virus, using "capture and kill" assays in plasma. Plasma comprises complement molecules or white blood cells that can produce complement molecules.

Briefly, buffy coat layers harvested from healthy donors are depleted of $CD8^+$ T cells. $CD8^-$ peripheral blood mononuclear cells (PBMCs) are isolated from the depleted buffy coats by Ficoll-Hypaque centrifugation, stimulated with phytohemagglutinin (PHA) and OKT3 (an anti-CD3e antibody), and used as feeder cells for virus cultivation. Live SARS-CoV-2 viruses (including those disclosed in Table 6) isolated from COVID-19 patient PBMCs or obtained from other sources are added to the CD8-PBMCs and used to produce SARS-CoV-2 virus inocula.

SARS-CoV-2 virus inocula are incubated with plasma mixed with various ACE2 mucoadhesive chimeric proteins (e.g., ACE2-Fc1-12K, ACE614-Fc1-12K, ACE614-Fc1-12H, ACE360-$CH_2$-6R, ACEΔ360-$CH_2$-12R, ACE200-Hinge-$CH_2$-6K, ACE420-Hinge-$CH_2$-6H, ACE19-Fc1-12K, and ACE12-Fc1-12H, separately) or control plasma (e.g., plasma that was not mixed with ACE2 mucoadhesive chimeric proteins) for 1 h at 37° C., generating a pre-incubation mixture. Stimulated PBMCs are subsequently mixed with aliquots of the pre-incubation mixture. After 72 h, cultures are washed 3 times, and supplemented with medium and newly stimulated PBMCs. Cultures are further incubated for 6 to 10 days and analyzed for S1 spike protein concentration. Production of S1 spike protein in the absence of ACE2 mucoadhesive peptides in the plasma is designated as 100%.

Plasma mixed with various ACE2 mucoadhesive chimeric proteins has decreased S1 spike protein concentration compared to the control plasma. The results demonstrate that ACE2 mucoadhesive chimeric peptides kill live SARS-CoV-2 viruses in plasma.

Example 11. ACE2 Mucoadhesive Chimeric Proteins with Various Positively Charged Peptide Fragments Bind Mucin In Vitro Several other ACE740-Fc1 mucoadhesive chimeric proteins were generated and characterized for mucin binding ability, S1-binding specificity, and ability to block pseudovirus infection. These chimeric proteins bear mucoadhesive peptides with a mixture of positively and non-positively charged amino acids of varying lengths. For example, mucoadhesive peptides as short as five amino acids (HHHHH, SEQ ID NO: 128) or six amino acids (HHHHHH, SEQ ID NO: 28) were tested, as well as peptides with positively charged amino acids other than lysine. In addition, mucoadhesive peptides with fewer than 5 consecutive positively charged amino acids were analyzed, such as peptides bearing two to three consecutive positively charged amino acids interspersed with a non-positively charged amino acid (KKKGKKK, SEQ ID NO: 129; KKAHHGKKAHHV, SEQ ID NO: 130; and, KKARRGKKARRV, SEQ ID NO: 131).

The mucin-binding ability of the ACE740-Fc1 mucoadhesive chimeric proteins was analyzed using the method described in Example 4. Briefly, mucin-coated plates were blocked overnight in BSA, washed, and 0.5 μg/well of the ACE740-Fc1 mucoadhesive chimeric protein was added to the plate. The plates were stained with HRP-conjugated goat-anti-human IgG and tested for HRP activity.

Figure 9:
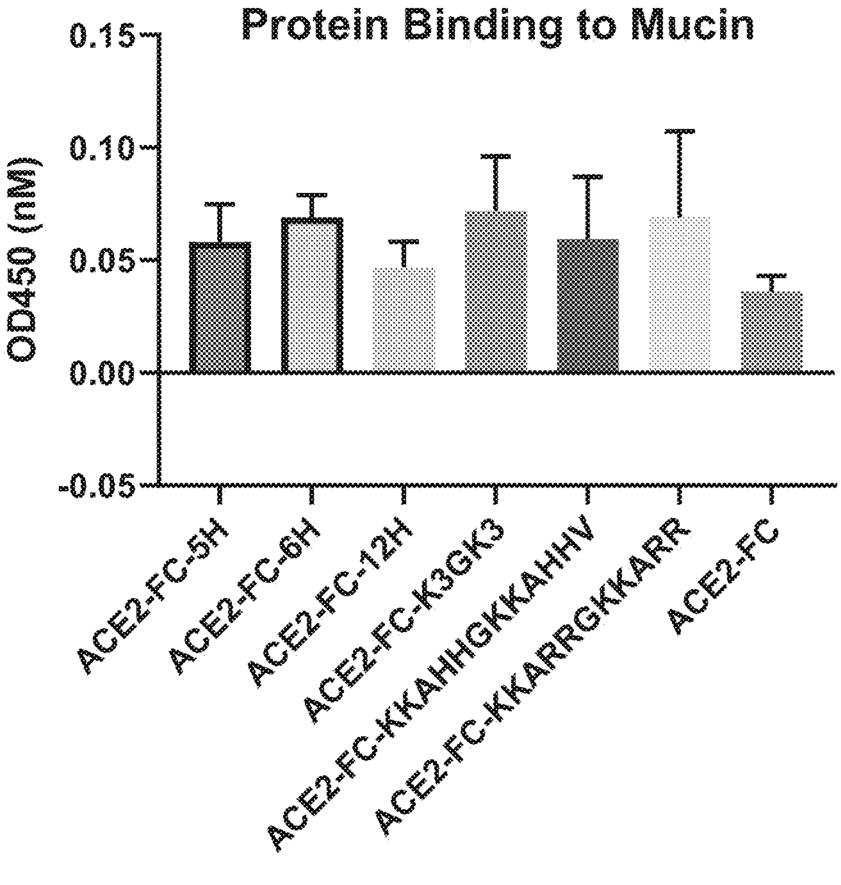
FIG. 9 demonstrates that the addition of various mucoadhesive peptides increases the attraction of ACE2-Fc1 to mucin proteins. An ELISA assay using mucin-coated plates was conducted to compare the mucin-binding ability of ACE2-Fc1 mucoadhesive chimeric proteins to that of ACE2-Fc1 without mucoadhesive peptide. Binding was detected using horseradish peroxidase (HRP)-conjugated goat anti-human IgG and staining was detected at $OD_{450}$.

FIG. 9 shows significant mucin binding for all tested ACE740-Fc1 mucoadhesive chimeric proteins, greater than ACE2-Fc1 protein lacking a positively charged mucoadhesive peptide.

Example 12. Binding Specificity of Various ACE740-Fc1 Mucoadhesive Chimeric Proteins to the BA.5 Spike Protein Using the method described in Example 3A, binding of mucoadhesive chimeric proteins bearing 12K or various mucoadhesive peptides described in Example 11 to a current SARS-CoV-2 variant BA.5 spike protein was analyzed by fluorescence activated cell sorting (FACS).

The mucoadhesive chimeric proteins were tested for binding to HEK293F cells transiently transfected with an expression vector encoding the BA.5 S1 protein. The cells were tested for S1 expression, harvested, and incubated with various ACE740-Fc1 mucoadhesive chimeric proteins followed by PE-anti-human-Fc secondary antibody, and then analyzed by FACS; binding specificity to the S1 protein of the SARS-CoV-2 Omicron variant BA.5 was measured by the amount of the secondary antibody (PE-A) bound to the cells. Untransfected HEK293 cells stained with secondary antibody PE-A alone served as a negative control (very small amount of PE-A bound to the cells).

Figure 10:
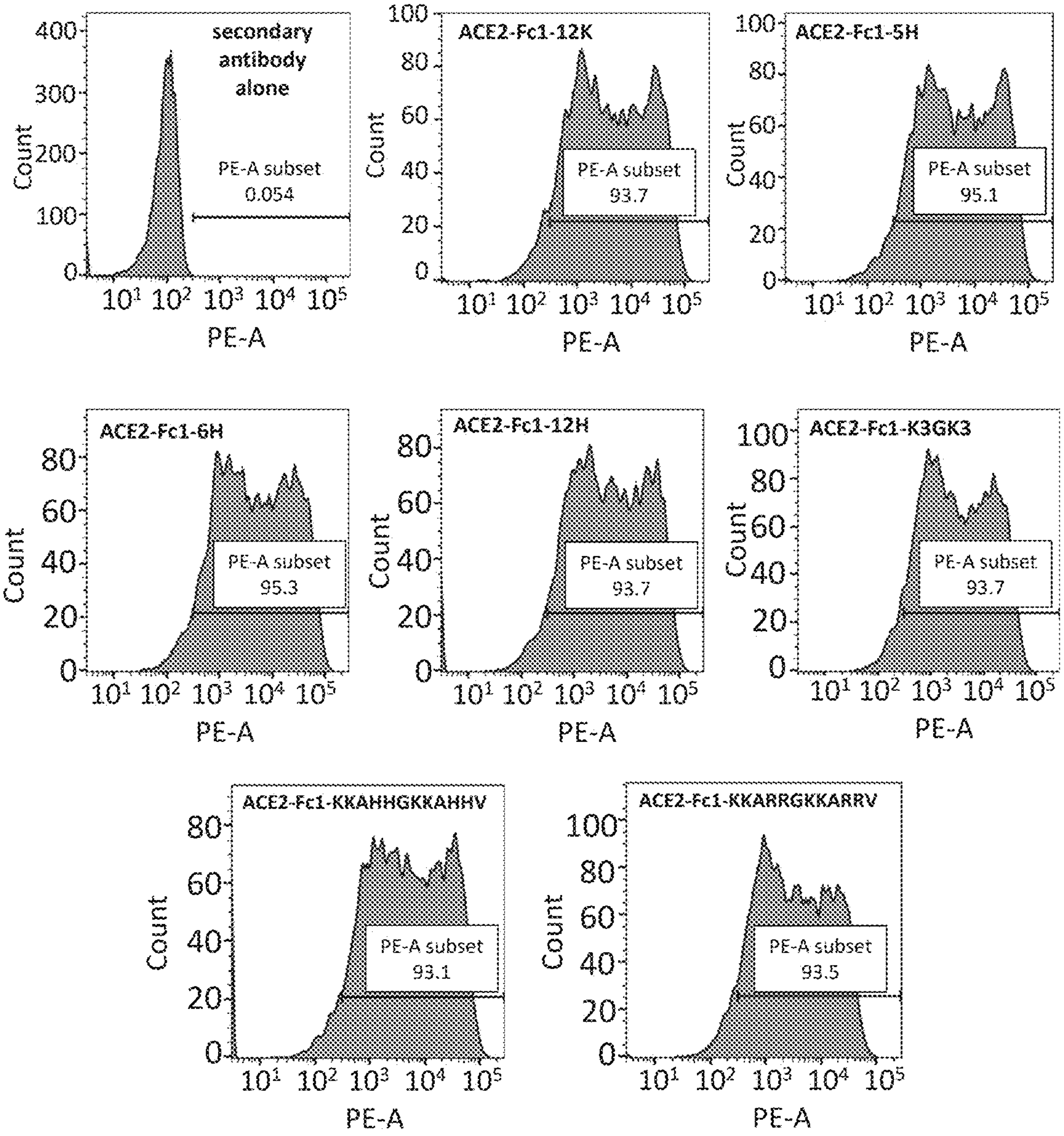
FIG. 10 shows that the exemplary ACE2-Fc1-12K and various other mucoadhesive chimeric proteins bind to spike protein S1 subunit protein. Spike protein S1 subunit proteins from the SARS-CoV-2 Omicron variant BA.5 were transiently expressed in HEK293F cells. Cells were incubated first with ACE2-Fc1 chimeric proteins followed by a PE-Fc secondary antibody, then sorted using fluorescence-activated cell sorting (FACS).

FIG. 10 shows that all the tested exemplary mucoadhesive chimeric proteins bound to cells expressing the S1 protein of the SARS-CoV-2 Omicron variant BA.5, the most transmissible variant circulating since 2021. FIG. 10 also shows similarly strong S1-binding profiles among all the tested exemplary mucoadhesive chimeric proteins with different lengths and compositions of positively charged peptide fragments, indicating that such mucoadhesive peptide fragments do not interfere with ACE2's binding to the SARS-CoV-2 S1 protein.

Example 13. Various ACE740-Fc1 Mucoadhesive Chimeric Proteins Block BA.5 Pseudovirus Infection In Vitro Using the method described in Example 3B, ACE740-Fc-1 mucoadhesive chimeric proteins bearing various mucoadhesive peptide fragments were assessed on their ability to block infection by the SARS-CoV-2 BA.5 variant. The BA.5 spike protein S1 subunit was introduced into HEK293F cells to generate pseudotyped lentivirus. The purified cell culture supernatants containing pseudotyped lentiviruses were incubated with a range of concentrations of ACE740-Fc1 mucoadhesive chimeric proteins for 30 min, and then added to HEK293F-hACE2 cells in 5% $CO_2$ at 37° C. for 48 h. The degree of cellular infection was determined by detecting the level of luciferase produced (normalized according to Example 3B) using untransduced HEK293-hACE2 cells as the negative control.

Figure 11:
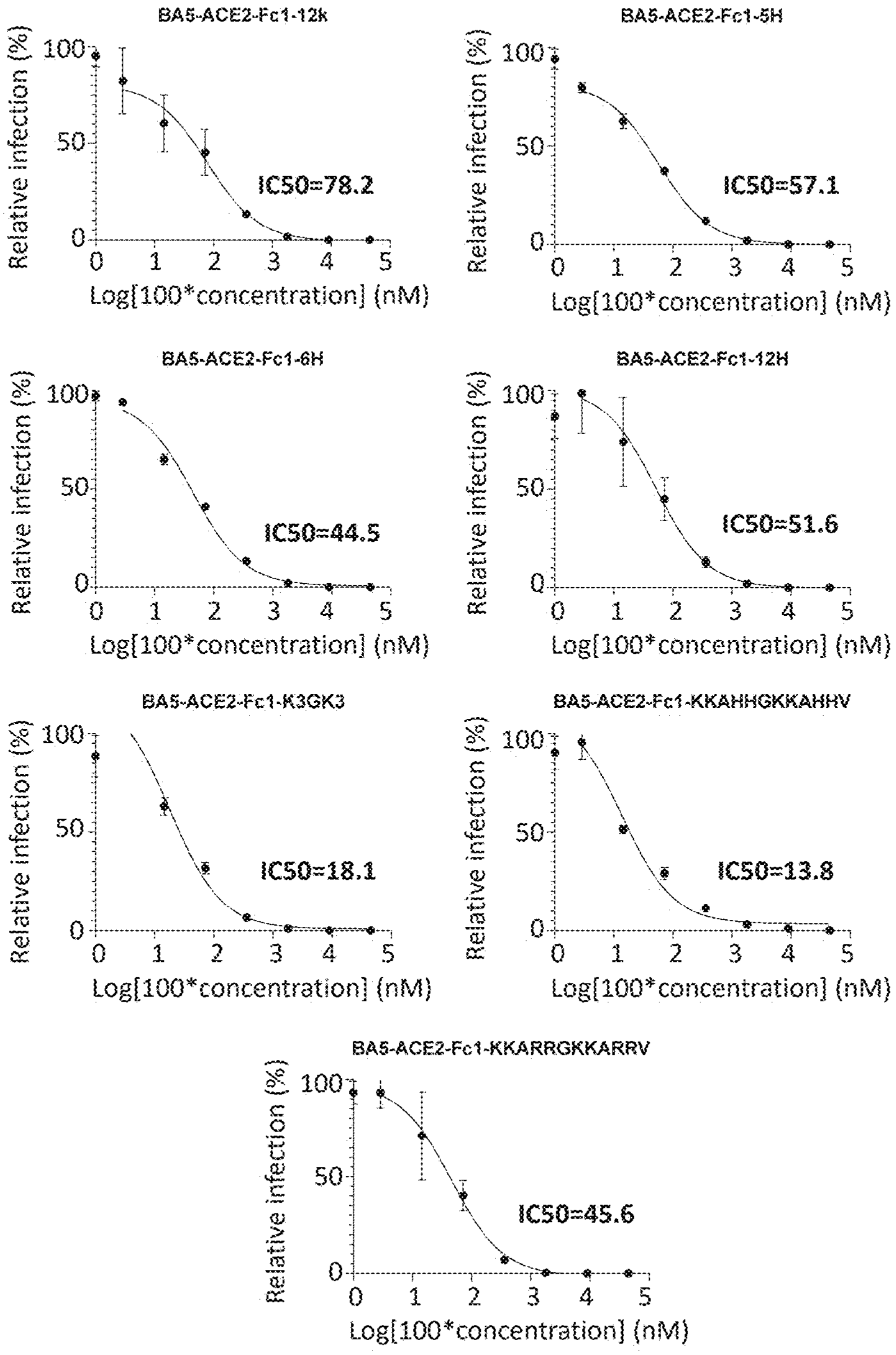
FIG. 11 shows that the exemplary ACE740-Fc1-12K and various other mucoadhesive chimeric proteins block SARS-CoV-2 pseudovirus infection of HEK293F cells expressing ACE2. ACE740-Fc1 chimeric proteins were incubated with pseudotyped lentivirus containing an EF1-α-driven luciferase and GFP reporter genes separated by a P2A self-cleaving peptide and then added to HEK293F-ACE2 cells. Infection was determined by detecting the luciferase level or by detecting GFP in infected cells.

FIG. 11 demonstrates that all mucoadhesive chimeric proteins tested were able to block infection by BA.5 pseudovirus infection at low protein concentrations, with curves comparable to ACE2-Fc1-12K.

SEQUENCE LISTING

| SEQ ID NO | ID | Sequence |
|---|---|---|
| 1 | Human ACE2 (hACE2) | MSSSSWLLLSLVAVTAAQSTIEEQAKTFLDKFNHEAEDLFYQSSLASWNYNT<br>NITEENVQNMNNAGDKWSAFLKEQSTLAQMYPLQEIQNLTVKLQLQALQQN<br>GSSVLSEDKSKRLNTILNTMSTIYSTGKVCNPDNPQECLLLEPGLNEIMANSL<br>DYNERLWAWESWRSEVGKQLRPLYEEYVVLKNEMARANHYEDYGDYWRG<br>DYEVNGVDGYDYSRGQLIEDVEHTFEEIKPLYEHLHAYVRAKLMNAYPSYIS<br>PIGCLPAHLLGDMWGRFWTNLYSLTVPFGQKPNIDVTDAMVDQAWDAQRIF |

-continued

SEQUENCE LISTING

| SEQ ID NO | ID | Sequence |
|---|---|---|
| | | KEAEKFFVSVGLPNMTQGFWENSMLTDPGNVQKAVCHPTAWDLGKGDFRI LMCTKVTMDDFLTAHHEMGHIQYDMAYAAQPFLLRNGANEGFHEAVGEIM SLSAATPKHLKSIGLLSPDFQEDNETEINFLLKQALTIVGTLPFTYMLEKWRW MVFKGEIPKDQWMKKWWEMKREIVGVVEPVPHDETYCDPASLFHVSNDYS FIRYYTRTLYQFQFQEALCQAAKHEGPLHKCDISNSTEAGQKLFNMLRLGKS EPWTLALENVVGAKNMNVRPLLNYFEPLFTWLKDQNKNSFVGWSTDWSPY ADQSIKVRISLKSALGDKAYEWNDNEMYLFRSSVAYAMRQYFLKVKNQMIL FGEEDVRVANLKPRISFNFFVTAPKNVSDIIPRTEVEKAIRMSRSRINDAFRLN DNSLEFLGIQPTLGPPNQPPVSIWLIVFGVVMGVIVVGIVILIFTGIRDRKKKNK ARSGENPYASIDISKGENNPGFQNTDDVQTSF |
| 2 | ACE614 | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGDYWRGDYEVNGVDGYDYSRGQL IEDVEHTFEEIKPLYEHLHAYVRAKLMNAYPSYISPIGCLPAHLLGDMWGRF WTNLYSLTVPFGQKPNIDVTDAMVDQAWDAQRIFKEAEKFFVSVGLPNMTQ GFWENSMLTDPGNVQKAVCHPTAWDLGKGDFRILMCTKVTMDDFLTAHHE MGHIQYDMAYAAQPFLLRNGANEGFHEAVGEIMSLSAATPKHLKSIGLLSPD FQEDNETEINFLLKQALTIVGTLPFTYMLEKWRWMVFKGEIPKDQWMKKW WEMKREIVGVVEPVPHDETYCDPASLFHVSNDYSFIRYYTRTLYQFQFQEAL CQAAKHEGPLHKCDISNSTEAGQKLFNMLRLGKSEPWTLALENVVGAKNM NVRPLLNYFEPLFTWLKDQNKNSFVGWSTDWSPYA |
| 3 | ACE360 | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGDYWRGDYEVNGVDGYDYSRGQL IEDVEHTFEEIKPLYEHLHAYVRAKLMNAYPSYISPIGCLPAHLLGDMWGRF WTNLYSLTVPFGQKPNIDVTDAMVDQAWDAQRIFKEAEKFFVSVGLPNMTQ GFWENSMLTDPGNVQKAVCHPTAWDLGKGDFRILM |
| 4 | ACEΔ360 | DKFNHEAEDLFYQSSLASWNYNTNITEENVQNMNNAGDKWSAFLKEQSTLA QMYPLQEIQNLTVKLQLQALQQNGSSVLSEDKSKRLNTILNTMSTIYSTGKV CNPDNPQECLLLEPGLNEIMANSLDYNERLWAWESWRSEVGKQLRPLYEEY VVLKNEMARANHYEDYGDYWRGDYEVNGVDGYDYSRGQLIEDVEHTFEEI KPLYEHLHAYVRAKLMNAYPSYISPIGCLPAHLLGDMWGRFWTNLYSLTVP FGQKPNIDVTDAMVDQAWDAQRIFKEAEKFFVSVGLPNMTQGFWENSMLT DPGNVQKAVCHPTAWDLGKGDFRILM |
| 5 | ACE732 | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGDYWRGDYEVNGVDGYDYSRGQL IEDVEHTFEEIKPLYEHLHAYVRAKLMNAYPSYISPIGCLPAHLLGDMWGRF WTNLYSLTVPFGQKPNIDVTDAMVDQAWDAQRIFKEAEKFFVSVGLPNMTQ GFWENSMLTDPGNVQKAVCHPTAWDLGKGDFRILMCTKVTMDDFLTAHHE MGHIQYDMAYAAQPFLLRNGANEGFHEAVGEIMSLSAATPKHLKSIGLLSPD FQEDNETEINFLLKQALTIVGTLPFTYMLEKWRWMVFKGEIPKDQWMKKW WEMKREIVGVVEPVPHDETYCDPASLFHVSNDYSFIRYYTRTLYQFQFQEAL CQAAKHEGPLHKCDISNSTEAGQKLFNMLRLGKSEPWTLALENVVGAKNM NVRPLLNYFEPLFTWLKDQNKNSFVGWSTDWSPYADQSIKVRISLKSALGDK AYEWNDNEMYLFRSSVAYAMRQYFLKVKNQMILFGEEDVRVANLKPRISFN FFVTAPKNVSDIIPRTEVEKAIRMSRSRINDAFRLNDNSLEFLGIQPTLG |
| 6 | ACE200 | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYG |
| 7 | ACEΔ420 | YQSSLASWNYNTNITEENVQNMNNAGDKWSAFLKEQSTLAQMYPLQEIQNL TVKLQLQALQQNGSSVLSEDKSKRLNTILNTMSTIYSTGKVCNPDNPQECLLL EPGLNEIMANSLDYNERLWAWESWRSEVGKQLRPLYEEYVVLKNEMARAN HYEDYGDYWRGDYEVNGVDGYDYSRGQLIEDVEHTFEEIKPLYEHLHAYVR AKLMNAYPSYISPIGCLPAHLLGDMWGRFWTNLYSLTVPFGQKPNIDVTDA MVDQAWDAQRIFKEAEKFFVSVGLPNMTQGFWENSMLTDPGNVQKAVCHP TAWDLGKGDFRILMCTKVTMDDFLTAHHEMGHIQYDMAYAAQPFLLRNGA NEGFHEAVGEIMSLSAATPKHLKS |
| 8 | ACE19 | QAKTFLDKFNHEAEDLFYQ |
| 9 | ACE2 K26R | MSSSSWLLLSLVAVTAAQSTIEEQARTFLDKFNHEAEDLFYQSSLASWNYNT NITEENVQNMNNAGDKWSAFLKEQSTLAQMYPLQEIQNLTVKLQLQALQQN GSSVLSEDKSKRLNTILNTMSTIYSTGKVCNPDNPQECLLLEPGLNEIMANSL |

-continued

SEQUENCE LISTING

| SEQ ID NO | ID | Sequence |
|---|---|---|
| | | DYNERLWAWESWRSEVGKQLRPLYEEYVVLKNEMARANHYEDYGDYWRG<br>DYEVNGVDGYDYSRGQLIEDVEHTFEEIKPLYEHLHAYVRAKLMNAYPSYIS<br>PIGCLPAHLLGDMWGRFWTNLYSLTVPFGQKPNIDVTDAMVDQAWDAQRIF<br>KEAEKFFVSVGLPNMTQGFWENSMLTDPGNVQKAVCHPTAWDLGKGDFRI<br>LMCTKVTMDDFLTAHHEMGHIQYDMAYAAQPFLLRNGANEGFHEAVGEIM<br>SLSAATPKHLKSIGLLSPDFQEDNETEINFLLKQALTIVGTLPFTYMLEKWRW<br>MVFKGEIPKDQWMKKWWEMKREIVGVVEPVPHDETYCDPASLFHVSNDYS<br>FIRYYTRTLYQFQFQEALCQAAKHEGPLHKCDISNSTEAGQKLFNMLRLGKS<br>EPWTLALENVVGAKNMNVRPLLNYFEPLFTWLKDQNKNSFVGWSTDWSPY<br>ADQSIKVRISLKSALGDKAYEWNDNEMYLFRSSVAYAMRQYFLKVKNQMIL<br>FGEEDVRVANLKPRISFNFFVTAPKNVSDIIPRTEVEKAIRMSRSRINDAFRLN<br>DNSLEFLGIQPTLGPPNQPPVSIWLIVFGVVMGVIVVGIVILIFTGIRDRKKKNK<br>ARSGENPYASIDISKGENNPGFQNTDDVQTSF |
| 10 | ACE2 I468V | MSSSSWLLLSLVAVTAAQSTIEEQAKTFLDKFNHEAEDLFYQSSLASWNYNT<br>NITEENVQNMNNAGDKWSAFLKEQSTLAQMYPLQEIQNLTVKLQLQALQQN<br>GSSVLSEDKSKRLNTILNTMSTIYSTGKVCNPDNPQECLLLEPGLNEIMANSL<br>DYNERLWAWESWRSEVGKQLRPLYEEYVVLKNEMARANHYEDYGDYWRG<br>DYEVNGVDGYDYSRGQLIEDVEHTFEEIKPLYEHLHAYVRAKLMNAYPSYIS<br>PIGCLPAHLLGDMWGRFWTNLYSLTVPFGQKPNIDVTDAMVDQAWDAQRIF<br>KEAEKFFVSVGLPNMTQGFWENSMLTDPGNVQKAVCHPTAWDLGKGDFRI<br>LMCTKVTMDDFLTAHHEMGHIQYDMAYAAQPFLLRNGANEGFHEAVGEIM<br>SLSAATPKHLKSIGLLSPDFQEDNETEINFLLKQALTIVGTLPFTYMLEKWRW<br>MVFKGEVPKDQWMKKWWEMKREIVGVVEPVPHDETYCDPASLFHVSNDY<br>SFIRYYTRTLYQFQFQEALCQAAKHEGPLHKCDISNSTEAGQKLFNMLRLGK<br>SEPWTLALENVVGAKNMNVRPLLNYFEPLFTWLKDQNKNSFVGWSTDWSP<br>YADQSIKVRISLKSALGDKAYEWNDNEMYLFRSSVAYAMRQYFLKVKNQMI<br>LFGEEDVRVANLKPRISFNFFVTAPKNVSDIIPRTEVEKAIRMSRSRINDAFRL<br>NDNSLEFLGIQPTLGPPNQPPVSIWLIVFGVVMGVIVVGIVILIFTGIRDRKKKN<br>KARSGENPYASIDISKGENNPGFQNTDDVQTSF |
| 11 | ACE2 N638S | MSSSSWLLLSLVAVTAAQSTIEEQAKTFLDKFNHEAEDLFYQSSLASWNYNT<br>NITEENVQNMNNAGDKWSAFLKEQSTLAQMYPLQEIQNLTVKLQLQALQQN<br>GSSVLSEDKSKRLNTILNTMSTIYSTGKVCNPDNPQECLLLEPGLNEIMANSL<br>DYNERLWAWESWRSEVGKQLRPLYEEYVVLKNEMARANHYEDYGDYWRG<br>DYEVNGVDGYDYSRGQLIEDVEHTFEEIKPLYEHLHAYVRAKLMNAYPSYIS<br>PIGCLPAHLLGDMWGRFWTNLYSLTVPFGQKPNIDVTDAMVDQAWDAQRIF<br>KEAEKFFVSVGLPNMTQGFWENSMLTDPGNVQKAVCHPTAWDLGKGDFRI<br>LMCTKVTMDDFLTAHHEMGHIQYDMAYAAQPFLLRNGANEGFHEAVGEIM<br>SLSAATPKHLKSIGLLSPDFQEDNETEINFLLKQALTIVGTLPFTYMLEKWRW<br>MVFKGEIPKDQWMKKWWEMKREIVGVVEPVPHDETYCDPASLFHVSNDYS<br>FIRYYTRTLYQFQFQEALCQAAKHEGPLHKCDISNSTEAGQKLFNMLRLGKS<br>EPWTLALENVVGAKNMNVRPLLNYFEPLFTWLKDQNKNSFVGWSTDWSPY<br>ADQSIKVRISLKSALGDKAYEWNDSEMYLFRSSVAYAMRQYFLKVKNQMIL<br>FGEEDVRVANLKPRISFNFFVTAPKNVSDIIPRTEVEKAIRMSRSRINDAFRLN<br>DNSLEFLGIQPTLGPPNQPPVSIWLIVFGVVMGVIVVGIVILIFTGIRDRKKKNK<br>ARSGENPYASIDISKGENNPGFQNTDDVQTSF |
| 12 | ACE2 N720D | MSSSSWLLLSLVAVTAAQSTIEEQAKTFLDKFNHEAEDLFYQSSLASWNYNT<br>NITEENVQNMNNAGDKWSAFLKEQSTLAQMYPLQEIQNLTVKLQLQALQQN<br>GSSVLSEDKSKRLNTILNTMSTIYSTGKVCNPDNPQECLLLEPGLNEIMANSL<br>DYNERLWAWESWRSEVGKQLRPLYEEYVVLKNEMARANHYEDYGDYWRG<br>DYEVNGVDGYDYSRGQLIEDVEHTFEEIKPLYEHLHAYVRAKLMNAYPSYIS<br>PIGCLPAHLLGDMWGRFWTNLYSLTVPFGQKPNIDVTDAMVDQAWDAQRIF<br>KEAEKFFVSVGLPNMTQGFWENSMLTDPGNVQKAVCHPTAWDLGKGDFRI<br>LMCTKVTMDDFLTAHHEMGHIQYDMAYAAQPFLLRNGANEGFHEAVGEIM<br>SLSAATPKHLKSIGLLSPDFQEDNETEINFLLKQALTIVGTLPFTYMLEKWRW<br>MVFKGEIPKDQWMKKWWEMKREIVGVVEPVPHDETYCDPASLFHVSNDYS<br>FIRYYTRTLYQFQFQEALCQAAKHEGPLHKCDISNSTEAGQKLFNMLRLGKS<br>EPWTLALENVVGAKNMNVRPLLNYFEPLFTWLKDQNKNSFVGWSTDWSPY<br>ADQSIKVRISLKSALGDKAYEWNDNEMYLFRSSVAYAMRQYFLKVKNQMIL<br>FGEEDVRVANLKPRISFNFFVTAPKNVSDIIPRTEVEKAIRMSRSRINDAFRLN<br>DNSLEFLGIQPTLGPPNQPPVSIWLIVFGVVMGVIVVGIVILIFTGIRDRKKKNK<br>ARSGENPYASIDISKGENNPGFQNTDDVQTSF |
| 13 | ACE2 HN-HN | MSSSSWLLLSLVAVTAAQSTIEEQAKTFLDKFNHEAEDLFYQSSLASWNYNT<br>NITEENVQNMNNAGDKWSAFLKEQSTLAQMYPLQEIQNLTVKLQLQALQQN<br>GSSVLSEDKSKRLNTILNTMSTIYSTGKVCNPDNPQECLLLEPGLNEIMANSL<br>DYNERLWAWESWRSEVGKQLRPLYEEYVVLKNEMARANHYEDYGDYWRG<br>DYEVNGVDGYDYSRGQLIEDVEHTFEEIKPLYEHLHAYVRAKLMNAYPSYIS<br>PIGCLPAHLLGDMWGRFWTNLYSLTVPFGQKPNIDVTDAMVDQAWDAQRIF<br>KEAEKFFVSVGLPNMTQGFWENSMLTDPGNVQKAVCHPTAWDLGKGDFRI<br>LMCTKVTMDDFLTAHNEMGNIQYDMAYAAQPFLLRNGANEGFHEAVGEIM<br>SLSAATPKHLKSIGLLSPDFQEDNETEINFLLKQALTIVGTLPFTYMLEKWRW |

-continued

SEQUENCE LISTING

| SEQ ID NO | ID | Sequence |
|---|---|---|
| | | MVFKGEIPKDQWMKKWWEMKREIVGVVEPVPHDETYCDPASLFHVSNDYS FIRYYTRTLYQFQFQEALCQAAKHEGPLHKCDISNSTEAGQKLFNMLRLGKS EPWTLALENVVGAKNMNVRPLLNYFEPLFTWLKDQNKNSFVGWSTDWSPY ADQSIKVRISLKSALGDKAYEWNDNEMYLFRSSVAYAMRQYFLKVKNQMIL FGEEDVRVANLKPRISFNFFVTAPKNVSDIIPRTEVEKAIRMSRSRINDAFRLN DNSLEFLGIQPTLGPPNQPPVSIWLIVFGVVMGVIVVGIVILIFTGIRDRKKKNK ARSGENPYASIDISKGENNPGFQNTDDVQTSF |
| 14 | ACE2 TY-HA | MSSSSWLLLSLVAVTAAQSTIEEQAKYFLDKFNAEAEDLFYQSSLASWNYNT NITEENVQNMNNAGDKWSAFLKEQSTLAQMYPLQEIQNLTVKLQLQALQQN GSSVLSEDKSKRLNTILNTMSTIYSTGKVCNPDNPQECLLLEPGLNEIMANSL DYNERLWAWESWRSEVGKQLRPLYEEYVVLKNEMARANHYEDYGDYWRG DYEVNGVDGYDYSRGQLIEDVEHTFEEIKPLYEHLHAYVRAKLMNAYPSYIS PIGCLPAHLLGDMWGRFWTNLYSLTVPFGQKPNIDVTDAMVDQAWDAQRIF KEAEKFFVSVGLPNMTQGFWENSMLTDPGNVQKAVCHPTAWDLGKGDFRI LMCTKVTMDDFLTAHHEMGHIQYDMAYAAQPFLLRNGANEGFHEAVGEIM SLSAATPKHLKSIGLLSPDFQEDNETEINFLLKQALTIVGTLPFTYMLEKWRW MVFKGEIPKDQWMKKWWEMKREIVGVVEPVPHDETYCDPASLFHVSNDYS FIRYYTRTLYQFQFQEALCQAAKHEGPLHKCDISNSTEAGQKLFNMLRLGKS EPWTLALENVVGAKNMNVRPLLNYFEPLFTWLKDQNKNSFVGWSTDWSPY ADQSIKVRISLKSALGDKAYEWNDNEMYLFRSSVAYAMRQYFLKVKNQMIL FGEEDVRVANLKPRISFNFFVTAPKNVSDIIPRTEVEKAIRMSRSRINDAFRLN DNSLEFLGIQPTLGPPNQPPVSIWLIVFGVVMGVIVVGIVILIFTGIRDRKKKNK ARSGENPYASIDISKGENNPGFQNTDDVQTSF |
| 15 | Mouse ACE2 UPKB:Q8R0I0 | MSSSSWLLLSLVAVTTAQSLTEENAKTFLNNFNQEAEDLSYQSSLASWNYNT NITEENAQKMSEAAAKWSAFYEEQSKTAQSFSLQEIQTPIIKRQLQALQQSGS SALSADKNKQLNTILNTMSTIYSTGKVCNPKNPQECLLLEPGLDEIMATSTDY NSRLWAWEGWRAEVGKQLRPLYEEYVVLKNEMARANNYNDYGDYWRGD YEAEGADGYNYNRNQLIEDVERTFAEIKPLYEHLHAYVRRKLMDTYPSYISP TGCLPAHLLGDMWGRFWTNLYPLTVPFAQKPNIDVTDAMMNQGWDAERIF QEAEKFFVSVGLPHMTQGFWANSMLTEPADGRKVVCHPTAWDLGHGDFRI KMCTKVTMDNFLTAHHEMGHIQYDMAYARQPFLLRNGANEGFHEAVGEIM SLSAATPKHLKSIGLLPSDFQEDSETEINFLLKQALTIVGTLPFTYMLEKWRW MVFRGEIPKEQWMKKWWEMKREIVGVVEPLPHDETYCDPASLFHVSNDYSF IRYYTRTIYQFQFQEALCQAAKYNGSLHKCDISNSTEAGQKLLKMLSLGNSEP WTKALENVVGARNMDVKPLLNYFQPLFDWLKEQNRNSFVGWNTEWSPYA DQSIKVRISLKSALGANAYEWTNNEMFLFRSSVAYAMRKYFSIIKNQTVPFLE EDVRVSDLKPRVSFYFFVTSPQNVSDVIPRSEVEDAIRMSRGRINDVFGLNDN SLEFLGIHPTLEPPYQPPVTIWLIIFGVVMALVVVGIIILIVTGIKGRKKKNETKR EENPYDSMDIGKGESNAGFQNSDDAQTSF |
| 16 | Guinea Pig ACE2 tr\|H0VSF6 | MSGSFWFLLNLVAVTTAQFNLEEQAKTFLDEFNLKAEDLYYQSSLASWNYN TNITDENVQKMSEAGGILSAFYEEQSNLAKAYPLQDIQNLTVKRQLRILQQSG SSGFSADKNKQLSTILNTMSTLYSTGKVCYPSDPQECLLLEPGLADIMSKSTD YNLRLWAWEGWRSKVGKQLRPLYEEYVALKNEMARANKYEDYGDYWRR DYEVEDMDGYNYSRNQLIEDVERTFAEIKPLYEQLHAYVRTKLMETYPSRIS PVGCLPAHLLGDMWGRFWTELYSLTVPFQQKPNIDVTDAMESQSWDAEKIF KEAEKFFVSVGLPPMTQGFWKNSMLTEPGDGQKVVCHPTAWDMGKNDFRI KMCTKVTMDHFLTAHHEMGHIQYDMAYAIQPFLLRDGANEGFHEAIGEIMS LSAATPEHLKSIGLLPPDFHEDNGTFFHGFTHALLGTLPFTFMLEKVERGWSS RVKIPKSSGLKNVADEVKIVGVVEPLPHDETYCDPASLFHVSNDYSFIRYYTR TIYQFQFQEALCKAANHVGPLHKCDISNSTEAGQKLLNMLKLGKSEPWTLAL ESIVGTKNMDVKPLLNYFQPLSTWLQDQNRNSFVGWNTEWSPYSEESIKVRI SLKSALGEDAYKWDDNEMYLFRSSVAYAMRKYFLDVKNQTVLFSWEDVRV SDWTHRVSFTFFVTEPNNVSNIIPKTEVEDAIRLSRSRINDVFLSGIYPTLSPPY EPPVTIWLIVFGVVMGLVVVGIVVLVITGIRDRRKKKQKQREENPYSSVDIGK GENNTAFQNSEDNQTSF |
| 17 | Equine ACE2 tr\|F6V9L3 | MSGSSWLLLSLVAVTAAQSTTEDLAKTFLEKFNSEAEELSHQSSLASWSYNT NITDENVQKMNEAGARWSAFYEEQCKLAKTYPLEEIQNLTVKRQLQALQQS GSSVLSADKSKRLNEILNTMSTIYSTGKVCNPSNPQECLLLEPGLDAIMENSK DYNQRLWAWEGWRSEVGKQLRPLYEEYVVLKNEMARANNYEDYGDYWR GDYEAEGPSGYDYSRDQLIEDVERTFAEIKPLYEHLHAYVRAKLMDTYPSHI NPTGCLPAHLLGDMWGRFWTNLYSLTVPFGQKPNIDVTDAMVDQSWDAKR IFEEAEKFFVSVGLPNMTQGFWENSMLTEPGDGRKVVCHPTAWDLGKGDFR IKMCTKVTMDDFLTAHHEMGHIQYDMAYAVQPYLLRNGANEGFHEAVGEI MSLSAATPNHLKAIGLLPPDFYEDSETEINFLLKQALTIVGTLPFTYMLEKWR WMVFKGEIPKEEWMKKWWEMKREIVGVVEPVPHDETYCDPAALFHVAND YSFIRYYTRTIYQFQFQEALCQTAKHEGPLHKCDISNSTEAGQKLLQMLSLGK SEPWTLALERIVGVKNMDVRPLLNYFEPLFTWLKDQNKNSFVGWSTNWSPY ADQSIKVRISLKSALGEKSYEWNDNEMYLFQSSVAYAMRVYFLKAKNQTILF |

-continued

SEQUENCE LISTING

| SEQ ID NO | ID | Sequence |
|---|---|---|
| | | GEEDVWVSDLKPRISFNFFVTSPKNASDIIPRTDVEEAIRMSRSRINDAFRLDD |
| | | NTLEFLGIQPTLGPPYQPPVTVWLIAFGVVMGLVVVGIVVLIATGIRGRRKKN |
| | | QARSEENPYASVDLSKGENNPGFQNGDDVQTSF |
| 18 | Macaque | MSGSSWLLLSLVAVTAAQSTIEEQAKTFLDKFNHEAEDLFYQSSLASWNYNT |
| | ACE2 | NITEENVQNMNNAGEKWSAFLKEQSTLAQMYPLQEIQNLTVKLQLQALQQN |
| | tr\|F7AH40 | GSSVLSEDKSKRLNTILNTMSTIYSTGKVCNPNNPQECLLLDPGLNEIMEKSL |
| | | DYNERLWAWEGWRSEVGKQLRPLYEEYVVLKNEMARANHYKDYGDYWR |
| | | GNYEVNGVDGYDYNRDQLIEDVERTFEEIKPLYEHLHAYVRAKLMNAYPSY |
| | | ISPTGCLPAHLLGDMWGRFWTNLYSLTVPFGQKPNIDVTDAMVNQAWNAQ |
| | | RIFKEAEKFFVSVGLPNMTQGFWENSMLTDPGNVQKVVCHPTAWDLGKGD |
| | | FRIIMCTKVTMDDFLTAHHEMGHIQYDMAYAAQPFLLRNGANEGFHEAVGE |
| | | IMSLSAATPKHLKSIGLLSPDFQEDNETEINFLLKQALTIVGTLPFTYMLEKWR |
| | | WMVFKGEIPKDQWMKKWWEMKREIVGVVEPVPHDETYCDPASLFHVSND |
| | | YSFIRYYTRTLYQFQFQEALCQAAKHEGPLHKCDISNSTEAGQKLLNMLKLG |
| | | KSEPWTLALENVVGAKNMNVRPLLNYFEPLFTWLKDQNKNSFVGWSTDWS |
| | | PYADQSIKVRISLKSALGDKAYEWNDNEMYLFRSSVAYAMRTYFLEIKHQTI |
| | | LFGEEDVRVADLKPRISFNFYVTAPKNVSDIIPRTEVEEAIRISRSRINDAFRLN |
| | | DNSLEFLGIQTTLAPPYQSPVTTWLIVFGVVMGVIVAGIVVLIFTGIRDRKKKN |
| | | QARSEENPYASIDINKGENNPGFQNTDDVQTSF |
| 19 | Chimpanzee | MSGSSWLLLSLVAVTAAQSTIEEQAKTFLDKFNHEAEDLFYQSSLASWNYNT |
| | ACE2 | NITEENVQNMNNAGDKWSAFLKEQSTLAQMYPLQEIQNLTVKLQLQALQQN |
| | tr\|A0A2J8KU96 | GSSVLSEDKSKRLNTILNTMSAIYSTGKVCNPNNPQECLLLEPGLNEIMANSL |
| | | DYNERLWAWESWRSEVGKQLRPLYEEYVVLKNEMARANHYEDYGDYWRG |
| | | DYEVNGVDGYDYSRGQLIEDVEHTFEEIKPLYEHLHAYVRAKLMNAYPSYIS |
| | | PIGCLPAHLLGDMWGRFWTNLYSLTVPFGQKPNIDVTDAMVDQAWDAQRIF |
| | | KEAEKFFVSVGLPNMTQGFWENSMLTDPGNVQKAVCHPTAWDLGKGDFRI |
| | | LMCTKVTMDDFLTAHHEMGHIQYDMAYAAQPFLLRNGANEGFHEAVGEIM |
| | | SLSAATPKHLKSIGLLSPDFQEDNETEINFLLKQALTIVGTLPFTYMLEKWRW |
| | | MVFKGEIPEDQWMKKWWEMKREIVGVVEPVPHDETYCDPASLFHVSNDYS |
| | | FIRYYTRTLYQFQFQEALCQAAKHEGPLHKCDISNSTEAGQKLFNMLRLGKS |
| | | EPWTLALENVVGAKNMNVRPLLNYFEPLFTWLKDQNKNSFVGWSTDWSPY |
| | | ADQSIKVRISLKSALGDKAYEWNDNEMYLFRSSVAYAMRQYFLKVKNQMIL |
| | | FGEEDVRVANLKPRISFNFFVTAPKNVSDIIPRTEVEKAIRKSRSRINDAFRLN |
| | | DNSLEFLGIQPTLGPPNQPPVSIWLIVFGVVMGVIVVGIVILIFTGIRDRKKKNK |
| | | ARSEENPYASVDTSKGENNPGFQNTDDVQTSF |
| 20 | Swine ACE2 | MSGSFWLLLSLIPVTAAQSTTEELAKTFLEKFNLEAEDLAYQSSLASWNYNT |
| | tr\|K7GLM4 | NITDENIQKMNDARAKWSAFYEEQSRIAKTYPLDEIQTLILKRQLQALQQSGT |
| | | SGLSADKSKRLNTILNTMSTIYSSGKVLDPNNPQECLVLEPGLDEIMENSKDY |
| | | SRRLWAWESWRAEVGKQLRPLYEEYVVLENEMARANNYEDYGDYWRGDY |
| | | EVTGTGDYDYSRNQLMEDVERTFAEIKPLYEHLHAYVRAKLMDAYPSRISPT |
| | | GCLPAHLLGDMWGRFWTNLYPLTVPFGEKPSIDVTEAMVNQSWDAIRIFEEA |
| | | EKFFVSIGLPNMTQGFWNNSMLTEPGDGRKVVCHPTAWDLGKGDFRIKM |
| | | CTKVTMDDFLTAHHEMGHIQYDMAYAIQPYLLRNGANEGFHEAVGEIMSLS |
| | | AATPHYLKALGLLPPDFYEDSETEINFLLKQALTIVGTLPFTYMLEKWRWMV |
| | | FKGEIPKEQWMQKWWEMKREIVGVVEPLPHDETYCDPACLFHVAEDYSFIR |
| | | YYTRTIYQFQFHEALCRTAKHEGPLYKCDISNSTEAGQKLLQMLSLGKSEPW |
| | | TLALENIVGVKTMDVKPLLSYFEPLLTWLKAQNGNSSVGWNTDWTPYADQS |
| | | IKVRISLKSALGKEAYEWNDNEMYLFRSSIAYAMRNYFSSAKNETIPFGAED |
| | | VWVSDLKPRISFNFFVTSPANMSDIIPRSDVEKAISMSRSRINDAFRLDDNTLE |
| | | FLGIQPTLGPPDEPPVTVWLIIFGVVMGLVVVGIVVLIFTGIRDRRKKKQASSE |
| | | ENPYGSMDLSKGESNSGFQNGDDIQTSF |
| 21 | Canine ACE2 | MSGSSWLLLSLAALTAAQSTEDLVKTFLEKFNYEAEELSYQSSLASWNYNINI |
| | tr\|J9P7Y2 | TDENVQKMNNAGAKWSAFYEEQSKLAKTYPLEEIQDSTVKRQLRALQHSGS |
| | | SVLSADKNQRLNTILNSMSTIYSTGKACNPSNPQECLLLEPGLDDIMENSKDY |
| | | NERLWAWEGWRSEVGKQLRPLYEEYVALKNEMARANNYEDYGDYWRGD |
| | | YEEEWENGYNYSRNQLIDDVEHTFTQIMPLYQHLHAYVRTKLMDTYPSYISP |
| | | TGCLPAHLLGDMWGRFWTNLYPLTVPFGQKPNIDVTNAMVNQSWDARKIF |
| | | KEAEKFFVSVGLPNMTQEFWENSMLTEPSDSRKVVCHPTAWDLGKGDFRIK |
| | | MCTKVTMDDFLTAHHEMGHIQYDMAYAAQPFLLRNGANEGFHEAVGEIMS |
| | | LSAATPNHLKNIGLLPPSFFEDSETEINFLLKQALTIVGTLPFTYMLEKWRWM |
| | | VFKGEIPKDQWMKTWWEMKRNIVGVVEPVPHDETYCDPASLFHVANDYSFI |
| | | RYYTRTIYQFQFQEALCQIAKHEGPLHKCDISNSSEAGQKLLEMLKLGKSKP |
| | | WTYALEIVVGAKNMDVRPLLNYFEPLFTWLKEQNRNSFVGWNTDWSPYAD |
| | | QSIKVRISLKSALGEKAYEWNNNEMYLFRSSIAYAMRQYFSEVKNQTIPFVE |
| | | DNVWVSDLKPRISFNFFVTSPGNVSDIIPRTEVEEAIRMYRSRINDVFRLDDNS |
| | | LEFLGIQPTLGPPYEPPVTIWLIVFGVVMGVVVVGIVLLIFSGIRNRRKNDQAR |
| | | GEENPYASVDLSKGENNPGFQNVDDAQTSF |

-continued

SEQUENCE LISTING

| SEQ ID NO | ID | Sequence |
|---|---|---|
| 22 | Feline ACE2<br>tr\|A0A5F5XDN9 | MSGSFWLLLSFAALTAAQSTTEELAKTFLEKFNHEAEELSYQSSLASWNYNT<br>NITDENVQKMNEAGAKWSAFYEEQSKLAKTYPLAEIHNTTVKRQLQALQQS<br>GSSVLSADKSQRLNTILNAMSTIYSTGKACNPNNPQECLLLEPGLDDIMENSK<br>DYNERLWAWEGWRAEVGKQLRPLYEEYVALKNEMAKSKQYEDYGDYWR<br>GDYEEEWTDGYNYSRSQLIKDVEHTFTQIKPLYQHL<br>HAYVRAKLMDTYPSRISPTGCLPAHLLGDMWGRFWTNLYPLTVPFGQKPNI<br>DVTDAMVNQSWDARRIFKEAEKFFVSVGLPNMTQGFWENSMLTEPGDSRK<br>VVCHPTAWDLGKGDFRIKMCTKVTMDDFLTAHHEMGHIQYDMAYAVQPFL<br>LRNGANEGFHEAVGEIMSLSAATPNHLKTIGLLSPGFSEDSETEINFLLKQALT<br>IVGTLPFTYMLEKWRWMVFKGEIPKEQWMQKWWEMKREIVGVVEPVPHDE<br>TYCDPASLFHVANDYSFIRYYTRTIYQFQFQEALCRIAKHEGPLHKCDISNSSE<br>AGKKLLQMLTLGKSKPWTLALEHVVGEKKMNVTPLLKYFEPLFTWLKEQN<br>RNSFVGWNTDWRPYADQSIKVRISLKSALGDEAYEWNDNEMYLFRSSVAYA<br>MREYFSKVKNQTIPFVEDNVWVSNLKPRISFNFFVTASKNVSDVIPRSEVEEA<br>IRMSRSRINDAFRLDDNSLEFLGIQPTLSPPYQPPVTIWLIVFGVVMGVVVVGI<br>VLLIVSGIRNRRKNNQARSEENPYASVDLSKGENNPGFQHADDVQTSF |
| 23 | Bovine ACE2<br>UPKB:Q58DD0 | MTGSFWLLLSLVAVTAAQSTTEEQAKTFLEKFNHEAEDLSYQSSLASWNYN<br>TNITDENVQKMNEARAKWSAFYEEQSRMAKTYSLEEIQNLTLKRQLKALQH<br>SGTSALSAEKSKRLNTILNKMSTIYSTGKVLDPNTQECLALEPGLDDIMENSR<br>DYNRRLWAWEGWRAEVGKQLRPLYEEYVVLENEMARANNYEDYGDYWR<br>GDYEVTGAGDYDYSRDQLMKDVERTFAEIKPLYEQLHAYVRAKLMHTYPS<br>YISPTGCLPAHLLGDMWGRFWTNLYSLTVPFEHKPSIDVTEKMENQSWDAE<br>RIFKEAEKFFVSISLPYMTQGFWDNSMLTEPGDGRKVVCHPTAWDLGKGDF<br>RIKMCTKVTMDDFLTAHHEMGHIQYDMAYAAQPYLLRNGANEGFHEAVGE<br>IMSLSAATPHYLKALGLLAPDFHEDNETEINFLLKQALTIVGTLPFTYMLEKW<br>RWMVFKGEIPKQQWMEKWWEMKREIVGVVEPLPHDETYCDPACLFHVAED<br>YSFIRYYTRTIYQFQFHEALCKTAKHEGALFKCDISNSTEAGQRLLQMLRLGK<br>SEPWTLALENIVGIKTMDVKPLLNYFEPLFTWLKEQNRNSFVGWSTEWTPYS<br>DQSIKVRISLKSALGENAYEWNDNEMYLFQSSVAYAMRKYFSEARNETVLF<br>GEDNVWVSDKKPRISFKFFVTSPNNVSDIIPRTEVENAIRLSRDRINDVFQLDD<br>NSLEFLGIQPTLGPPYEPPVTIWLIIFGVVMGVVVIGIVVLIFTGIRNRRKKNQA<br>SSEENPYGSVDLNKGENNSGFQNIDDVQTSL |
| 24 | Rabbit ACE2<br>tr\|G1TEF4 | MSGSSWLLLSLVAVTAAQSTIEELAKTFLEKFNQEAEDLSYQSALASWDYNT<br>NITEENVQKMNDAEAKWSAFYEEQSKLAKTYPSQEVQNLTVKRQLQALQQS<br>GSSALSADKSKQLNTILSTMSTIYSTGKVCNQSNPQECFLLEPGLDEIMAKST<br>DYNERLWAWEGWRSVVGKQLRPLYEEYVVLKNEMARANNYEDYGDYWR<br>ADYEAEGADGYDYSRSQLIDDVERTFSEIKPLYEQLHAFVRTKLMDAYPSRIS<br>PTGCLPAHLLGDMWGRFWTNLYSLTVPFGQKPNIDVTDTMVNQGWDAERIF<br>KEAEKFFVSVGLPSMTQGFWENSMLTEPGDGRKVVCHPTAWDLGKGDFRIK<br>MCTKVTMDNFLTAHHEMGHIQYDMAYATQPFLLRNGANEGFHEAVGEIMS<br>LSAATPEHLKSIGLLPYDFHEDNETEINFLLKQALTIVGTLPFTYMLEKWRWM<br>VFKGEIPKEQWMQKWWEMKREIVGVVEPMPHDETYCDPAALFHVANDYSF<br>IRYYTRTIYQFQFQEALCQAAQHEGPLHKCDISNSTEAGQKLLNMLRLGRSEP<br>WTLALENVVGAKNMDVRPLLNYFEPLFTWLKEQNRNSFVGWSTEWTPYAD<br>QSIKVRISLKTALGDQAYEWNDSEMYLFRSSVAYAMRKYFSEVKNQTILFGE<br>EDVRVSDLKPRISFNFFVTAPNNVNDIIPRNEVEEAISMSRSRINDIFRLDDNSL<br>EFVGIQPTLEPPYESPVPIWLVVFGVVMGMIVIGIVVLIFTGIKDRRKQKQAKR<br>EENPYGFVDMSKGENNSGFQNSDDIQTSF |
| 25 | Ferret ACE2<br>UPKB:Q2WG88 | MLGSSWLLLSLAALTAAQSTTEDLAKTFLEKFNYEAEELSYQNSLASWNYNT<br>NITDENIQKMNIAGAKWSAFYEEESQHAKTYPLEEIQDPIIKRQLRALQQSGSS<br>VLSADKRERLNTILNAMSTIYSTGKACNPNNPQECLLLEPGLDDIMENSKDY<br>NERLWAWEGWRSEVGKQLRPLYEEYVALKNEMARANNYEDYGDYWRGD<br>YEEEWADGYSYSRNQLIEDVEHTFTQIKPLYEHLHAYVRAKLMDAYPSRISP<br>TGCLPAHLLGDMWGRFWTNLYPLMVPFRQKPNIDVTDAMVNQSWDARRIF<br>EEAETFFVSVGLPNMTEGFWQNSMLTEPGDNRKVVCHPTAWDLGKRDFRIK<br>MCTKVTMDDFLTAHHEMGHIQYDMAYAEQPFLLRNGANEGFHEAVGEIMS<br>LSAATPNHLKNIGLLPPDFSEDSETDINFLLKQALTIVGTLPFTYMLEKWRWM<br>VFKGEIPKEQWMQKWWEMKRDIVGVVEPLPHDETYCDPAALFHVANDYSFI<br>RYYTRTIYQFQFQEALCQIAKHEGPLYKCDISNSSEAGQKLHEMLSLGRSKP<br>WTFALERVVGAKTMDVRPLLNYFEPLFTWLKEQNRNSFVGWNTDWSPYAD<br>QSIKVRISLKSALGEKAYEWNDNEMYFFQSSIAYAMREYFSKVKNQTIPFVG<br>KDVRVSDLKPRISFNFIVTSPENMSDIIPRADVEEAIRKSRGRINDAFRLDDNSL<br>EFLGIQPTLEPPYQPPVTIWLIVFGVVMGVVVVGIFLLIFSGIRNRRKNNQARS<br>EENPYASVDLSKGENNPGFQNVDDVQTSF |
| 26 | Mink ACE2<br>UPKB:<br>A0A7T0Q2W2 | MLGSSWLLLSLAALTAAQSTTEDLAKTFLEKFNYEAEELSYQNSLASWNYNT<br>NITDENIQKMNIAGAKWSAFYEEESQHAKTYPLEEIQDPIIKRQLRALQQSGSS<br>VLSADKRERLNTILNAMSTIYSTGKACNPNNPQECLLLEPGLDDIMENSKDY<br>NERLWAWEGWRSEVGKQLRPLYEEYVALKNEMARANNYEDYGDYWRGD<br>YEEEWADGYNYSRNQLIEDVEHTFTQIKPLYEHLHAYVRAKLMDAYPSRISP |

-continued

SEQUENCE LISTING

| SEQ ID NO | ID | Sequence |
|---|---|---|
| | | TGCLPAHLLGDMWGRFWTNLYPLMVPFGQKPNIDVTDAMVNQSWDARRIF KEAEKFFVSVGLPNMTEGFWQNSMLTEPGDNRKVVCHPTAWDLGKHDFRI KMCTKVTMDDFLTAHHEMGHIQYDMAYAAQPFLLRNGANEGFHEAVGEIM SLSAATPNHLKNIGLLPPDFSEDSETDINFLLKQALTIVGTLPFTYMLEKWRW MVFKGEIPKEQWMQKWWEMKRDIVGVVEPLPHDETYCDPAALFHVANDYS FIRYYTRTIYQFQFQEALCQIAKHEGPLYKCDISNSREAGQKLHEMLSLGRSK PWTFALERVVGAKTMDVRPLLNYFEPLFTWLKEQNRNSFVGWNTDWSPYA DQSIKVRISLKSALGEKAYEWNDNEMYFFQSSIAYAMREYFSKVKKQTIPFV DKDVRVSDLKPRISFNFIVTSPENMSDIIPRADVEEAIRKSRGRINDAFRLDDN SLEFLGIQPTLEPPYQPPVTIWLIVFGVVMGVVVVGIFLLIFSGIRNRRKNNQA RSEENPYASVDLSKGENNPGFQNVDDVQTSF |
| 27 | Chicken ACE2 tr\|F1NHR4 | MLLHFWLLCGLSAVVTPQDVTQEAQTFLAEFNVRAEDISYENSLASWNYNT NITEETARKMSEAGAKWAAFYEEASRNASRFSLANIQDAVTRLQIQSLQDRG SSVLSPEKYSRLNSVMNSMSTIYSTGVVCKATEPFDCLVLEPGLDDIMANSID YHERLWAWEGWRADVGRMMRPLYEEYVELKNEAARLNNYSDYGDYWRA NYETDYPEEYKYSRDQLVQDVEKTFEQIKPLYQHLHAYVRHRLEQVYGSELI NPTGCLPAHLLGDMWGRFWTNLYNLTVPYPEKPNIDVTSAMAQKNWDAM KIFKTAEAFFASIGLYNMTEGFWTNSMLTEPTDNRKVVCHPTAWDMGKNDY RIKMCTKVTMDDFLTAHHEMGHIEYDMAYSVQPFLLRNGANEGFHEAVGEI MSLSAATPQHLKSLDLLEPTFQEDEETEINFLLKQALTIVGTMPFTYMLEKWR WMVFNGEITKQEWTKRWWKMKREIVGVVEPVPHDETYCDPAALFHVAND YSFIRYYTRTIYQFQFQEALCKAANHTGPLHKCDITNSTAAGGNLRQLLELGK SKPWTQALESATGEKYMNATPLLHYFEPLFNWLQKNNSGRSIGWNTDWTPY SDNAIKVRISLKAALGDDAYVWDASELFLFKSSIAYAMRKYFAKEKEQNVDF QVTDIHVGEETQRVSFYLTVSMPGNVSDIVPRADVEKAIRMSRGRISEAFRLD DNTLEFDGIVPTLATPYKPPVTIWLILFGVVMSLIVIGVIVLIITGQRDKRKKAR GRANEAGSNCEVNPYDEDGRSNKGFEQSEETQTSF |
| 28 | 6H | HHHHHH |
| 29 | 12H | HHHHHHHHHHHH |
| 30 | 30H | HHHHHHHHHHHHHHHHHHHHHHHHHHHHHH |
| 31 | 6K | KKKKKK |
| 32 | 12K | KKKKKKKKKKKK |
| 33 | 30K | KKKKKKKKKKKKKKKKKKKKKKKKKKKKKK |
| 34 | 6R | RRRRRR |
| 35 | 12R | RRRRRRRRRRRR |
| 36 | 30R | RRRRRRRRRRRRRRRRRRRRRRRRRRRRRR |
| 37 | 6O | OOOOOO |
| 38 | 12O | OOOOOOOOOOOO |
| 39 | 30O | OOOOOOOOO |
| 40 | 6X-1 | HHKKOO |
| 41 | 6X-2 | HORKHR |
| 42 | 6X-3 | HKRSOH |
| 43 | 6X-4 | RRHTHR |
| 44 | 6X-5 | KKOORR |
| 45 | 6X-5 | KKHHRR |
| 46 | 6X-6 | OORRHH |
| 47 | 12X-1 | HHHKKKRRROOO |
| 48 | 12X-2 | HHOAKKRCOOQH |
| 49 | 12X-3 | HRKOORKHHRKK |
| 50 | 12X-4 | KRAHOKCORKSH |

-continued

SEQUENCE LISTING

| SEQ ID NO | ID | Sequence |
|---|---|---|
| 51 | 12X-5 | KKRROOHHHRRR |
| 52 | 12X-6 | OOORRRKKKHHH |
| 53 | 30X-1 | HKROHKROHKROHKROHKROHKROHKROHK |
| 54 | 30X-2 | KOHRSOKRHTORHKAHORKCKROKQRKHOS |
| 55 | 30X-3 | KKROSRRHOTOOHHAROKHCKHROTRHKKS |
| 56 | 30X-4 | HRKQOHRSOOKTRRRAHROCHHHSRHOTHR |
| 57 | 35X-1 | GRHKAKNHIRRPKSRWKKWHKYRKVHRHKVHKGRR |
| 58 | 40X-2 | WRKVHHYKKQHKNRAHGKLKLRAKIHQRSRMHGKQKHYHR |
| 59 | 42X-1 | AHHKCRRGHKQKILHRRPHKFHRWKRVHKGRHGKKHRRHKHR |
| 60 | 45X-1 | QHRGKAKYHRTHHVKKQRHGRKNHKVHRHARKFHKIRRLKCHKKH |
| 61 | 50X-1 | HNKRFKKGRHVRHSRHKSHRRTHKYHHWRHYRKVHRCKKAHKSHHRVHH<br>K |
| 62 | 50X-2 | AHGRPHOFKROCKAHOVKHILKRTOSHOYKOVHQRNKOAOKMRKIRGGHK |
| 63 | Immunoglobulin Fc region ($CH_2CH_3$) | TCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPSDIAVE<br>WESNGQPENNYKTTPPVLDSDGSFFLYSKLTVDKSRWQQGNVFSCSVMHEA<br>LHNHYTQKSLSLSPGK |
| 64 | Immunoglobulin $C_L$ | GQPKANPTVTLFPPSSEELQANKATLVCLISDFYPGAVTVAWKADGSPVKAG<br>VETTKPSKQSNNKYAASSYLSLTPEQWKSHRSYSCQVTHEGSTVEKTVAPTE<br>CS |
| 65 | Immunoglobulin $CH_1$ | ASTKGPSVFPLAPSSKSTSGGTAALGCLVKDYFPEPVTVSWNSGALTSGVHTF<br>PAVLQSSGLYSLSSVVTVPSSSLGTQTYICNVNHKPSNTKVDKRVEPKSC |
| 66 | Immunoglobulin $CH_2$ | TCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKA<br>LPAPIEKTISKAKGQPRE |
| 67 | Immunoglobulin $CH_3$ | PQVYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| 68 | Immunoglobulin $CH_4$ | PDVYLLPPAREQLNLRESATITCLVTGFSPADVFVQWMQRGQPLSPEKYVTS<br>APMPEPQAPGRYFAHSILTVSEEEWNTGETYTCVVAHEALPNRVTERTVDKS<br>TGK |
| 69 | Alkaline phosphatase | MWWRLWWLLLLLLLLWGSSASAAIIPVEEENPDFWNREAAEALGAAKKLQ<br>PAQTAAKNLIIFLGDGMGVSTVTAARILKGQKKDKLGPEIPLAMDRFPYVAL<br>SKTYNVDKHVPDSGATATAYLCGVKGNFQTIGLSAAARFNQCNTTRGNEVIS<br>VMNRAKKAGKSVGVVTTTRVQHASPAGTYAHTVNRNWYSDADVPASARQ<br>EGCQDIATQLISNMDIDVILGGGRKYMFRMGTPDPEYPDDYSQGGTRLDGKN<br>LVQEWLAKRQGARYVWNRTELMQASLDPSVTHLMGLFEPGDMKYEIHRDS<br>TLDPSLMEMTEAALRLLSRNPRGFFLFVEGGRIDHGHHESRAYRALTETIMFD<br>DAIERAGQLTSEEDTLSLVTADHSHVFSFGGYPLRGSSIFGLAPGKARDRKAY<br>TVLLYGNGPGYVLKDGARPDVTESESGSPEYRQQSAVPLDEETHAGEDVAV<br>FARGPQAHLVHGVQEQTFIAHVMAFAACLEPYTACDLAPPAGTTDAAHPGY<br>SRVGAAGRFEQT |
| 70 | Glutathione-s-transferase (GST) | MKLVGSYTSPFVRKLSILLLEKGITFEFINELPYNADNGVAQFNPLGKVPVLV<br>TEEGECWFDSPIIAEYIELMNVAPAMLPRDPLESLRVRKIEALADGIMDAGLV<br>SVREQARPAAQQSEDELLRQREKINRSLDVLEGYLVDGTLKTDTVNLATIAIA<br>CAVGYLNFRRVAPGWCVDRPHLVKLVENLFSRESFARTEPPKA |
| 71 | bHLH-Leucine Zipper | LENHSRRLEMTNKQLWLRIQEL |
| 72 | Leucine/Isoleucine Zipper | LSIIAICLGSLGLILIILLSVVVWKLL |

-continued

SEQUENCE LISTING

| SEQ ID NO | ID | Sequence |
|---|---|---|
| 73 | Collagen-like Peptide | GPP(GPP)$_n$, where n ≥ 0 |
| 74 | T4 Fibritin | GYIPEAPRDGQAYVRKDGEWVLLSTFL |
| 75 | p53 Tetramerization Domain | EYFTLQIRGRERFEMFRELNEALELKDAQAG |
| 76 | Streptavidin (SA) | MAEAGITGTWYNQLGSTFIVTAGADGALTGTYESAVGNAEGDYVLTGRYDS APATDGSGTALGWTVAWKNNYRNAHSATTWSGQYVGGAEARINTQWLLTS GTTEANAWKSTLVGHDTFTKVKPSAAS |
| 77 | COMP (cartilage oligomeric matrix protein) | GPQMLRELGETNAALQDVRELLRQQVREITFLKNTVMEBDAC |
| 78 | Linker A | SRGGGGSGGGGSGGGGSLEMA |
| 79 | Linker 1 | GGGGS |
| 80 | Linker 2 | GS(GS)$_n$, where n ≥ 0 |
| 81 | Linker 3 | (GSGGS)$_n$, where n ≥ 1 |
| 82 | Linker 4 | (GGGGS)$_n$, where n ≥ 1 |
| 83 | Linker 5 | (GGGS)$_n$, where n ≥ 1 |
| 84 | ACE614-Fc1-12K | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGDYWRGDYEVNGVDGYDYSRGQL IEDVEHTFEEIKPLYEHLHAYVRAKLMNAYPSYISPIGCLPAHLLGDMWGRF WTNLYSLTVPFGQKPNIDVTDAMVDQAWDAQRIFKEAEKFFVSVGLPNMTQ GFWENSMLTDPGNVQKAVCHPTAWDLGKGDFRILMCTKVTMDDFLTAHHE MGHIQYDMAYAAQPFLLRNGANEGFHEAVGEIMSLSAATPKHLKSIGLLSPD FQEDNETEINFLLKQALTIVGTLPFTYMLEKWRWMVFKGEIPKDQWMKKW WEMKREIVGVVEPVPHDETYCDPASLFHVSNDYSFIRYYTRTLYQFQFQEAL CQAAKHEGPLHKCDISNSTEAGQKLFNMLRLGKSEPWTLALENVVGAKNM NVRPLLNYFEPLFTWLKDQNKNSFVGWSTDWSPYATCPPCPAPELLGGPSVF LFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK GGGGSKKKKKKKKKKKK |
| 85 | ACE614-Fc1-12H | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGDYWRGDYEVNGVDGYDYSRGQL IEDVEHTFEEIKPLYEHLHAYVRAKLMNAYPSYISPIGCLPAHLLGDMWGRF WTNLYSLTVPFGQKPNIDVTDAMVDQAWDAQRIFKEAEKFFVSVGLPNMTQ GFWENSMLTDPGNVQKAVCHPTAWDLGKGDFRILMCTKVTMDDFLTAHHE MGHIQYDMAYAAQPFLLRNGANEGFHEAVGEIMSLSAATPKHLKSIGLLSPD FQEDNETEINFLLKQALTIVGTLPFTYMLEKWRWMVFKGEIPKDQWMKKW WEMKREIVGVVEPVPHDETYCDPASLFHVSNDYSFIRYYTRTLYQFQFQEAL CQAAKHEGPLHKCDISNSTEAGQKLFNMLRLGKSEPWTLALENVVGAKNM NVRPLLNYFEPLFTWLKDQNKNSFVGWSTDWSPYATCPPCPAPELLGGPSVF LFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK HHHHHHHHHHHH |
| 86 | ACE200-bIZIP-35X-1 | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGLSIIAICLGSLGLILIIILLSVVVWKLL GRHKAKNHIRRPKSRWKKWHKYRKVHRHKVHKGRR |

-continued

SEQUENCE LISTING

| SEQ ID NO | ID | Sequence |
|---|---|---|
| 87 | ACE200-$CH_2$-$CH_2$-12X-4 | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGTCPPCPAPELLGGPSVFLFPPKPKD TLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREKRAHOK CORKSH |
| 88 | ACE19-SA-50X-1 | QAKTFLDKFNHEAEDLFYQMAEAGITGTWYNQLGSTFIVTAGADGALTGTY ESAVGNAEGDYVLTGRYDSAPATDGSGTALGWTVAWKNNYRNAHSATTW SGQYVGGAEARINTQWLLTSGTTEANAWKSTLVGHDTFTKVKPSAASHNKR FKKGRHVRHSRHKSHRRTHKYHHWRHYRKVHRCKKAHKSHHRVHHK |
| 89 | cACE614-Fc1-12H | STEDLVKTFLEKFNYEAEELSYQSSLASWNYNINITDENVQKMNNAGAKWS AFYEEQSKLAKTYPLEEIQDSTVKRQLRALQHSGSSVLSADKNQRLNTILNS MSTIYSTGKACNPSNPQECLLLEPGLDDIMENSKDYNERLWAWEGWRSEVG KQLRPLYEEYVALKNEMARANNYEDYGDATCPPCPAPELLGGPSVFLFPPKP KDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGS FFLYSKLTVDKSRWQQGNVFSCSVMHEALHNHYTQKSLSLSPGKHHHHHHH HHHHH |
| 90 | cACE200-$(GPP)_{10}$-40X-2 | STEDLVKTFLEKFNYEAEELSYQSSLASWNYNINITDENVQKMNNAGAKWS AFYEEQSKLAKTYPLEEIQDSTVKRQLRALQHSGSSVLSADKNQRLNTILNS MSTIYSTGKACNPSNPQECLLLEPGLDDIMENSKDYNERLWAWEGWRSEVG KQLRPLYEEYVALKNEMARANNYEDYGDGPPGPPGPPGPPGPPGPPGPPGPP GPPGPPWRKVHHYKKQHKNRAHGKLKLRAKIHQRSRMHGKQKHYHR |
| 91 | mACE614-COMP-6X-5 | SLTEENAKTFLNNFNQEAEDLSYQSSLASWNYNTNITEENAQKMSEAAAKW SAFYEEQSKTAQSFSLQEIQTPIIKRQLQALQQSGSSALSADKNKQLNTILNTM STIYSTGKVCNPKNPQECLLLEPGLDEIMATSTDYNSRLWAWEGWRAEVGK QLRPLYEEYVVLKNEMARANNYNDYGDYWRGDYEAEGADGYNYNRNQLI EDVERTFAEIKPLYEHLHAYVRRKLMDTYPSYISPTGCLPAHLLGDMWGRF WTNLYPLTVPFAQKPNIDVTDAMMNQGWDAERIFQEAEKFFVSVGLPHMTQ GFWANSMLTEPADGRKVVCHPTAWDLGHGDFRIKMCTKVTMDNFLTAHHE MGHIQYDMAYARQPFLLRNGANEGFHEAVGEIMSLSAATPKHLKSIGLLPSD FQEDSETEINFLLKQALTIVGTLPFTYMLEKWRWMVFRGEIPKEQWMKKWW EMKREIVGVVEPLPHDETYCDPASLFHVSNDYSFIRYYTRTIYQFQFQEALCQ AAKYNGSLHKCDISNSTEAGQKLLKMLSLGNSEPWTKALENVVGARNMDV KPLLNYFQPLFDWLKEQNRNSFVGWNTEWSPYAGPQMLRELGETNAALQD VRELLRQQVREITFLKNTVMEBDACKKHHRR |
| 92 | gACEΔ360-FC1-12O | AEFNVRAEDISYENSLASWNYNTNITEETARKMSEAGAKWAAFYEEASRNA SRFSLANIQDAVTRLQIQSLQDRGSSVLSPEKYSRLNSVMNSMSTIYSTGVVC KATEPFDCLVLEPGLDDIMANSIDYHERLWAWEGWRADVGRMMRPLYEEY VELKNEAARLNNYSDYGDYWRANYETDYPEEYKYSRDQLVQDVEKTFEQI KPLYQHLHAYVRHRLEQVYGSELINPTGCLPAHLLGDMWGRFWTNLYNLTV PYPEKPNIDVTSAMAQKNWDAMKIFKTAEAFFASIGLYNMTEGFWTNSMLT EPTDNRKVVCHPTAWDMGKNDYRIKMATCPPCPAPELLGGPSVFLFPPKPKD TLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLP PSRDELTKNQVSLTCLVKGFYPSDIAVEWESNGQPENNYKTTPPVLDSDGSFF LYSKLTVDKSRWQQGNVFSCSVMHEALHNHYTQKSLSLSPGKOOOOOOOOOOOO |
| 93 | nACEΔ420-T4F-12X-1 | YQNSLASWNYNTNITDENIQKMNIAGAKWSAFYEEESQHAKTYPLEEIQDPII KRQLRALQQSGSSVLSADKRERLNTILNAMSTIYSTGKACNPNNPQECLLLEP GLDDIMENSKDYNERLWAWEGWRSEVGKQLRPLYEEYVALKNEMARANN YEDYGDYWRGDYEEEWADGYNYSRNQLIEDVEHTFTQIKPLYEHLHAYVR AKLMDAYPSRISPTGCLPAHLLGDMWGRFWTNLYPLMVPFGQKPNIDVTDA MVNQSWDARRIFKEAEKFFVSVGLPNMTEGFWQNSMLTEPGDNRKVVCHP TAWDLGKHDFRIKMCTKVTMDDFLTAHHEMGHIQYDMAYAAQPFLLRNGA NEGFHEAVGEIMSLSAATPNHLKFGYIPEAPRDGQAYVRKDGEWVLLSTFLH HKKOOHHKKOO |
| 94 | Immunoglobulin Fc region ($CH_2CH_3CH_4$) | PPKVSVFVPPRDGFFGNPRKSKLICQATGFSPRQIQVSWLREGKQVGSGVTTD QVQAEAKESGPTTYKVTSTLTIKESDWLSQSMFTCRVDHRGLTFQQNASSMC VPDQDTAIRVFAIPPSFASIFLTKSTKLTCLVTDLTTYDSVTISWTRQNGEAVK THTNISESHPNATFSAVGEASICEDDWNSGERFTCTVTHTDLPSPLKQTISRPK GVALHRPDVYLLPPAREQLNLRESATITCLVTGFSPADVFVQWMQRGQPLSP EKYVTSAPMPEPQAPGRYFAHSILTVSEEEWNTGETYTCVVAHEALPNRVTE RTVDKSTGKPTLYNVSLVMSDTAGTCY |

-continued

SEQUENCE LISTING

| SEQ ID NO | ID | Sequence |
|---|---|---|
| 95 | Flag-His(6)-tag | DYKDDDDKHHHHHH |
| 96 | WIV4 Receptor Binding Domain (319-541)(aa319-541) | RVQPTESIVRFPNITNLCPFGEVFNATRFASVYAWNRKRISNCVADYSVLYNS ASFSTFKCYGVSPTKLNDLCFTNVYADSFVIRGDEVRQIAPGQTGKIADYNY KLPDDFTGCVIAWNSNNLDSKVGGNYNYLYRLFRKSNLKPFERDISTEIYQA GSTPCNGVEGFNCYFPLQSYGFQPTNGVGYQPYRVVVLSFELLHAPATVCGP KKSTNLVKNKCVNF |
| 97 | Delta Receptor Binding Domain (319-541) | RVQPTESIVRFPNITNLCPFGEVFNATRFASVYAWNRKRISNCVADYSVLYNS ASFSTFKCYGVSPTKLNDLCFTNVYADSFVIRGDEVRQIAPGQTGKIADYNY KLPDDFTGCVIAWNSNNLDSKVGGNYNYRYRLFRKSNLKPFERDISTEIYQA GSKPCNGVEGFNCYFPLQSYGFQPTNGVGYQPYRVVVLSFELLHAPATVCGP KKSTNLVKNKCVNF |
| 98 | Omicron BA.1 Receptor Binding Domain (319-541) | RVQPTESIVRFPNITNLCPFDEVFNATRFASVYAWNRKRISNCVADYSVLYNL APFFTFKCYGVSPTKLNDLCFTNVYADSFVIRGDEVRQIAPGQTGNIADYNY KLPDDFTGCVIAWNSNKLDSKVSGNYNYLYRLFRKSNLKPFERDISTEIYQA GNKPCNGVAGFNCYFPLRSYSFRPTYGVGHQPYRVVVLSFELLHAPATVCGP KKSTNLVKNKCVNF |
| 99 | Omicron BA.2 Receptor Binding Domain (319-541) | RVQPTESIVRFPNITNLCPFDEVFNATRFASVYAWNRKRISNCVADYSVLYNF APFFAFKCYGVSPTKLNDLCFTNVYADSFVIRGNEVSQIAPGQTGNIADYNY KLPDDFTGCVIAWNSNKLDSKVGGNYNYLYRLFRKSNLKPFERDISTEIYQA GNKPCNGVAGFNCYFPLRSYGFRPTYGVGHQPYRVVVLSFELLHAPATVCG PKKSTNLVKNKCVNF |
| 100 | Bat Receptor Binding Domain (319-541) | RVLPSTEVVRFPNITNFCPFDKVFNATRFPNVYAWQRTKISDCIADYTVLYNS TSFSTFKCYGVSPSKLIDLCFTSVYADTFLIRFSEVRQIAPGETGVIADYNYKLP DDFTGCVLAWNTAQQDIGSYFYRSHRAVKLKPFERDLSSDENGVRTLSTYDF NPNVPLDYQATRVVVLSFELLNAPATVCGPKLSTQLVKNRCVNF |
| 101 | Extracellular binding domain (EBD) of human ACE2 | QSTIEEQAKTFLDKFNHEAEDLFYQSSLASWNYNTNITEENVQNMNNAGDK WSAFLKEQSTLAQMYPLQEIQNLTVKLQLQALQQNGSSVLSEDKSKRLNTIL NTMSTIYSTGKVCNPDNPQECLLLEPGLNEIMANSLDYNERLWAWESWRSE VGKQLRPLYEEYVVLKNEMARANHYEDYGDYWRGDYEVNGVDGYDYSRG QLIEDVEHTFEEIKPLYEHLHAYVRAKLMNAYPSYISPIGCLPAHLLGDMWG RFWTNLYSLTVPFGQKPNIDVTDAMVDQAWDAQRIFKEAEKFFVSVGLPNM TQGFWENSMLTDPGNVQKAVCHPTAWDLGKGDFRILMCTKVTMDDFLTAH HEMGHIQYDMAYAAQPFLLRNGANEGFHEAVGEIMSLSAATPKHLKSIGLLS PDFQEDNETEINFLLKQALTIVGTLPFTYMLEKWRWMVFKGEIPKDQWMKK WWEMKREIVGVVEPVPHDETYCDPASLFHVSNDYSFIRYYTRTLYQFQFQEA LCQAAKHEGPLHKCDISNSTEAGQKLFNMLRLGKSEPWTLALENVVGAKNM NVRPLLNYFEPLFTWLKDQNKNSFVGWSTDWSPYADQSIKVRISLKSALGDK AYEWNDNEMYLFRSSVAYAMRQYFLKVKNQMILFGEEDVRVANLKPRISFN FFVTAPKNVSDIIPRTEVEKAIRMSRSRINDAFRLNDNSLEFLGIQPTLGPPNQP PVS |
| 102 | ACE12 [a spike protein binding site] | DKFNHEAEDLFY |
| 103 | SARS-CoV RBD ABD75332.1 | VTPTQEVVRFPNITNRCPFDKVFNASRFPNVYAWERTKISDCVADYTVLYNS TSFSTFKCYGVSPSKLIDLCFTSVYADTFLIRSSEVRQVAPGETGVIADYNYKL PDDFTGCVIAWNTAQQDQGQYYYRSYRKEKLKPFERDLSSDENGVYTLSTY DFYPSIPVEYQATRVVVLSFELLNAPATVCGPKLSTQLVKNQCVNF |
| 104 | cACE614 | STEDLVKTFLEKFNYEAEELSYQSSLASWNYNINITDENVQKMNNAGAKWS AFYEEQSKLAKTYPLEEIQDSTVKRQLRALQHSGSSVLSADKNQRLNTILNS MSTIYSTGKACNPSNPQECLLLEPGLDDIMENSKDYNERLWAWEGWRSEVG KQLRPLYEEYVALKNEMARANNYEDYGDYWRGDYEEEWENGYNYSRNQLI DDVEHTFTQIMPLYQHLHAYVRTKLMDTYPSYISPTGCLPAHLLGDMWGRF WTNLYPLTVPFGQKPNIDVTNAMVNQSWDARKIFKEAEKFFVSVGLPNMTQ EFWENSMLTEPSDSRKVVCHPTAWDLGKGDFRIKMCTKVTMDDFLTAHHE MGHIQYDMAYAAQPFLLRNGANEGFHEAVGEIMSLSAATPNHLKNIGLLPPS FFEDSETEINFLLKQALTIVGTLPFTYMLEKWRWMVFKGEIPKDQWMKTWW EMKRNIVGVVEPVPHDETYCDPASLFHVANDYSFIRYYTRTIYQFQFQEALC QIAKHEGPLHKCDISNSSEAGQKLLEMLKLGKSKPWTYALEIVVGAKNMDV RPLLNYFEPLFTWLKEQNRNSFVGWNTDWSPYADQSIKVRISLKSALGEKAY |

-continued

SEQUENCE LISTING

| SEQ ID NO | ID | Sequence |
|---|---|---|
| | | EWNNNEMYLFRSSIAYAMRQYFSEVKNQTIPFVEDNVWVSDLKPRISFNFFV TSPGNVSDIIPRTEVEEAIRMYRSRINDVFRLDDNSLEFLGIQPTLGPPYEPPVTI WLIVFGVVMGVVVVGIVLLIFSGIRNRRKNDQARGEENPYASVDLSKGENNP GFQNVDDAQT |
| 105 | cACE200 | STEDLVKTFLEKFNYEAEELSYQSSLASWNYNINITDENVQKMNNAGAKWS AFYEEQSKLAKTYPLEEIQDSTVKRQLRALQHSGSSVLSADKNQRLNTILNS MSTIYSTGKACNPSNPQECLLLEPGLDDIMENSKDYNERLWAWEGWRSEVG KQLRPLYEEYVALKNEMARANNYEDYGD |
| 106 | mACE614 | SLTEENAKTFLNNFNQEAEDLSYQSSLASWNYNTNITEENAQKMSEAAAKW SAFYEEQSKTAQSFSLQEIQTPIIKRQLQALQQSGSSALSADKNKQLNTILNTM STIYSTGKVCNPKNPQECLLLEPGLDEIMATSTDYNSRLWAWEGWRAEVGK QLRPLYEEYVVLKNEMARANNYNDYGDYWRGDYEAEGADGYNYNRNQLI EDVERTFAEIKPLYEHLHAYVRRKLMDTYPSYISPTGCLPAHLLGDMWGRF WTNLYPLTVPFAQKPNIDVTDAMMNQGWDAERIFQEAEKFFVSVGLPHMTQ GFWANSMLTEPADGRKVVCHPTAWDLGHGDFRIKMCTKVTMDNFLTAHHE MGHIQYDMAYARQPFLLRNGANEGFHEAVGEIMSLSAATPKHLKSIGLLPSD FQEDSETEINFLLKQALTIVGTLPFTYMLEKWRWMVFRGEIPKEQWMKKWW EMKREIVGVVEPLPHDETYCDPASLFHVSNDYSFIRYYTRTIYQFQFQEALCQ AAKYNGSLHKCDISNSTEAGQKLLKMLSLGNSEPWTKALENVVGARNMDV KPLLNYFQPLFDWLKEQNRNSFVGWNTEWSPYA |
| 107 | gACEΔ360 | ASRNASRFSLANIQDAVTRLQIQSLQDRGSSVLSPEKYSRLNSVMNSMSTIYS TGVVCKATEPFDCLVLEPGLDDIMANSIDYHERLWAWEGWRADVGRMMRP LYEEYVELKNEAARLNNYSDYGDYWRANYETDYPEEYKYSRDQLVQDVEK TFEQIKPLYQHLHAYVRHRLEQVYGSELINPTGCLPAHLLGDMWGRFWTNL YNLTVPYPEKPNIDVTSAMAQKNWDAMKIFKTAEAFFASIGLYNMTEGFWT NSMLTEPTDNRKVVCHPTAWDMGKNDYRIKM |
| 108 | nACEΔ420 | YQNSLASWNYNTNITDENIQKMNIAGAKWSAFYEEESQHAKTYPLEEIQDPII KRQLRALQQSGSSVLSADKRERLNTILNAMSTIYSTGKACNPNNPQECLLLEP GLDDIMENSKDYNERLWAWEGWRSEVGKQLRPLYEEYVALKNEMARANN YEDYGDYWRGDYEEEWADGYNYSRNQLIEDVEHTFTQIKPLYEHLHAYVR AKLMDAYPSRISPTGCLPAHLLGDMWGRFWTNLYPLMVPFGQKPNIDVTDA MVNQSWDARRIFKEAEKFFVSVGLPNMTEGFWQNSMLTEPGDNRKVVCHP TAWDLGKHDFRIKMCTKVTMDDFLTAHHEMGHIQYDMAYAAQPFLLRNGA NEGFHEAVGEIMSLSAATPNHLKF |
| 109 | $(GPP)_{10}$ | GPPGPPGPPGPPGPPGPPGPPGPPGPPGPP |
| 110 | ACE12-2 aa 29-40 of full-length chicken ACE2 protein | AEFNVRAEDISY |
| 111 | ACE12-3 aa 30-41 of guinea pig ACE2 protein | DEFNLKAEDLYY |
| 112 | ACE12-4 aa 30-41 of mouse ACE2 protein | NNFNQEAEDLSY |
| 113 | ACE12-5 aa 30-41 of swine ACE2 protein | EKFNLEAEDLAY |
| 114 | ACE12-6 aa 30-41 of bovine ACE2 protein | EKFNHEAEDLSY |
| 115 | ACE12-7 aa 30-41 of rabbit ACE2 protein | EKFNQEAEDLSY |

-continued

SEQUENCE LISTING

| SEQ ID NO | ID | Sequence |
|---|---|---|
| 116 | ACE12-8 aa 30-41 of macaque ACE2 protein | DKFNHEAEDLFY |
| 117 | ACE12-9 aa 30-41 of chimpanzee ACE2 protein | DKFNHEAEDLFY |
| 118 | ACE12-10 aa 30-41 of equine ACE2 protein | EKFNSEAEELSH |
| 119 | ACE12-11 aa 30-41 of ferret ACE2 protein | EKFNYEAEELSY |
| 120 | ACE12-12 aa 30-41 of mink ACE2 protein | EKFNYEAEELSY |
| 121 | ACE12-13 aa 29-40 of canine ACE2 protein | EKFNYEAEELSY |
| 122 | ACE12-14 aa 30-41 of feline ACE2 protein | EKFNHEAEELSY |
| 123 | S1 RBD Alpha 7EKF_B N501Y | RVQPTESIVRFPNITNLCPFGEVFNATRFASVYAWNRKRISNCVADYSVLYNS ASFSTFKCYGVSPTKLNDLCFTNVYADSFVIRGDEVRQIAPGQTGKIADYNY KLPDDFTGCVIAWNSNNLDSKVGGNYNYLYRLFRKSNLKPFERDISTEIYQA GSTPCNGVEGFNCYFPLQSYGFQPTYGVGYQPYRVVVLSFELLHAPATVCGP KKSTNLVKNKCVNF |
| 124 | S1 RBD Beta 7EKG_B K417N, E484K | RVQPTESIVRFPNITNLCPFGEVFNATRFASVYAWNRKRISNCVADYSVLYNS ASFSTFKCYGVSPTKLNDLCFTNVYADSFVIRGDEVRQIAPGQTGKIADYNY KLPDDFTGCVIAWNSNNLDSKVGGNYNYLYRLFRKSNLKPFERDISTEIYQA GSTPCNGVEGFNCYFPLQSYGFQPTYGVGYQPYRVVVLSFELLHAPATVCGP KKSTNLVKNKCVNF |
| 125 | BA.5.1.1 L452R, F486V | RVQPTESIVRFPNITNLCPFDEVFNATRFASVYAWNRKRISNCVADYSVLYNF APFFAFKCYGVSPTKLNDLCFTNVYADSFVIRGNEVSQIAPGQTGNIADYNY KLPDDFTGCVIAWNSNKLDSKVGGNYNYRYRLFRKSNLKPFERDISTEIYQA GNKPCNGVAGVNCYFPLQSYGFRPTYGVGHQPYRVVVLSFELLHAPATVCG PKKSTNLVKNKCVNF |
| 126 | BQ.1 R346T, K444T, N460K | RVQPTESIVRFPNITNLCPFDEVFNATRFASVYAWNRKRISNCVADYSVLYNF APFFAFKCYGVSPTKLNDLCFTNVYADSFVIRGNEVSQIAPGQTGNIADYNY KLPDDFTGCVIAWNSNKLDSTVGGNYNYRYRLFRKSKLKPFERDISTEIYQA GNKPCNGVAGVNCYFPLQSYGFRPTYGVGHQPYRVVVLSFELLHAPATVCG PKKSTNLVKNKCVNF |
| 127 | XBB.1.5 G339H, R346T, L368I, V445P, G446S, N460K, F486S, F490S, R493Q | RVQPTESIVRFPNITNLCPFHEVFNATTFASVYAWNRKRISNCVADYSVIYNF APFFAFKCYGVSPTKLNDLCFTNVYADSFVIRGNEVSQIAPGQTGNIADYNY KLPDDFTGCVIAWNSNKLDSKPSGNYNYLYRLFRKSKLKPFERDISTEIYQAG NKPCNGVAGPNCYSPLQSYGFRPTYGVGHQPYRVVVLSFELLHAPATVCGP KKSTNLVKNKCVNF |
| 128 | 5H | HHHHH |
| 129 | 7X-1 | KKKGKKK |

-continued

SEQUENCE LISTING

| SEQ ID NO | ID | Sequence |
|---|---|---|
| 130 | 12X-7 | KKAHHGKKAHHV |
| 131 | 12X-8 | KKARRGKKARRV |
| 132 | 12X-9 | KLIHKKARVRGK |
| 133 | 15X-1 | ILRRKAHHGKIKKVR |
| 134 | 15X-2 | GHRVKKAVRHIKRL |
| 135 | ACE740 | STIEEQAKTFLDKFNHEAEDLFYQSSLASWNYNTNITEENVQNMNNAGDKW<br>SAFLKEQSTLAQMYPLQEIQNLTVKLQLQALQQNGSSVLSEDKSKRLNTILNT<br>MSTIYSTGKVCNPDNPQECLLLEPGLNEIMANSLDYNERLWAWESWRSEVG<br>KQLRPLYEEYVVLKNEMARANHYEDYGDYWRGDYEVNGVDGYDYSRGQL<br>IEDVEHTFEEIKPLYEHLHAYVRAKLMNAYPSYISPIGCLPAHLLGDMWGRF<br>WTNLYSLTVPFGQKPNIDVTDAMVDQAWDAQRIFKEAEKFFVSVGLPNMTQ<br>GFWENSMLTDPGNVQKAVCHPTAWDLGKGDFRILMCTKVTMDDFLTAHHE<br>MGHIQYDMAYAAQPFLLRNGANEGFHEAVGEIMSLSAATPKHLKSIGLLSPD<br>FQEDNETEINFLLKQALTIVGTLPFTYMLEKWRWMVFKGEIPKDQWMKKW<br>WEMKREIVGVVEPVPHDETYCDPASLFHVSNDYSFIRYYTRTLYQFQFQEAL<br>CQAAKHEGPLHKCDISNSTEAGQKLFNMLRLGKSEPWTLALENVVGAKNM<br>NVRPLLNYFEPLFTWLKDQNKNSFVGWSTDWSPYADQSIKVRISLKSALGDK<br>AYEWNDNEMYLFRSSVAYAMRQYFLKVKNQMILFGEEDVRVANLKPRISFN<br>FFVTAPKNVSDIIPRTEVEKAIRMSRSRINDAFRLNDNSLEFLGIQPTLGPPNQP<br>PVS |
| 136 | ACE740-Fc1-5H | STIEEQAKTFLDKFNHEAEDLFYQSSLASWNYNTNITEENVQNMNNAGDKW<br>SAFLKEQSTLAQMYPLQEIQNLTVKLQLQALQQNGSSVLSEDKSKRLNTILNT<br>MSTIYSTGKVCNPDNPQECLLLEPGLNEIMANSLDYNERLWAWESWRSEVG<br>KQLRPLYEEYVVLKNEMARANHYEDYGDYWRGDYEVNGVDGYDYSRGQL<br>IEDVEHTFEEIKPLYEHLHAYVRAKLMNAYPSYISPIGCLPAHLLGDMWGRF<br>WTNLYSLTVPFGQKPNIDVTDAMVDQAWDAQRIFKEAEKFFVSVGLPNMTQ<br>GFWENSMLTDPGNVQKAVCHPTAWDLGKGDFRILMCTKVTMDDFLTAHHE<br>MGHIQYDMAYAAQPFLLRNGANEGFHEAVGEIMSLSAATPKHLKSIGLLSPD<br>FQEDNETEINFLLKQALTIVGTLPFTYMLEKWRWMVFKGEIPKDQWMKKW<br>WEMKREIVGVVEPVPHDETYCDPASLFHVSNDYSFIRYYTRTLYQFQFQEAL<br>CQAAKHEGPLHKCDISNSTEAGQKLFNMLRLGKSEPWTLALENVVGAKNM<br>NVRPLLNYFEPLFTWLKDQNKNSFVGWSTDWSPYADQSIKVRISLKSALGDK<br>AYEWNDNEMYLFRSSVAYAMRQYFLKVKNQMILFGEEDVRVANLKPRISFN<br>FFVTAPKNVSDIIPRTEVEKAIRMSRSRINDAFRLNDNSLEFLGIQPTLGPPNQP<br>PVSTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVS<br>NKALPAPIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFSCSVMH<br>EALHNHYTQKSLSLSPGHHHHH |
| 137 | ACE740-Fc1-6H | STIEEQAKTFLDKFNHEAEDLFYQSSLASWNYNTNITEENVQNMNNAGDKW<br>SAFLKEQSTLAQMYPLQEIQNLTVKLQLQALQQNGSSVLSEDKSKRLNTILNT<br>MSTIYSTGKVCNPDNPQECLLLEPGLNEIMANSLDYNERLWAWESWRSEVG<br>KQLRPLYEEYVVLKNEMARANHYEDYGDYWRGDYEVNGVDGYDYSRGQL<br>IEDVEHTFEEIKPLYEHLHAYVRAKLMNAYPSYISPIGCLPAHLLGDMWGRF<br>WTNLYSLTVPFGQKPNIDVTDAMVDQAWDAQRIFKEAEKFFVSVGLPNMTQ<br>GFWENSMLTDPGNVQKAVCHPTAWDLGKGDFRILMCTKVTMDDFLTAHHE<br>MGHIQYDMAYAAQPFLLRNGANEGFHEAVGEIMSLSAATPKHLKSIGLLSPD<br>FQEDNETEINFLLKQALTIVGTLPFTYMLEKWRWMVFKGEIPKDQWMKKW<br>WEMKREIVGVVEPVPHDETYCDPASLFHVSNDYSFIRYYTRTLYQFQFQEAL<br>CQAAKHEGPLHKCDISNSTEAGQKLFNMLRLGKSEPWTLALENVVGAKNM<br>NVRPLLNYFEPLFTWLKDQNKNSFVGWSTDWSPYADQSIKVRISLKSALGDK<br>AYEWNDNEMYLFRSSVAYAMRQYFLKVKNQMILFGEEDVRVANLKPRISFN<br>FFVTAPKNVSDIIPRTEVEKAIRMSRSRINDAFRLNDNSLEFLGIQPTLGPPNQP<br>PVSTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVS<br>NKALPAPIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFSCSVMH<br>EALHNHYTQKSLSLSPGHHHHHH |
| 138 | ACE740-Fc1-7X-1 | STIEEQAKTFLDKFNHEAEDLFYQSSLASWNYNTNITEENVQNMNNAGDKW<br>SAFLKEQSTLAQMYPLQEIQNLTVKLQLQALQQNGSSVLSEDKSKRLNTILNT<br>MSTIYSTGKVCNPDNPQECLLLEPGLNEIMANSLDYNERLWAWESWRSEVG<br>KQLRPLYEEYVVLKNEMARANHYEDYGDYWRGDYEVNGVDGYDYSRGQL<br>IEDVEHTFEEIKPLYEHLHAYVRAKLMNAYPSYISPIGCLPAHLLGDMWGRF<br>WTNLYSLTVPFGQKPNIDVTDAMVDQAWDAQRIFKEAEKFFVSVGLPNMTQ<br>GFWENSMLTDPGNVQKAVCHPTAWDLGKGDFRILMCTKVTMDDFLTAHHE |

-continued

SEQUENCE LISTING

| SEQ ID NO | ID | Sequence |
|---|---|---|
| | | MGHIQYDMAYAAQPFLLRNGANEGFHEAVGEIMSLSAATPKHLKSIGLLSPD FQEDNETEINFLLKQALTIVGTLPFTYMLEKWRWMVFKGEIPKDQWMKKW WEMKREIVGVVEPVPHDETYCDPASLFHVSNDYSFIRYYTRTLYQFQFQEAL CQAAKHEGPLHKCDISNSTEAGQKLFNMLRLGKSEPWTLALENVVGAKNM NVRPLLNYFEPLFTWLKDQNKNSFVGWSTDWSPYADQSIKVRISLKSALGDK AYEWNDNEMYLFRSSVAYAMRQYFLKVKNQMILFGEEDVRVANLKPRISFN FFVTAPKNVSDIIPRTEVEKAIRMSRSRINDAFRLNDNSLEFLGIQPTLGPPNQP PVSTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMH EALHNHYTQKSLSLSPGKKKGKKK |
| 139 | ACE740-Fc1-12X-7 | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGDYWRGDYEVNGVDGYDYSRGQL IEDVEHTFEEIKPLYEHLHAYVRAKLMNAYPSYISPIGCLPAHLLGDMWGRF WTNLYSLTVPFGQKPNIDVTDAMVDQAWDAQRIFKEAEKFFVSVGLPNMTQ GFWENSMLTDPGNVQKAVCHPTAWDLGKGDFRILMCTKVTMDDFLTAHHE MGHIQYDMAYAAQPFLLRNGANEGFHEAVGEIMSLSAATPKHLKSIGLLSPD FQEDNETEINFLLKQALTIVGTLPFTYMLEKWRWMVFKGEIPKDQWMKKW WEMKREIVGVVEPVPHDETYCDPASLFHVSNDYSFIRYYTRTLYQFQFQEAL CQAAKHEGPLHKCDISNSTEAGQKLFNMLRLGKSEPWTLALENVVGAKNM NVRPLLNYFEPLFTWLKDQNKNSFVGWSTDWSPYADQSIKVRISLKSALGDK AYEWNDNEMYLFRSSVAYAMRQYFLKVKNQMILFGEEDVRVANLKPRISFN FFVTAPKNVSDIIPRTEVEKAIRMSRSRINDAFRLNDNSLEFLGIQPTLGPPNQP PVSTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMH EALHNHYTQKSLSLSPGKKAHHGKKAHHV |
| 140 | ACE740-Fc1-12X-8 | STIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNT MSTIYSTGKVCNPDNPQECLLLEPGLNEIMANSLDYNERLWAWESWRSEVG KQLRPLYEEYVVLKNEMARANHYEDYGDYWRGDYEVNGVDGYDYSRGQL IEDVEHTFEEIKPLYEHLHAYVRAKLMNAYPSYISPIGCLPAHLLGDMWGRF WTNLYSLTVPFGQKPNIDVTDAMVDQAWDAQRIFKEAEKFFVSVGLPNMTQ GFWENSMLTDPGNVQKAVCHPTAWDLGKGDFRILMCTKVTMDDFLTAHHE MGHIQYDMAYAAQPFLLRNGANEGFHEAVGEIMSLSAATPKHLKSIGLLSPD FQEDNETEINFLLKQALTIVGTLPFTYMLEKWRWMVFKGEIPKDQWMKKW WEMKREIVGVVEPVPHDETYCDPASLFHVSNDYSFIRYYTRTLYQFQFQEAL CQAAKHEGPLHKCDISNSTEAGQKLFNMLRLGKSEPWTLALENVVGAKNM NVRPLLNYFEPLFTWLKDQNKNSFVGWSTDWSPYADQSIKVRISLKSALGDK AYEWNDNEMYLFRSSVAYAMRQYFLKVKNQMILFGEEDVRVANLKPRISFN FFVTAPKNVSDIIPRTEVEKAIRMSRSRINDAFRLNDNSLEFLGIQPTLGPPNQP PVSTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMH EALHNHYTQKSLSLSPGKKARRGKKARRV |
| 141 | WEF43315.1 S1 subunit, surface glycoprotein BA.5.1.1 | RVQPTESIVRFPNITNLCPFDEVFNATRFASVYAWNRKRISNCVADYSVLYNF APFFAFKCYGVSPTKLNDLCFTNVYADSFVIRGNEVSQIAPGQTGNIADYNY KLPDDFTGCVIAWNSNKLDSKVGGNYNYRYRLFRKSNLKPFERDISTEIYQA GNKPCNGVAGVNCYFPLQSYGFRPTYGVGHQPYRVVVLSFELLHAPATVCG PKKSTNLVKNKCVNF |
| 142 | WEJ42036.1 S1 subunit, surface glycoprotein BQ.1 | RVQPTESIVRFPNITNLCPFDEVFNATTFASVYAWNRKRISNCVADYSVLYNF APFFAFKCYGVSPTKLNDLCFTNVYADSFVIRGNEVSQIAPGQTGNIADYNY KLPDDFTGCVIAWNSNKLDSTVGGNYNYRYRLFRKSKLKPFERDISTEIYQA GNKPCNGVAGVNCYFPLQSYGFRPTYGVGHQPYRVVVLSFELLHAPATVCG PKKSTNLVKNKCVNF |
| 143 | WEI68632.1 S1 subunit, surface glycoprotein XBB.1.5 | RVQPTESIVRFPNITNLCPFHEVFNATTFASVYAWNRKRISNCVADYSVIYNF APFFAFKCYGVSPTKLNDLCFTNVYADSFVIRGNEVSQIAPGQTGNIADYNY KLPDDFTGCVIAWNSNKLDSKPSGNYNYLYRLFRKSKLKPFERDISTEIYQAG NKPCNGVAGPNCYSPLQSYGFRPTYGVGHQPYRVVVLSFELLHAPATVCGP KKSTNLVKNKCVNF |

What is claimed is:

1. A chimeric protein comprising:

(a) a target-binding moiety comprising an extracellular binding domain (EBD) of an angiotensin-converting enzyme 2 (ACE2) protein or a fragment or a variant thereof that specifically binds to a spike(S) protein; and (b) a mucoadhesive peptide fragment comprising at least 5 positively charged amino acid residues, wherein the mucoadhesive peptide fragment does not comprise six consecutive histidines; and wherein the mucoadhesive peptide fragment facilitates attachment of the chimeric protein to a mucosa.

2. The chimeric protein of claim 1, wherein the chimeric protein comprises:

(i) a single polypeptide chain; or (ii) two or more polypeptide chains, and wherein the chimeric protein comprises two or more mucoadhesive peptide fragments.

3. The chimeric protein of claim 1, wherein the mucoadhesive peptide fragment comprises at least 6 positively charged amino acid residues.

4. The chimeric protein of claim 1, wherein the positively charged amino acid residues are selected from the group consisting of lysine, arginine, histidine, ornithine, and combinations thereof.

5. The chimeric protein of claim 1, wherein:

(i) the mucoadhesive peptide fragment comprises at least 5 contiguous positively charged amino acid residues;

(ii) the positively charged amino acid residues are interspersed with one or more non-positively charged amino acid residues;

(iii) the mucoadhesive peptide fragment is no more than about 15 kD; and/or (iv) the mucoadhesive peptide fragment has an isoelectric point (pI) higher than the pH of the mucosa.

6. The chimeric protein of claim 1, wherein the mucoadhesive peptide fragment comprises an amino acid sequence of any one of SEQ ID NOs: 31-62 and 128-134, or a variant thereof having at least about 90% sequence identity to the amino acid sequence of any one of SEQ ID NOs: 31-62 and 128-134.

7. The chimeric protein of claim 1, wherein the mucoadhesive peptide fragment is fused to the target-binding moiety via a peptide linker.

8. The chimeric protein of claim 1, wherein the mucoadhesive peptide fragment is fused to a C-terminus of the target-binding moiety.

9. The chimeric protein of claim 1, wherein the target-binding moiety comprises the EBD of a human ACE2 (hACE2) protein or a fragment or a variant thereof that specifically binds to a spike(S) protein.

10. The chimeric protein of claim 9, wherein the target-binding moiety comprises:

(a) (i) amino acids 30-41 of a full-length hACE2 protein, or a variant thereof having at least about 90% sequence identity to amino acids 30-41 of a full-length hACE2 protein; and/or (ii) the amino acid sequence of SEQ ID NO: 102, or a variant thereof having at least about 90% sequence identity to the amino acid sequence of SEQ ID NO: 102;

(b) (i) amino acids 24-42 of a full-length hACE2 protein, or a variant thereof having at least about 90% sequence identity to amino acids 24-42 of a full-length hACE2 protein; and/or (ii) The amino acid sequence of SEQ ID NO: 8, or a variant thereof having at least about 90% sequence identity to the amino acid sequence of SEQ ID NO: 8; or (c) the amino acid sequence of any one of SEQ ID NOs: 1-7, 9-14, and 135, or a variant thereof having at least about 90% sequence identity to the amino acid sequence of any one of SEQ ID NOs: 1-7, 9-14, and 135.

11. The chimeric protein of claim 10, wherein the chimeric protein comprises the amino acid sequence of any one of SEQ ID NOs: 84, 86-88, 136, and 138-140, or a variant thereof having at least about 90% sequence identity to the amino acid sequence of any one of SEQ ID NOs: 84, 86-88, 136, and 138-140.

12. The chimeric protein of claim 1, wherein the target-binding moiety comprises the EBD of an animal ACE2 protein or a fragment or a variant thereof that specifically binds to a spike (S) protein.

13. The chimeric protein of claim 12, wherein the target-binding moiety comprises:

(a) (i) amino acids 30-41 of a full-length animal ACE2 protein, or a variant thereof having at least about 90% sequence identity to amino acids 30-41 of a full-length animal ACE2 protein, wherein the full-length animal ACE2 protein is not a chicken or canine ACE2 protein; or (ii) amino acids 29-40 of a full-length animal ACE2 protein, or a variant thereof having at least about 90% sequence identity to amino acids 29-40 of a full-length animal ACE2 protein, wherein the full-length animal ACE2 protein is a chicken or canine ACE2 protein; or (b) the amino acid sequence of any one of SEQ ID NOs: 15-27 and 110-122, or a variant thereof having at least about 90% sequence identity to any one of SEQ ID NOs: 15-27 and 110-122.

14. The chimeric protein of claim 13, wherein the chimeric protein comprises the amino acid sequence of any one of SEQ ID NOs: 90-93, or a variant thereof having at least about 90% sequence identity to the amino acid sequence of any one of SEQ ID NOs: 90-93.

15. A pharmaceutical composition comprising the chimeric protein of claim 1, and a pharmaceutically acceptable carrier.

16. The chimeric protein of claim 12, wherein the animal ACE2 protein is a murine, guinea pig, equine, ferret, macaque, chimpanzee, swine, canine, feline, bovine, rabbit, mink, or chicken ACE2 protein or a fragment or a variant thereof.

17. The chimeric protein of claim 1, wherein the S protein is a coronavirus S protein, and wherein the coronavirus is selected from the group consisting of SARS-COV, SARS-COV-2, and HCoV-NL63.

18. The chimeric protein of claim 17, wherein the S protein comprises the amino acid sequence of any one of SEQ ID NOs: 96-100, 103, 123-127, and 141-143, or a variant thereof having at least about 90% sequence identity to the amino acid sequence of any one of SEQ ID NOs: 96-100, 103, 123-127, and 141-143.

19. The chimeric protein of claim 7, wherein the peptide linker comprises an oligomerization or multimerization domain.

20. The chimeric protein of claim 19, wherein the oligomerization or multimerization domain is an Fc region or a fragment thereof.

21. An isolated nucleic acid or a vector encoding the chimeric protein of claim 1.

22. A host cell expressing the chimeric protein of claim 1.

23. A method of preparing a chimeric protein, comprising:

(a) culturing the host cell of claim 22 under a condition effective to express the chimeric protein; and (b) obtaining the expressed chimeric protein from the host cell.

24. A method of preventing or treating an infection caused by a virus in an individual, comprising administering to the individual an effective amount of the pharmaceutical composition of claim 15, wherein the chimeric protein specifically binds to a spike(S) protein of the virus.

25. An in vitro method of killing or neutralizing a virus, comprising contacting the virus with the chimeric protein of claim 1 in the presence of at least one component of the complement system, wherein the chimeric protein specifically binds to a spike(S) protein of the virus.

26. A method of killing or neutralizing a virus in an individual, comprising administering to the individual an effective amount of the pharmaceutical composition of claim 15, wherein the chimeric protein specifically binds to a spike(S) protein of the virus.

27. A method of activating the complement pathway in an individual, comprising administering to the individual an effective amount of the pharmaceutical composition of claim 15.

28. The method of claim 24, wherein the virus is a coronavirus.

29. The method of claim 28, wherein the S protein comprises the amino acid sequence of any one of SEQ ID NOs: 96-100, 103, 123-127, and 141-143, or a variant thereof having at least about 90% sequence identity to the amino acid sequence of any one of SEQ ID NOs: 96-100, 103, 123-127, and 141-143.

30. The method of claim 28, wherein the coronavirus is selected from the group consisting of SARS-COV, SARS-COV-2, and HCoV-NL63.

* * * * *

SEQUENCE LISTING

Sequence total quantity: 143
SEQ ID NO: 1 moltype = AA length = 805
FEATURE Location/Qualifiers
source 1..805
mol_type = protein
organism = Homo sapiens
SEQUENCE: 1
MSSSSWLLLS LVAVTAAQST IEEQAKTFLD KFNHEAEDLF YQSSLASWNY NTNITEENVQ 60
NMNNAGDKWS AFLKEQSTLA QMYPLQEIQN LTVKLQLQAL QQNGSSVLSE DKSKRLNTIL 120
NTMSTIYSTG KVCNPDNPQE CLLLEPGLNE IMANSLDYNE RLWAWESWRS EVGKQLRPLY 180
EEYVVLKNEM ARANHYEDYG DYWRGDYEVN GVDGYDYSRG QLIEDVEHTF EEIKPLYEHL 240
HAYVRAKLMN AYPSYISPIG CLPAHLLGDM WGRFWTNLYS LTVPFGQKPN IDVTDAMVDQ 300
AWDAQRIFKE AEKFFVSVGL PNMTQGFWEN SMLTDPGNVQ KAVCHPTAWD LGKGDFRILM 360
CTKVTMDDFL TAHHEMGHIQ YDMAYAAQPF LLRNGANEGF HEAVGEIMSL SAATPKHLKS 420
IGLLSPDFQE DNETEINFLL KQALTIVGTL PFTYMLEKWR WMVFKGEIPK DQWMKKWWEM 480
KREIVGVVEP VPHDETYCDP ASLFHVSNDY SFIRYYTRTL YQFQFQEALC QAAKHEGPLH 540
KCDISNSTEA GQKLFNMLRL GKSEPWTLAL ENVVGAKNMN VRPLLNYFEP LFTWLKDQNK 600
NSFVGWSTDW SPYADQSIKV RISLKSALGD KAYEWNDNEM YLFRSSVAYA MRQYFLKVKN 660
QMILFGEEDV RVANLKPRIS FNFFVTAPKN VSDIIPRTEV EKAIRMSRSR INDAFRLNDN 720
SLEFLGIQPT LGPPNQPPVS IWLIVFGVVM GVIVVGIVIL IFTGIRDRKK KNKARSGENP 780
YASIDISKGE NNPGFQNTDD VQTSF 805

SEQ ID NO: 2 moltype = AA length = 596
FEATURE Location/Qualifiers
source 1..596
mol_type = protein
organism = synthetic construct
SEQUENCE: 2
STIEEQAKTF LDKFNHEAED LFYQSSLASW NYNTNITEEN VQNMNNAGDK WSAFLKEQST 60
LAQMYPLQEI QNLTVKLQLQ ALQQNGSSVL SEDKSKRLNT ILNTMSTIYS TGKVCNPDNP 120
QECLLLEPGL NEIMANSLDY NERLWAWESW RSEVGKQLRP LYEEYVVLKN EMARANHYED 180
YGDYWRGDYE VNGVDGYDYS RGQLIEDVEH TFEEIKPLYE HLHAYVRAKL MNAYPSYISP 240
IGCLPAHLLG DMWGRFWTNL YSLTVPFGQK PNIDVTDAMV DQAWDAQRIF KEAEKFFVSV 300
GLPNMTQGFW ENSMLTDPGN VQKAVCHPTA WDLGKGDFRI LMCTKVTMDD FLTAHHEMGH 360
IQYDMAYAAQ PFLLRNGANE GFHEAVGEIM SLSAATPKHL KSIGLLSPDF QEDNETEINF 420
LLKQALTIVG TLPFTYMLEK WRWMVFKGEI PKDQWMKKWW EMKREIVGVV EPVPHDETYC 480
DPASLFHVSN DYSFIRYYTR TLYQFQFQEA LCQAAKHEGP LHKCDISNST EAGQKLFNML 540
RLGKSEPWTL ALENVVGAKN MNVRPLLNYF EPLFTWLKDQ NKNSFVGWST DWSPYA 596

SEQ ID NO: 3 moltype = AA length = 342
FEATURE Location/Qualifiers
source 1..342
mol_type = protein
organism = synthetic construct
SEQUENCE: 3
STIEEQAKTF LDKFNHEAED LFYQSSLASW NYNTNITEEN VQNMNNAGDK WSAFLKEQST 60
LAQMYPLQEI QNLTVKLQLQ ALQQNGSSVL SEDKSKRLNT ILNTMSTIYS TGKVCNPDNP 120
QECLLLEPGL NEIMANSLDY NERLWAWESW RSEVGKQLRP LYEEYVVLKN EMARANHYED 180
YGDYWRGDYE VNGVDGYDYS RGQLIEDVEH TFEEIKPLYE HLHAYVRAKL MNAYPSYISP 240
IGCLPAHLLG DMWGRFWTNL YSLTVPFGQK PNIDVTDAMV DQAWDAQRIF KEAEKFFVSV 300
GLPNMTQGFW ENSMLTDPGN VQKAVCHPTA WDLGKGDFRI LM 342

SEQ ID NO: 4 moltype = AA length = 331
FEATURE Location/Qualifiers
source 1..331
mol_type = protein
organism = synthetic construct
SEQUENCE: 4
DKFNHEAEDL FYQSSLASWN YNTNITEENV QNMNNAGDKW SAFLKEQSTL AQMYPLQEIQ 60
NLTVKLQLQA LQQNGSSVLS EDKSKRLNTI LNTMSTIYST GKVCNPDNPQ ECLLLEPGLN 120
EIMANSLDYN ERLWAWESWR SEVGKQLRPL YEEYVVLKNE MARANHYEDY GDYWRGDYEV 180
NGVDGYDYSR GQLIEDVEHT FEEIKPLYEH LHAYVRAKLM NAYPSYISPI GCLPAHLLGD 240
MWGRFWTNLY SLTVPFGQKP NIDVTDAMVD QAWDAQRIFK EAEKFFVSVG LPNMTQGFWE 300
NSMLTDPGNV QKAVCHPTAW DLGKGDFRIL M 331

SEQ ID NO: 5 moltype = AA length = 714
FEATURE Location/Qualifiers
source 1..714
mol_type = protein
organism = synthetic construct
SEQUENCE: 5
STIEEQAKTF LDKFNHEAED LFYQSSLASW NYNTNITEEN VQNMNNAGDK WSAFLKEQST 60
LAQMYPLQEI QNLTVKLQLQ ALQQNGSSVL SEDKSKRLNT ILNTMSTIYS TGKVCNPDNP 120
QECLLLEPGL NEIMANSLDY NERLWAWESW RSEVGKQLRP LYEEYVVLKN EMARANHYED 180
YGDYWRGDYE VNGVDGYDYS RGQLIEDVEH TFEEIKPLYE HLHAYVRAKL MNAYPSYISP 240
IGCLPAHLLG DMWGRFWTNL YSLTVPFGQK PNIDVTDAMV DQAWDAQRIF KEAEKFFVSV 300
GLPNMTQGFW ENSMLTDPGN VQKAVCHPTA WDLGKGDFRI LMCTKVTMDD FLTAHHEMGH 360
IQYDMAYAAQ PFLLRNGANE GFHEAVGEIM SLSAATPKHL KSIGLLSPDF QEDNETEINF 420

```
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYADQSI  600
KVRISLKSAL GDKAYEWNDN EMYLFRSSVA YAMRQYFLKV KNQMILFGEE DVRVANLKPR  660
ISFNFFVTAP KNVSDIIPRT EVEKAIRMSR SRINDAFRLN DNSLEFLGIQ PTLG        714

SEQ ID NO: 6            moltype = AA  length = 182
FEATURE                 Location/Qualifiers
source                  1..182
                        mol_type = protein
                        organism = synthetic construct
SEQUENCE: 6
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YG                                                                182

SEQ ID NO: 7            moltype = AA  length = 380
FEATURE                 Location/Qualifiers
source                  1..380
                        mol_type = protein
                        organism = synthetic construct
SEQUENCE: 7
YQSSLASWNY NTNITEENVQ NMNNAGDKWS AFLKEQSTLA QMYPLQEIQN LTVKLQLQAL  60
QQNGSSVLSE DKSKRLNTIL NTMSTIYSTG KVCNPDNPQE CLLLEPGLNE IMANSLDYNE  120
RLWAWESWRS EVGKQLRPLY EEYVVLKNEM ARANHYEDYG DYWRGDYEVN GVDGYDYSRG  180
QLIEDVEHTF EEIKPLYEHL HAYVRAKLMN AYPSYISPIG CLPAHLLGDM WGRFWTNLYS  240
LTVPFGQKPN IDVTDAMVDQ AWDAQRIFKE AEKFFVSVGL PNMTQGFWEN SMLTDPGNVQ  300
KAVCHPTAWD LGKGDFRILM CTKVTMDDFL TAHHEMGHIQ YDMAYAAQPF LLRNGANEGF  360
HEAVGEIMSL SAATPKHLKS                                             380

SEQ ID NO: 8            moltype = AA  length = 19
FEATURE                 Location/Qualifiers
source                  1..19
                        mol_type = protein
                        organism = synthetic construct
SEQUENCE: 8
QAKTFLDKFN HEAEDLFYQ                                              19

SEQ ID NO: 9            moltype = AA  length = 805
FEATURE                 Location/Qualifiers
source                  1..805
                        mol_type = protein
                        organism = synthetic construct
SEQUENCE: 9
MSSSSWLLLS LVAVTAAQST IEEQARTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 10           moltype = AA  length = 805
FEATURE                 Location/Qualifiers
source                  1..805
                        mol_type = protein
                        organism = synthetic construct
SEQUENCE: 10
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEVPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
```

```
YASIDISKGE NNPGFQNTDD VQTSF                                        805

SEQ ID NO: 11          moltype = AA  length = 805
FEATURE                Location/Qualifiers
source                 1..805
                       mol_type = protein
                       organism = synthetic construct
SEQUENCE: 11
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDSEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                        805

SEQ ID NO: 12          moltype = AA  length = 805
FEATURE                Location/Qualifiers
source                 1..805
                       mol_type = protein
                       organism = synthetic construct
SEQUENCE: 12
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                        805

SEQ ID NO: 13          moltype = AA  length = 805
FEATURE                Location/Qualifiers
source                 1..805
                       mol_type = protein
                       organism = synthetic construct
SEQUENCE: 13
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHNEMGNIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                        805

SEQ ID NO: 14          moltype = AA  length = 805
FEATURE                Location/Qualifiers
source                 1..805
                       mol_type = protein
                       organism = synthetic construct
SEQUENCE: 14
MSSSSWLLLS LVAVTAAQST IEEQAKYFLD KFNAEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
```

```
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                        805

SEQ ID NO: 15          moltype = AA  length = 805
FEATURE                Location/Qualifiers
source                 1..805
                       mol_type = protein
                       organism = Mus musculus
SEQUENCE: 15
MSSSSWLLLS LVAVTTAQSL TEENAKTFLN NFNQEAEDLS YQSSLASWNY NTNITEENAQ  60
KMSEAAAKWS AFYEEQSKTA QSFSLQEIQT PIIKRQLQAL QQSGSSALSA DKNKQLNTIL  120
NTMSTIYSTG KVCNPKNPQE CLLLEPGLDE IMATSTDYNS RLWAWEGWRA EVGKQLRPLY  180
EEYVVLKNEM ARANNYNDYG DYWRGDYEAE GADGYNYNRN QLIEDVERTF AEIKPLYEHL  240
HAYVRRKLMD TYPSYISPTG CLPAHLLGDM WGRFWTNLYP LTVPFAQKPN IDVTDAMMNQ  300
GWDAERIFQE AEKFFVSVGL PHMTQGFWAN SMLTEPADGR KVVCHPTAWD LGHGDFRIKM  360
CTKVTMDNFL TAHHEMGHIQ YDMAYARQPF LLRNGANEGF HEAVGEIMSL SAATPKHLKS  420
IGLLPSDFQE DSETEINFLL KQALTIVGTL PFTYMLEKWR WMVFRGEIPK EQWMKKWWEM  480
KREIVGVVEP LPHDETYCDP ASLFHVSNDY SFIRYYTRTI YQFQFQEALC QAAKYNGSLH  540
KCDISNSTEA GQKLLKMLSL GNSEPWTKAL ENVVGARNMD VKPLLNYFQP LFDWLKEQNR  600
NSFVGWNTEW SPYADQSIKV RISLKSALGA NAYEWTNNEM FLFRSSVAYA MRKYFSIIKN  660
QTVPFLEEDV RVSDLKPRVS FYFFVTSPQN VSDVIPRSEV EDAIRMSRGR INDVFGLNDN  720
SLEFLGIHPT LEPPYQPPVT IWLIIFGVVM ALVVVGIIIL IVTGIKGRKK KNETKREENP  780
YDSMDIGKGE SNAGFQNSDD AQTSF                                        805

SEQ ID NO: 16          moltype = AA  length = 794
FEATURE                Location/Qualifiers
source                 1..794
                       mol_type = protein
                       organism = Cavia porcellus
SEQUENCE: 16
MSGSFWFLLN LVAVTTAQFN LEEQAKTFLD EFNLKAEDLY YQSSLASWNY NTNITDENVQ  60
KMSEAGGILS AFYEEQSNLA KAYPLQDIQN LTVKRQLRIL QQSGSSGFSA DKNKQLSTIL  120
NTMSTLYSTG KVCYPSDPQE CLLLEPGLAD IMSKSTDYNL RLWAWEGWRS KVGKQLRPLY  180
EEYVALKNEM ARANKYEDYG DYWRRDYEVE DMDGYNYSRN QLIEDVERTF AEIKPLYEQL  240
HAYVRTKLME TYPSRISPVG CLPAHLLGDM WGRFWTELYS LTVPFQQKPN IDVTDAMESQ  300
SWDAEKIFKE AEKFFVSVGL PPMTQGFWKN SMLTEPGDGQ KVVCHPTAWD MGKNDFRIKM  360
CTKVTMDHFL TAHHEMGHIQ YDMAYAIQPF LLRDGANEGF HEAIGEIMSL SAATPEHLKS  420
IGLLPPDFHE DNGTFFHGFT HALLGTLPFT FMLEKVERGW SSRVKIPKSS GLKNVADEVK  480
IVGVVEPLPH DETYCDPASL FHVSNDYSFI RYYTRTIYQF QFQEALCKAA NHVGPLHKCD  540
ISNSTEAGQK LLNMLKLGKS EPWTLALESI VGTKNMDVKP LLNYFQPLST WLQDQNRNSF  600
VGWNTEWSPY SEESIKVRIS LKSALGDAY KWDDNEMYLF RSSVAYAMRK YFLDVKNQTV  660
LFSWEDVRVS DWTHRVSFTF FVTEPNNVSN IIPKTEVEDA IRLSRSRIND VFLSGIYPTL  720
SPPYEPPVTI WLIVFGVVMG LVVVGIVVLV ITGIRDRRKK KQKQREENPY SSVDIGKGEN  780
NTAFQNSEDN QTSF                                                    794

SEQ ID NO: 17          moltype = AA  length = 805
FEATURE                Location/Qualifiers
source                 1..805
                       mol_type = protein
                       organism = Equus sp.
SEQUENCE: 17
MSGSSWLLLS LVAVTAAQST TEDLAKTFLE KFNSEAEELS HQSSLASWSY NTNITDENVQ  60
KMNEAGARWS AFYEEQCKLA KTYPLEEIQN LTVKRQLQAL QQSGSSVLSA DKSKRLNEIL  120
NTMSTIYSTG KVCNPSNPQE CLLLEPGLDA IMENSKDYNQ RLWAWEGWRS EVGKQLRPLY  180
EEYVVLKNEM ARANNYEDYG DYWRGDYEAE GPSGYDYSRD QLIEDVERTF AEIKPLYEHL  240
HAYVRAKLMD TYPSHINPTG CLPAHLLGDM WGRFWTNLYS LTVPFGQKPN IDVTDAMVDQ  300
SWDAKRIFEE AEKFFVSVGL PNMTQGFWEN SMLTEPGDGR KVVCHPTAWD LGKGDFRIKM  360
CTKVTMDDFL TAHHEMGHIQ YDMAYAVQPY LLRNGANEGF HEAVGEIMSL SAATPNHLKA  420
IGLLPPDFYE DSETEINFLL KQALTIVGTL PFTYMLEKWR WMVFKGEIPK EEWMKKWWEM  480
KREIVGVVEP VPHDETYCDP AALFHVANDY SFIRYYTRTI YQFQFQEALC QTAKHEGPLH  540
KCDISNSTEA GQKLLQMLSL GKSEPWTLAL ERIVGVKNMD VRPLLNYFEP LFTWLKDQNK  600
NSFVGWSTNW SPYADQSIKV RISLKSALGE KSYEWNDNEM YLFQSSVAYA MRVYFLKAKN  660
QTILFGEEDV WVSDLKPRIS FNFFVTSPKN ASDIIPRTDV EEAIRMSRSR INDAFRLDDN  720
TLEFLGIQPT LGPPYQPPVT VWLIAFGVVM GLVVVGIVVL IATGIRGRRK KNQARSEENP  780
YASVDLSKGE NNPGFQNGDD VQTSF                                        805

SEQ ID NO: 18          moltype = AA  length = 805
FEATURE                Location/Qualifiers
source                 1..805
                       mol_type = protein
                       organism = Macaca sp.
SEQUENCE: 18
MSGSSWLLLS LVAVTAAQST IEEQAKTFLD KFNHEAEDLF YQSSLASWNY NTNITEENVQ  60
NMNNAGEKWS AFLKEQSTLA QMYPLQEIQN LTVKLQLQAL QQNGSSVLSE DKSKRLNTIL  120
NTMSTIYSTG KVCNPNNPQE CLLLDPGLNE IMEKSLDYNE RLWAWEGWRS EVGKQLRPLY  180
```

```
EEYVVLKNEM ARANHYKDYG DYWRGNYEVN GVDGYDYNRD QLIEDVERTF EEIKPLYEHL  240
HAYVRAKLMN AYPSYISPTG CLPAHLLGDM WGRFWTNLYS LTVPFGQKPN IDVTDAMVNQ  300
AWNAQRIFKE AEKFFVSVGL PNMTQGFWEN SMLTDPGNVQ KVVCHPTAWD LGKGDFRIIM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLLNMLKL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRTYFLEIKH  660
QTILFGEEDV RVADLKPRIS FNFYVTAPKN VSDIIPRTEV EEAIRISRSR INDAFRLNDN  720
SLEFLGIQTT LAPPYQSPVT TWLIVFGVVM GVIVAGIVVL IFTGIRDRKK KNQARSEENP  780
YASIDINKGE NNPGFQNTDD VQTSF                                        805

SEQ ID NO: 19          moltype = AA  length = 805
FEATURE                Location/Qualifiers
source                 1..805
                       mol_type = protein
                       organism = Pan troglodytes
SEQUENCE: 19
MSGSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSAIYSTG KVCNPNNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPE DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRKSRSR INDAFRLNDN  720
SLEFLGIQPT LGPPNQPPVS IWLIVFGVVM GVIVVGIVIL IFTGIRDRKK KNKARSEENP  780
YASVDTSKGE NNPGFQNTDD VQTSF                                        805

SEQ ID NO: 20          moltype = AA  length = 805
FEATURE                Location/Qualifiers
source                 1..805
                       mol_type = protein
                       note = Sus domesticus
                       organism = unidentified
SEQUENCE: 20
MSGSFWLLLS LIPVTAAQST TEELAKTFLE KFNLEAEDLA YQSSLASWNY NTNITDENIQ  60
KMNDARAKWS AFYEEQSRIA KTYPLDEIQT LILKRQLQAL QQSGTSGLSA DKSKRLNTIL  120
NTMSTIYSSG KVLDPNNPQE CLVLEPGLDE IMENSKDYSR RLWAWESWRA EVGKQLRPLY  180
EEYVVLENEM ARANNYEDYG DYWRGDYEVT GTGDYDYSRN QLMEDVERTF AEIKPLYEHL  240
HAYVRAKLMD AYPSRISPTG CLPAHLLGDM WGRFWTNLYP LTVPFGEKPS IDVTEAMVNQ  300
SWDAIRIFEE AEKFFVSIGL PNMTQGFWNN SMLTEPGDGR KVVCHPTAWD LGKGDFRIKM  360
CTKVTMDDFL TAHHEMGHIQ YDMAYAIQPY LLRNGANEGF HEAVGEIMSL SAATPHYLKA  420
LGLLPPDFYE DSETEINFLL KQALTIVGTL PFTYMLEKWR WMVFKGEIPK EQWMQKWWEM  480
KREIVGVVEP LPHDETYCDP ACLFHVAEDY SFIRYYTRTI YQFQFHEALC RTAKHEGPLY  540
KCDISNSTEA GQKLLQMLSL GKSEPWTLAL ENIVGVKTMD VKPLLSYFEP LLTWLKAQNG  600
NSSVGWNTDW TPYADQSIKV RISLKSALGK EAYEWNDNEM YLFRSSIAYA MRNYFSSAKN  660
ETIPFGAEDV WVSDLKPRIS FNFFVTSPAN MSDIIPRSDV EKAISMSRSR INDAFRLDDN  720
TLEFLGIQPT LGPPDEPPVT VWLIIFGVVM GLVVVGIVVL IFTGIRDRRK KKQASSEENP  780
YGSMDLSKGE SNSGFQNGDD IQTSF                                        805

SEQ ID NO: 21          moltype = AA  length = 804
FEATURE                Location/Qualifiers
source                 1..804
                       mol_type = protein
                       organism = Canis sp.
SEQUENCE: 21
MSGSSWLLLS LAALTAAQST EDLVKTFLEK FNYEAEELSY QSSLASWNYN INITDENVQK  60
MNNAGAKWSA FYEEQSKLAK TYPLEEIQDS TVKRQLRALQ HSGSSVLSAD KNQRLNTILN  120
SMSTIYSTGK ACNPSNPQEC LLLEPGLDDI MENSKDYNER LWAWEGWRSE VGKQLRPLYE  180
EYVALKNEMA RANNYEDYGD YWRGDYEEEW ENGYNYSRNQ LIDDVEHTFT QIMPLYQHLH  240
AYVRTKLMDT YPSYISPTGC LPAHLLGDMW GRFWTNLYPL TVPFGQKPNI DVTNAMVNQS  300
WDARKIFKEA EKFFVSVGLP NMTQEFWENS MLTEPSDSRK VVCHPTAWDL GKGDFRIKMC  360
TKVTMDDFLT AHHEMGHIQY DMAYAAQPFL LRNGANEGFH EAVGEIMSLS AATPNHLKNI  420
GLLPPSFFED SETEINFLLK QALTIVGTLP FTYMLEKWRW MVFKGEIPKD QWMKTWWEMK  480
RNIVGVVEPV PHDETYCDPA SLFHVANDYS FIRYYTRTIY QFQFQEALCQ IAKHEGPLHK  540
CDISNSSEAG QKLLEMLKLG KSKPWTYALE IVVGAKNMDV RPLLNYFEPL FTWLKEQNRN  600
SFVGWNTDWS PYADQSIKVR ISLKSALGEK AYEWNNNEMY LFRSSIAYAM RQYFSEVKNQ  660
TIPFVEDNVW VSDLKPRISF NFFVTSPGNV SDIIPRTEVE EAIRMYRSRI NDVFRLDDNS  720
LEFLGIQPTL GPPYEPPVTI WLIVFGVVMG VVVVGIVLLI FSGIRNRRKN DQARGEENPY  780
ASVDLSKGEN NPGFQNVDDA QTSF                                         804

SEQ ID NO: 22          moltype = AA  length = 805
FEATURE                Location/Qualifiers
source                 1..805
```

```
                         mol_type = protein
                         organism = Felis sp.
SEQUENCE: 22
MSGSFWLLLS FAALTAAQST TEELAKTFLE KFNHEAEELS YQSSLASWNY NTNITDENVQ  60
KMNEAGAKWS AFYEEQSKLA KTYPLAEIHN TTVKRQLQAL QQSGSSVLSA DKSQRLNTIL  120
NAMSTIYSTG KACNPNNPQE CLLLEPGLDD IMENSKDYNE RLWAWEGWRA EVGKQLRPLY  180
EEYVALKNEM AKSKQYEDYG DYWRGDYEEE WTDGYNYSRS QLIKDVEHTF TQIKPLYQHL  240
HAYVRAKLMD TYPSRISPTG CLPAHLLGDM WGRFWTNLYP LTVPFGQKPN IDVTDAMVNQ  300
SWDARRIFKE AEKFFVSVGL PNMTQGFWEN SMLTEPGDSR KVVCHPTAWD LGKGDFRIKM  360
CTKVTMDDFL TAHHEMGHIQ YDMAYAVQPF LLRNGANEGF HEAVGEIMSL SAATPNHLKT  420
IGLLSPGFSE DSETEINFLL KQALTIVGTL PFTYMLEKWR WMVFKGEIPK EQWMQKWWEM  480
KREIVGVVEP VPHDETYCDP ASLFHVANDY SFIRYYTRTI YQFQFQEALC RIAKHEGPLH  540
KCDISNSSEA GKKLLQMLTL GKSKPWTLAL EHVVGEKKMN VTPLLKYFEP LFTWLKEQNR  600
NSFVGWNTDW RPYADQSIKV RISLKSALGD EAYEWNDNEM YLFRSSVAYA MREYFSKVKN  660
QTIPFVEDNV WVSNLKPRIS FNFFVTASKN VSDVIPRSEV EEAIRMSRSR INDAFRLDDN  720
SLEFLGIQPT LSPPYQPPVT IWLIVFGVVM GVVVVGIVLL IVSGIRNRRK NNQARSEENP  780
YASVDLSKGE NNPGFQHADD VQTSF                                       805

SEQ ID NO: 23            moltype = AA  length = 804
FEATURE                  Location/Qualifiers
source                   1..804
                         mol_type = protein
                         note = Bovinae
                         organism = unidentified
SEQUENCE: 23
MTGSFWLLLS LVAVTAAQST TEEQAKTFLE KFNHEAEDLS YQSSLASWNY NTNITDENVQ  60
KMNEARAKWS AFYEEQSRMA KTYSLEEIQN LTLKRQLKAL QHSGTSALSA EKSKRLNTIL  120
NKMSTIYSTG KVLDPNTQEC LALEPGLDDI MENSRDYNRR LWAWEGWRAE VGKQLRPLYE  180
EYVVLENEMA RANNYEDYGD YWRGDYEVTG AGDYDYSRDQ LMKDVERTFA EIKPLYEQLH  240
AYVRAKLMHT YPSYISPTGC LPAHLLGDMW GRFWTNLYSL TVPFEHKPSI DVTEKMENQS  300
WDAERIFKEA EKFFVSISLP YMTQGFWDNS MLTEPGDGRK VVCHPTAWDL GKGDFRIKMC  360
TKVTMDDFLT AHHEMGHIQY DMAYAAQPYL LRNGANEGFH EAVGEIMSLS AATPHYLKAL  420
GLLAPDFHED NETEINFLLK QALTIVGTLP FTYMLEKWRW MVFKGEIPKQ QWMEKWWEMK  480
REIVGVVEPL PHDETYCDPA CLFHVAEDYS FIRYYTRTIY QFQFHEALCK TAKHEGALFK  540
CDISNSTEAG QRLLQMLRLG KSEPWTLALE NIVGIKTMDV KPLLNYFEPL FTWLKEQNRN  600
SFVGWSTEWT PYSDQSIKVR ISLKSALGEN AYEWNDNEMY LFQSSVAYAM RKYFSEARNE  660
TVLFGEDNVW VSDKKPRISF KFFVTSPNNV SDIIPRTEVE NAIRLSRDRI NDVFQLDDNS  720
LEFLGIQPTL GPPYEPPVTI WLIIFGVVMG VVVIGIVVLI FTGIRNRRKK NQASSEENPY  780
GSVDLNKGEN NSGFQNIDDV QTSL                                        804

SEQ ID NO: 24            moltype = AA  length = 805
FEATURE                  Location/Qualifiers
source                   1..805
                         mol_type = protein
                         organism = Oryctolagus cuniculus
SEQUENCE: 24
MSGSSWLLLS LVAVTAAQST IEELAKTFLE KFNQEAEDLS YQSALASWDY NTNITEENVQ  60
KMNDAEAKWS AFYEEQSKLA KTYPSQEVQN LTVKRQLQAL QQSGSSALSA DKSKQLNTIL  120
STMSTIYSTG KVCNQSNPQE CFLLEPGLDE IMAKSTDYNE RLWAWEGWRS VVGKQLRPLY  180
EEYVVLKNEM ARANNYEDYG DYWRADYEAE GADGYDYSRS QLIDDVERTF SEIKPLYEQL  240
HAFVRTKLMD AYPSRISPTG CLPAHLLGDM WGRFWTNLYS LTVPFGQKPN IDVTDTMVNQ  300
GWDAERIFKE AEKFFVSVGL PSMTQGFWEN SMLTEPGDGR KVVCHPTAWD LGKGDFRIKM  360
CTKVTMDNFL TAHHEMGHIQ YDMAYATQPF LLRNGANEGF HEAVGEIMSL SAATPEHLKS  420
IGLLPYDFHE DNETEINFLL KQALTIVGTL PFTYMLEKWR WMVFKGEIPK EQWMQKWWEM  480
KREIVGVVEP MPHDETYCDP AALFHVANDY SFIRYYTRTI YQFQFQEALC QAAQHEGPLH  540
KCDISNSTEA GQKLLNMLRL GRSEPWTLAL ENVVGAKNMD VRPLLNYFEP LFTWLKEQNR  600
NSFVGWSTEW TPYADQSIKV RISLKTALGD QAYEWNDSEM YLFRSSVAYA MRKYFSEVKN  660
QTILFGEEDV RVSDLKPRIS FNFFVTAPNN VNDIIPRNEV EEAISMSRSR INDIFRLDDN  720
SLEFVGIQPT LEPPYESPVP IWLVVFGVVM GMIVIGIVVL IFTGIKDRRK QKQAKREENP  780
YGFVDMSKGE NNSGFQNSDD IQTSF                                       805

SEQ ID NO: 25            moltype = AA  length = 805
FEATURE                  Location/Qualifiers
source                   1..805
                         mol_type = protein
                         note = Mustela furo
                         organism = unidentified
SEQUENCE: 25
MLGSSWLLLS LAALTAAQST TEDLAKTFLE KFNYEAEELS YQNSLASWNY NTNITDENIQ  60
KMNIAGAKWS AFYEEESQHA KTYPLEEIQD PIIKRQLRAL QQSGSSVLSA DKRERLNTIL  120
NAMSTIYSTG KACNPNNPQE CLLLEPGLDD IMENSKDYNE RLWAWEGWRS EVGKQLRPLY  180
EEYVALKNEM ARANNYEDYG DYWRGDYEEE WADGYSYSRN QLIEDVEHTF TQIKPLYEHL  240
HAYVRAKLMD AYPSRISPTG CLPAHLLGDM WGRFWTNLYP LMVPFRQKPN IDVTDAMVNQ  300
SWDARRIFEE AETFFVSVGL PNMTEGFWQN SMLTEPGDNR KVVCHPTAWD LGKRDFRIKM  360
CTKVTMDDFL TAHHEMGHIQ YDMAYAEQPF LLRNGANEGF HEAVGEIMSL SAATPNHLKN  420
IGLLPPDFSE DSETDINFLL KQALTIVGTL PFTYMLEKWR WMVFKGEIPK EQWMQKWWEM  480
KRDIVGVVEP LPHDETYCDP AALFHVANDY SFIRYYTRTI YQFQFQEALC QIAKHEGPLY  540
KCDISNSSEA GQKLHEMLSL GRSKPWTFAL ERVVGAKTMD VRPLLNYFEP LFTWLKEQNR  600
NSFVGWNTDW SPYADQSIKV RISLKSALGE KAYEWNDNEM YFFQSSIAYA MREYFSKVKN  660
```

```
QTIPFVGKDV RVSDLKPRIS FNFIVTSPEN MSDIIPRADV EEAIRKSRGR INDAFRLDDN  720
SLEFLGIQPT LEPPYQPPVT IWLIVFGVVM GVVVVGIFLL IFSGIRNRRK NNQARSEENP  780
YASVDLSKGE NNPGFQNVDD VQTSF                                        805

SEQ ID NO: 26          moltype = AA  length = 805
FEATURE                Location/Qualifiers
source                 1..805
                       mol_type = protein
                       organism = Neovison vison
SEQUENCE: 26
MLGSSWLLLS LAALTAAQST TEDLAKTFLE KFNYEAEELS YQNSLASWNY NTNITDENIQ  60
KMNIAGAKWS AFYEEESQHA KTYPLEEIQD PIIKRQLRAL QQSGSSVLSA DKRERLNTIL  120
NAMSTIYSTG KACNPNNPQE CLLLEPGLDD IMENSKDYNE RLWAWEGWRS EVGKQLRPLY  180
EEYVALKNEM ARANNYEDYG DYWRGDYEEE WADGYNYSRN QLIEDVEHTF TQIKPLYEHL  240
HAYVRAKLMD AYPSRISPTG CLPAHLLGDM WGRFWTNLYP LMVPFGQKPN IDVTDAMVNQ  300
SWDARRIFKE AEKFFVSVGL PNMTEGFWQN SMLTEPGDNR KVVCHPTAWD LGKHDFRIKM  360
CTKVTMDDFL TAHHEMGHIQ YDMAYAAQPF LLRNGANEGF HEAVGEIMSL SAATPNHLKN  420
IGLLPPDFSE DSETDINFLL KQALTIVGTL PFTYMLEKWR WMVFKGEIPK EQWMQKWWEM  480
KRDIVGVVEP LPHDETYCDP AALFHVANDY SFIRYYTRTI YQFQFQEALC QIAKHEGPLY  540
KCDISNSREA GQKLHEMLSL GRSKPWTFAL ERVVGAKTMD VRPLLNYFEP LFTWLKEQNR  600
NSFVGWNTDW SPYADQSIKV RISLKSALGE KAYEWNDNEM YFFQSSIAYA MREYFSKVKK  660
QTIPFVDKDV RVSDLKPRIS FNFIVTSPEN MSDIIPRADV EEAIRKSRGR INDAFRLDDN  720
SLEFLGIQPT LEPPYQPPVT IWLIVFGVVM GVVVVGIFLL IFSGIRNRRK NNQARSEENP  780
YASVDLSKGE NNPGFQNVDD VQTSF                                        805

SEQ ID NO: 27          moltype = AA  length = 808
FEATURE                Location/Qualifiers
source                 1..808
                       mol_type = protein
                       note = Gallus domesticus
                       organism = unidentified
SEQUENCE: 27
MLLHFWLLCG LSAVVTPQDV TQEAQTFLAE FNVRAEDISY ENSLASWNYN TNITEETARK  60
MSEAGAKWAA FYEEASRNAS RFSLANIQDA VTRLQIQSLQ DRGSSVLSPE KYSRLNSVMN  120
SMSTIYSTGV VCKATEPFDC LVLEPGLDDI MANSIDYHER LWAWEGWRAD VGRMMRPLYE  180
EYVELKNEAA RLNNYSDYGD YWRANYETDY PEEYKYSRDQ LVQDVEKTFE QIKPLYQHLH  240
AYVRHRLEQV YGSELINPTG CLPAHLLGDM WGRFWTNLYN LTVPYPEKPN IDVTSAMAQK  300
NWDAMKIFKT AEAFFASIGL YNMTEGFWTN SMLTEPTDNR KVVCHPTAWD MGKNDYRIKM  360
CTKVTMDDFL TAHHEMGHIE YDMAYSVQPF LLRNGANEGF HEAVGEIMSL SAATPQHLKS  420
LDLLEPTFQE DEETEINFLL KQALTIVGTM PFTYMLEKWR WMVFNGEITK QEWTKRWWKM  480
KREIVGVVEP VPHDETYCDP AALFHVANDY SFIRYYTRTI YQFQFQEALC KAANHTGPLH  540
KCDITNSTAA GGNLRQLLEL GKSKPWTQAL ESATGEKYMN ATPLLHYFEP LFNWLQKNNS  600
GRSIGWNTDW TPYSDNAIKV RISLKAALGD DAYVWDASEL FLFKSSIAYA MRKYFAKEKE  660
QNVDFQVTDI HVGEETQRVS FYLTVSMPGN VSDIVPRADV EKAIRMSRGR ISEAFRLDDN  720
TLEFDGIVPT LATPYKPPVT IWLILFGVVM SLIVIGVIVL IITGQRDKRK KARGRANEAG  780
SNCEVNPYDE DGRSNKGFEQ SEETQTSF                                     808

SEQ ID NO: 28          moltype = AA  length = 6
FEATURE                Location/Qualifiers
source                 1..6
                       mol_type = protein
                       organism = synthetic construct
SEQUENCE: 28
HHHHHH                                                             6

SEQ ID NO: 29          moltype = AA  length = 12
FEATURE                Location/Qualifiers
source                 1..12
                       mol_type = protein
                       organism = synthetic construct
SEQUENCE: 29
HHHHHHHHHH HH                                                      12

SEQ ID NO: 30          moltype = AA  length = 30
FEATURE                Location/Qualifiers
source                 1..30
                       mol_type = protein
                       organism = synthetic construct
SEQUENCE: 30
HHHHHHHHHH HHHHHHHHHH HHHHHHHHHH                                   30

SEQ ID NO: 31          moltype = AA  length = 6
FEATURE                Location/Qualifiers
source                 1..6
                       mol_type = protein
                       organism = synthetic construct
SEQUENCE: 31
KKKKKK                                                             6
```

```
SEQ ID NO: 32          moltype = AA  length = 12
FEATURE                Location/Qualifiers
source                 1..12
                       mol_type = protein
                       organism = synthetic construct
SEQUENCE: 32
KKKKKKKKKK KK                                                   12

SEQ ID NO: 33          moltype = AA  length = 30
FEATURE                Location/Qualifiers
source                 1..30
                       mol_type = protein
                       organism = synthetic construct
SEQUENCE: 33
KKKKKKKKKK KKKKKKKKKK KKKKKKKKKK                                30

SEQ ID NO: 34          moltype = AA  length = 6
FEATURE                Location/Qualifiers
source                 1..6
                       mol_type = protein
                       organism = synthetic construct
SEQUENCE: 34
RRRRRR                                                          6

SEQ ID NO: 35          moltype = AA  length = 12
FEATURE                Location/Qualifiers
source                 1..12
                       mol_type = protein
                       organism = synthetic construct
SEQUENCE: 35
RRRRRRRRRR RR                                                   12

SEQ ID NO: 36          moltype = AA  length = 30
FEATURE                Location/Qualifiers
source                 1..30
                       mol_type = protein
                       organism = synthetic construct
SEQUENCE: 36
RRRRRRRRRR RRRRRRRRRR RRRRRRRRRR                                30

SEQ ID NO: 37          moltype = AA  length = 6
FEATURE                Location/Qualifiers
source                 1..6
                       mol_type = protein
                       organism = synthetic construct
SEQUENCE: 37
OOOOOO                                                          6

SEQ ID NO: 38          moltype = AA  length = 12
FEATURE                Location/Qualifiers
source                 1..12
                       mol_type = protein
                       organism = synthetic construct
SEQUENCE: 38
OOOOOOOOOO OO                                                   12

SEQ ID NO: 39          moltype = AA  length = 30
FEATURE                Location/Qualifiers
source                 1..30
                       mol_type = protein
                       organism = synthetic construct
SEQUENCE: 39
OOOOOOOOOO OOOOOOOOOO OOOOOOOOOO                                30

SEQ ID NO: 40          moltype = AA  length = 6
FEATURE                Location/Qualifiers
source                 1..6
                       mol_type = protein
                       organism = synthetic construct
SEQUENCE: 40
HHKKOO                                                          6

SEQ ID NO: 41          moltype = AA  length = 6
FEATURE                Location/Qualifiers
source                 1..6
                       mol_type = protein
                       organism = synthetic construct
SEQUENCE: 41
HORKHR                                                          6
```

```
SEQ ID NO: 42          moltype = AA  length = 6
FEATURE                Location/Qualifiers
source                 1..6
                       mol_type = protein
                       organism = synthetic construct
SEQUENCE: 42
HKRSOH                                                       6

SEQ ID NO: 43          moltype = AA  length = 6
FEATURE                Location/Qualifiers
source                 1..6
                       mol_type = protein
                       organism = synthetic construct
SEQUENCE: 43
RRHTHR                                                       6

SEQ ID NO: 44          moltype = AA  length = 6
FEATURE                Location/Qualifiers
source                 1..6
                       mol_type = protein
                       organism = synthetic construct
SEQUENCE: 44
KKOORR                                                       6

SEQ ID NO: 45          moltype = AA  length = 6
FEATURE                Location/Qualifiers
source                 1..6
                       mol_type = protein
                       organism = synthetic construct
SEQUENCE: 45
KKHHRR                                                       6

SEQ ID NO: 46          moltype = AA  length = 6
FEATURE                Location/Qualifiers
source                 1..6
                       mol_type = protein
                       organism = synthetic construct
SEQUENCE: 46
OORRHH                                                       6

SEQ ID NO: 47          moltype = AA  length = 12
FEATURE                Location/Qualifiers
source                 1..12
                       mol_type = protein
                       organism = synthetic construct
SEQUENCE: 47
HHHKKKRRRO OO                                                12

SEQ ID NO: 48          moltype = AA  length = 12
FEATURE                Location/Qualifiers
source                 1..12
                       mol_type = protein
                       organism = synthetic construct
SEQUENCE: 48
HHOAKKRCOO QH                                                12

SEQ ID NO: 49          moltype = AA  length = 12
FEATURE                Location/Qualifiers
source                 1..12
                       mol_type = protein
                       organism = synthetic construct
SEQUENCE: 49
HRKOORKHHR KK                                                12

SEQ ID NO: 50          moltype = AA  length = 12
FEATURE                Location/Qualifiers
source                 1..12
                       mol_type = protein
                       organism = synthetic construct
SEQUENCE: 50
KRAHOKCORK SH                                                12

SEQ ID NO: 51          moltype = AA  length = 12
FEATURE                Location/Qualifiers
source                 1..12
                       mol_type = protein
                       organism = synthetic construct
SEQUENCE: 51
```

```
KKRROOHHHR RR                                                     12

SEQ ID NO: 52           moltype = AA  length = 12
FEATURE                 Location/Qualifiers
source                  1..12
                        mol_type = protein
                        organism = synthetic construct
SEQUENCE: 52
OOORRRKKKH HH                                                     12

SEQ ID NO: 53           moltype = AA  length = 30
FEATURE                 Location/Qualifiers
source                  1..30
                        mol_type = protein
                        organism = synthetic construct
SEQUENCE: 53
HKROHKROHK ROHKROHKRO HKROHKROHK                                  30

SEQ ID NO: 54           moltype = AA  length = 30
FEATURE                 Location/Qualifiers
source                  1..30
                        mol_type = protein
                        organism = synthetic construct
SEQUENCE: 54
KOHRSOKRHT ORHKAHORKC KROKQRKHOS                                  30

SEQ ID NO: 55           moltype = AA  length = 30
FEATURE                 Location/Qualifiers
source                  1..30
                        mol_type = protein
                        organism = synthetic construct
SEQUENCE: 55
KKROSRRHOT OOHHAROKHC KHROTRHKKS                                  30

SEQ ID NO: 56           moltype = AA  length = 30
FEATURE                 Location/Qualifiers
source                  1..30
                        mol_type = protein
                        organism = synthetic construct
SEQUENCE: 56
HRKQOHRSOO KTRRRAHROC HHHSRHOTHR                                  30

SEQ ID NO: 57           moltype = AA  length = 35
FEATURE                 Location/Qualifiers
source                  1..35
                        mol_type = protein
                        organism = synthetic construct
SEQUENCE: 57
GRHKAKNHIR RPKSRWKKWH KYRKVHRHKV HKGRR                            35

SEQ ID NO: 58           moltype = AA  length = 40
FEATURE                 Location/Qualifiers
source                  1..40
                        mol_type = protein
                        organism = synthetic construct
SEQUENCE: 58
WRKVHHYKKQ HKNRAHGKLK LRAKIHQRSR MHGKQKHYHR                       40

SEQ ID NO: 59           moltype = AA  length = 42
FEATURE                 Location/Qualifiers
source                  1..42
                        mol_type = protein
                        organism = synthetic construct
SEQUENCE: 59
AHHKCRRGHK QKILHRRPHK FHRWKRVHKG RHGKKHRRHK HR                    42

SEQ ID NO: 60           moltype = AA  length = 45
FEATURE                 Location/Qualifiers
source                  1..45
                        mol_type = protein
                        organism = synthetic construct
SEQUENCE: 60
QHRGKAKYHR THHVKKQRHG RKNHKVHRHA RKFHKIRRLK CHKKH                 45

SEQ ID NO: 61           moltype = AA  length = 50
FEATURE                 Location/Qualifiers
source                  1..50
                        mol_type = protein
                        organism = synthetic construct
```

```
SEQUENCE: 61
HNKRFKKGRH VRHSRHKSHR RTHKYHHWRH YRKVHRCKKA HKSHHRVHHK             50

SEQ ID NO: 62           moltype = AA  length = 50
FEATURE                 Location/Qualifiers
source                  1..50
                        mol_type = protein
                        organism = synthetic construct
SEQUENCE: 62
AHGRPHOFKR OCKAHOVKHI LKRTOSHOYK OVHQRNKOAO KMRKIRGGHK             50

SEQ ID NO: 63           moltype = AA  length = 223
FEATURE                 Location/Qualifiers
source                  1..223
                        mol_type = protein
                        organism = synthetic construct
SEQUENCE: 63
TCPPCPAPEL LGGPSVFLFP PKPKDTLMIS RTPEVTCVVV DVSHEDPEVK FNWYVDGVEV  60
HNAKTKPREE QYNSTYRVVS VLTVLHQDWL NGKEYKCKVS NKALPAPIEK TISKAKGQPR  120
EPQVYTLPPS RDELTKNQVS LTCLVKGFYP SDIAVEWESN GQPENNYKTT PPVLDSDGSF  180
FLYSKLTVDK SRWQQGNVFS CSVMHEALHN HYTQKSLSLS PGK                    223

SEQ ID NO: 64           moltype = AA  length = 106
FEATURE                 Location/Qualifiers
source                  1..106
                        mol_type = protein
                        organism = synthetic construct
SEQUENCE: 64
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                 106

SEQ ID NO: 65           moltype = AA  length = 103
FEATURE                 Location/Qualifiers
source                  1..103
                        mol_type = protein
                        organism = synthetic construct
SEQUENCE: 65
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSC                    103

SEQ ID NO: 66           moltype = AA  length = 121
FEATURE                 Location/Qualifiers
source                  1..121
                        mol_type = protein
                        organism = synthetic construct
SEQUENCE: 66
TCPPCPAPEL LGGPSVFLFP PKPKDTLMIS RTPEVTCVVV DVSHEDPEVK FNWYVDGVEV  60
HNAKTKPREE QYNSTYRVVS VLTVLHQDWL NGKEYKCKVS NKALPAPIEK TISKAKGQPR  120
E                                                                  121

SEQ ID NO: 67           moltype = AA  length = 102
FEATURE                 Location/Qualifiers
source                  1..102
                        mol_type = protein
                        organism = synthetic construct
SEQUENCE: 67
PQVYTLPPSR DELTKNQVSL TCLVKGFYPS DIAVEWESNG QPENNYKTTP PVLDSDGSFF  60
LYSKLTVDKS RWQQGNVFSC SVMHEALHNH YTQKSLSLSP GK                     102

SEQ ID NO: 68           moltype = AA  length = 107
FEATURE                 Location/Qualifiers
source                  1..107
                        mol_type = protein
                        organism = synthetic construct
SEQUENCE: 68
PDVYLLPPAR EQLNLRESAT ITCLVTGFSP ADVFVQWMQR GQPLSPEKYV TSAPMPEPQA  60
PGRYFAHSIL TVSEEEWNTG ETYTCVVAHE ALPNRVTERT VDKSTGK                107

SEQ ID NO: 69           moltype = AA  length = 525
FEATURE                 Location/Qualifiers
source                  1..525
                        mol_type = protein
                        organism = synthetic construct
SEQUENCE: 69
MWWRLWWLLL LLLLLWGSSA SAAIIPVEEE NPDFWNREAA EALGAAKKLQ PAQTAAKNLI  60
IFLGDGMGVS TVTAARILKG QKKDKLGPEI PLAMDRFPYV ALSKTYNVDK HVPDSGATAT  120
AYLCGVKGNF QTIGLSAAAR FNQCNTTRGN EVISVMNRAK KAGKSVGVVT TTRVQHASPA  180
GTYAHTVNRN WYSDADVPAS ARQEGCQDIA TQLISNMDID VILGGGRKYM FRMGTPDPEY  240
PDDYSQGGTR LDGKNLVQEW LAKRQGARYV WNRTELMQAS LDPSVTHLMG LFEPGDMKYE  300
```

```
IHRDSTLDPS LMEMTEAALR LLSRNPRGFF LFVEGGRIDH GHHESRAYRA LTETIMFDDA  360
IERAGQLTSE EDTLSLVTAD HSHVFSFGGY PLRGSSIFGL APGKARDRKA YTVLLYGNGP  420
GYVLKDGARP DVTESESGSP EYRQQSAVPL DEETHAGEDV AVFARGPQAH LVHGVQEQTF  480
IAHVMAFAAC LEPYTACDLA PPAGTTDAAH PGYSRVGAAG RFEQT                  525

SEQ ID NO: 70          moltype = AA  length = 202
FEATURE                Location/Qualifiers
source                 1..202
                       mol_type = protein
                       organism = synthetic construct
SEQUENCE: 70
MKLVGSYTSP FVRKLSILLL EKGITFEFIN ELPYNADNGV AQFNPLGKVP VLVTEEGECW  60
FDSPIIAEYI ELMNVAPAML PRDPLESLRV RKIEALADGI MDAGLVSVRE QARPAAQQSE  120
DELLRQREKI NRSLDVLEGY LVDGTLKTDT VNLATIAIAC AVGYLNFRRV APGWCVDRPH  180
LVKLVENLFS RESFARTEPP KA                                           202

SEQ ID NO: 71          moltype = AA  length = 22
FEATURE                Location/Qualifiers
source                 1..22
                       mol_type = protein
                       organism = synthetic construct
SEQUENCE: 71
LENHSRRLEM TNKQLWLRIQ EL                                           22

SEQ ID NO: 72          moltype = AA  length = 27
FEATURE                Location/Qualifiers
source                 1..27
                       mol_type = protein
                       organism = synthetic construct
SEQUENCE: 72
LSIIAICLGS LGLILIILLS VVVWKLL                                      27

SEQ ID NO: 73          moltype = AA  length = 6
FEATURE                Location/Qualifiers
source                 1..6
                       mol_type = protein
                       organism = synthetic construct
VARIANT                4..6
                       note = can be absent or present in repeats of any integer
SEQUENCE: 73
GPPGPP                                                             6

SEQ ID NO: 74          moltype = AA  length = 27
FEATURE                Location/Qualifiers
source                 1..27
                       mol_type = protein
                       organism = synthetic construct
SEQUENCE: 74
GYIPEAPRDG QAYVRKDGEW VLLSTFL                                      27

SEQ ID NO: 75          moltype = AA  length = 31
FEATURE                Location/Qualifiers
source                 1..31
                       mol_type = protein
                       organism = synthetic construct
SEQUENCE: 75
EYFTLQIRGR ERFEMFRELN EALELKDAQA G                                 31

SEQ ID NO: 76          moltype = AA  length = 128
FEATURE                Location/Qualifiers
source                 1..128
                       mol_type = protein
                       organism = synthetic construct
SEQUENCE: 76
MAEAGITGTW YNQLGSTFIV TAGADGALTG TYESAVGNAE GDYVLTGRYD SAPATDGSGT  60
ALGWTVAWKN NYRNAHSATT WSGQYVGGAE ARINTQWLLT SGTTEANAWK STLVGHDTFT  120
KVKPSAAS                                                           128

SEQ ID NO: 77          moltype = AA  length = 42
FEATURE                Location/Qualifiers
source                 1..42
                       mol_type = protein
                       organism = synthetic construct
SEQUENCE: 77
GPQMLRELGE TNAALQDVRE LLRQQVREIT FLKNTVMEBD AC                     42

SEQ ID NO: 78          moltype = AA  length = 21
FEATURE                Location/Qualifiers
source                 1..21
```

```
                        mol_type = protein
                        organism = synthetic construct
SEQUENCE: 78
SRGGGGSGGG GSGGGGSLEM A                                              21

SEQ ID NO: 79           moltype = AA  length = 5
FEATURE                 Location/Qualifiers
source                  1..5
                        mol_type = protein
                        organism = synthetic construct
SEQUENCE: 79
GGGGS                                                                5

SEQ ID NO: 80           moltype = AA  length = 4
FEATURE                 Location/Qualifiers
source                  1..4
                        mol_type = protein
                        organism = synthetic construct
VARIANT                 3..4
                        note = can be absent or present in repeats of any integer
SEQUENCE: 80
GSGS                                                                 4

SEQ ID NO: 81           moltype = AA  length = 5
FEATURE                 Location/Qualifiers
source                  1..5
                        mol_type = protein
                        organism = synthetic construct
VARIANT                 1..5
                        note = can be present in repeats of any integer
SEQUENCE: 81
GSGGS                                                                5

SEQ ID NO: 82           moltype = AA  length = 5
FEATURE                 Location/Qualifiers
source                  1..5
                        mol_type = protein
                        organism = synthetic construct
VARIANT                 1..5
                        note = can be present in repeats of any integer
SEQUENCE: 82
GGGGS                                                                5

SEQ ID NO: 83           moltype = AA  length = 4
FEATURE                 Location/Qualifiers
source                  1..4
                        mol_type = protein
                        organism = synthetic construct
VARIANT                 1..4
                        note = can be present in repeats of any integer
SEQUENCE: 83
GGGS                                                                 4

SEQ ID NO: 84           moltype = AA  length = 836
FEATURE                 Location/Qualifiers
source                  1..836
                        mol_type = protein
                        organism = synthetic construct
SEQUENCE: 84
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYATCPP  600
CPAPELLGGP SVFLFPPKPK DTLMISRTPE VTCVVVDVSH EDPEVKFNWY VDGVEVHNAK  660
TKPREEQYNS TYRVVSVLTV LHQDWLNGKE YKCKVSNKAL PAPIEKTISK AKGQPREPQV  720
YTLPPSRDEL TKNQVSLTCL VKGFYPSDIA VEWESNGQPE NNYKTTPPVL DSDGSFFLYS  780
KLTVDKSRWQ QGNVFSCSVM HEALHNHYTQ KSLSLSPGKG GGGSKKKKKK KKKKKK      836

SEQ ID NO: 85           moltype = AA  length = 831
FEATURE                 Location/Qualifiers
source                  1..831
                        mol_type = protein
                        organism = synthetic construct
```

```
SEQUENCE: 85
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYATCPP  600
CPAPELLGGP SVFLFPPKPK DTLMISRTPE VTCVVVDVSH EDPEVKFNWY VDGVEVHNAK  660
TKPREEQYNS TYRVVSVLTV LHQDWLNGKE YKCKVSNKAL PAPIEKTISK AKGQPREPQV  720
YTLPPSRDEL TKNQVSLTCL VKGFYPSDIA VEWESNGQPE NNYKTTPPVL DSDGSFFLYS  780
KLTVDKSRWQ QGNVFSCSVM HEALHNHYTQ KSLSLSPGKH HHHHHHHHHH H          831

SEQ ID NO: 86          moltype = AA  length = 244
FEATURE                Location/Qualifiers
source                 1..244
                       mol_type = protein
                       organism = synthetic construct
SEQUENCE: 86
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGLSIIAICL GSLGLILIIL LSVVVWKLLG RHKAKNHIRR PKSRWKKWHK YRKVHRHKVH  240
KGRR                                                              244

SEQ ID NO: 87          moltype = AA  length = 315
FEATURE                Location/Qualifiers
source                 1..315
                       mol_type = protein
                       organism = synthetic construct
SEQUENCE: 87
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGTCPPCPAP ELLGGPSVFL FPPKPKDTLM ISRTPEVTCV VVDVSHEDPE VKFNWYVDGV  240
EVHNAKTKPR EEQYNSTYRV VSVLTVLHQD WLNGKEYKCK VSNKALPAPI EKTISKAKGQ  300
PREKRAHOKC ORKSH                                                  315

SEQ ID NO: 88          moltype = AA  length = 197
FEATURE                Location/Qualifiers
source                 1..197
                       mol_type = protein
                       organism = synthetic construct
SEQUENCE: 88
QAKTFLDKFN HEAEDLFYQM AEAGITGTWY NQLGSTFIVT AGADGALTGT YESAVGNAEG  60
DYVLTGRYDS APATDGSGTA LGWTVAWKNN YRNAHSATTW SGQYVGGAEA RINTQWLLTS  120
GTTEANAWKS TLVGHDTFTK VKPSAASHNK RFKKGRHVRH SRHKSHRRTH KYHHWRHYRK  180
VHRCKKAHKS HHRVHHK                                                197

SEQ ID NO: 89          moltype = AA  length = 418
FEATURE                Location/Qualifiers
source                 1..418
                       mol_type = protein
                       organism = synthetic construct
SEQUENCE: 89
STEDLVKTFL EKFNYEAEEL SYQSSLASWN YNINITDENV QKMNNAGAKW SAFYEEQSKL  60
AKTYPLEEIQ DSTVKRQLRA LQHSGSSVLS ADKNQRLNTI LNSMSTIYST GKACNPSNPQ  120
ECLLLEPGLD DIMENSKDYN ERLWAWEGWR SEVGKQLRPL YEEYVALKNE MARANNYEDY  180
GDATCPPCPA PELLGGPSVF LFPPKPKDTL MISRTPEVTC VVVDVSHEDP EVKFNWYVDG  240
VEVHNAKTKP REEQYNSTYR VVSVLTVLHQ DWLNGKEYKC KVSNKALPAP IEKTISKAKG  300
QPREPQVYTL PPSRDELTKN QVSLTCLVKG FYPSDIAVEW ESNGQPENNY KTTPPVLDSD  360
GSFFLYSKLT VDKSRWQQGN VFSCSVMHEA LHNHYTQKSL SLSPGKHHHH HHHHHHHH    418

SEQ ID NO: 90          moltype = AA  length = 252
FEATURE                Location/Qualifiers
source                 1..252
                       mol_type = protein
                       organism = synthetic construct
SEQUENCE: 90
STEDLVKTFL EKFNYEAEEL SYQSSLASWN YNINITDENV QKMNNAGAKW SAFYEEQSKL  60
AKTYPLEEIQ DSTVKRQLRA LQHSGSSVLS ADKNQRLNTI LNSMSTIYST GKACNPSNPQ  120
ECLLLEPGLD DIMENSKDYN ERLWAWEGWR SEVGKQLRPL YEEYVALKNE MARANNYEDY  180
GDGPPGPPGP PGPPGPPGPP GPPGPPGPPG PPWRKVHHYK KQHKNRAHGK LKLRAKIHQR  240
SRMHGKQKHY HR                                                     252

SEQ ID NO: 91          moltype = AA  length = 644
```

```
FEATURE                Location/Qualifiers
source                 1..644
                       mol_type = protein
                       organism = synthetic construct
SEQUENCE: 91
SLTEENAKTF LNNFNQEAED LSYQSSLASW NYNTNITEEN AQKMSEAAAK WSAFYEEQSK  60
TAQSFSLQEI QTPIIKRQLQ ALQQSGSSAL SADKNKQLNT ILNTMSTIYS TGKVCNPKNP  120
QECLLLEPGL DEIMATSTDY NSRLWAWEGW RAEVGKQLRP LYEEYVVLKN EMARANNYND  180
YGDYWRGDYE AEGADGYNYN RNQLIEDVER TFAEIKPLYE HLHAYVRRKL MDTYPSYISP  240
TGCLPAHLLG DMWGRFWTNL YPLTVPFAQK PNIDVTDAMM NQGWDAERIF QEAEKFFVSV  300
GLPHMTQGFW ANSMLTEPAD GRKVVCHPTA WDLGHGDFRI KMCTKVTMDN FLTAHHEMGH  360
IQYDMAYARQ PFLLRNGANE GFHEAVGEIM SLSAATPKHL KSIGLLPSDF QEDSETEINF  420
LLKQALTIVG TLPFTYMLEK WRWMVFRGEI PKEQWMKKWW EMKREIVGVV EPLPHDETYC  480
DPASLFHVSN DYSFIRYYTR TIYQFQFQEA LCQAAKYNGS LHKCDISNST EAGQKLLKML  540
SLGNSEPWTK ALENVVGARN MDVKPLLNYF QPLFDWLKEQ NRNSFVGWNT EWSPYAGPQM  600
LRELGETNAA LQDVRELLRQ QVREITFLKN TVMEBDACKK HHRR                  644

SEQ ID NO: 92          moltype = AA  length = 568
FEATURE                Location/Qualifiers
source                 1..568
                       mol_type = protein
                       organism = synthetic construct
SEQUENCE: 92
AEFNVRAEDI SYENSLASWN YNTNITEETA RKMSEAGAKW AAFYEEASRN ASRFSLANIQ  60
DAVTRLQIQS LQDRGSSVLS PEKYSRLNSV MNSMSTIYST GVVCKATEPF DCLVLEPGLD  120
DIMANSIDYH ERLWAWEGWR ADVGRMMRPL YEEYVELKNE AARLNNYSDY GDYWRANYET  180
DYPEEYKYSR DQLVQDVEKT FEQIKPLYQH LHAYVRHRLE QVYGSELINP TGCLPAHLLG  240
DMWGRFWTNL YNLTVPYPEK PNIDVTSAMA QKNWDAMKIF KTAEAFFASI GLYNMTEGFW  300
TNSMLTEPTD NRKVVCHPTA WDMGKNDYRI KMATCPPCPA PELLGGPSVF LFPPKPKDTL  360
MISRTPEVTC VVVDVSHEDP EVKFNWYVDG VEVHNAKTKP REEQYNSTYR VVSVLTVLHQ  420
DWLNGKEYKC KVSNKALPAP IEKTISKAKG QPREPQVYTL PPSRDELTKN QVSLTCLVKG  480
FYPSDIAVEW ESNGQPENNY KTTPPVLDSD GSFFLYSKLT VDKSRWQQGN VFSCSVMHEA  540
LHNHYTQKSL SLSPGKOOOO OOOOOOOO                                    568

SEQ ID NO: 93          moltype = AA  length = 419
FEATURE                Location/Qualifiers
source                 1..419
                       mol_type = protein
                       organism = synthetic construct
SEQUENCE: 93
YQNSLASWNY NTNITDENIQ KMNIAGAKWS AFYEEESQHA KTYPLEEIQD PIIKRQLRAL  60
QQSGSSVLSA DKRERLNTIL NAMSTIYSTG KACNPNNPQE CLLLEPGLDD IMENSKDYNE  120
RLWAWEGWRS EVGKQLRPLY EEYVALKNEM ARANNYEDYG DYWRGDYEEE WADGYNYSRN  180
QLIEDVEHTF TQIKPLYEHL HAYVRAKLMD AYPSRISPTG CLPAHLLGDM WGRFWTNLYP  240
LMVPFGQKPN IDVTDAMVNQ SWDARRIFKE AEKFFVSVGL PNMTEGFWQN SMLTEPGDNR  300
KVVCHPTAWD LGKHDFRIKM CTKVTMDDFL TAHHEMGHIQ YDMAYAAQPF LLRNGANEGF  360
HEAVGEIMSL SAATPNHLKF GYIPEAPRDG QAYVRKDGEW VLLSTFLHHK KOOHHKKOO   419

SEQ ID NO: 94          moltype = AA  length = 344
FEATURE                Location/Qualifiers
source                 1..344
                       mol_type = protein
                       organism = synthetic construct
SEQUENCE: 94
PPKVSVFVPP RDGFFGNPRK SKLICQATGF SPRQIQVSWL REGKQVGSGV TTDQVQAEAK  60
ESGPTTYKVT STLTIKESDW LSQSMFTCRV DHRGLTFQQN ASSMCVPDQD TAIRVFAIPP  120
SFASIFLTKS TKLTCLVTDL TTYDSVTISW TRQNGEAVKT HTNISESHPN ATFSAVGEAS  180
ICEDDWNSGE RFTCTVTHTD LPSPLKQTIS RPKGVALHRP DVYLLPPARE QLNLRESATI  240
TCLVTGFSPA DVFVQWMQRG QPLSPEKYVT SAPMPEPQAP GRYFAHSILT VSEEEWNTGE  300
TYTCVVAHEA LPNRVTERTV DKSTGKPTLY NVSLVMSDTA GTCY                  344

SEQ ID NO: 95          moltype = AA  length = 14
FEATURE                Location/Qualifiers
source                 1..14
                       mol_type = protein
                       organism = synthetic construct
SEQUENCE: 95
DYKDDDDKHH HHHH                                                   14

SEQ ID NO: 96          moltype = AA  length = 223
FEATURE                Location/Qualifiers
source                 1..223
                       mol_type = protein
                       organism = SARS-CoV-2
SEQUENCE: 96
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNF                   223
```

```
SEQ ID NO: 97          moltype = AA  length = 223
FEATURE                Location/Qualifiers
source                 1..223
                       mol_type = protein
                       organism = SARS-CoV-2
SEQUENCE: 97
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYRYRLFRK SNLKPFERDI STEIYQAGSK PCNGVEGFNC YFPLQSYGFQ  180
PTNGVGYQPY RVVVLSFELL HAPATVCGPK KSTNLVKNKC VNF                   223

SEQ ID NO: 98          moltype = AA  length = 223
FEATURE                Location/Qualifiers
source                 1..223
                       mol_type = protein
                       organism = SARS-CoV-2
SEQUENCE: 98
RVQPTESIVR FPNITNLCPF DEVFNATRFA SVYAWNRKRI SNCVADYSVL YNLAPFFTFK  60
CYGVSPTKLN DLCFTNVYAD SFVIRGDEVR QIAPGQTGNI ADYNYKLPDD FTGCVIAWNS  120
NKLDSKVSGN YNYLYRLFRK SNLKPFERDI STEIYQAGNK PCNGVAGFNC YFPLRSYSFR  180
PTYGVGHQPY RVVVLSFELL HAPATVCGPK KSTNLVKNKC VNF                   223

SEQ ID NO: 99          moltype = AA  length = 223
FEATURE                Location/Qualifiers
source                 1..223
                       mol_type = protein
                       organism = SARS-CoV-2
SEQUENCE: 99
RVQPTESIVR FPNITNLCPF DEVFNATRFA SVYAWNRKRI SNCVADYSVL YNFAPFFAFK  60
CYGVSPTKLN DLCFTNVYAD SFVIRGNEVS QIAPGQTGNI ADYNYKLPDD FTGCVIAWNS  120
NKLDSKVGGN YNYLYRLFRK SNLKPFERDI STEIYQAGNK PCNGVAGFNC YFPLRSYGFR  180
PTYGVGHQPY RVVVLSFELL HAPATVCGPK KSTNLVKNKC VNF                   223

SEQ ID NO: 100         moltype = AA  length = 204
FEATURE                Location/Qualifiers
source                 1..204
                       mol_type = protein
                       organism = Bat coronavirus
SEQUENCE: 100
RVLPSTEVVR FPNITNFCPF DKVFNATRFP NVYAWQRTKI SDCIADYTVL YNSTSFSTFK  60
CYGVSPSKLI DLCFTSVYAD TFLIRFSEVR QIAPGETGVI ADYNYKLPDD FTGCVLAWNT  120
AQQDIGSYFY RSHRAVKLKP FERDLSSDEN GVRTLSTYDF NPNVPLDYQA TRVVVLSFEL  180
LNAPATVCGP KLSTQLVKNR CVNF                                        204

SEQ ID NO: 101         moltype = AA  length = 723
FEATURE                Location/Qualifiers
source                 1..723
                       mol_type = protein
                       organism = Homo sapiens
SEQUENCE: 101
QSTIEEQAKT FLDKFNHEAE DLFYQSSLAS WNYNTNITEE NVQNMNNAGD KWSAFLKEQS  60
TLAQMYPLQE IQNLTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
LRLGKSEPWT LALENVVGAK NMNVRPLLNY FEPLFTWLKD QNKNSFVGWS TDWSPYADQS  600
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVS                                                               723

SEQ ID NO: 102         moltype = AA  length = 12
FEATURE                Location/Qualifiers
source                 1..12
                       mol_type = protein
                       organism = Homo sapiens
SEQUENCE: 102
DKFNHEAEDL FY                                                     12

SEQ ID NO: 103         moltype = AA  length = 203
FEATURE                Location/Qualifiers
source                 1..203
                       mol_type = protein
                       organism = SARS-CoV coronavirus
SEQUENCE: 103
```

```
VTPTQEVVRF PNITNRCPFD KVFNASRFPN VYAWERTKIS DCVADYTVLY NSTSFSTFKC  60
YGVSPSKLID LCFTSVYADT FLIRSSEVRQ VAPGETGVIA DYNYKLPDDF TGCVIAWNTA  120
QQDQGQYYYR SYRKEKLKPF ERDLSSDENG VYTLSTYDFY PSIPVEYQAT RVVVLSFELL  180
NAPATVCGPK LSTQLVKNQC VNF                                          203

SEQ ID NO: 104          moltype = AA  length = 784
FEATURE                 Location/Qualifiers
source                  1..784
                        mol_type = protein
                        organism = synthetic construct
SEQUENCE: 104
STEDLVKTFL EKFNYEAEEL SYQSSLASWN YNINITDENV QKMNNAGAKW SAFYEEQSKL  60
AKTYPLEEIQ DSTVKRQLRA LQHSGSSVLS ADKNQRLNTI LNSMSTIYST GKACNPSNPQ  120
ECLLLEPGLD DIMENSKDYN ERLWAWEGWR SEVGKQLRPL YEEYVALKNE MARANNYEDY  180
GDYWRGDYEE EWENGYNYSR NQLIDDVEHT FTQIMPLYQH LHAYVRTKLM DTYPSYISPT  240
GCLPAHLLGD MWGRFWTNLY PLTVPFGQKP NIDVTNAMVN QSWDARKIFK EAEKFFVSVG  300
LPNMTQEFWE NSMLTEPSDS RKVVCHPTAW DLGKGDFRIK MCTKVTMDDF LTAHHEMGHI  360
QYDMAYAAQP FLLRNGANEG FHEAVGEIMS LSAATPNHLK NIGLLPPSFF EDSETEINFL  420
LKQALTIVGT LPFTYMLEKW RWMVFKGEIP KDQWMKTWWE MKRNIVGVVE PVPHDETYCD  480
PASLFHVAND YSFIRYYTRT IYQFQFQEAL CQIAKHEGPL HKCDISNSSE AGQKLLEMLK  540
LGKSKPWTYA LEIVVGAKNM DVRPLLNYFE PLFTWLKEQN RNSFVGWNTD WSPYADQSIK  600
VRISLKSALG EKAYEWNNNE MYLFRSSIAY AMRQYFSEVK NQTIPFVEDN VWVSDLKPRI  660
SFNFFVTSPG NVSDIIPRTE VEEAIRMYRS RINDVFRLDD NSLEFLGIQP TLGPPYEPPV  720
TIWLIVFGVV MGVVVVGIVL LIFSGIRNRR KNDQARGEEN PYASVDLSKG ENNPGFQNVD  780
DAQT                                                               784

SEQ ID NO: 105          moltype = AA  length = 182
FEATURE                 Location/Qualifiers
source                  1..182
                        mol_type = protein
                        organism = synthetic construct
SEQUENCE: 105
STEDLVKTFL EKFNYEAEEL SYQSSLASWN YNINITDENV QKMNNAGAKW SAFYEEQSKL  60
AKTYPLEEIQ DSTVKRQLRA LQHSGSSVLS ADKNQRLNTI LNSMSTIYST GKACNPSNPQ  120
ECLLLEPGLD DIMENSKDYN ERLWAWEGWR SEVGKQLRPL YEEYVALKNE MARANNYEDY  180
GD                                                                 182

SEQ ID NO: 106          moltype = AA  length = 596
FEATURE                 Location/Qualifiers
source                  1..596
                        mol_type = protein
                        organism = synthetic construct
SEQUENCE: 106
SLTEENAKTF LNNFNQEAED LSYQSSLASW NYNTNITEEN AQKMSEAAAK WSAFYEEQSK  60
TAQSFSLQEI QTPIIKRQLQ ALQQSGSSAL SADKNKQLNT ILNTMSTIYS TGKVCNPKNP  120
QECLLLEPGL DEIMATSTDY NSRLWAWEGW RAEVGKQLRP LYEEYVVLKN EMARANNYND  180
YGDYWRGDYE AEGADGYNYN RNQLIEDVER TFAEIKPLYE HLHAYVRRKL MDTYPSYISP  240
TGCLPAHLLG DMWGRFWTNL YPLTVPFAQK PNIDVTDAMM NQGWDAERIF QEAEKFFVSV  300
GLPHMTQGFW ANSMLTEPAD GRKVVCHPTA WDLGHGDFRI KMCTKVTMDN FLTAHHEMGH  360
IQYDMAYARQ PFLLRNGANE GFHEAVGEIM SLSAATPKHL KSIGLLPSDF QEDSETEINF  420
LLKQALTIVG TLPFTYMLEK WRWMVFRGEI PKEQWMKKWW EMKREIVGVV EPLPHDETYC  480
DPASLFHVSN DYSFIRYYTR TIYQFQFQEA LCQAAKYNGS LHKCDISNST EAGQKLLKML  540
SLGNSEPWTK ALENVVGARN MDVKPLLNYF QPLFDWLKEQ NRNSFVGWNT EWSPYA      596

SEQ ID NO: 107          moltype = AA  length = 286
FEATURE                 Location/Qualifiers
source                  1..286
                        mol_type = protein
                        organism = synthetic construct
SEQUENCE: 107
ASRNASRFSL ANIQDAVTRL QIQSLQDRGS SVLSPEKYSR LNSVMNSMST IYSTGVVCKA  60
TEPFDCLVLE PGLDDIMANS IDYHERLWAW EGWRADVGRM MRPLYEEYVE LKNEAARLNN  120
YSDYGDYWRA NYETDYPEEY KYSRDQLVQD VEKTFEQIKP LYQHLHAYVR HRLEQVYGSE  180
LINPTGCLPA HLLGDMWGRF WTNLYNLTVP YPEKPNIDVT SAMAQKNWDA MKIFKTAEAF  240
FASIGLYNMT EGFWTNSMLT EPTDNRKVVC HPTAWDMGKN DYRIKM                 286

SEQ ID NO: 108          moltype = AA  length = 380
FEATURE                 Location/Qualifiers
source                  1..380
                        mol_type = protein
                        organism = synthetic construct
SEQUENCE: 108
YQNSLASWNY NTNITDENIQ KMNIAGAKWS AFYEEESQHA KTYPLEEIQD PIIKRQLRAL  60
QQSGSSVLSA DKRERLNTIL NAMSTIYSTG KACNPNNPQE CLLLEPGLDD IMENSKDYNE  120
RLWAWEGWRS EVGKQLRPLY EEYVALKNEM ARANNYEDYG DYWRGDYEEE WADGYNYSRN  180
QLIEDVEHTF TQIKPLYEHL HAYVRAKLMD AYPSRISPTG CLPAHLLGDM WGRFWTNLYP  240
LMVPFGQKPN IDVTDAMVNQ SWDARRIFKE AEKFFVSVGL PNMTEGFWQN SMLTEPGDNR  300
KVVCHPTAWD LGKHDFRIKM CTKVTMDDFL TAHHEMGHIQ YDMAYAAQPF LLRNGANEGF  360
HEAVGEIMSL SAATPNHLKF                                              380
```

```
SEQ ID NO: 109          moltype = AA  length = 30
FEATURE                 Location/Qualifiers
source                  1..30
                        mol_type = protein
                        organism = synthetic construct
SEQUENCE: 109
GPPGPPGPPG PPGPPGPPGP PGPPGPPGPP                                   30

SEQ ID NO: 110          moltype = AA  length = 12
FEATURE                 Location/Qualifiers
source                  1..12
                        mol_type = protein
                        note = Gallus domesticus
                        organism = unidentified
SEQUENCE: 110
AEFNVRAEDI SY                                                      12

SEQ ID NO: 111          moltype = AA  length = 12
FEATURE                 Location/Qualifiers
source                  1..12
                        mol_type = protein
                        organism = Cavia porcellus
SEQUENCE: 111
DEFNLKAEDL YY                                                      12

SEQ ID NO: 112          moltype = AA  length = 12
FEATURE                 Location/Qualifiers
source                  1..12
                        mol_type = protein
                        organism = Mus musculus
SEQUENCE: 112
NNFNQEAEDL SY                                                      12

SEQ ID NO: 113          moltype = AA  length = 12
FEATURE                 Location/Qualifiers
source                  1..12
                        mol_type = protein
                        note = Sus domesticus
                        organism = unidentified
SEQUENCE: 113
EKFNLEAEDL AY                                                      12

SEQ ID NO: 114          moltype = AA  length = 12
FEATURE                 Location/Qualifiers
source                  1..12
                        mol_type = protein
                        note = Bovinae+G116 (cow)
                        organism = unidentified
SEQUENCE: 114
EKFNHEAEDL SY                                                      12

SEQ ID NO: 115          moltype = AA  length = 12
FEATURE                 Location/Qualifiers
source                  1..12
                        mol_type = protein
                        organism = Oryctolagus cuniculus
SEQUENCE: 115
EKFNQEAEDL SY                                                      12

SEQ ID NO: 116          moltype = AA  length = 12
FEATURE                 Location/Qualifiers
source                  1..12
                        mol_type = protein
                        organism = Macaca sp.
SEQUENCE: 116
DKFNHEAEDL FY                                                      12

SEQ ID NO: 117          moltype = AA  length = 12
FEATURE                 Location/Qualifiers
source                  1..12
                        mol_type = protein
                        organism = Pan troglodytes
SEQUENCE: 117
DKFNHEAEDL FY                                                      12

SEQ ID NO: 118          moltype = AA  length = 12
FEATURE                 Location/Qualifiers
source                  1..12
```

```
                        mol_type = protein
                        organism = Equus sp.
SEQUENCE: 118
EKFNSEAEEL SH                                                12

SEQ ID NO: 119          moltype = AA  length = 12
FEATURE                 Location/Qualifiers
source                  1..12
                        mol_type = protein
                        note = Mustela furo
                        organism = unidentified
SEQUENCE: 119
EKFNYEAEEL SY                                                12

SEQ ID NO: 120          moltype = AA  length = 12
FEATURE                 Location/Qualifiers
source                  1..12
                        mol_type = protein
                        organism = Neovison vison
SEQUENCE: 120
EKFNYEAEEL SY                                                12

SEQ ID NO: 121          moltype = AA  length = 12
FEATURE                 Location/Qualifiers
source                  1..12
                        mol_type = protein
                        organism = Canis sp.
SEQUENCE: 121
EKFNYEAEEL SY                                                12

SEQ ID NO: 122          moltype = AA  length = 12
FEATURE                 Location/Qualifiers
source                  1..12
                        mol_type = protein
                        organism = Felis sp.
SEQUENCE: 122
EKFNHEAEEL SY                                                12

SEQ ID NO: 123          moltype = AA  length = 223
FEATURE                 Location/Qualifiers
source                  1..223
                        mol_type = protein
                        organism = SARS-CoV-2
SEQUENCE: 123
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTYGVGYQPY RVVVLSFELL HAPATVCGPK KSTNLVKNKC VNF                   223

SEQ ID NO: 124          moltype = AA  length = 223
FEATURE                 Location/Qualifiers
source                  1..223
                        mol_type = protein
                        organism = SARS-CoV-2
SEQUENCE: 124
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTYGVGYQPY RVVVLSFELL HAPATVCGPK KSTNLVKNKC VNF                   223

SEQ ID NO: 125          moltype = AA  length = 223
FEATURE                 Location/Qualifiers
source                  1..223
                        mol_type = protein
                        organism = SARS-CoV-2
SEQUENCE: 125
RVQPTESIVR FPNITNLCPF DEVFNATRFA SVYAWNRKRI SNCVADYSVL YNFAPFFAFK  60
CYGVSPTKLN DLCFTNVYAD SFVIRGNEVS QIAPGQTGNI ADYNYKLPDD FTGCVIAWNS  120
NKLDSKVGGN YNYRYRLFRK SNLKPFERDI STEIYQAGNK PCNGVAGVNC YFPLQSYGFR  180
PTYGVGHQPY RVVVLSFELL HAPATVCGPK KSTNLVKNKC VNF                   223

SEQ ID NO: 126          moltype = AA  length = 223
FEATURE                 Location/Qualifiers
source                  1..223
                        mol_type = protein
                        organism = SARS-CoV-2
SEQUENCE: 126
RVQPTESIVR FPNITNLCPF DEVFNATRFA SVYAWNRKRI SNCVADYSVL YNFAPFFAFK  60
CYGVSPTKLN DLCFTNVYAD SFVIRGNEVS QIAPGQTGNI ADYNYKLPDD FTGCVIAWNS  120
```

```
NKLDSTVGGN YNYRYRLFRK SKLKPFERDI STEIYQAGNK PCNGVAGVNC YFPLQSYGFR  180
PTYGVGHQPY RVVVLSFELL HAPATVCGPK KSTNLVKNKC VNF                   223

SEQ ID NO: 127         moltype = AA  length = 223
FEATURE                Location/Qualifiers
source                 1..223
                       mol_type = protein
                       organism = SARS-CoV-2
SEQUENCE: 127
RVQPTESIVR FPNITNLCPF HEVFNATTFA SVYAWNRKRI SNCVADYSVI YNFAPFFAFK  60
CYGVSPTKLN DLCFTNVYAD SFVIRGNEVS QIAPGQTGNI ADYNYKLPDD FTGCVIAWNS  120
NKLDSKPSGN YNYLYRLFRK SKLKPFERDI STEIYQAGNK PCNGVAGPNC YSPLQSYGFR  180
PTYGVGHQPY RVVVLSFELL HAPATVCGPK KSTNLVKNKC VNF                   223

SEQ ID NO: 128         moltype = AA  length = 5
FEATURE                Location/Qualifiers
source                 1..5
                       mol_type = protein
                       organism = synthetic construct
SEQUENCE: 128
HHHHH                                                             5

SEQ ID NO: 129         moltype = AA  length = 7
FEATURE                Location/Qualifiers
source                 1..7
                       mol_type = protein
                       organism = synthetic construct
SEQUENCE: 129
KKKGKKK                                                           7

SEQ ID NO: 130         moltype = AA  length = 12
FEATURE                Location/Qualifiers
source                 1..12
                       mol_type = protein
                       organism = synthetic construct
SEQUENCE: 130
KKAHHGKKAH HV                                                     12

SEQ ID NO: 131         moltype = AA  length = 12
FEATURE                Location/Qualifiers
source                 1..12
                       mol_type = protein
                       organism = synthetic construct
SEQUENCE: 131
KKARRGKKAR RV                                                     12

SEQ ID NO: 132         moltype = AA  length = 12
FEATURE                Location/Qualifiers
source                 1..12
                       mol_type = protein
                       organism = synthetic construct
SEQUENCE: 132
KLIHKKARVR GK                                                     12

SEQ ID NO: 133         moltype = AA  length = 15
FEATURE                Location/Qualifiers
source                 1..15
                       mol_type = protein
                       organism = synthetic construct
SEQUENCE: 133
ILRRKAHHGK IKKVR                                                  15

SEQ ID NO: 134         moltype = AA  length = 14
FEATURE                Location/Qualifiers
source                 1..14
                       mol_type = protein
                       organism = synthetic construct
SEQUENCE: 134
GHRVKKAVRH IKRL                                                   14

SEQ ID NO: 135         moltype = AA  length = 722
FEATURE                Location/Qualifiers
source                 1..722
                       mol_type = protein
                       organism = synthetic construct
SEQUENCE: 135
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
```

```
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYADQSI  600
KVRISLKSAL GDKAYEWNDN EMYLFRSSVA YAMRQYFLKV KNQMILFGEE DVRVANLKPR  660
ISFNFFVTAP KNVSDIIPRT EVEKAIRMSR SRINDAFRLN DNSLEFLGIQ PTLGPPNQPP  720
VS                                                                722

SEQ ID NO: 136          moltype = AA  length = 949
FEATURE                 Location/Qualifiers
source                  1..949
                        mol_type = protein
                        organism = synthetic construct
SEQUENCE: 136
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYADQSI  600
KVRISLKSAL GDKAYEWNDN EMYLFRSSVA YAMRQYFLKV KNQMILFGEE DVRVANLKPR  660
ISFNFFVTAP KNVSDIIPRT EVEKAIRMSR SRINDAFRLN DNSLEFLGIQ PTLGPPNQPP  720
VSTCPPCPAP ELLGGPSVFL FPPKPKDTLM ISRTPEVTCV VVDVSHEDPE VKFNWYVDGV  780
EVHNAKTKPR EEQYNSTYRV VSVLTVLHQD WLNGKEYKCK VSNKALPAPI EKTISKAKGQ  840
PREPQVYTLP PSRDELTKNQ VSLTCLVKGF YPSDIAVEWE SNGQPENNYK TTPPVLDSDG  900
SFFLYSKLTV DKSRWQQGNV FSCSVMHEAL HNHYTQKSLS LSPGHHHHH             949

SEQ ID NO: 137          moltype = AA  length = 950
FEATURE                 Location/Qualifiers
source                  1..950
                        mol_type = protein
                        organism = synthetic construct
SEQUENCE: 137
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYADQSI  600
KVRISLKSAL GDKAYEWNDN EMYLFRSSVA YAMRQYFLKV KNQMILFGEE DVRVANLKPR  660
ISFNFFVTAP KNVSDIIPRT EVEKAIRMSR SRINDAFRLN DNSLEFLGIQ PTLGPPNQPP  720
VSTCPPCPAP ELLGGPSVFL FPPKPKDTLM ISRTPEVTCV VVDVSHEDPE VKFNWYVDGV  780
EVHNAKTKPR EEQYNSTYRV VSVLTVLHQD WLNGKEYKCK VSNKALPAPI EKTISKAKGQ  840
PREPQVYTLP PSRDELTKNQ VSLTCLVKGF YPSDIAVEWE SNGQPENNYK TTPPVLDSDG  900
SFFLYSKLTV DKSRWQQGNV FSCSVMHEAL HNHYTQKSLS LSPGHHHHHH            950

SEQ ID NO: 138          moltype = AA  length = 951
FEATURE                 Location/Qualifiers
source                  1..951
                        mol_type = protein
                        organism = synthetic construct
SEQUENCE: 138
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYADQSI  600
KVRISLKSAL GDKAYEWNDN EMYLFRSSVA YAMRQYFLKV KNQMILFGEE DVRVANLKPR  660
ISFNFFVTAP KNVSDIIPRT EVEKAIRMSR SRINDAFRLN DNSLEFLGIQ PTLGPPNQPP  720
VSTCPPCPAP ELLGGPSVFL FPPKPKDTLM ISRTPEVTCV VVDVSHEDPE VKFNWYVDGV  780
EVHNAKTKPR EEQYNSTYRV VSVLTVLHQD WLNGKEYKCK VSNKALPAPI EKTISKAKGQ  840
PREPQVYTLP PSRDELTKNQ VSLTCLVKGF YPSDIAVEWE SNGQPENNYK TTPPVLDSDG  900
SFFLYSKLTV DKSRWQQGNV FSCSVMHEAL HNHYTQKSLS LSPGKKKGKK K           951
```

```
SEQ ID NO: 139          moltype = AA  length = 956
FEATURE                 Location/Qualifiers
source                  1..956
                        mol_type = protein
                        organism = synthetic construct
SEQUENCE: 139
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYADQSI  600
KVRISLKSAL GDKAYEWNDN EMYLFRSSVA YAMRQYFLKV KNQMILFGEE DVRVANLKPR  660
ISFNFFVTAP KNVSDIIPRT EVEKAIRMSR SRINDAFRLN DNSLEFLGIQ PTLGPPNQPP  720
VSTCPPCPAP ELLGGPSVFL FPPKPKDTLM ISRTPEVTCV VVDVSHEDPE VKFNWYVDGV  780
EVHNAKTKPR EEQYNSTYRV VSVLTVLHQD WLNGKEYKCK VSNKALPAPI EKTISKAKGQ  840
PREPQVYTLP PSRDELTKNQ VSLTCLVKGF YPSDIAVEWE SNGQPENNYK TTPPVLDSDG  900
SFFLYSKLTV DKSRWQQGNV FSCSVMHEAL HNHYTQKSLS LSPGKKAHHG KKAHHV      956

SEQ ID NO: 140          moltype = AA  length = 956
FEATURE                 Location/Qualifiers
source                  1..956
                        mol_type = protein
                        organism = synthetic construct
SEQUENCE: 140
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYADQSI  600
KVRISLKSAL GDKAYEWNDN EMYLFRSSVA YAMRQYFLKV KNQMILFGEE DVRVANLKPR  660
ISFNFFVTAP KNVSDIIPRT EVEKAIRMSR SRINDAFRLN DNSLEFLGIQ PTLGPPNQPP  720
VSTCPPCPAP ELLGGPSVFL FPPKPKDTLM ISRTPEVTCV VVDVSHEDPE VKFNWYVDGV  780
EVHNAKTKPR EEQYNSTYRV VSVLTVLHQD WLNGKEYKCK VSNKALPAPI EKTISKAKGQ  840
PREPQVYTLP PSRDELTKNQ VSLTCLVKGF YPSDIAVEWE SNGQPENNYK TTPPVLDSDG  900
SFFLYSKLTV DKSRWQQGNV FSCSVMHEAL HNHYTQKSLS LSPGKKARRG KKARRV      956

SEQ ID NO: 141          moltype = AA  length = 223
FEATURE                 Location/Qualifiers
source                  1..223
                        mol_type = protein
                        organism = synthetic construct
SEQUENCE: 141
RVQPTESIVR FPNITNLCPF DEVFNATRFA SVYAWNRKRI SNCVADYSVL YNFAPFFAFK  60
CYGVSPTKLN DLCFTNVYAD SFVIRGNEVS QIAPGQTGNI ADYNYKLPDD FTGCVIAWNS  120
NKLDSKVGGN YNYRYRLFRK SNLKPFERDI STEIYQAGNK PCNGVAGVNC YFPLQSYGFR  180
PTYGVGHQPY RVVVLSFELL HAPATVCGPK KSTNLVKNKC VNF                    223

SEQ ID NO: 142          moltype = AA  length = 223
FEATURE                 Location/Qualifiers
source                  1..223
                        mol_type = protein
                        organism = synthetic construct
SEQUENCE: 142
RVQPTESIVR FPNITNLCPF DEVFNATTFA SVYAWNRKRI SNCVADYSVL YNFAPFFAFK  60
CYGVSPTKLN DLCFTNVYAD SFVIRGNEVS QIAPGQTGNI ADYNYKLPDD FTGCVIAWNS  120
NKLDSTVGGN YNYRYRLFRK SKLKPFERDI STEIYQAGNK PCNGVAGVNC YFPLQSYGFR  180
PTYGVGHQPY RVVVLSFELL HAPATVCGPK KSTNLVKNKC VNF                    223

SEQ ID NO: 143          moltype = AA  length = 223
FEATURE                 Location/Qualifiers
source                  1..223
                        mol_type = protein
                        organism = synthetic construct
```

-continued

```
SEQUENCE: 143
RVQPTESIVR FPNITNLCPF HEVFNATTFA SVYAWNRKRI SNCVADYSVI YNFAPFFAFK  60
CYGVSPTKLN DLCFTNVYAD SFVIRGNEVS QIAPGQTGNI ADYNYKLPDD FTGCVIAWNS  120
NKLDSKPSGN YNYLYRLFRK SKLKPFERDI STEIYQAGNK PCNGVAGPNC YSPLQSYGFR  180
PTYGVGHQPY RVVVLSFELL HAPATVCGPK KSTNLVKNKC VNF                   223
```